(12) United States Patent
Shao et al.

(10) Patent No.: US 11,332,751 B2
(45) Date of Patent: May 17, 2022

(54) METHODS AND COMPOSITIONS FOR PRODUCTION OF AROMATIC AND OTHER COMPOUNDS IN YEAST

(71) Applicant: Iowa State University Research Foundation, Inc., Ames, IA (US)

(72) Inventors: Zengyi Shao, Ames, IA (US); Mingfeng Cao, Ames, IA (US); Miguel Suastegui, Ames, IA (US); Meirong Gao, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 22 days.

(21) Appl. No.: 16/947,304

(22) Filed: Jul. 28, 2020

(65) Prior Publication Data

US 2021/0040490 A1 Feb. 11, 2021

Related U.S. Application Data

(62) Division of application No. 16/019,822, filed on Jun. 27, 2018, now Pat. No. 10,787,672.

(60) Provisional application No. 62/526,223, filed on Jun. 28, 2017.

(51) Int. Cl.

| C12N 15/00 | (2006.01) |
| A01N 63/00 | (2020.01) |
| C12N 15/81 | (2006.01) |
| C12N 15/10 | (2006.01) |
| C12N 9/10 | (2006.01) |
| C12N 9/02 | (2006.01) |
| C12P 5/00 | (2006.01) |
| C12N 9/88 | (2006.01) |
| C12P 7/44 | (2006.01) |
| C12P 7/42 | (2006.01) |

(52) U.S. Cl.
CPC ........... *C12N 15/81* (2013.01); *C12N 9/0004* (2013.01); *C12N 9/10* (2013.01); *C12N 9/88* (2013.01); *C12N 15/102* (2013.01); *C12P 5/007* (2013.01); *C12P 7/42* (2013.01); *C12P 7/44* (2013.01); *C12N 2830/002* (2013.01); *C12N 2830/008* (2013.01); *C12N 2830/702* (2013.01)

(58) Field of Classification Search
CPC .............................. C12N 15/81; C12N 15/102
See application file for complete search history.

(56) References Cited

U.S. PATENT DOCUMENTS

| 8,609,382 B1 | 12/2013 | Hughes et al. |
| 9,297,027 B1 | 3/2016 | Slininger et al. |
| 2014/0370594 A1 | 12/2014 | Dumesic et al. |

OTHER PUBLICATIONS

Suastegui et al., "Investigating Strain Dependency in the Production of Aromatic Compounds in *Saccharomyces cerevisiae*", Biotechnology and Bioengineering, vol. 113, No. 12, pp. 2676-2685, Dec. 12, 2016.
Saustegui et al., "Yeast factories for the production of aromatic compounds: from building blocks to plant secondary metabolites", J Ind. Microbiol. Biotechnol., 14 pages, Aug. 31, 2016.
Gao et al., "Innovating a Nonconventional Yeast Platform for Producing Shikimte as the Building Block of High-Value Aromatics", ACS SyntheticBiology, 10 pages, Apr. 29, 2016.
GenEmbl Accession No. CP000499, May 14, 2014.
Jeffries et al., Nat. Biotechnol. 25 (3), pp. 319-326, 2007.

*Primary Examiner* — Gary B Nickol
*Assistant Examiner* — Lakia J Jackson-Tongue
(74) *Attorney, Agent, or Firm* — McKee, Voorhees & Sease, PLC

(57) ABSTRACT

The present disclosure includes methods and components for production of valuable industrial compounds in yeast. In an embodiment, the present invention provides a nucleic acid construct with increased stability for gene expression or gene editing comprising: a nucleic acid sequence encoding one or more of SEQ ID NO: 1-8 (CENs 1-8); and one or more regulatory elements functional in a yeast cell. In an embodiment of the present invention the nucleic acid constructs are vectors, preferably episomal vectors. High expression promoters, as well as methods for increasing production of compounds such as aromatics are disclosed.

12 Claims, 29 Drawing Sheets
(29 of 29 Drawing Sheet(s) Filed in Color)

Specification includes a Sequence Listing.

| Organism name | GC₃ analysis ratio |
|---|---|
| Scheffersomyces stipitis | 8/8 |
| Hansenula polymorpha | 7/7 |
| Candida lusitaniae | 8/8 |
| Yarrowia lipolytica | 6/6 |
| Ashbya gossypii | 3/7 |
| Aspergillus oryzae | 3/8 |
| Coprinopsis cinerea | 1/13 |
| Candida glabrata | 6/13 |
| Candida orthopsilosis | 4/8 |
| Candida tropicalis | 4/12 |
| Gibberella zeae | 2/11 |
| Kazachstania naganishii | 4/13 |
| Kluyveromyces lactis | 2/6 |
| Kazachstania africana | 4/12 |
| Lachancea thermotolerans | 1/8 |
| Lodderomyces elongisporus | 1/11 |
| Millerozyma farinosa | 6/13 |
| Naumovozyma dairenensis | 3/11 |
| Naumovozyma castellii | 2/10 |
| Pyrenophora tritici-repentis | 3/18 |
| Saccharomyces cerevisiae | 4/12 |
| Saccharomyces kudriavzevii | 3/16 |
| Saccharomyces uvarum | 4/16 |
| Saccharomyces kluyveri | 3/8 |
| Saccharomyces mikatae | 8/16 |
| Sporisorium reilianum | 3/23 |
| Tetrapisispora phaffii | 6/16 |
| Tetrapisispora blattae | 3/10 |
| Torulaspora delbrueckii | 2/8 |
| Zymoseptoria tritici | 2/21 |

*FIG. 2A*

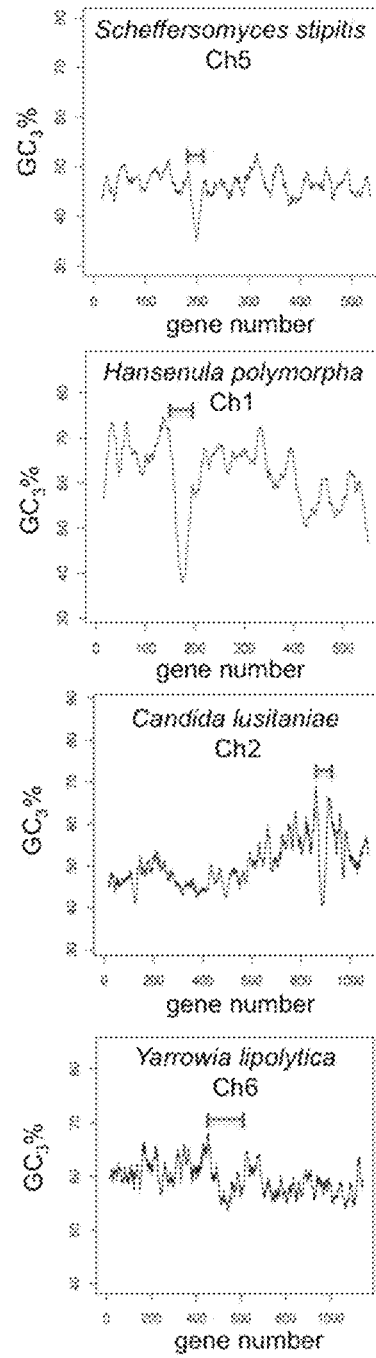

*FIG. 2B*

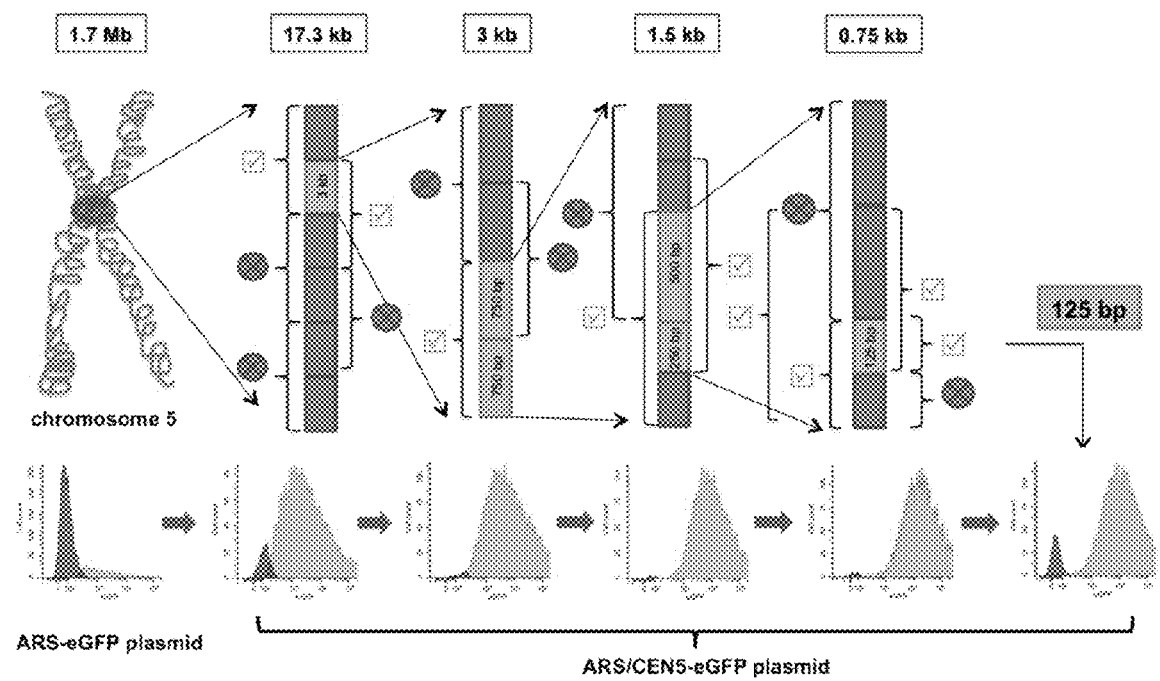
*FIG. 3A*
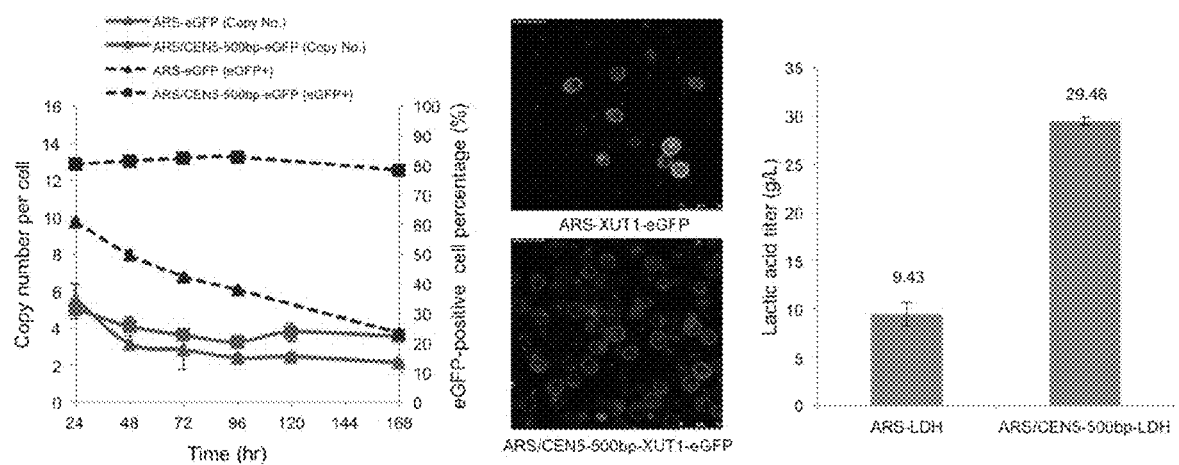
*FIG. 3B*  *FIG. 3C*  *FIG. 3D*

| | ade2Δ | trp1Δ | ade2Δtrp1Δ |
|---|---|---|---|
| Colony-1 | — | + | — |
| Colony-2 | + | — | — |
| Colony-3 | — | + | — |
| Colony-4 | + | + | + |
| Colony-5 | + | + | + |
FIG. 28A
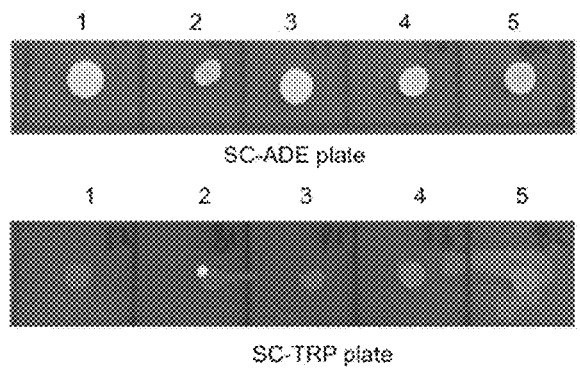
FIG. 28B
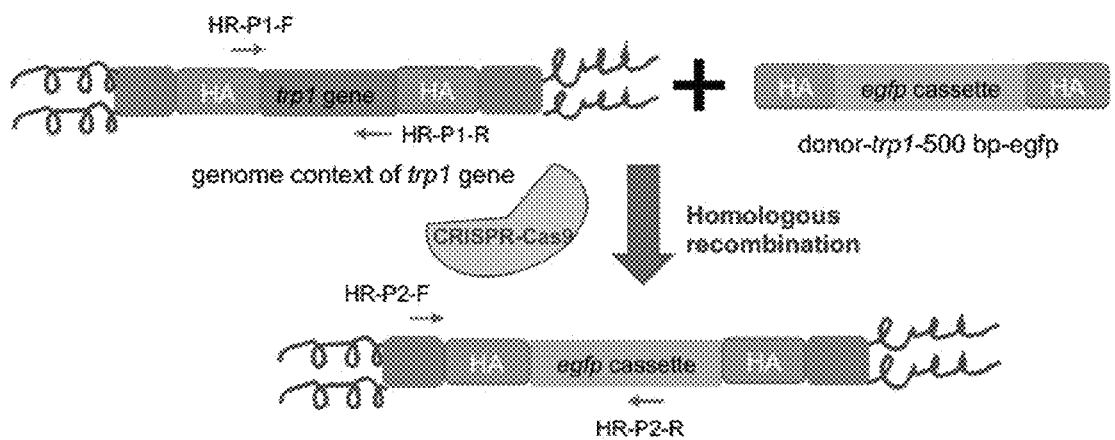
FIG. 29A
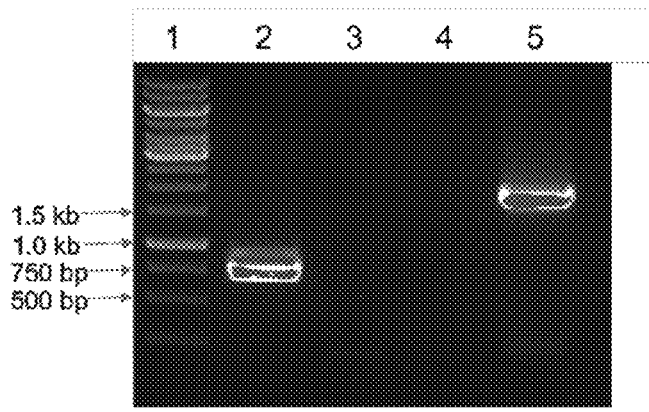
FIG. 29B

METHODS AND COMPOSITIONS FOR PRODUCTION OF AROMATIC AND OTHER COMPOUNDS IN YEAST

CROSS-REFERENCE TO RELATED APPLICATIONS

This is a divisional application of U.S. Ser. No. 16/019,822, filed Jun. 27, 2018, which claims priority to provisional application U.S. Ser. No. 62/526,223 filed Jun. 28, 2017, the entire contents of which are incorporated herein by reference in their entirety.

GRANT REFERENCE

This invention was made with government support under contract NSF Grant No. EEC0813570. The Government has certain rights in this invention.

FIELD OF THE INVENTION

The present invention is directed to method and compositions for producing aromatic compounds in yeast. In particular, engineered yeast strains are provided which produce high titers of compounds derived from the aromatic amino acid pathway. Methods and compositions for producing the modified yeast, and methods of uses thereof are also provided.

BACKGROUND OF THE INVENTION

Aromatic compounds represent a plethora of commercially relevant chemicals with diverse industrial applications. An assorted range of products are made with the help of aromatics, including, pharmaceuticals, clothing, cosmetics, computers, paints, vehicle components, fabrics, sports equipment, and the like. The aromatic, or arene, chemicals are recognized as cyclic six-carbon structures with delocalized electrons that generally possess a sweet or pleasant aroma, the property from which this class of molecule gets its name. This vast family of compounds is of great importance to the chemical industry; benzene, for instance, serves as the aromatic building block of many other chemicals such as toluene, phenol, and other polycyclic aromatics. Unfortunately, traditional techniques relying on petroleum to derive aromatics such as, benzene, xylenes and toluene, rise significant sustainability and safety concerns. Acute and chronic exposure to benzene has proven to be carcinogenic, furthermore, the synthesis of benzene derivatives usually entails the release of toxic gases into the environment. For these reasons, there has been much interest in the construction and optimization of alternative means capable of utilizing renewable feedstocks and production of aromatic compounds.

The metabolic pathways for the biosynthesis of aromatic compounds are present in many microorganisms and plants. In nature, the aromatic amino acids serve as building blocks for the biosynthesis of polypeptides, though, the aromatic amino acid biosynthesis pathway also represents a source to a plethora of commercially relevant chemicals with very diverse industrial applications. Examples include the polymer precursor muconic acid, as well as nutraceuticals (flavonoids and stilbenoids), and opium-derived pharmaceuticals (benzylisoquinoline alkaloids). In several plants, these amino acids serve as the precursors to produce highly sought-after nutraceuticals, fragrances, and drugs. Although these secondary metabolites encompass a market in the billion-dollar range, extraction from plant tissues requires high amounts of biomass and cumbersome separation processes, leading to low yields. Production of aromatic compounds through microorganisms has been a research focus in recent years, and significant progress has been made in this area. At the same time, the intrinsic complexity of the genetic and metabolic regulations and reportedly low yields remain limiting factors.

Shikimate Pathway

The shikimate pathway serves an essential role in many organisms. Not only are the three aromatic amino acids synthesized through this pathway, but many secondary metabolites also derive from it. Decades of effort have been invested into engineering *S. cerevisiae* to produce shikimate and its derivatives. However, the intrinsically complicated regulations involved in central metabolism and the low precursor availability in *S. cerevisiae* has limited production levels.

Shikimate is an essential precursor for many alkaloid and flavonoid types of secondary metabolites. These biologically active compounds are derived via decarboxylation or deamination of aromatic amino acids, the synthesis of which originates from the shikimate pathway. In addition to its ability to express P450 enzymes, *S. cerevisiae* is generally recognized as safe (GRAS) for producing compounds for use as nutraceutical and pharmaceutical ingredients. Breakthroughs include the production of the antioxidant naringenin (113 mg/L), and the recent complete biosynthesis of analgesic opioids (6.4 mg/L for thebaine and 0.3 µg/L for hydrocodone). Although the low titers are caused mainly by stepwise loss at incomplete conversion steps in the pathways, the relatively low precursor availability provided by the shikimate pathway was noticed in *S. cerevisiae* as opposed to bacterial production hosts. To the best of our knowledge, none of the shikimate pathway derived compounds developed in yeast batch fermentation have yielded titers even close to 1 g/L, the minimal level required for progression from lab-scale proof-of-concept research to small-scale process development, with the ultimate goal of attracting future commercial interest.

Shikimate itself is also a versatile enantiomeric precursor for the chemical synthesis of many biologically active compounds because it has a highly functionalized six-carbon ring with three chiral carbons. Oseltamivir phosphate, more commonly known as Tamiflu®, is used for the treatment of seasonal influenza, and is synthesized from shikimate via ten chemical conversions. The current processes used to synthesize shikimate, which was commercialized by Roche, include the extraction from Chinese star anise, the fruit of the *Illicium verum* plant. It is estimated that 30 billion doses of Tamiflu®, equivalent to 3.9 million kg of shikimate, would be required to treat a severe influenza outbreak. However, approximately 30 kg of fruit are needed to produce merely 1 kg of shikimate, and it takes 6 years of growth before *Illicium verum* bears fruit. Open-field crop growth and the resulting price is also inevitably susceptible to environmental factors, which is often associated with variability in product yield and composition.

Roche also ferments genetically engineered *Escherichia coli* to produce shikimate as an alternative to the plant extraction process, which offers a much more abundant supply in a timelier manner and confined space. After a decade of research development, the production in *E. coli* has been improved to 87 g/L. Nonetheless, considering the ultimate goal of reconstituting complex pathways to synthesize shikimate-derived natural products with nutraceutical and pharmaceutical applications, exploring the potential of shikimate production in yeasts is still of importance.

As can be seen there is a continuing need to develop and engineer yeast strains for improved production of valuable aromatic compounds.

BRIEF SUMMARY OF THE INVENTION

In an embodiment, the present invention provides a nucleic acid construct for gene expression or gene editing in yeast comprising: a nucleic acid sequence encoding one or more of SEQ ID NO: 1-8 (CENs 1-8); and one or more regulatory elements functional in a yeast cell. In an embodiment, the present invention the nucleic acid construct further comprises an autonomously replicating sequence (ARS).

In an embodiment, the present invention the nucleic acid construct includes a multiple cloning site for insertion of gene of interest operably linked to the regulatory elements. In an embodiment, the regulatory element is a promoter. In another embodiment, the regulatory element is a terminator sequence. In another embodiment, a nucleic acid of the present invention comprises a gene of interest is inserted in a multiple cloning site. In an embodiment of the invention the promoters are selected from the group consisting of: sADH1p, sENO1p, sPIR1p, sTDH2p, sAOX1p, and sTEF1p (SEQ ID NO: 9-14). In an embodiment of the invention the terminators are selected from the group consisting of: ADH1t, sAOX1t, ENO1t, sGLN1t, sUAGt, sOLE1t, PGK1t, sPIR1t, sTDH2t, and TEF1t (SEQ ID NO: 19-28). In other embodiments, gene of interest is one or more of RKI1, TKL1, aro4$_{K220L}$, aro1$_{D920A}$, or aro1$_{D902A\text{-}D1409A}$. In other embodiments, the genes RIC1, ARO1, and ARO4 are downregulated or absent.

In an embodiment of the present invention the nucleic acid constructs are vectors. In one embodiment, the vector is an episomal plasmid vector, which beneficially provides increased stability compared to the same plasmid vector lacking one or more of SEQ ID NO:1-8 (CENs 1-8).

In further embodiments, the present invention includes a cell, tissue, or organ comprising the nucleic acid construct of the invention. In an embodiment, the modified recombinant yeast cell comprises, an expression system that comprises at least one nucleotide sequence that encodes a transketolase, TLK1, capable of being expressed; an expression system that comprises at least one nucleotide sequence that encodes mutant ARO1, wherein said mutation is aro1D920A, capable of being expressed; wherein the expression of RIC1, ARO1 and ARO4 are downregulated or absent, and wherein said modified yeast cell produces higher titers of aromatic compounds compared to wild-type yeast cell of the same strain. In an embodiment, the yeast cell further comprises a third expression system that comprises at least on nucleotide sequence that encodes RKI1. In a preferred embodiment the modified yeast cell is of Saccharomyces spp.

In an embodiment of the invention provides a modified recombinant yeast cell for producing aromatic compounds comprises, an expression system that comprises at least one nucleotide sequence that encodes a transketolase, TLK1, capable of being expressed; an expression system that comprises at least one nucleotide sequence that encodes mutant ARO1, wherein said mutation is aro1D920A, capable of being expressed; an expression system that comprises at least one nucleotide sequence that encodes aro4K220L; and wherein the expression of ARO1 and ARO4 are downregulated or absent, and wherein said modified yeast cell produces higher titers of aromatic compounds compared to wild-type yeast cell of the same strain. In an preferred embodiment, the yeast cell is S. stipitis.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1A shows a comparison of enhanced green fluorescence protein (eGFP)-expression profiles between S. stipitis carrying the ARS-eGFP plasmid and S. cerevisiae carrying the ARS/CEN-eGFP plasmid. FIG. 1B shows number analysis over 7 days. Fluorescence-activated cell sorting (FACS) was performed to separate cells into groups with three different fluorescence levels.

FIGS. 2A-B show $GC_3$ chromosome scanning of yeast species with full genome sequences deposited in public databases. FIG. 2A shows 30 out of 73 analyzed yeast species displayed the signature $GC_3$ valley in at least one of their chromosomes. $GC_3$ analysis ratio is the number of chromosomes that have pronouncedly low $GC_3$ valleys with respect to the total number of chromosomes. FIG. 2B shows representative $GC_3$ chromosome scanning profiles of four yeast species that have a $GC_3$ valley on each of the chromosomes. The boundaries of each $GC_3$ valley were marked in red. See FIGS. 3A-D show incorporation of a functional CEN into the autonomously replicating sequences (ARS) backbone significantly improved its stability. FIG. 3A shows stepwise identification of the minimal CEN from S. stipitis chromosome 5. FIG. 3B shows copy number and mitotic stability analysis. FIG. 3C shows homogenous protein expression enabled by the ARS/CEN vector. The two images had nearly identical cell densities. FIG. 3D shows lactic acid production was tripled when lactate dehydrogenase (LDH) was expressed from the ARS/CEN-500 bp vector.

FIG. 7A shows incorporation of an active promoter immediately upstream of a CEN disrupted the interactions between the segregation machinery and the CEN due to the local transcriptional activity. FIG. 7B shows arranging two copies of CEN on one plasmid led to plasmid breakage during plasmid segregation.

FIG. 11A shows intergenic promoters, and (b) FIG. 11B shows shortened promoters. All data were normalized by $OD_{600}$. Error bars represent standard deviations of three biological replicates.

FIG. 15A shows the scheme of DSBs DNA repair by donor DNA after CRISPR-Cas9 targeting ade2 and trp1 loci: ade2-donor-100 bp contains TAG stop codon and misses 1 bp to disrupt the ORF; while trp1-500 bp-egfp has up/down 500 bp homologous arms of trp1 gene and egfp cassette was inserted to replace trp1. FIG. 15B shows HR efficiency of ade2 and trp1 repair in S. stipitis and S. stipitis Δku, pCasAde2* and pCasTrp1* were used to measure transformation efficiency.

FIG. 16A shows the cell density (OD600 nm) of pdCas-Random, pdCas9-eGFP-ORF, and pdCas9-Mxi1-eGFP-ORF transformants at 20 h and 44 h in SC-URA medium. FIG. 16B shows the relative eGFP fluorescence value for pdCas-Random, pdCas9-eGFP-ORF, and pdCas9-Mxi1-eGFP-ORF transformants at 20 h and 44 h in SC-URA medium.

FIG. 17A shows the CRISPR-Cas9 system for single gene targeting. FIG. 17B shows double gene targeting of ade2 and trp1 by CRISPR-Cas9. FIG. 17C shows CRISPR-dCas9 system targeting egfp-ORF. FIG. 17D shows dCas9 fusion expression with transcription repressor Mxi1 to target egfp-ORF.

FIG. 19A shows the minimal genetic cassettes for the production of SA. The transcription of the mutant aro1D920A was controlled by the native ARO1p promoter or the constitutive GPD1p promoter. FIG. 19B shows production of SA from strains with ARO1p (SA1) and GPD1p (SA2) promoters for expression of aro1D920A. FIG. 19C shows fermentation results from TF KO strains. "SA2" represents the control strain. The variation is represented by the standard deviation from three biological replicates. Statistical groups are depicted by * and ** (p-value <0.05).

FIG. 21A is a simplified map of central carbon metabolism depicting the upstream pathway (glycolysis and PPP) leading towards the aromatic amino acid pathway. The flux ranges (in mmol gDW-1 h-1) obtained through flux variability analysis are shown for the wild-type (top, purple) and the overproducer (bottom, blue) when glucose uptake is 100 mmol g DW-1 h-1. The sign of the flux values corresponds to the direction of the arrow (i.e. a negative value indicates that the net flux traverses in the reverse direction). FIG. 21B shows maximum yield achievable by downregulation (⁻), deletion (D), or overexpression (−) of the selected novel genes. The values on top of each bar graph indicate the percentage of the theoretical maximum yield (i.e. 0.615 g SA g-1). FIG. 21C shows in silico strain construction of the maximum SA producing strain. The overexpression of the genes RKI1, TKL1, aro1D920A (DHQS), in combination with deletion of aro1 (SHKK), led to a yield equivalent to 98.97% of the maximum the theoretical yield. Green and red arrows represent overexpression and deletion of genes, respectively. The maximum theoretical yield was determined after constraining the model with flux values from 13C labeling experiments.

FIG. 25A shows the scheme of DSB repair by donor DNA after Cas9 targeting the selected locus. FIG. 25B shows evaluation of the transformation efficiency between UC7 and UC7 kuΔ strains when transforming a CRISPR plasmid targeting trp1 or ade2 gene. The number of transformants obtained with the kuΔ strain was normalized to the one obtained with the parental strain without ku deletion. Statistical analysis was performed between the two strains (t-test,  value <0.01). FIG. 25C shows evaluation of HR-mediated trp1 and ade2 disruption in the kuΔ strain and the parental strain without ku deletion. Statistical analysis was performed between the two strains (t-test,  p-value <0.01). FIG. 25D shows verification of eGFP repression by flow cytometry analysis and real-time PCR. Three SgRNA were designed targeting different regions of the eGFP expression cassette. Cells were cultured in SC-URA media and collected at 44 hr. The reads were normalized to the cells carrying the control plasmid pdCas9-Random. Plasmid pdCas9-eGFP-ORF-1 expressed dCas9 by itself whereas pdCas9-Mxi1-eGFP-ORF-1, pdCas9-Mxi1-eGFP-ORF-0, and pdCas9-Mxi1-eGFP-ORF-2 expressed dCas9 fused with the transcriptional repressor Mxi1. The N20 and PAM sequences were marked on the partial sequence of the egfp-ORF (SEQ ID NO: 77). Statistical analysis was performed between individual targeted repression and the control with the results depicted by * and ** (t-test, *p-value <0.05, **p-value <0.01). All the results are shown as the mean±standard deviation from three biological replicates.

FIG. 26A shows the CRISPR-Cas9 system for the single-gene knockout. FIG. 26B shows the CRISPR-Cas9 system for double-gene knockout targeting ade2 and trp1. FIG. 26C shows CRISPR-dCas9 system targeting egfp-ORF-1. FIG. 26D shows dCas9 fusion expression with the transcription repressor Mxi1 to target the locus egfp-ORF-0, 1, or 2. The corresponding plasmid shares the same design, only differing in the sequence of N20.

FIGS. 28A-B show the screening of double-gene knockout targeting ade2 and trp1 by CRISPR-Cas9. FIG. 28A shows the genotypes of five colonies confirmed by DNA sequencing. FIG. 28B shows the colonies growing on SC-ADE (containing a low concentration of adenine at 10 mg/L; #4 displayed slightly pink color) and SC-TRP selection plates to confirm the phenotype.

FIGS. 29A-B show HR-mediated gene knockout at the trp1 locus in S. stipitis. FIG. 29A shows the scheme of DSB repair by donor DNA. The donor DNA, named donor-trp1-500 bp-egfp, has homologous arms (HAs) designed based on the 500 bp upstream and downstream regions of the trp1 gene. A successful knockout will have the egfp expression cassette inserted to the original trp1 locus. The positions of the verification primers were marked. FIG. 29B shows a representative gel-image of PCR verification of the HR-mediated trp1 knockout. The expected sizes are 723 bp (using HR-P1-F/R targeting trp1) and 1668 bp (using HR-P2-F/R targeting the inserted egfp). Lane 1. 1 kb DNA Ladder (GeneRuler, Thermo Scientific); Lane 2. A 723-bp amplicon was obtained using the primers HR-P1-F/R if the trp1 was intact; Lane 3. No specific amplification occurred using the primers HR-P2-F/R if the trp1 was intact; Lane 4. No specific amplification occurred using the primers HR-P1-F/R if the trp1 was replaced by egfp; Lane 5. A 1668-bp amplicon was obtained using the primers HR-P2-F/R if the trp1 was replaced by egfp.

FIG. 30A shows effect of the lengths of HAs on HR efficiency. HR efficiency was calculated by the ratio of the number of eGFP positive clones to the total number of colonies. FIG. 30B shows effect of the lengths of HAs on transformation efficiency. The numbers of colonies obtained for HAs at different lengths were normalized to the one with HA-50 bp. The transformation efficiencies are shown as the mean±standard deviation from three biological replicates (n=3).

DETAILED DESCRIPTION OF THE INVENTION

Figure 1A:
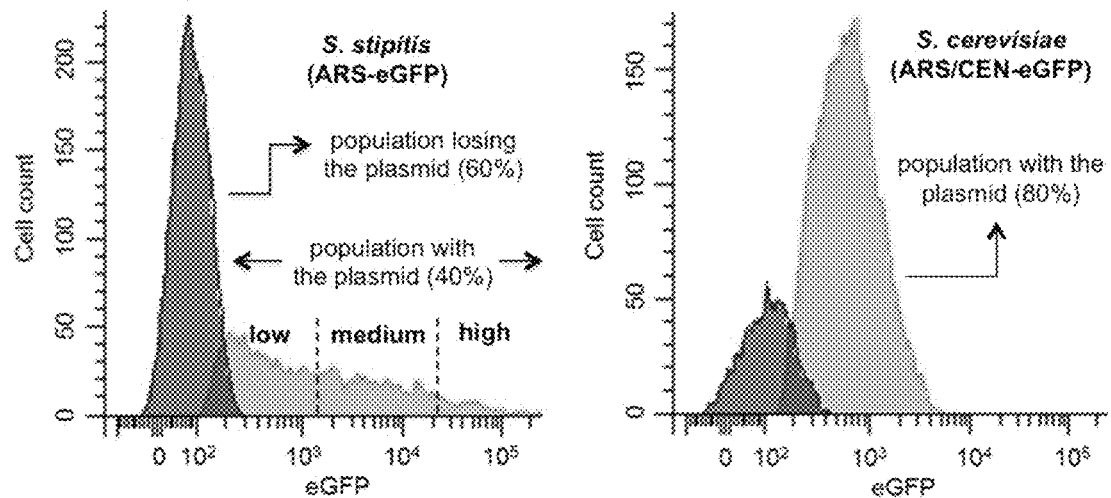
FIGS. 1A-B show instability of the S. stipitis plasmid in the absence of a functional centromere (CEN).

The following definitions and introductory matters are provided to facilitate an understanding of the present invention.

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), The Encyclopedia of Cell Biology and Molecular Medicine, published by Wiley-VCH in 16 volumes, 2008; and other similar references. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, e.g., Sambrook et al. MOLECULAR CLONING: A LABORATORY MANUAL, 2d ed., Cold Spring Harbor Laboratory Press, 1989; 3d ed., 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Numeric ranges recited within the specification, including ranges of "greater than," "at least," or "less than" a numeric value, are inclusive of the numbers defining the range and include each integer within the defined range.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, a conservatively modified variant refers to those nucleic acids, which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid, which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, generation of immune response, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids, which are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company. Further, the term "amino acid substitutions" means the replacement of one amino acid in a polypeptide with a different amino acid or with no amino acid (i.e., a deletion). In some examples, an amino acid in a polypeptide is substituted with an amino acid from a homologous polypeptide.

As used herein "expression" refers to transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA.

In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression control sequences refer to nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, and maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., Methods in Enzymology 153:516-544, 1987). For example, when cloning in bacterial systems, inducible promoters such as pL of bacteriophage lambda, plac, ptrp, ptac (ptrp-lac hybrid promoter) and the like may be used. When cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein, "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adenoa-associated viruses) that incorporate the recombinant polynucleotide.

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, "operably linked" is a first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

The term "heterologous" as used herein describes a relationship between two or more elements which indicates that the elements are not normally found in proximity to one another in nature. Thus, for example, a polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g., a genetically engineered coding sequence or an allele from a different ecotype or variety). An example of a heterologous polypeptide is a polypeptide expressed from a recombinant polynucleotide in a transgenic organism. Heterologous polynucleotides and polypeptides are forms of recombinant molecules.

As used herein, "sequence identity" refers to the similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CAB/OS 5:151-3, 1989; Corpet et al., Nuc. Acids Res. 16:10881-90, 1988; Huang et al. Computer Appls. In the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations. Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166/1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Homologs and variants of a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of Pearson & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, 4th ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, J. Mol. Evol. 35:351-360, 1987. The method used is similar to the method described by Higgins & Sharp, CAB/OS 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395, 1984.

Another example of algorithms that are suitable for determining percent sequence identity and sequence similarity are the BLAST and the BLAST 2.0 algorithm, which are described in Altschul et al., J. Mol. Biol. 215:403-410, 1990 and Altschul et al., Nucleic Acids Res. 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, Proc. Natl. Acad.

Sci. USA 89:10915, 1989). An oligonucleotide is a linear polynucleotide sequence of up to about 100 nucleotide bases in length.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possess catalytic activity for DNA cleavage. A cleavage domain can be contained in a single polypeptide chain or cleavage activity can result from the association of two (or more) polypeptides.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present in cells only during the early stages of development of a flower is an exogenous molecule with respect to the cells of a fully developed flower. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species that is an ortholog of an endogenous gene in the host cell.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases. Thus, the term includes "transgenes" or "genes of interest" which are exogenous sequences introduced into a host cell.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

As used herein, "gene editing," "gene edited" "genetically edited" and "gene editing effectors" refer to the use of naturally occurring or artificially engineered nucleases, also referred to as "molecular scissors." The nucleases create specific double-stranded break (DSBs) at desired locations in the genome, which in some cases harnesses the cell's endogenous mechanisms to repair the induced break by natural processes of homologous recombination (HR) and/or nonhomologous end-joining (NHEJ). Gene editing effectors include Zinc Finger Nucleases (ZFNs), Transcription Activator-Like Effector Nucleases (TALENs), the Clustered Regularly Interspaced Short Palindromic Repeats/CAS9 (CRISPR/Cas9) system, and meganuclease re-engineered as homing endonucleases. The terms also include the use of transgenic procedures and techniques, including, for example, where the change is relatively small and/or does not introduce DNA from a foreign species.

The terms "genetic manipulation" and "genetically manipulated" include gene editing techniques, as well as and/or in addition to other techniques and processes that alter or modify the nucleotide sequence of a gene or gene, or modify or alter the expression of a gene or genes.

As used herein, "isolated" means free from contamination by other microbes. An isolated yeast can exist in the presence of a small fraction of other yeast which do not interfere with the properties and function of the isolated yeast. An isolated yeast will generally be at least 30%, 40%, 50%, 60%, 70%, 80%, 85%, 90%, 95%, 98%, or 99% pure. Preferably, an isolated yeast according to the invention will be at least 98% or at least 99% pure.

As used herein, "yeast" includes "non-recombinant yeast", "recombinant yeast" and "modified yeast".

As used herein, "non-recombinant yeast" includes a yeast cell that does not contain heterologous polynucleotide sequences, and is suitable for further modification using the compositions and methods of the invention, e.g. suitable for genetic manipulation, e.g., which can incorporate heterologous polynucleotide sequences, e.g., which can be transfected.

As used herein, "recombinant" as it refers to yeast, means a yeast cell that is suitable for, or subjected to, genetic manipulation, or incorporates a heterologous polynucleotide sequence, or that has been treated such that a native polynucleotide sequence has been mutated or deleted. The term is intended to include progeny of the cell originally transfected. In particular embodiments, the cell is a *Saccharomyces* spp. cell or a *Scheffersomyces* spp., in particular *S. stipitis*.

As used herein, "modified" as it refers to yeast, means a yeast cell that is not identical to a reference bacterium, as defined herein below.

A "modified" yeast includes a "recombinant" yeast.

As used herein, "aromatic production" means the production of aromatic compounds from a precursor of the aromatic amino acid biosynthetic pathway.

As used herein, "capable of producing aromatic compounds" means capable of "aromatic production" as defined herein.

The term "sugar" is intended to include any carbohydrate source comprising a sugar molecule(s). Such sugars are potential sources of sugars for depolymerization (if required) and subsequent bioconversion to acetaldehyde and subsequently to ethanol by fermentation according to the products and methods of the present invention. Sources of sugar include starch, the chief form of fuel storage in most organisms, hemicellulose, and cellulose, the main extracellular structural component of the rigid cell walls and the fibrous and woody tissues of organisms. The term is intended to include monosaccharides, also called simple sugars, oligosaccharides and polysaccharides. In certain embodiments, sugars include, e.g., glucose, xylose, arabinose, mannose, galactose, sucrose, and lactose. In other embodiments, the sugar is glucose.

As used herein, "modified nucleic acid molecule" or "modified gene" is intended to include a nucleic acid molecule or gene having a nucleotide sequence which includes at least one alteration (e.g., substitution, insertion, deletion) such that the polypeptide or polypeptide that can be encoded by the modified exhibits an activity or property that differs from the polypeptide or polypeptide encoded by the wild-type nucleic acid molecule or gene.

As used herein, "mutation" as it refers to a nucleic acid molecule or gene means alteration, insertion or deletion of a nucleic acid or a gene, or an increase or decrease in the level of expression of a nucleic acid or a gene, wherein the increase or decrease in expression results in a respective increase or decrease in the expression of the polypeptide that can be encoded by the nucleic acid molecule or gene. A mutation also means a nucleic acid molecule or gene having a nucleotide sequence which includes at least one alteration (e.g., substitution, insertion, deletion) such that the polypeptide or polypeptide that can be encoded by the modified exhibits an activity or property that differs from the polypeptide or polypeptide encoded by the wild-type nucleic acid molecule or gene.

As used herein, "modified protein" or "modified protein or amino acid sequence" is intended to include an amino acid sequence which includes at least one alteration (e.g., substitution, insertion, deletion) such that the polypeptide or polypeptide that can be encoded by the modified amino acid sequence exhibits an activity or property that differs from the polypeptide or polypeptide encoded by the wild-type amino acid sequence.

As used herein, "mutation" as it refers to a protein or amino acid sequence means alteration, insertion or deletion of an amino acid of an amino acid sequence, or an increase or decrease in the level of expression of an amino acid sequence, wherein the increase or decrease in expression results in an increase or decrease in the expression of the polypeptide that can be encoded by amino acid sequence. A mutation also means a protein or amino acid sequence having an amino acid sequence which includes at least one alteration (e.g., substitution, insertion, deletion) such that the polypeptide or polypeptide that can be encoded by the modified exhibits an activity or property that differs from the polypeptide or polypeptide encoded by the wild-type amino acid sequence.

As used herein, "fragment" or "subsequence" is intended to include a portion of parental or reference nucleic acid sequence or amino acid sequence, or a portion of polypeptide or gene, which encodes or retains a biological function or property of the parental or reference sequence, polypeptide or gene.

A "modified" yeast includes a yeast of its ancestors which comprise a "mutation" as defined hereinabove.

As used herein, "reference" or "reference yeast" includes, at least, a wild-type yeast and a parental yeast.

As used herein, "wild-type" means the typical form of an organism or strain, for example a yeast gene, or characteristic as it occurs in nature, in the absence of mutations. "Wild type" refers to the most common phenotype in the natural population. Wild type is the standard of reference for the genotype and phenotype.

As used herein, "parental" or "parental yeast" refers to the yeast that gives rise to a bacterium of interest.

A "gene," as used herein, is a nucleic acid that can direct synthesis of an enzyme or other polypeptide molecule, e.g., can comprise coding sequences, for example, a contiguous open reading frame (ORF) that encodes a polypeptide, a subsequence thereof, or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. In addition, the term "gene" is intended to include a specific gene for a selected purpose. A gene can be endogenous to the host cell or can be recombinantly introduced into the host cell, e.g., as a plasmid maintained episomally or a plasmid (or fragment thereof) that is stably integrated into the genome. A heterologous gene is a gene that is introduced into a cell and is not native to the cell.

The term "nucleic acid" is intended to include nucleic acid molecules, e.g., polynucleotides which include an open reading frame encoding a polypeptide, a subsequence thereof, and can further include non-coding regulatory sequences, and introns. In addition, the terms are intended to include one or more genes that map to a functional locus. In addition, the terms are intended to include a specific gene for a selected purpose.

As used herein, "increasing" or "increases" or "increased" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, for example, as compared to the level of expression of the tlk1 genes in a yeast cell, having an increased expression of a tlk1 gene, as compared to a reference yeast.

As used herein, "increasing" or "increases" or "increased" also means increases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of expression of the tlk1 genes in a yeast cell, having an increased expression of a tlk1 gene, as compared to a reference yeast.

As used herein, "decreasing" or "decreases" or "decreased" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the decreased level of expression of a aro1/aro4 genes in a cell, as compared to a reference yeast.

As used herein, "decreasing" or "decreases" or "decreased" also means decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of expression of a aro1/aro4 genes in a yeast cell, as compared to a reference yeast.

"Decreased" or "reduced" also means eliminated such that there is no detectable level of activity, expression, etc., for example no detectable level of expression of, for example aro1/aro4 genes or no detectable activity of, for example the aro1/aro4 proteins.

As used herein, "activity" refers to the activity of a gene, for example the level of transcription of a gene. "Activity" also refers to the activity of an mRNA, for example, the level of translation of an mRNA. "Activity" also refers to the activity of a protein, for example aro1/aro4 genes An "increase in activity" includes an increase in the rate and/or the level of activity. As used herein, "expression" refers to the expression of the protein product of a gene of interest.

"Altering", as it refers to expression levels, means decreasing expression of a gene, mRNA or protein of interest, for example aro1/aro4 genes.

As used herein, "not expressed" means there are no detectable levels of the product of a gene or mRNA of interest, for example, aro1/aro4 genes.

As used herein, "growth" means an increase, as defined herein, in the number or mass of a yeast over time.

As used herein, "derived from" means originates from.

The term "amino acid" is intended to include the 20 alpha-amino acids that regularly occur in proteins. Basic charged amino acids include arginine, asparagine, glutamine, histidine and lysine. Neutral charged amino acids include alanine, cysteine, glycine, isoleucine, leucine, methionine, phenylalanine, proline, serine, threonine, tryptophan, tyrosine, and valine. Acidic amino acids include aspartic acid and glutamic acid.

As used herein, "selecting" refers to the process of determining that an identified yeast strain produces aromatics compounds.

As used herein, "identifying" refers to the process of assessing a yeast strain and determining that the yeast strain produces adequate yields of aromatics.

As used herein, "increasing concentrations of furfural" means increments from 0 to 5 g/L, for example, 1 .mu.g/L increments, 1 mg/L increments or 1 g/L increments.

In this disclosure, "comprises," "comprising," "containing" and "having" and the like have the open-ended meaning ascribed to them in U.S. patent law and mean "includes," "including," and the like.

A "purified protein" refers to a protein that has been separated from other proteins, lipids, and nucleic acids with which it is naturally associated. Preferably, the protein constitutes at least 10, 20, 50 70, 80, 90, 95, 99-100% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic-fragment, a fragment produced by polymerase chain reaction (PCR), or a restriction fragment; and (d) a recombinant nucleotide sequence that is part of a hybridgene, i. e., a gene encoding a fusion protein. Isolated nucleic acid molecules according to the present disclosure further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides the nucleic acid molecule, the two phrases can be used interchangeably The term "substantially pure" in reference to a given polypeptide means that the polypeptide is substantially free from other biological macromolecules. The substantially pure polypeptide is at least 75% (e.g., at least 80, 85, 95, or 99%) pure by dry weight Purity can be measured by any appropriate standard method, for example, by column chromatography, polyacrylamide gel electrophoresis, or HPLC analysis.

A "heterologous promoter", when operably linked to a nucleic acid sequence, refers to a promoter which is not naturally associated with the nucleic acid sequence.

The terms "express" and "over-express" are used to denote the fact that, in some cases, a cell useful in the method herein may inherently express some of the factor that it is to be genetically altered to produce, in which case the addition of the polynucleotide sequence results in over-expression of the factor. That is, more factor is expressed by the altered cell than would be, under the same conditions, by a wild type cell. Similarly, if the cell does not inherently express the factor that it is genetically altered to produce, the term used would be to merely "express" the factor since the wild type cell did not express the factor at all.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

As used herein, the term "metabolic pathway" includes catabolic pathways and anabolic pathways both natural and engineered i.e. synthetic. Anabolic pathways involve constructing a larger molecule from smaller molecules, a process requiring energy. Catabolic pathways involve breaking down of larger molecules, often releasing energy. An anabolic pathway is referred to herein as "a biosynthetic pathway."

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella* ozaenae which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a. β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

Yeast Cells

Yeast strains that can be used in the compositions and methods described herein include, but are not limited to, *Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*. Although much of the discussion herein relates to *Saccharomyces cerevisiae* which ectopically expresses an abnormally processed protein, this is merely for illustrative purposes. Other yeast strains can be substituted for *S. cerevisiae*.

A nucleic acid encoding a polypeptide described herein may be transfected into a yeast cell using nucleic acid vectors that include, but are not limited to, plasmids, linear nucleic acid molecules, artificial chromosomes, and episomal vectors.

Three well known systems used for recombinant plasmid expression and replication in yeast cells include integrative plasmids, low-copy-number ARS-CEN plasmids, and high-copy-number 2.mu. plasmids. See Sikorski, "Extrachromosomal cloning vectors of *Saccharomyces cerevisiae*," in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994.

An example of the integrative plasmids is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells.

An example of the low-copy-number ARS-CEN plasmids is YCp, which contains the autonomous replicating sequence (ARS1) and a centromeric sequence (CEN4). These plasmids are usually present at 1-2 copies per cell. Removal of the CEN sequence yields a YRp plasmid, which is typically present in 100-200 copies per cell. However, this plasmid is both mitotically and meiotically unstable.

An example of the high-copy-number 2.mu. plasmids is YEp, which contains a sequence approximately 1 kb in length (named the 2μ sequence). The 2μ sequence acts as a yeast replicon giving rise to higher plasmid copy number. However, these plasmids are unstable and require selection for maintenance. Copy number is increased by having on the plasmid a selection gene operatively linked to a crippled promoter.

A wide variety of plasmids can be used in the compositions and methods described herein. In one embodiment, the plasmid is an integrative plasmid (e.g., pRS303, pRS304, pRS305, pRS306, or a derivative thereof). See, e.g., Alberti et al. (2007) "A suite of Gateway cloning vectors for high-throughput genetic analysis in *Saccharomyces cerevisiae*" Yeast 24(10):913-19. In further embodiments, the plasmid is an episomal plasmid (e.g., p426GPD, p416GPD, p426TEF, p423GPD, p425GPD, p424GPD or p426GAL).

Regardless of the type of plasmid used, yeast cells are typically transformed by chemical methods (e.g., as described by Rose et al., 1990, Methods in Yeast Genetics, Cold Spring Harbor Laboratory Press, Cold Spring Harbor, N.Y.). The cells are typically treated with lithium acetate to achieve transformation efficiencies of approximately $10^4$ colony-forming units (transformed cells)/µg of DNA. Yeast perform homologous recombination such that the cut, selectable marker recombines with the mutated (usually a point mutation or a small deletion) host gene to restore function. Transformed cells are then isolated on selective media. Of course, any suitable means of introducing nucleic acids into yeast cells can be used.

The yeast vectors (plasmids) described herein typically contain a yeast origin of replication, an antibiotic resistance gene, a bacterial origin of replication (for propagation in bacterial cells), multiple cloning sites, and a yeast nutritional gene for maintenance in yeast cells. The nutritional gene (or "auxotrophic marker") is most often one of the following: 1) TRP1 (Phosphoribosylanthranilate isomerase); 2) URA3 (Orotidine-5'-phosphate decarboxylase); 3) LEU2 (3-Isopropylmalate dehydrogenase); 4) HIS3 (Imidazoleglycerol-phosphate dehydratase or IGP dehydratase); or 5) LYS2 α.-aminoadipate-semialdehyde dehydrogenase).

For example, various yeast-specific promoters (elements) may be employed to regulate the expression of an RNA in yeast cells. Examples of inducible yeast promoters include GAL1-10, GAL1, GALL, GALS, TET, VP16 and VP16-ER. Examples of repressible yeast promoters include Met25. Examples of constitutive yeast promoters include glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), and MRP7. Autonomously replicating expression vectors of yeast containing promoters inducible by glucocorticoid hormones have also been described (Picard et al., 1990), including the glucocorticoid responsive element (GRE). These and other examples are described in Mumber et al., 1995; Ronicke et al., 1997; Gao, 2000, all incorporated herein by reference. Yet other yeast vectors containing constitutive or inducible promoters such as alpha factor, alcohol oxidase, and PGH may be used. For reviews, see Ausubel et al. and Grant et al., 1987.

In some embodiments, a yeast strain is used that allows for expression, e.g., inducible expression, from GAL promoters on carbon sources other than galactose. In some embodiments, the strain carries an integrated or episomal (e.g., plasmid-borne) gene encoding a fusion protein, wherein the Gal4 DNA binding domain is fused to a transcriptional activation domain and a regulatory domain. The fusion protein is characterized in that its ability to activate transcription is regulated by binding of a small molecule to the regulatory domain. For example, in some embodiments, the fusion protein does not activate transcription in the absence of the small molecule, whereas in the presence of the small molecule, the fusion protein activates transcription. Exemplary small molecules include, e.g., steroid hormones, wherein the corresponding regulatory domain comprises at least a portion of a receptor for the small molecule. For example, the small molecule may be an estrogen (e.g., estradiol), or analog thereof (e.g., tamoxifen), and the corresponding regulatory domain comprises at least a portion of the estrogen receptor (ER). Exemplary activation domains include, e.g., viral protein activation domains such as the herpes simplex virus protein VP16 activation domain. In some embodiments, the strain carries an integrated or episomal (e.g., plasmid-borne) gene encoding a Gal4-ER-VP16 fusion protein. Presence of an estrogen receptor ligand, e.g., estradiol, in the medium, allows for expression from GAL promoters on carbon sources other than galactose. One of skill in the art will appreciate that numerous ways exist to render expression of a molecule of interest, e.g., an amyloid beta peptide, conditional, e.g., on culture media containing galactose or other carbon sources.

CRISPR

The vectors of the invention also may be used for genetic modification using gene editing systems such as CRISPRS and the like. The invention thus provides for the possibilities that the guide-polynucleotide and the Cas protein are provided as such, or that they are encoded on or present on a vector. In the latter case, the encoding polynucleotides may each be on a separate vector or may both be on a single vector. The present invention, as depicted elsewhere herein, also provides for an exogenous polynucleotide, also referred to as a donor polynucleotide, a donor DNA when the polynucleotide is a DNA, or repair template, that upon cleavage of the target-polynucleotide by the CRISPR-Cas complex recombines with the target-polynucleotide, resulting in a modified target-polynucleotide. Such exogenous polynucleotide is herein referred to as an exogenous polynucleotide according to the present invention and may be single-stranded or double-stranded. Accordingly, a composition according to the present invention may further comprise an exogenous polynucleotide according to the present invention; a composition according to the invention may comprise one or more distinct exogenous polynucleotides. Such one or more distinct exogenous polynucleotides may encode different expression products or may encode identical expression products while a part of the exogenous polynucleotide has sequence identity to a part of the target-polynucleotide. In an embodiment, the composition according to the invention comprises one or more distinct exogenous polynucleotides, said exogenous polynucleotide comprise one or more regions of sequence identity to the target polynucleotide to allow, upon cleavage of the target-polynucleotide by the CRISPR-Cas complex, homologous recombination with the cleaved target-polynucleotide, resulting in a modified target-polynucleotide. Such compositions according to the invention allow for a multiplex CRISPR-CAS system according to the invention as referred to elsewhere herein. In an embodiment, in a composition according to the invention where at least two distinct exogenous polynucleotides are present that upon cleavage of the target-polynucleotide by the CRISPR-Cas complex recombine with the target-polynucleotides, resulting in a modified target-polynucleotide, said at least two distinct exogenous polynucleotides may comprise sequence identity with each other such that recombination of said distinct exogenous polynucleotides is facilitated, wherein the recombination preferably is in vivo recombination in the host cell. In an embodiment, in the composition according to the invention comprising at least two distinct exogenous polynucleotides, each of said at least two distinct exogenous polynucleotides comprise at least one region of sequence identity with another exogenous polynucleotide and optionally with the target polynucleotide, to allow upon cleavage of the target-polynucleotide by the CRISPR-Cas complex, homologous recombination of said at least two distinct exogenous polynucleotides with one another and with the cleaved target-polynucleotide, resulting in a modified target-polynucleotide, wherein the recombination preferably is in vivo recombination in the host cell.

The exogenous polynucleotide according to the present invention may be present on a vector or may be present as such, may be encoded by another polynucleotide or may be operably linked to the guide-polynucleotide and may have sequence identity to a part of the target-polynucleotide upstream of the PAM associated with the guide-sequence (i.e. on the 5' side of the PAM) or may have sequence identity to a part of the target-polynucleotide downstream of the PAM associated with the guide-sequence (i.e. on the 5' side of the PAM). The vector may be a separate vector for the exogenous polynucleotide.

In the context of all embodiments of the present invention, a vector may be any vector (e.g., a plasmid or virus), which can conveniently be subjected to recombinant DNA procedures and can mediate expression of a polynucleotide according to the invention. The choice of the vector will typically depend on the compatibility of the vector with the host cell into which the vector is to be introduced. Preferred vectors are the vectors used in the examples herein. A vector may be a linear polynucleotide or a linear or closed circular plasmid. A vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome. Preferably, in the composition according to the present invention, at least one vector is an autonomously replicating vector, or any autonomously replicating vector suitable to be used in a yeast host cell.

A vector may be one which, when introduced into the host cell, becomes integrated into the genome and replicated together with the chromosome(s) into which it has been integrated. An integrative vector may integrate at random or at a predetermined target locus in a chromosome of the host cell. A preferred integrative vector comprises a DNA fragment, which is homologous to a DNA sequence in a predetermined target locus in the genome of the host cell for targeting the integration of the vector to this predetermined locus. In order to promote targeted integration, a vector is preferably linearized prior to transformation of the cell.

Linearization is preferably performed such that at least one but preferably either end of the vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the host cell, i.e. integration in a predetermined target locus, is increased by augmented homologous recombination abilities of the host cell.

The homologous flanking DNA sequences in the vector (which are homologous to the target locus) may be derived from a highly expressed locus, meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (e.g. as described in EP 357 127 B1).

More than one copy of a polynucleotide according to the present invention may be inserted into the microbial host cell to mediate production of the product encoded by said polynucleotide. This can be done, preferably by integrating multiple copies of the polynucleotide into the genome of the host cell, more preferably by targeting the integration of the polynucleotide at one of the highly expressed loci defined in the former paragraph. Alternatively, integration of multiple copies can be achieved by including an amplifiable selectable marker gene with a polynucleotide according to the present invention, such that cells containing amplified copies of the selectable marker gene (and thereby additional copies of the nucleic acid sequence) can be selected for by cultivating the cells in the presence of the appropriate selectable agent. To increase the number of copies of a polynucleotide according the present invention even more, the technique of gene conversion as described in WO98/46772 may be used.

When a polynucleotide according to the present invention encoding a Cas protein according to the present invention and/or a guide-polynucleotide according to the present invention is integrated into the genome of the host cell, it may be desirable to excise the polynucleotide from the genome, e.g. when the desired genome editing has taken place. The excision of a polynucleotide can be performed by any means known to the person skilled in art; one preferred means is using Amds as a selection marker and counter-selecting with e.g. fluoroacetamide to excise the polynucleotide from the genome such as described in EP0635574. Another means for excision would be to use the well-known Cre/lox system; the polynucleotide sequence encoding the Cas-protein according to the present invention may e.g. be flanked by lox66/71 or loxP/loxP. A further means for excision would be to the use the CRISPR-Cas system according to the present invention.

A vector according to the present invention may be a single vector or plasmid or a vector system comprising two or more vectors or plasmids, which together contain the polynucleotides according to the present invention to be introduced into the host cell host cell.

A Cas protein in the context of all embodiments of the present invention refers to any Cas protein suitable for the purpose of the invention. A Cas protein may comprise enzymatic activity or may not comprise enzymatic activity. Non-limiting examples of Cas proteins include CasI, CasI B, Cas2, Cas3, Cas4, Cas5, Cas6, Cas7, Cas8, Cas9 (also known as CsnI and CsxI2), CasIO, CsyI, Csy2, Csy3, CseI, Cse2, CscI, Csc2, Csa5, Csn2, Csm2, Csm3, Csm4, Csm5, Csm6, CmrI, Cmr3, Cmr4, Cmr5, Cmr6, CsbI, Csb2, Csb3, CsxI7, CsxI4, CsxIO, CsxI6, CsaX, Csx3, CsxI, CsxIS, CsfI, Csf2, Csf3, Csf4, homologs thereof or modified versions thereof. These Cas proteins are known to the person skilled in the art; for example, the amino acid sequence of *S. pyogenes* Cas9 protein may be found in the SwissProt database under accession number Q99ZW2. Preferably, an unmodified Cas protein according to the present invention has DNA cleavage activity, such as e.g. Cas9. Preferably, a Cas protein according to the present invention is Cas9, and may be Cas9 from *S. pyogenes* or *S. pneumoniae*. Preferably, a Cas protein according to the present invention directs cleavage of one or both polynucleotide strands at the location of the target-polynucleotide, such as within the target-polynucleotide and/or within the reverse complement of the target-polynucleotide. At the location of the target-polynucleotide is herein defined as within about 1, 2, 3, 4, 5, 6, 7, 8, 9, 10, 15, 20, 25, 50, 100, 200, 500, or more nucleotides from the first or last nucleotide of a target-polynucleotide; more preferably, within 1, 2, 3, 4, 5, 6, 7, 8, 9, 10, 15, 20, 25, 50, 100, 200, 500, or more nucleotides from the first or last nucleotide of a target-polynucleotide; even more preferably, within 1, 2, 3, 4, 5, 6, 7, 8, 9, 10, 15, 20, 25, 50 nucleotides from the first or last nucleotide of a target-polynucleotide. Accordingly, a Cas protein according to the present invention preferably directs cleavage of one or both polynucleotide strands within about 1, 2, 3, 4, 5, 6, 7, 8, 9, 10, 15, 20, 25, 50, 100, 200, 500, or more nucleotides from the first or last nucleotide of a target-polynucleotide; more preferably, within 1, 2, 3, 4, 5, 6, 7, 8, 9, 10, 15, 20, 25, 50, 100, 200, 500, or more nucleotides from the first or last nucleotide of a target-polynucleotide; even more preferably, within 1, 2, 3, 4, 5, 6, 7, 8, 9, 10, 15, 20, 25, 50 nucleotides from the first or last nucleotide of a target-polynucleotide. Typically, a target-polynucleotide according to the present invention is associated with a PAM sequence (defined elsewhere herein) and the PAM sequence is preferably immediately downstream (3') of the target-sequence; the formation of the CRISPR-Cas complex typically results in cleavage of one or both polynucleotide strands 3 base pairs upstream (5') of the PAM sequence.

A Cas protein according to the present invention may comprise two or more mutated catalytic domains of Cas9, such as RuvC I, RuvC II and/or RuvC III to result in a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. Preferably, a Cas protein is considered to substantially lack all DNA cleavage activity when the DNA cleavage activity of the mutated enzyme is less than about 25%, 10%, 5%, 1%, 0.1%, 0.01%, or lower with respect to its non-mutated form. A Cas protein lacking substantially all enzyme activity can conveniently be used for gene silencing or down regulation of expression since the CRISPR-CAS complex will hamper transcription from the target-polynucleotide. Other mutations may be useful; where the Cas9 or other Cas protein is from a species other than S. pyogenes, mutations in corresponding amino acids may be made to achieve similar effects; the person skilled in the art knows how to identify these corresponding amino acids.

A Cas protein according to the present invention may be a fusion protein and comprise at least one heterologous functional domain, such domain preferably is a domain comprising FokI activity such as described by Aggarwal et al (Aggarwal, A. K.; Wah, D. A.; Hirsch, J. A.; Dorner, L. F.; Schildkraut, I. (1997). "Structure of the multimodular endonuclease FokI bound to DNA". Nature 388 (6637): 97-100). The enzyme FokI is naturally found in *Flavobacterium okeanokoites* and is a bacterial type IIS restriction endonuclease consisting of an N-terminal DNA-binding domain and a non-specific DNA cleavage domain at the C-terminal (Durai et al., 2005). When the FokI protein is bound to double stranded DNA via its DNA-binding domain at the 5'-GGATG-3':3'-CATCC-5' recognition site, the DNA cleavage domain is activated and cleaves, without further sequence specificity, the first strand 9 nucleotides downstream and the second strand 13 nucleotides upstream of the nearest nucleotide of the recognition site (Wah et al., 1998. Cas9-FokI fusions have been described inter alia in Guilinger et al., 2014; and in Tsai et al., 2014.

Various applications can be considered by the person skilled in the art for the compositions and methods according to the present invention. A polynucleotide (or gene) in a genome may be modified, edited or disrupted using compositions and methods according to the present invention. E.g. when a fully active Cas protein is used that cuts in both strands of the target-polynucleotide and when no exogenous polynucleotide is present as a suitable repair template, the double strand break is repaired by non-homologous end joining repair (NHEJ). During NHEJ insertions and/or deletions (which may be construed as substitution in some cases) of one or several nucleotides may occur, these are randomly inserted or deleted at the repair site; this is characteristic for NHEJ. Such insertions and/or deletions may impact the reading frame of the coding sequence, resulting amino acid changes in the gene product or even a truncated protein in case of genesis of a (premature) stop codon or alteration of a splice site.

A polynucleotide (or gene) in a genome may be modified, edited or disrupted using compositions and methods according to the present invention using homologous end joining repair (HEJ), also known as homology-directed repair (HDR), when an exogenous polynucleotide is present as repair template. E.g. when an exogenous polynucleotide having sequence identity to the target-polynucleotide (i.e. upstream (5') and downstream (3') of the double strand break) is present together with a CRISPR-Cas system according to the present invention, HDR will introduce (or actually reproduce) the corresponding nucleotides of the exogenous polynucleotide at the double strand break in the target-polynucleotide. Preferably, an exogenous polynucleotide according to the present invention does not contain the target sequence itself followed by a functional PAM sequence to avoid the risk of the exogenous polynucleotide itself or the modified target-polynucleotide being (re)cut by the CRISPR-CAS system.

In the embodiments of the present invention, when a CRISPR-Cas system according to the present invention comprises an exogenous polynucleotide (donor polynucleotide, donor DNA, repair template), the CRISPR-Cas system according to the present invention preferably comprises two or more guide-polynucleotides encoded by or present on one or more separate polynucleotides or vectors, and two or more exogenous polynucleotides are provided together with said CRISPR-Cas system enabling the formation of two or more CRISPR-CAS complexes. In a method according to the present invention, such CRISPR-Cas systems according to the present invention can conveniently be used to modulate expression at two or more target-polynucleotides, i.e. a method to target multiple target sites. Such CRISPR-Cas system according to the present invention will by chance form one, two or more CRISPR-CAS complexes at one or more target-polynucleotides. Such method can be used to generate one or more insertions, deletions, substitutions, optionally in combination with the one or more exogenous polynucleotides, in the genome of the host cell, or to modulate expression of genes via the formed CRISPR-CAS complexes.

In a fourth aspect, the present invention provides a method of producing a host cell, comprising contacting a host cell with the composition according to the first aspect of the present invention, wherein the guide-polynucleotide directs binding of the Cas protein at the target-polynucleotide in the host cell to form a CRISPR-Cas complex. In an embodiment, the contacting with the composition according to the first aspect of the invention may be performed in two steps, wherein the host cell is first contacted with a source of a Cas protein according to the invention and subsequently the host cell is contacted with a source of a guide-polynucleotide according to the invention and optionally an exogenous polynucleotide according to the invention. A host cell in this embodiment of the present invention may be any type of host cell as defined herein and may comprise a polynucleotide encoding a compound of interest as defined elsewhere herein. A preferred method of producing a host cell according to the present invention comprises a step to produce an offspring host cell, wherein in said offspring host cell no components of a CRISPR-Cas system according to the present invention are present anymore. A further preferred host cell is a modified host cell wherein expression of a component associated with NHEJ as depicted here above is altered compared to the corresponding wild-type host cell; preferably expression of the component associated with NHEJ is lowered.

The composition according to the first aspect of the present invention may be any such composition as defined herein. Contacting a host cell with a composition according to the present invention may be performed by any means known to the person skilled in the art. A host cell according to the present invention may simply be brought into a solution comprising a composition according to the present invention. Specific means of delivering a composition according to the present invention into a host cell may be used. The person skilled in the art is aware of such methods (see e.g. Sambrook & Russell; Ausubel, supra)., which include but are not limited to electroporation methods, particle bombardment or microprojectile bombardment, protoplast methods and *Agrobacterium* mediated transformation (AMT Yeast may be transformed using any method known in the art such as the procedures described by Becker and Guarente, In Abelson, J. N. and Simon, 1983; Hinnen et al., 1978, and Gietz R D, Woods R A. 2002.

The present invention provides for a method for the production of a compound of interest, comprising culturing under conditions conducive to the compound of interest a host cell according to the third or fourth aspect of the present invention or a host cell obtained by a method according to the second aspect of the present invention, or a host cell obtainable by a method according to the fourth aspect of the present invention and optionally purifying or isolating the compound of interest.

A compound of interest in the context of all embodiments of the present invention may be any biological compound. The biological compound may be biomass or a biopolymer or a metabolite. The biological compound may be encoded by a single polynucleotide or a series of polynucleotides composing a biosynthetic or metabolic pathway or may be the direct result of the product of a single polynucleotide or products of a series of polynucleotides, the polynucleotide may be a gene, the series of polynucleotide may be a gene cluster. In all embodiments of the present invention, the single polynucleotide or series of polynucleotides encoding the biological compound of interest or the biosynthetic or metabolic pathway associated with the biological compound of interest, are preferred targets for the compositions and methods according to the present invention. The biological compound may be native to the host cell or heterologous to the host cell.

The term "heterologous biological compound" is defined herein as a biological compound which is not native to the cell; or a native biological compound in which structural modifications have been made to alter the native biological compound. The term "biopolymer" is defined herein as a chain (or polymer) of identical, similar, or dissimilar subunits (monomers). The biopolymer may be any biopolymer. The biopolymer may for example be, but is not limited to, a nucleic acid, polyamine, polyol, polypeptide (or polyamide), or polysaccharide. The biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. The term polypeptide refers to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. Polypeptides further include naturally occurring allelic and engineered variations of the above-mentioned polypeptides and hybrid polypeptides. The polypeptide may be native or may be heterologous to the host cell. The polypeptide may be a collagen or gelatine, or a variant or hybrid thereof. The polypeptide may be an antibody or parts thereof, an antigen, a clotting factor, an enzyme, a hormone or a hormone variant, a receptor or parts thereof, a regulatory protein, a structural protein, a reporter, or a transport protein, protein involved in secretion process, protein involved in folding process, chaperone, peptide amino acid transporter, glycosylation factor, transcription factor, synthetic peptide or oligopeptide, intracellular protein. The intracellular protein may be an enzyme such as, a protease, ceramidases, epoxide hydrolase, aminopeptidase, acylases, aldolase, hydroxylase, aminopeptidase, lipase. The polypeptide may also be an enzyme secreted extracellularly. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, asparaginase, amylase, a maltogenic amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, galactolipase, chlorophyllase, polyphenoloxidase, ribonuclease, transglutaminase, or glucose oxidase, hexose oxidase, monooxygenase.

According to the present invention, a compound of interest can be a polypeptide or enzyme with improved secretion features as described in WO2010/102982. According to the present invention, a compound of interest can be a fused or hybrid polypeptide to which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the host cell. Example of fusion polypeptides and signal sequence fusions are for example as described in WO2010/121933.

The biopolymer may be a polysaccharide. The polysaccharide may be any polysaccharide, including, but not limited to, a mucopolysaccharide (e.g., heparin and hyaluronic acid) and nitrogen-containing polysaccharide (e.g., chitin). In a preferred option, the polysaccharide is hyaluronic acid.

A polynucleotide coding for the compound of interest or coding for a compound involved in the production of the compound of interest according to the invention may encode an enzyme involved in the synthesis of a primary or secondary metabolite, such as organic acids, carotenoids, (beta-lactam) antibiotics, and vitamins. Such metabolite may be considered as a biological compound according to the present invention.

The term "metabolite" encompasses both primary and secondary metabolites; the metabolite may be any metabolite. Preferred metabolites are citric acid, gluconic acid, adipic acid, fumaric acid, itaconic acid and succinic acid.

A metabolite may be encoded by one or more genes, such as in a biosynthetic or metabolic pathway. Primary metabolites are products of primary or general metabolism of a cell, which are concerned with energy metabolism, growth, and structure. Secondary metabolites are products of secondary metabolism (see, for example, R. B. Herbert, The Biosynthesis of Secondary Metabolites, Chapman and Hall, New York, 1981).

A primary metabolite may be, but is not limited to, an amino acid, fatty acid, nucleoside, nucleotide, sugar, triglyceride, or vitamin.

A secondary metabolite may be, but is not limited to, an alkaloid, coumarin, flavonoid, polyketide, quinine, steroid, peptide, or terpene. The secondary metabolite may be an antibiotic, antifeedant, attractant, bacteriocide, fungicide, hormone, insecticide, or rodenticide. Preferred antibiotics are cephalosporins and beta-lactams. Other preferred metabolites are exo-metabolites. Examples of exo-metabolites are Aurasperone B, Funalenone, Kotanin, Nigragillin, Orlandin, Other naphtho-γ-pyrones, Pyranonigrin A, Tensidol B, Fumonisin B2 and Ochratoxin A.

EXAMPLES

Example 1: Hubs to Facilitate Nonconventional Yeast Engineering

*Saccharomyces cerevisiae* is far from being the only yeast of economic importance. Many of the 1800 other known yeast species have highly unusual metabolic, biosynthetic, physiological, and fermentative capacities that make them attractive in various biotech applications. As outcomes of long-term natural evolution in particular environments, these high-performance characteristics are conferred by a network of genes via a hierarchy of regulations that are intrinsically complex, making horizontal transfer of these functions into model hosts very challenging. With the advancement of platform technologies (e.g., next-generation sequencing and CRISPR-Cas9 genome editing), great interest has recently emerged in engineering native hosts to directly leverage this enormous fortune inherited from nature.

In general, stable episomal expression platforms and precise genome-editing tools are the two foundational technologies used for engineering nonconventional species. The availability of a stable episomal expression vector is advantageous because of its unmatchable flexibility in assembling genetic information and its capacity for facilitating downstream strain-development steps, which shortens the time required from months to weeks. To trick cells into recognizing extra-chromosomal DNA as their own genetic material, most yeast species are manipulated with episomal vectors composed of an autonomously replicating sequence (ARS) and a centromere (CEN) to direct the replication and segregation of episomal DNA, respectively. An ARS is a DNA replication starting point, and hundreds of such sequences are normally found in a yeast genome. Nowadays, the technique used for ARS isolation is simple and quite mature, whereas challenges remain in identifying a functional CEN in an efficient manner. A CEN is the partitioning element present on each chromosome that directs the formation of a kinetochore, the multi-protein complex that interacts with the spindle microtubules to enable stable chromosome segregation during cell division. In the absence of a CEN, extra-chromosomal DNA containing an ARS can replicate, but is mitotically unstable and lost with a high frequency due to the strong maternal segregation bias (i.e., plasmids tend to stay in mother cells).

It is generally accepted that CEN formation is modulated in an epigenetic manner in eukaryotes, conferring a heritable phenotype that is not based solely on a genotype. To date no cis-acting CEN-specific DNA sequences have been found conserved across yeast species, or even among chromosomes belonging to a single species. The traditional CEN isolation strategies, including (a) chromatin immunoprecipitation followed by next-generation sequencing (ChIP-Seq) and (b) functional selection based on toxic gene lethality at a high copy number set specific prerequisites for a centromeric protein-specific antibody and a high transformation efficiency, respectively, which are fairly challenging with some yeasts. Here the inventors present a third approach involving the integration of in silico GC3-chromosome scanning with high-throughput functional screening. This innovation proved to be highly efficient; all eight *S. stipitis* CENs were isolated from the genome within just one month. Our results illustrate that in some yeast species, the CEN-proximal regions display unique chromosome features, 'GC3 valleys', which can be implemented to approximate the CEN locations, therefore significantly reducing the screening efforts required in the subsequent validation step. This finding not only facilitates technology development for exploiting high potential yeast species, but also provokes profound discussion regarding CEN-specific genome features that have been rarely recognized in the past.

Results

Instability of the *S. stipitis* Vector Lacking a CEN

Figure 1B:
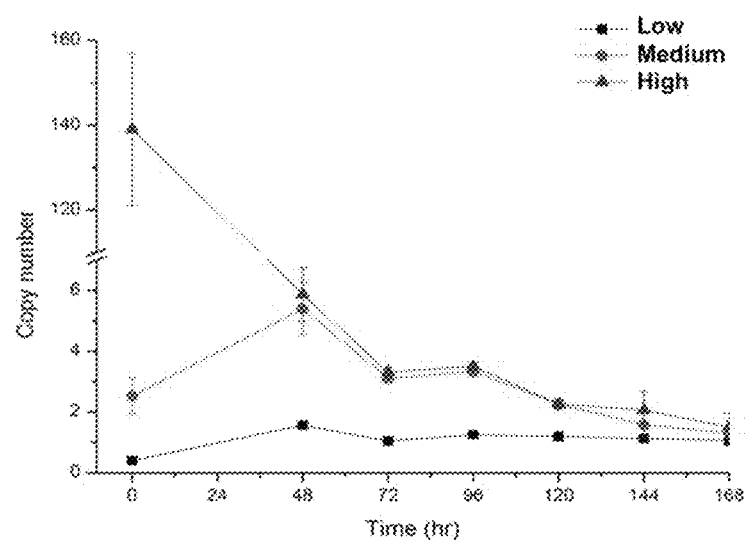

*S. stipitis* is one of the most important microbes in the field of biorenewables due to its high native capacity for converting xylose, the second most abundant sugar in lignocellulosic biomass. It has served as a repository for isolating genes involved in xylose transport and utilization, but its direct implementation as a fermenting host is limited by missing genetic manipulation tools. We noticed a lethal issue related to vector instability when we failed experimentally in knocking out a common auxotrophic marker, overexpressing exogenous genes, and even evaluating promoter strength. *S. stipitis* transformed with the vector carrying an ARS and an enhanced green-fluorescence protein (eGFP) expression cassette generated an unusually broad fluorescence range. This is in great contrast to the sharp, uniform eGFP expression peak observed in *S. cerevisiae* transformed with a plasmid containing both a CEN and an ARS (FIG. 1a). Fluorescence-activated cell sorting (FACS) was performed to separate cells into three groups with differing levels of fluorescence. Copy number analysis of each group indicated that the ARS-eGFP plasmid was present at 0-140 copies per cell (FIG. 1b); in high-eGFP signal cells, the plasmid dropped quickly from 140 to 6 copies per cell within 48 h, at which time approximately 60% of the entire population had completely lost eGFP expression. To the best of our knowledge, all the episomal plasmids developed for S. stipitis to date were designed based on the same backbone, varying only in the selection marker, but all missing the key CEN element. In addition, neither the S. cerevisiae CEN nor the 2μ, origin functioned in S. stipitis.

To isolate the S. stipitis CEN, classical approaches involving ChIP-Seq and SUP11 lethality assay. However, these methods were fruitless, either due to the failures in kinetochore protein overexpression and immune-tag insertion, or due to the low transformation efficiency observed when attempting to establish a genomic DNA library.

GC$_3$ Chromosome Scanning and CEN Prediction

It was previously found that the genomic GC content is correlated with meiotic recombination, when genetic materials are exchanged via the sequential occurrence of double strand breaks and chromosome crossovers. Meiotic recombination spots in S. cerevisiae were mapped based on the association between recombination hotspots and GC-rich regions. A possible explanation for this phenomenon is that high-GC-content regions bind relevant proteins needed to form a chromatin structure that supports the recruitment of recombination machinery. In contrast, centromeres and telomeres show reduced crossover with nearby genes, making them non-randomly associated with cold spots. The evolutionary decrease in GC content is particularly more evident at wobble positions because mutations occurring here are often silent, allowing the maintenance of a genome structure feature without affecting gene functions.

Evidence in this regard can be found from Lynch et al.'s bioinformatics analysis, where they calculated the GC percentage of the third positions of codons (GC$_3$) on each chromosome for a group of yeasts, including *Candida lusitaniae*, *S. stipitis*, and *Yarrowia lipolytica*. Their results showed that in silico prediction was effective for five of the six *Y. lipolytica* chromosomes; the five CENs that were previously characterized by another group coincided with the single markedly reduced GC$_3$ trough in each chromosome. Considering that CEN epigeneticity has been a long-standing mystery and the only commonality found is that some yeasts have "point CENs" defined by centromere DNA element (CDE) I/II/III blocks, Lynch's work delivered a very important message to the comparative genomics field that some yeasts might contain signature 'GC$_3$ valleys' featuring centromeric functions. However, due to the lack of functional characterization following this bioinformatics prediction, this hypothesis has not been widely appreciated.

To demonstrate that GC$_3$ valleys represent a second chromosomal feature shared by a set of yeast species, we performed a more comprehensive examination, calculating the GC$_3$ percentage for each chromosome of 73 yeast species whose full genome sequences have been deposited in one of the five databases (*Candida* Genome Database, FungiDB, National Center for Biotechnology Information, Ensembl Genome Browser, and Yeast Gene Order Browser). Very interestingly, 30 species had a single pronounced GC$_3$ valley occurring on at least one of the chromosomes, among which, *Hansenula polymorpha*, *S. stipitis*, *C. lusitaniae*, and *Y. lipolytica* showed a unique GC$_3$ valley on each of the chromosomes (FIG. 2). *S. stipitis* was chosen to validate due to the aforementioned plasmid instability issue in this species.

Stepwise Identification of the Minimal CEN5 for *S. stipitis*

Although they appeared as sharp GC$_3$ valleys, these regions spanned chromosomal segments ranging from 92-194 kb in length on each chromosome of *S. stipitis* (Table 1). An unusually long intergenic region ranging from 14,594-38,042 bp was located within each valley, whereas the average length of the other intergenic regions was only 732 bp to 1976 bp. The inventors hypothesized that the CENs are located within these abnormally long intergenic sequences. The sequence from chromosome 5 was first selected based on its relatively short length (17,264 bp), and more importantly, on the observation that several genes flanking this target location are homologs of the open reading frames proximal to the CENs isolated from *C. albicans* and *C. dubliniensis*. Flow cytometry analysis of the yeast cells containing this 17.3-kb region in the backbone of the ARS-eGFP vector displayed a symmetric eGFP expression peak, with the eGFP-positive population increasing from 40% to 90% relative to the yeast cells transformed with the ARS-eGFP vector (FIG. 3a). In experiments with a series of variants with shortened CENs, we found that the core CEN sequence could be reduced stepwise from 17.3 kb to 125 bp while maintaining the enhanced eGFP expression profile. The colonies with a functional CEN revealed a uniformly medium growth rate, whereas those without a CEN displayed a range of sizes, indicating a variable copy number among the cells. It was also noticed that cells harboring CENs shorter than 500 bp formed colonies much more slowly (almost 7 days on a SC-Ura plate for cells with the 125-bp CEN). This result was likely caused by an inefficient interaction between the CEN core and the kinetochore components when the proximal regions were trimmed off, as special 3D structures are likely formed to facilitate CEN-kinetochore binding. The 500-bp fragment (named CEN5-500 bp) was therefore chosen as the minimal stabilizing element for future plasmid manipulations.

Copy number and mitotic stability analysis of the ARS/CEN5-500 bp-eGFP plasmid showed ~3-5 copies per cell, with at least 80% of the cells being eGFP-positive; in both measurements stability was observed for at least 168 h, in sharp contrast to the rapid decline of the eGFP positive population belonging to the cells transformed with the ARS-eGFP plasmid (FIG. 3b). Note that although the copy number of the ARS-eGFP plasmid also appeared stable at 2-3 copies/cell, this number simply reflected a weighted average from a range of 0-140 copies per cell. To test the expression uniformity enabled by the CEN-containing plasmid, a putative xylose transporter (XUT1) containing a C-terminal eGFP tag was expressed, and the results were examined by confocal microscope (FIG. 3c). Homogeneous expression was only observed when the fusion protein was expressed using the ARS/CEN5-500 bp vector, with a distinctive fluorescent halo observed at the cell periphery via membranous localization of the xylose transporter. This result was in contrast to the case when the fusion protein was expressed in the ARS vector, only brightest cells could be observed. In addition, a codon-optimized lactate dehydrogenase (LDH) gene from *Lactobacillus helveticus* was cloned into the ARS/CEN5-500 bp vector, leading to lactate production at a titer of 29.5±0.4 g/L, which was 3-fold higher than the level achieved with the corresponding plasmid lacking the CEN (9.4±1.2 g/L, FIG. 3d). This ARS/CEN5-500 bp vector should be particularly useful for producing valuable chemicals in *S. stipitis* considering that alterations in most biosynthetic pathways interfere with cellular metabolism and therefore inhibit the hosts' growth rate to a certain degree; an unstable plasmid would be quickly lost during cultivation.

Rapid Library-Based Identification of the Other Seven *S. stipitis* CENs

Figure 4:
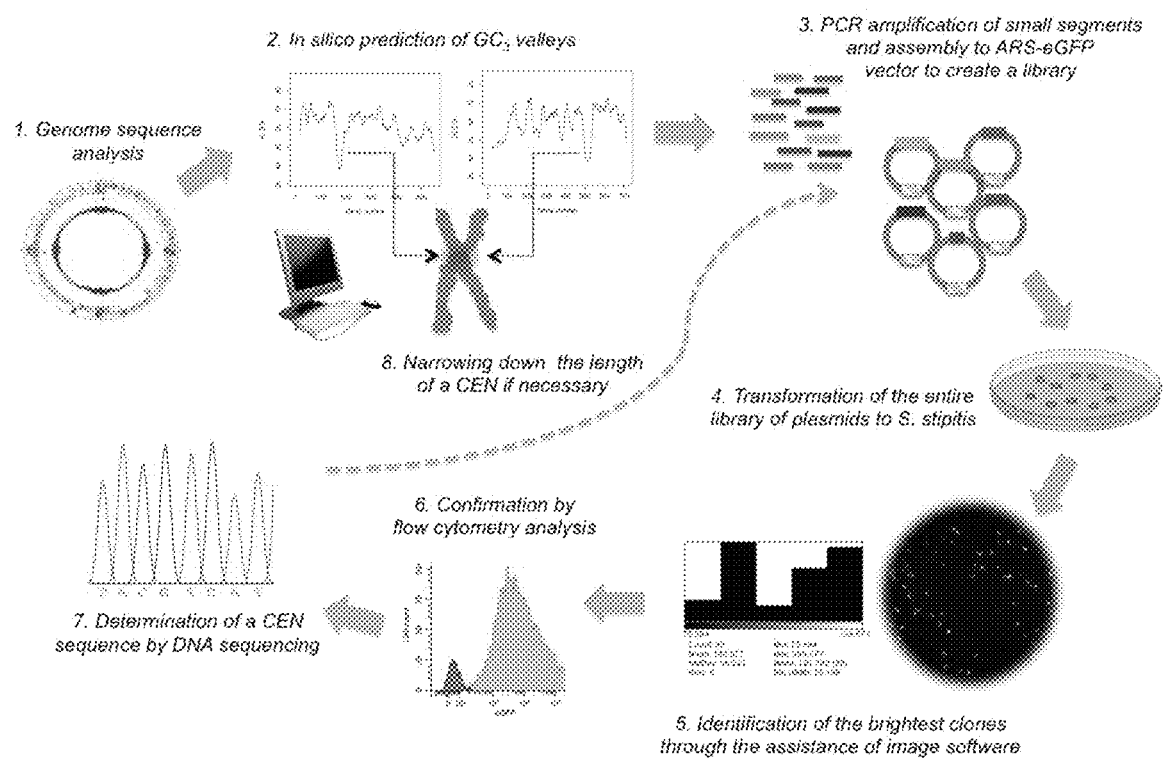
FIG. 4 is a flowchart describing the rapid library-based CEN identification procedures.
Figure 5:
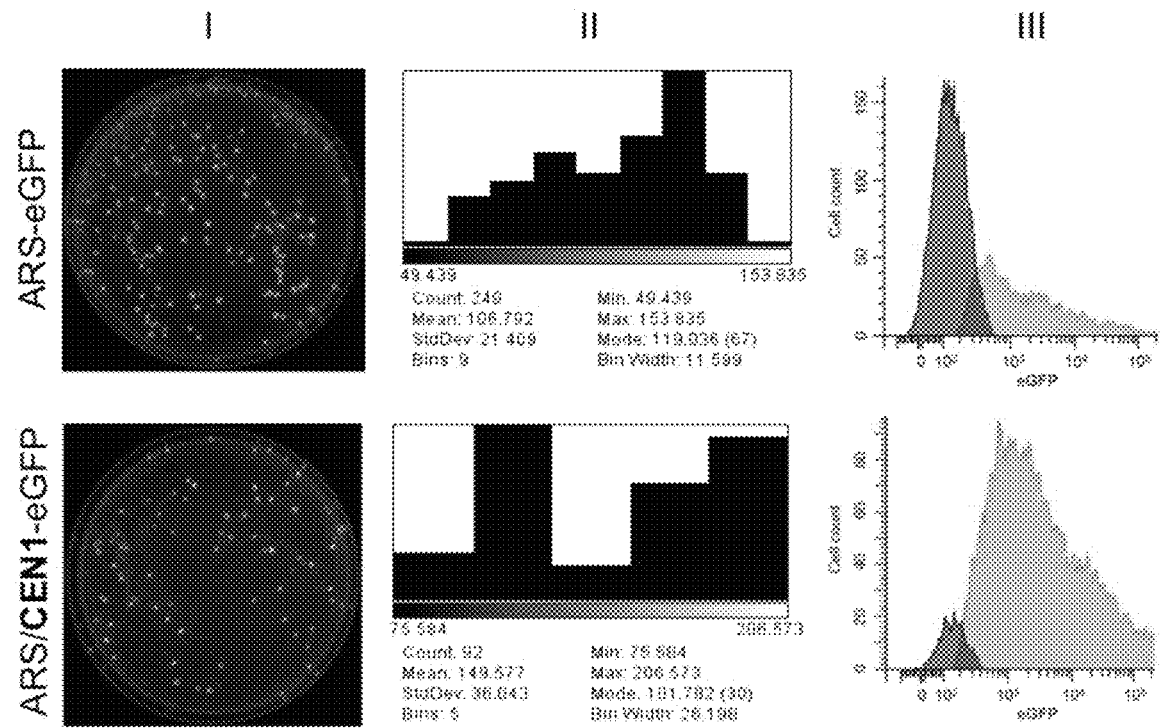
FIG. 5 shows analysis of the fluorescence displayed by each colony to identify clones carrying CENs. Only the results of CEN1 library and the negative control clones carrying the ARS-eGFP plasmid are shown here with the rest of the other CEN libraries summarized in FIG. 6. II. Processing of each picture and quantification of the fluorescence intensity of individual colonies using ImageJ software. III. Flow cytometric analysis of the brightest clones to confirm CEN function.

Encouraged by the success in narrowing down the *S. stipitis* CEN5 to several hundred base pairs, we next examined the minimal CEN elements in the other seven chromosomes. It is important to validate the accuracy of tagging a $GC_3$ valley to a CEN neighbor on a broader scale because, to date, very little information is available regarding common features of yeast CENs. Furthermore, we sought to streamline the identification protocol for the remaining seven chromosomes, so that the method could be effectively used by researchers in general. To do so, we amplified 5-13 segments of approximately 3-kb from each $GC_3$ valley in the remaining seven predicted sequences (14.6 kb to 38.0 kb; Table 1) and created seven libraries with the 3-kb amplicons inserted into the ARS-eGFP backbone (FIG. 4). Segments from each of the seven libraries endowed their transformants with different fluorescence levels, with the mean fluorescence value for each plate varying from 141±29 to 175±37, whereas that observed with the control ARS-eGFP plasmid was 107±21 (FIG. 5). Fifteen colonies, including ten colonies with high fluorescence values and five colonies with low fluorescence values, were picked for further screening by flow cytometry. The results revealed that only the colonies with maximum values (~200, for CENT: 183) showed single and symmetric fluorescence peaks, with more than 90% of the entire population being eGFP-positive, whereas the colonies picked from low-signal groups invariably showed broad peaks similar to those of cells transformed with the control ARS-eGFP vector. The likelihood of obtaining a functional CEN based on the fluorescence intensity of each colony was estimated. For CEN1, CEN3, CEN4, CEN6, and CEN8, at least eight of the ten selected colonies with high fluorescence showed symmetric peaks, although for CEN2 and CENT, only two of the ten colonies displayed the desired eGFP peaks (Table 1). The associated inserts were subsequently sequenced to ascertain the CEN positions in the corresponding $GC_3$ valleys, which were designated as CEN1-3 kb to CEN8-3 kb. This library based method, integrated with $GC_3$ chromosome scanning, was highly effective for pinpointing CENs, requiring less than four weeks to determine all functional CENs in the *S. stipitis* genome.

Determination of the CEN Core in *S. stipitis*

Although the eight 3-kb CEN sequences differed markedly from each other, sequences almost identical to the functional CEN5-125 bp (98.4% similarity) were identified in seven out of eight functional 3-kb regions. The only exception (CEN5-3 kb) was found to have one region of 139 bp sharing low similarity (54.7%) with CEN5-125 bp. The centromeric functions of these highly similar 125-bp fragments were validated by re-cloning them into the ARS-eGFP backbone followed by flow cytometry analysis, all of which showed symmetrically-shaped eGFP fluorescence peaks, whereas CEN8-139 bp resulted in a broad range of eGFP fluorescence, as was observed with the ARS-eGFP plasmid. These results indicated that the 125-bp sequence is the minimal CEN, which interestingly classified the *S. stipitis* CENs into the "point CENs" category (less than a few hundred bp), in contrast to the previous suggestions that *S. stipitis* contains "regional CENs" (several kb to Mb).

Surprisingly, we observed 2-4 repeats of the core CEN in each of the eight $GC_3$ valleys (FIG. 6 and Table 1), leaving a question as to why most segments containing this core sequence were not identified either in the step-wise shortening process (for CEN5) or the 3-kb library screening (for the other seven CENs). We re-cloned a 3-kb segment from each chromosome that was not identified in library screening but contained the core 125-bp CEN sequence. We found that only the segment from CEN1 showed the enhanced fluorescence peak (95% eGFP-positive cells) whereas the 3-kb segments from CENs 2-8 did not display well-shaped eGFP expression peaks, indicating that the 3-kb CEN genome context in fact played an essential role in defining CEN function. In addition, another 2.6-kb fragment cloned from CEN1 (named CEN1-2.6 kb') and a 3-kb fragment cloned from CEN5 (named CEN5-3 kb') were functionally identified, even though they did not possess the homologous 125-bp core sequence, similar to CEN8-3 kb. Collectively, these observations convey the important information regarding the aforementioned CEN epigeneticity, indicating the indispensability of integrating in silico prediction and library screening for rapid and accurate CEN searches.

Additional Evidence to Confirm the CEN Identity

Figure 7A:
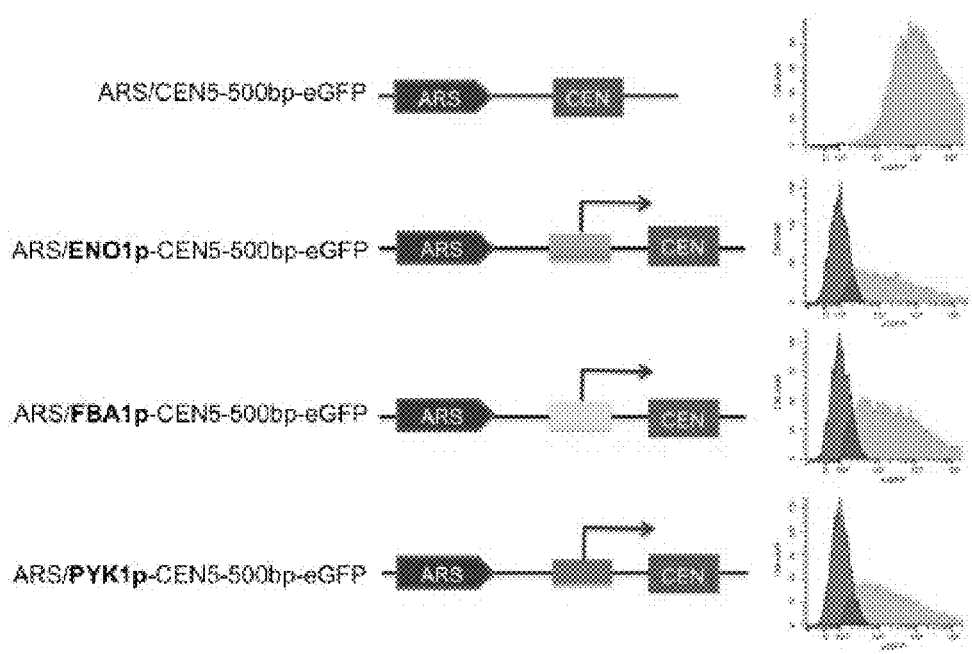
FIGS. 7A-B show additional lines of evidence used to confirm the CEN identity.
Figure 7B:
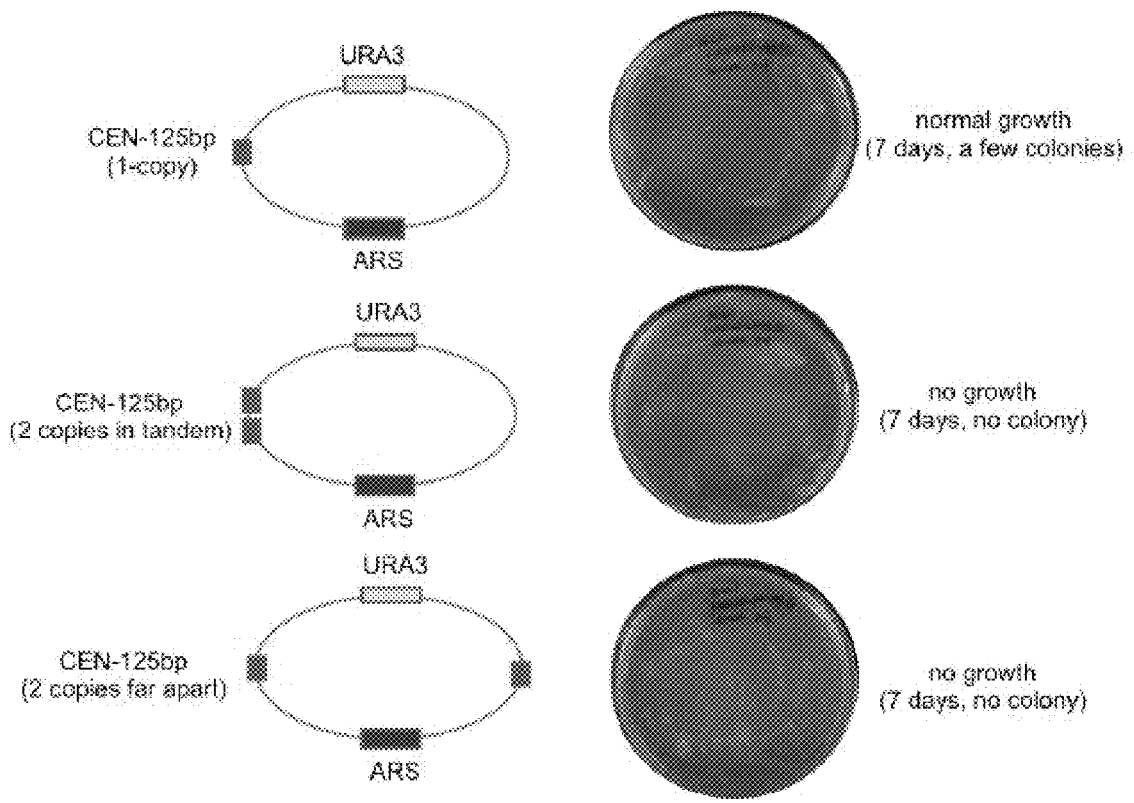
Figure 8A:
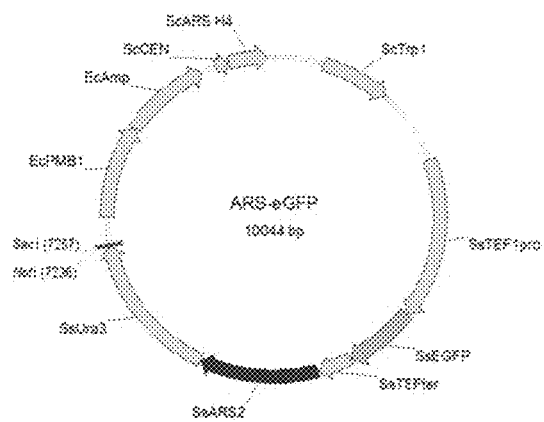
FIG. 8A shows the plasmid map of ARS-eGFP.
Figure 8B:
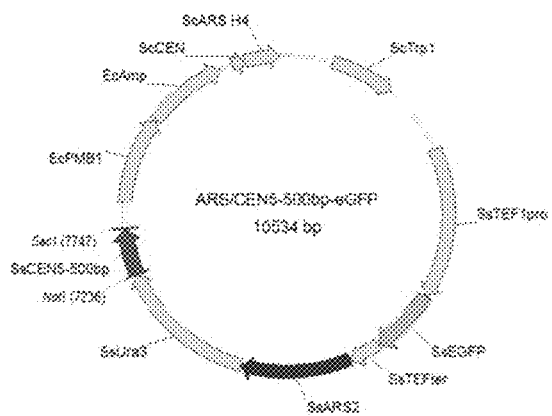
FIG. 8B shows the plasmid map of ARS/CEN5-500 bp-eGFP.
Figure 8C:
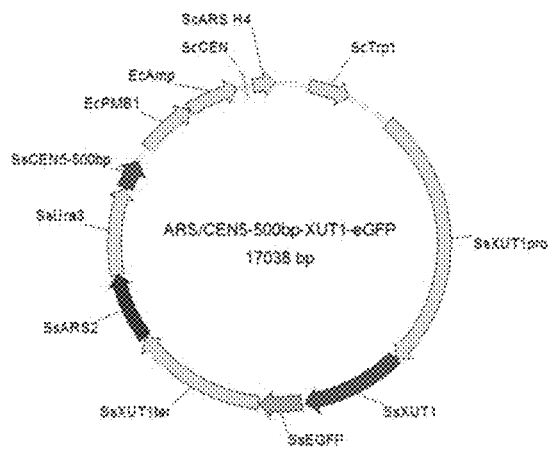
FIG. 8C shows the plasmid map of ARS/CEN5-500 bp-XUT1-eGFP.
Figure 8D:
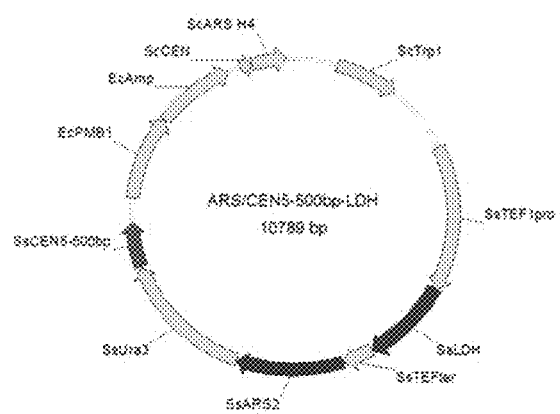
FIG. 8D shows the plasmid map of ARS/CEN5-500 bp-LDH.

The CEN identity was supported by two additional lines of evidence. First, a constitutive promoter was inserted upstream of CEN5-500 bp, which completely abolished the nearby CEN function. This may have occurred through a mechanism involving transcriptional CEN inactivation, wherein active local transcriptional activity interrupts functional interactions between CEN and the segregation machinery (FIG. 7a). Second, while one CEN is required for stable plasmid segregation, the presence of two copies of 125-bp core CEN either in tandem or separated on a plasmid showed a detrimental effect (i.e., no transformants; FIG. 7b). This is because the mitotic spindle apparatuses attached to both CENs and tore the plasmid under the opposing forces in two directions 46. These observations evidently confirmed that the identified elements are indeed CENs, rather than sequences that contribute to plasmid stability through directly tempering ARS function (i.e., low-copy autonomously replicative plasmids can be maintained more stably than high-copy plasmids).

Methods $GC_3$ Chromosome Scanning.

The whole genome sequences of 73 yeast species were downloaded from five databases including *Candida* Genome Database, FungiDB, National Center for Biotechnology Information, Ensembl Genome Browsers, and Yeast Gene Order Browser along with their annotations (in fasta and GFF format, respectively). The coding sequences (CDS) were then extracted from the genome using BEDTools (v2.20.1)60. CodonW (v1.4.4)61 was used to calculate the $GC_3$ percentage for each CDS sequence and a line graph was generated with a moving average of 15 genes corresponding to each chromosome. The genes with less than 100 codons, or whose coding region lengths were not multiples of three base pairs, were not included in $GC_3$ analysis.

Plasmid Construction and Yeast Transformation.

Majority of the plasmids used in this study were constructed using the DNA assembler method. In brief, the PCR-amplified fragments with overlapping ends were co-transformed with a digested plasmid backbone into *S. cerevisiae* for plasmid assembly via electroporation or lithium acetate-mediated methods. The isolated yeast plasmids were then transformed into *E. coli* for enrichment, and their identities were verified by restriction digestion or sequencing. The correctly assembled plasmids were subsequently transformed into *S. stipitis* for target gene expression. Codon-optimized genes, CEN-containing sequences, and plasmid maps are summarized in FIG. 8 and Table 2.

Flow Cytometry Analysis and Cell Sorting.

The transformed *S. stipitis* cells were cultured in SC-Ura medium for ~36-48 h and then centrifuged for 2 min at 2,000×g to remove the supernatant. The cell pellets were resuspended in 10 mM phosphate-buffered saline (pH 7.4) to an optical density at 600 nm ($OD_{600\ nm}$) between 0.1 and 0.2, and then analyzed by flow cytometry at 488 nm on a FACSCanto flow cytometer (BD Biosciences, San Jose, Calif.). The fluorescence-intensity distribution of each clonal population was calculated by BD FACSCanto Clinical Software. FACS was performed on a BD FACSAria III for copy number analysis. Three groups of cells, with high-level (mean fluorescence=77,014), medium-level (mean fluorescence=3,430) and low-level (mean fluorescence=329) signals were sorted (FIG. 1); 105 cells were collected for each group and re-inoculated into SC-Ura medium for time-dependent copy-number assays.

Step-Wise Determination of the Minimal CEN5.

Based on $GC_3$ chromosome scanning results, the longest intergenic region located in the $GC_3$-valley of chromosome 5 was hypothesized to harbour a functional CEN. To clone this 17,264-bp sequence, eight overlapping fragments, with lengths of 2.4 kb to 2.6 kb, were amplified from *S. stipitis* genomic DNA and assembled into the ARS-eGFP plasmid linearized by SacI and NotI using the DNA assembler method 62. To ensure high assembly efficiency, 400-bp overlaps between adjacent fragments were maintained through carefully designing primer-annealing positions 64. The ARS/CEN5-eGFP plasmid conferred a symmetric fluorescence peak in transformed cells and was therefore deemed to contain a functional CEN. The 17,264-bp sequence was subsequently divided into three segments of ~6-kb, each of which was cloned to the ARS-eGFP plasmid backbone. The segment that conferred a robust, symmetrical eGFP expression peak was continuously shortened to trim away the unnecessary sequences.

TABLE 1

Summary of the library-based and the stepwise CEN identification approaches.

| | Library approach | | | | |
|---|---|---|---|---|---|
| | CEN1 | CEN2 | CEN3 | CEN4 | CEN6 |
| Size of each chromosome (Mbp) | 3.51 | 2.74 | 1.84 | 1.80 | 1.72 |
| Length of the $GC_3$-valley (bp) | 194,092 | 119,392 | 130,977 | 93,962 | 128,639 |
| Length of the longest intergenic region located in each $GC_3$-valley 9 bp) | 14,594 | 38,042 | 24,208 | 26,877 | 30,037 |
| Average length of the remaining intergenic regions in each $GC_2$-valley (bp) | 930 | 1976 | 1070 | 1163 | 1027 |
| Number of 3-kb fragments used to create the corresponding library | 5 | 13 | 8 | 9 | 10 |
| Number of clones giving the desired eGFP peak among 10 randomly picked colonies | 8 | 2 | 4 | 2 | 4 |
| Repeat number of the 125-bp CEN core in the entire predicted $GC_3$-valley | 3 | 2 | 4 | 2 | 4 |
| Additional repeat number of the 125-bp CEN in each chromosome outside the $GC_3$ valley (bp) | 0 | 0 | 1/2929/ | 1/900/ | 0 |
| Chromosomal location of the longest intergenic region identified in each $GC_3$-valley | 2293090-2307683 | 1668602-1706643 | 1426116-1450323 | 1030956-1057832 | 886494-916530 |

| | Library approach | | Stepwise approach |
|---|---|---|---|
| | CEN7 | CEN8 | CEN5 |
| Size of each chromosome (Mbp) | 1.11 | .98 | 1.73 |
| Length of the $GC_3$-valley (bp) | 118,669 | 91,786 | 105,828 |
| Length of the longest intergenic region located in each $GC_3$-valley 9 bp) | 15,698 | 36,077 | 17,264 |

TABLE 1-continued

Summary of the library-based and the stepwise CEN identification approaches.

| | | | |
|---|---|---|---|
| Average length of the remaining intergenic regions in each GC$_2$-valley (bp) | 1230 | 1529 | 732 |
| Number of 3-kb fragments used to create the corresponding library | 5 | 12 | 0.8 |
| Number of clones giving the desired eGFP peak among 10 randomly picked colonies | 4 | 3 | 2 |
| Repeat number of the 125-bp CEN core in the entire predicted GC3-valley | 4 | 3 | 2 |
| Additional repeat number of the 125-bp CEN in each chromosome outside the GC$_3$ valley (bp) | 1/15606/ | 0 | 1/5056/ |
| Chromosomal location of the longest intergenic region identified in each GC$_3$-valley | 273467-289164 | 290537-326613 | 652653-669916 |

TABLE 2

The sequences of the key genetic elements in this work. The 125-bp CEN cores are highlighted.

| Genetic elements | Sequences(5'□3') |
|---|---|
| cgfp (codon-optimized) | (SEQ ID NO: 29) atgtctaaaggtgaagaattattcactggtgttgtcccaatttggttgaattagatggtgatgttaatggtcacaaattttctgtctccggtgaaggtgaaggtgatgctacttacggtaaattgaccttaaaatttatttgtactactggtaaattgccagttccatggccaaccttagtcactactttcggttatggtgttcaatgtttgctagatacccagatcatatgaaacaacatgactttttcaagtctgccatgccagaaggttatgttcaagaaagaactatttttttcaaagatgacggtaactacaagaccagagctgaagtcaagtttgaaggtgataccttagttaatagaatcgaattaaaaggtattgattttaaagaagatggtaacatttaggtcacaaattggaatacaactataactctcacaatgtttacatcatggctgacaaacaaaagaatggtatcaaagttaacttcaaaattagacacaacattgaagatggttctgttcaattagctgaccattatcaacaaaatactccaattggtgatggtccagtcttgttaccagacaaccattacttatccactcaatctgccttatccaaagatccaaacgaaaagagagaccacatggtcttgttagaatttgttactgctgctggtattacccatggtatggatgaattgtacaaataa |
| ldh (codon-optimized) | (SEQ ID NO: 30) atggccagagaagaaaagccaagaaaggtcatcttggtcggtgatggtgctgtcggttctacttcgctttctctatggttcagcagggtatcgccaagaattgggtatcatcgatatcgccaaagaacacgtcgaaggtgacgctatcgatttggctgatgctactccatggaccctccccaaagaatatctacgctgctgattacccagactgtaaggacgctgacttggttgttatcactgctggtgctccacaaaagccaggtgaaactagattggacttggtcaacaagaacttgaagatcttgtcctccatcgtcgaaccagtcgtcgaatctggttcgaaggtatcttcttggtcgtcgctaacccagtcgacatcttgactcatgctacttggagaatgtccggtttcccaaaggacagagttatcggttctggtacttcttggacaccggtagattgcaaaaggtcatcggtaagatggaaaacgtcgacccatcttctgtcaacgcctacatgtttgggtgaacacggtgatactgaattccagcctggtcttacaacaacgttgctggtgttaaggttgccgactgggttaaggctcataacatgccagaatccaagttggaagatatccaccaagaggtcaaggacatggcctacgacatcatcaacaagaagggtgctaccttctacggtatcggtactgcttctgctatgatcgctaaggccatcttgaacgacgaacacagagtcttgccattgtctgttccaatggacggtgaatacggattgcacgacttgcatatcggtactccagctgttgttggtagaaagggtttggaacaggtcatcgaaatgccattgtccgacaaagaacaagaattgatgaccgcttctgccgaccagttgaagaaagttatggacaaggccttcaaagaaccggtgtcaaggttagacagtaa |

TABLE 2-continued

The sequences of the key genetic elements in this work. The 125-bp CEN cores are highlighted.

| Genetic elements | Sequences(5'→3') |
|---|---|

CEN1-3kb (SEQ ID NO: 1)
aaacttgttatctctcatgatgacattgttcaccctaagtatggccaact tgctaccagagacctgagaaatctttacttgctgtgtctcgaaattgtcc gcccctagactgtctcgcgggctaaccactctgcctactcggcbcccgct cctgttacggtcgctgctcctgctgaggaccctggtgtggcacctatttc tgcctctgctcttgtccatgctcgccttggccaccttctccgactgtht gttcgtctggccttgaaatatccgaacatgbctcgcacggctgttcacga ctcgattcatgtgaagcatgtcttagctccaagaacactangttattccc aaaacgaccaccggtccagtcacatctgctcccttgcaacttcttcactg tgatttgtccggtcctcatgccggtggtccctcctcgttgttttatttg tattcttcttgacgactttactagcttcaaggctgttggccctattctca agaaatcggatgctgcggacttcattatcaaagttattaaggcatggaca aaccacttctccagtcgtggtggctaccgtgtctgtaacttcgttctgac aatggaggtgagttgtcaatctgacgcttacttcttctttgaggcagaag ggatccagacccagctcactgtgcctggtaactcacaccaaaatggacgt gctgaaagagcgattcgctccgttcttgacaaaacgcgtaccatgatcac tgcgtgttctcttccttcaccgctcttcccgcatgcactccaacatgctg catttctcctaaaccggctaccaacacctgttctccaaaatcgctcgcca tttgaactctggcatggcgcgaggcctatcttatctcaacttaaagtgtt gggtgtgctgcctttgtgaatgttccacccaatcaccgtcaactgaagtt ggtcgctcgtgcaatcaagggtgttatcttggatctgatccgttcggaag gctcatcttgtttatgatctcgctaccagacaagtgattacctcttctca tgttcggttccaggaaaatgtctttccttgtaagacctctgacgtcaac tgtcgtgtcggctacctccattggtggtgagggtagtggtggtggaagtt tccttctattctggcacctgctccatttgaagttcagaagcattcatagt gtcttacgtgtaataattgttaacagtaaaagtagaacttgtaagttgtt ctagttatcgttattaaaacatttgaaagtctatctaactctaaggggat accaccattatttatgttgttgtctcacactcacatgctccatgtgattc ttgttcaatatctcatggatcctattctctgcatcacgttcatctcatag ctgtggggttgagaccttctcccacatctgttccatatgtccgtgtgggt tctcctatcatctctgtataccctgccattgtgtttctattaccaccatat ccttattatgatatttgattggctctcacaagaattgcagccaaatctat tagattatcaatatccggtatctacgatatttccgaatcatgcatatact catgcattatcaaactttatctaataccggatttcgacaaacttctcctc acagatgtggggtttgaccttctccacatctatttccatatatatatta tatatccgtgtgggattctcctctcatctctgtataccagcdttatgttt ctgttactaccatattcttatcatgatcatttgattggctctcacaagaa ttgcaaccaaatctattagattatcaatatccggtatatactgtatttat catgcatattcatgcataccaacttatctcataccggatttcaacagttc ataggttatgttgttcaatagtgtttctgaattcagacatatttggagca tccagattcatacagaactcgatttcagtgcttcgttacctaggtagaaa atttgacgaattgggtgaccaccaaacdttagttttatttttatgtggatt tgtgaaattcagcatttgttcttcttgaaacggtgttgattattcttctt gttgtgttgtagatgttgtgttggatggttctatgaacgctgaatcaccg tgaattttcatggaagttttgacttatgtcgaccgcaccttgtttggaaag gggcttttatacttgaaactgttcattctattgtcgacccaagactttat attgttagcttcaccgctgttccgacaaagatacagtattcaatagagta atgagggtctattgtcttgaagaacagtttggtgtatcatcgtgatttga tgtcaactgttcaggattatttcacgttcggttgttttgagagacttact tttttcataaatcctttgatgtaattaatgattcttctgaagcatctttt cttcattatttcaatgtacggttattcattcaaaataggttcttaagatt ccttattgatagcctcttctgttttgtcatcaatatgcatttgactgaat aggccaaatatttgtaatataatgcttagtaatcgcattgtgacttcttg attgaatttaatgttgaagtcattcagaataacctttttaaatgttgtaaa tgcttccaatattccatccaatttatactttgtttcgaactatccaaatt tggcaaattctcaagttctcgttatgcacaatcattacagcgcttaccgc ttttgaattcttcttactacgttcttgattccttgaattcattgggcgta agagtgtcaacaccatccagcagatcttcttcttcaggctccagcgatga ctccgaatttcagcgtagacctgatccgttccagcgtttgtaccgtcaac cttttccatctcgttaaacaactcccgaattgtctttaggatgtcatc CEN2-3kb (SEQ ID NO: 2)
gaagatgacaaagaaagtgagatatgaatacattgaagatgacaatgagt ttggaacgagactttagaatcgaatagcgatgatccgaatgatgatacat atgatgaagctaatatttgcatccaaggtcatgcttatcaaatgtaggtt gaatctacagagagcaagaaagtaccaaacacatacgaagaagccattaa ttcttcagattctgagaaatggattgaagccatgaataccgaaatggctg ctcattctgaaaatgacacatggacattagtggatctcccggaaaagaaa acgaaagtccttggagtaagatgggtgtacaccatcaaggatggaggaaa atacaaagctaggcttgtggtacgaggattcaacaaagatatggagttga ttacaaagagcgtttgctccagtaattaggagtgagagtgtcaagttgt tacttgcacttgcggccatgtatggaaagaaggtacaccagatggatgtg tcaactgcattcttgaatggtaagattgatcttaagatctacatgaagca accatctgggtaccaggattgtagtgccttgagaaggtgtgtcagcttaa taagtccttgtacggattgaaacaggctccattgatatggaatgaaacaa tgaatagttccttgagaagatcggtttaaaaggtctttgtcagagtatgg TABLE 2-continued The sequences of the key genetic elements in this work. The 125-bp CEN cores are highlighted.

| Genetic elements | Sequences(5'→3') | actatacacgagaagaagtgtgatcattggactttatgtcgatgatttat
tgattgctggagacaatcagaatgagataaaagaaatcaagggacagttg
agtgcccagttcaagatgaaagatcttggaatagctaggaagttcctagg
cattaatatcactcaagggagtgatggaataaaagcagacttaggggatt
atattgataagatcctagaagagttaggaatggagaactgtaacccagta
tcaacaccaggttgcctggattgaaacttgaaaataacgagactgcgtta
ttggagaatcctaccttataccgatcaatagttggaaagttgctatatgc
tagcaacacggtaagaggagacataagtttattacaggagttctcagtag
atactttaaagagccaagagaggcacatcttacagcagcgaagcatgttc
ttcgatatctcaagggaaccaggtctcttgggcaacgttactcaaagact
ggacaacttgaagtattgtagacgcagattggggatcttcaacagacaat
aggaaatccatcacgggctatgcagtgaagttcggaggaggattgattct
tggaaatcgaagaagcaagctatagtcgcaacttctaccactgaagccga
atatatcgcactagcagaagccgtgaaagaagtgcttggttaagaacct
atttggtgaactacagataccactaacattacctataggaattcatgagg
ataatgtatcctgtataaaactaagtgaacatccaaccgttcatctgagg
actaagcatatcgacataagataccattcatccgtgaaaggataaaagag
gagaccataaaattaatacctgtcaaatctgaattcaatatagccgacat
attcacaaaggcgctagcaaaaccacaacacataaaattaagagcgttag
cagggatttcgtgaagagactattagattaagggaggctgttgaaatccg
gtattagataaagtttgataatgcatgaatatgcatgatctagaaaatat
cgtagataccggatattgataatctaatagattggctgcaacttcttgtga
gagcaaatcatatatcataataaggatatggtggtaatagaaaacacaat
ggcaggtatacagagaggataatagaaccccacacggacatatggaaaca
gatgtggagaaaggtdcaaccccacagctatgagatgaacgtgatgttga
aattcagagaattgaaactataattgtaatctaacaatcagataactatg
tgcagtactggctgcaaatttacaaataaggaagttccactggtcctatc
tctgagaataggagtaacccdtatcagacccgcctcaacggaatagaact
tatccgtaatgaaattggaggcgggctagagataagaataggggagata
agaatatgaataaggggaagataaggggttctgaacaatataaatatgg
taggatattctccaatatcagaagaataatcagaacttgaaattgaactt
cattatcaagagttaactatatcttattaatatacaatgtctaatttcaa
caggttatgagccaatccgtdcaaacatcaagttgatgactcccagaaac
tagttcgcgttcaactatcgtgaatggcgtacgcgtatggaggtcactat
tgggactcttggtatggagttccggggttcattgaaaaatctgaaccacc
taccgaggcttcgttgttattcttttaacctgacgcttcagdgcttattg
acaagacggtgtctaaagagattgttgattctcttcttgccgagaatctt ctggtcaggctcttgggaggctatccacgtcaattattcggttatgacgt
actctgagaaggtcgagtacgttactggttggtcgctaagattagtgaca
cgtaggtcagtactactgttcagttatcggctgccaagctgcttctacct
actttgctgagcagcctcctactgacattcctggtctcctctatcttaca
cactgtaagctggaccatattttgtctaagttcaaggaacttggtgctac
cttggatctcactgacctcaaatcgttcctaaaacggatcgatgcctcac
tgtcttccacgcctgggtctgtgttcacggtgactactctctcctctgct
ggactgaagtdcaccagaaagctcctgccacctctcctatctggaatacc
cgttgctatacgtgctctggt CEN3-3kb
(SEQ ID NO: 3)
atacataagtgactacgaaggagattctcctgagtcttgaatgatgatcc
aaatgatgaagattaccaaatgtcagaagcaaatgtggtaattcgaggac
atgcgttcacggctacaacaagtgtttaggtagccccaagattcccagaa
gctatagcgaagctgtcggaagccaagagctgggaaatggatagaagca
atgaacgatgaaatgtctgcacatgaaatgaaccagacgtgggttcttgc
agacaagccaaatgataaaacaaaagtgttaggtgtgagatgggtgtata
ccatcaaggatgatggtcgatacaaagcaagattagtcgcaagaggtttc
aacagagatatggtgttgattacgaagaaacctttgctccagtaatcaga
agtgagagtgtaaaggtgctactctccgtatctgctgtgtatgggatgaa
agttcatcagatgatgtaacgacagcattcctaaatggaaaaatcgatt
taccaatattcatgaatcaaccagatggattcaagcatacaaatgaactt
gggaaagtatgcaaactcaacaagtcactctatggtctaaagcaagctcc
gttgatatggaacaagacaataaatgcgttctcgagaaggtggggttgtt
aggtcacaagctgaattcggattatacaaaagaaagaacactattgtcgg
ttatatgtggatgacctattgatagcaagcagtaatgaaaatgagatcaa
ggctatcaaagaattgttgaagaaggaattcaaaatgaaagacctaggca
ttgcacagaaattccttggaataaacatacagcaatcagaaaaggtatt
agagcccattgggagactacattgacaaaatcttggaggaattctcaatg
caagattgcaacccagttggaactgcagcaattccaaatgctcagttaga
taaagatgaaaccaagattcttgccaatcctacaatttacagatccattg
ttggcaagttattatatgctagtaacaccattcggggagatattagcttc
attactggcatgctcagccggtacttcagaatcctagagagggacatcta
gtagcagctaagcatgtacttcggtacctaaaaggaacaaagactgtggg
ccaggtatatggaaaactggataaattcgaggtgtacgttgatgcagatt
ggggttcttcgctgtcagatagaaaatcaataacaggatatgcaattaag
ttcggaggaagtctaatctcgtggaaatcaaagaaacaaccaacagttgc
actatctacaacgaagccgagtatatggcacttgctgaagcagttaagg
aggtcctctggttggtgactctatttaaagaattggaaatccctgtaacc TABLE 2-continued The sequences of the key genetic elements in this work. The 125-bp CEN cores are highlighted.

| Genetic elements | Sequences(5'→3') |
|---|---| dtccaattatagtacatgaagataatacgtcatgtattaacttaacgaat
catccaacaactcatcaacgtacaaaacacattgatatcagatatcactt
tataagagagcaggtacagaaagaattgatcaaggttgtccaagttcagt
caacaaataatatcgcggacatcttacgaaggcagttcccaagccattac
tccagcaactacgaaactcagcaggaatgatggatattgaataatccgat
tattagattatgggggatgttgaaattcagagaattgaaactataattg
taatctaacaatcagataactatgtgcagtactggctgcaaatttacaaa
taaggaagttccactggtcctatctctgagaataggagtaacccdtatca
gacccgcctcaacggaatagaacttatccgtaatgaaattggaggcgggc
tagagataagaatagggggagataagaatatgaataaggggg aagataag
gggatctgaacaatataaatatggtaggatattctccaatatcagaagaa
taatcagaacttgaaattgaacttcattatcaagagttaactatatctta
ttaatatacaatgtctaatttcaacagaacttgtaagttgttctcgttat
cgttattaaaacattaagaaagtctatctaactctgagaggataccaccd
tatttatggtgttgtctcacattcacatgctccacggattcttgttctca
tgttcacatttgttcatagctgtggtattgaaaccttt ctccacatctat
ttccgtatgtccgtgtggggttctattatcctctctgtataccttgccatt
gtgtttctattaccaccatatccttattatgatatatgaatggctctcac
aagagttgcagccaaatctattagataatcaatatccggtatctacgata
tttctagatcatgcatattcatgcattatcaaactttatctaataccgga
tttcaacaacagagaggtacgggacgacaggaaatgtccagtacgaacag
gagaaggacagctagtggccttgtggccattaccaagacaattggtacac
ttgagaacaggggaagtacaaacattcgaacggtggcccttaccagagca
cgtatagcaacgggtattccagataggagaggtggcaggagctttctgt
gagacttcagtccagcagaggagagagtagtcaccgtgaacacagaccca
ggcgtggaagacagtgaggcatcgatccgtttaggaacgatttgaggtca
gtgagatccaaggtagcaccaagttccttgaacttagacaaaatatggtc
cagcttacagtgtgtaagatagaggagaccaggaatgtcagtaggaggct
gctcagcaaagtaggtagaaagcagcttggcagccgataactgaacagta
gtactgaccgacgtgtcactaatcttagcgaccaaaccagtaacgtacta
gaccttctcagagtacgtcataacccaataattgacgtggatagcctccc
aaagagcctgaccagaaagattctaggcaag CEN4-3.3kb
(SEQ ID NO: 4)
ctagttttgacaatccactgactgattctcgttagtcctgtgtgaatagt
tgctattgttagtcacttgtgactatgctgctagtactgtaggaccattt
actgtgggtgacgagtaattacttcctgtcagctctatgtgaccatttgc
agtggtcgttcccatctgttactgcaagctcataatggttacttgcttcg
gtctgttattactacttactattattcctttgcgactagttatagaagac
tgccactatttattgatgctagtcttctataactatatcatctgatatga
gagatccccgagtgttctcctattatttattgctgagcctgccgtggctc
cctactgtagtccgttacgactacctctcgtcttacccaacaaacttggg
tattccttctgtattttaaagtgacacccggtcattcttaattctttacg
attaattgctacagtctactgtgactgtattctctgtattctgcgagaaa
cctgattgtgttctcgcttacctagaatgatacactcgcagtcattccat
ggttgcggtggtatttggaaccttatgtcgcgttccatttaacctacaat
atggtgctccgagagtccatattaaccatatgattccacgtcagtctgtt
gggcccatgcagtctacgtgtatcatctgaattacttctactccaaattc
aaggagtatctgctaaagatagcaaccctattctcgaatatagaatagta
tgcgctgttataaaatctgcacaagcggtgcagtactcaccggttctgat
aagaaacatgagtctatgttctgactgaaactatcatcactacctttatt
tactgtgaggatgatagtgaacattgcgtgtgcaaactacaaatctgtga
attacgaatgttgtacttttagattatggggaatgtgaatagattgctg
ttctaatccaagagtacttgattacacagttgccdtacaaaatgtgtaag
agtaaaatgaacgactattagattaagagcaggagtattgaacattggaa
atatcaaatgatctaatctaatagtaatgttgaattgattcatcgttaga
tatggttatgtctacagtgtgccgtacacacaaataacctcattcttata
tctacattataccatactaacatcgttataggatataatgttgatctcga
taatcacaacacaatgtgggtatcctacccaacaacaatgaccatcac
gtaagtgatggaatactactcctggatgaaatttaacaggaaatttaaga
aataatcactagtgatcaagatgctccaaatggaatctgaaaataaggac
tatacatcacgaagattattaccagtctatcaggaagtgcaaagagtgaa
agttcacaaatacttcaaaacagatgctactgatttgaactaagagctgg
atcagatgcaaacttcaataaccattagattatggggaatgttgagatt
ggaaatctagagtaatccaatagattgaagtttagttatataacaagaaa
ctgagcgtgcaagaaactgagaatgcaagaaataatattcagattagaag
cattattcagaaacgcacaggttgcaaattaagccgcactgatgtgcagg
caactctgaggtataaaagaaagctgaaatcctcaaagtcttgaaaagt
tatacgtttataatgaatcaatttacgattcatttgagggaggttattct
agagatgtagagaataacatattgaacaactgtaggatacgctgtatcca
tatagacaagttgcgcgccttgttaaacagttgtatcaagataaagaaga
agacagacaaattacaacatggataggcaatcaagaggtctacataaact
agagtccatcatatcaacaattcactttcaatatgaaaccccggaactc
cataccaagagtcccaatagtgacctccatacgcgtacgccattcacgat
agttgaaacgcgaaactagttctgggagtcatcaaacttgatgtttgaga
cggattggctcataacctgttgaaaattagacattgtatattaataaaga TABLE 2-continued The sequences of the key genetic elements in this work. The 125-bp CEN cores are highlighted.

| Genetic elements | Sequences(5'→3') |
|---|---| tatagttaactcttgataatgaagttcaatttcaagttctgattattctt ctgatattggagaatatcctaccatatttatattgttcagatcccttat cttccccdtattcatattcttatctcccctattcttatctctagcccgc ctccaatttcattacggataagttctattccgttgaggcgggtctgataa ggggttactcctattctcagagataggaccagtggaacttccttatttgt aaatttgcagccagtactgcacatagttatctgattgttagattacaatt atagtttcaattctctgaatttcaacaagtcggacataattgattctcat tggtagatgttatcttatcacattactgtgcacaattatgtctgaatggc tgcaaatcctgcattcataaagtttacgcattggattaaaaatagaatat agaatatgctttaggttgatatcagcatattcaacagaatatgcatgatc tagaaaatatcatagataccggatattgataatctaatagatttggctgc aactcttgtgagagcaaatcatatatcataataaggatatggtggtaata gaaaacacaatggcaggtatacagagatgataggagaacccacacggac atatggaaacagatgtggagaaaggtdcaaccccacagctatgagatgaa cgtgatgcagagaataggatccatgagatattgaacaagaatacacatgga gcatgtgagtgtgagacaacaacataaataagggtggtatcccdtagagt tagatagacttctaaatgttaataacgataactagaacaacttacaagtt ctaccttactgttaacaattattacacgtaagacactatgaatgcttctg aacttcaacatctattaccatcatatccttaatatgatatgtgattggct atcacaagagttgcagccaaatctattagattatcaatatccggtatcta cgatattttctagatcatgcatattcatgcattatcaaacttatctatta ccggatttcaacagcctcccttaatctaatagtctcttcacgaaatccct gctaacgctcttaattttatgtgttgtggtttgctagcgccttgtgaata tgtcggctatattgaattcagatttgac CEN5-3kb (SEQ ID NO: 5)

aacagttcaacaggttatgagccaattaaattccggcctcatggtcattg atactcttcttctcagaggccgtgagaacttctggaatggaaagactgga tgactggtatgttcagtagctgtgtcttggctacagagattgctgcttat ctttcagagaaagaactttccatcaccttacggaccagcaggcgttgagc cacaagctccgtgagcttattctcaagtgtatgaagcctgacgttcagtc attgttcacgcactactctctgggtgtagaaacttggaaagctgtcgaaa ctgttgaaattcagagaattgaaactataattgtaatctaacaatcagat aactatgtgcagtactggctgcaaatttacaaataaggaaattccactgg tcctatctctgagaataggagtaacccdtatcagacccgcctcaacggaa tagaacttatccgtaatgaaattggaggcgggctagagattgttgattct cttcttgccgagaatcttctggtcagggctcataacctgttgaaaattag acattgtatattaataaagatatagttaactcttgataatgaagttcaat tcaagttctgattattcttctgatattggagaatatcctaccatatttat attgttcagaaccccttatcttccccdtattcatattcttatctccccct ataggagcttgctttagaccatagagtgacttgttgagttgcatacttcc caagttcatttgtatgcttgaatccatctggttgattcatgaatattggt aaatcgattttccatttaggaatgctgtcgttacatccatctgatgaact ttcatcccatacacagcagatacggagagtagccctttacactdcactt ctgattactggagcaaaggttctccgtaatcaacaccatatctctgttga aaacctcttgagactaatcttgctttgtatcgaccatcatccttgatggt atacacccatctcacacctaacacttgttttattattggcttgtctgcaa gaacccacgtctggttcatttcatgtgcagacatttcatcatccgcctca ggagaaatatccgagtcataagaatagcacagacgacagcatacggcaag aacacagcaggcaccgaaccatgagtcagaagagttcgggctttatcaag aatggtacgaatactaccgacacggtatccaccacgagtggagaagaaag aatgaaagagctcggcattgcacagaaattccttggaataaacatacagc aatcagaaaaggtattagagcccatttgggagactacattgacaaaatc ttggaggaattctcaatgcaagattgcaacccagttggaactgcagcaat tccaaatgctcagttagataaagatgaaaccaagattcttgccaatccta caatttacagatccattgttggcaagttatgttgagattggaaatctaga gtaatccaatagattgaagtttagttatataacaagaaactgagcgtgca agaaactacgaatgcaagaaataatattcagattagaagcattattcaga aacgcacaggttgcaaattaagccgcactgatgtgcaggcaactctgagg tataaaagaaagctgaaatcctcaaagtcttgaaaaagtttatacgttta taattaatcaatttacgattcatttgatggaggttattctagagatgcag agaataacatattgaacgactgtaggatacgctgtatccatatagacaag ttgcgcgccttgttaaacagttgtatcaagataaagaagaagacagacaa attacaacatggataggcaatcaagaggtctacataaactagagtccatc atatcaacaattcacattcaaaatgctcagcaaagtaggtagaaaagcagc ttggcagccgataactgaacagtagtactgaccgacgtgtcactaatctt agcgaccaaaccagtaacgtactcgaccttctcagagtacgtcataaccg aataattgacgtggatagcctcccaaagagcctgaccagaaagattctcg gcaagaagagaatcaacaatctctttagacaccgtcttgtcaataagctg ttgaagttcagaagcattcatagtgtcttacgtgtaataattgttaacag taaaggtagaacttgtaagttgttctcgttatcgttattaaaacatttag aaagtctatctaactctaaggggataccaccdtatttatgttgttgtdca cactcacatgctccatgtgattcttgttcaatatctcatggatcctattc tctgcatcacgttcatctcatagctgtggggttgagaccttctccacatc tgttccatatgtccgtgtggggttctcctatcatctctgtatacctgcca ttgtgtttctattaccaccatatcctcattatgatatatgattggctdca TABLE 2-continued The sequences of the key genetic elements in this work. The 125-bp CEN cores are highlighted.

| Genetic elements | Sequences(5'→3') |
|---|---| caagagttgcagccaaatctattagattatcaatatccggtatctacgat atttctagatcatgcatattcatgcattatcaaactttatctaataccgg atttcaacagcctcccttaatctaatagtctcttcacgaaatccctgcta acgctcttaattttatgtgttgcggtttgctagcgccttgtgaatatgtc ggctatattgaattcagatttgacaggtattaattttatggtctcctctt tatcctttcacggatgaaatggtatcttatgtcgatatgcttagtcctca gatgaacggttggatgttcacttagtttatacaggatacattatcctcat gaattcctataggtaatgttagtggtatctgtagttcaccaaatagggtt ctcaaccaaagcacttcttcacggcttctgctagtgcgatatattcggct tcagtggtagaagttgagacta CEN6-3.4kb
(SEQ ID NO: 6)
cgaggtgcaatagttcgaacagcgtcttgtcagcaatagtcctggaggga agcctattcaataaatatgcggcacatttaacagcgtagggccagaatgc ttgaggaacagaagcatgtccaagtagcgtcctggccttatcgattaccg agcggatcgaacgctctgcggttccattctgataagaattgtgagcaacc gtacgctgatgtgctataccttcctgttcaaggaagctcctgagactatg gttgacaaattcaccccccattatctgtacgaagagcaccaacacgatatc caccacgagtagagaaaaatgagtgtaatagccgaatatggataataatc tggtgggccacatccgacttcctaacgattgggaacacccacttaaactt gctataatcatccacaagcacacagaaataaactttcagaagagattcctg gcgtattatgagggccggagacatccgagtgaagaattgtaaaggagttg ttgtatccgatttatgggaaaccttcgggatactacgtgtcttcttatat tccagacagctggcacaactcttcgttacatcaccaatttctcaatatca gcaagcgagtaattgtcacgaagaacttgctgttcaatagcctgatgagg atgaccaagacggttatgaagaacagataaggcggagactaaaggtggta caggtgtcatatcaaggacggaaagtccaagatcgtccctatagacacca aaacgaccaatccgtggatgatagattccgtctacttggtggtaaggggc gaaccagagacacgaacagcagcatgcacggagataagattttagtgcat tctggaacatagcatacttcctgaaggactatagtdcatcagcagaccta aacttgatagaccdctacctaagcaggaagacgaactccgccagcacaa gaaacaaaactaccggactccggtttaaaagtccaaaacaaggaccgatc atgacaaatgtgaatcgaagcaccagagtcaaagatgaactccggtgaat gagatgtcgtggagccggtggttgtagtgagcacgaaggcactttcgtta acagcaaatttgcagtagcacctgacttgtattgcttcttgcgctcatt gtcactaaaggagcgcttcttggacgtattggtcagccatccagtatact taccaacacgaataggcgagcaacacacatcacgtctgtgaccacgacca ccacagttgtaacacttagtgttccaaagcggatcattggcatcaacaga aggacgtctggtgtcagtggaaaaggtagcagcaagaactgatggagcag taggagttcggtagaattctctgctttgctagaaatttgaaaacatcatc atacttcaacgattcgttgcccaggtggaagtaatttgcatgagattagg ggaacttcgagtaactagaaggtgaagacccttaattcatcaaaggtata ggattcgttcaaggaataaagagagtcaaaaaccggcttaacaacgtcag ttgtcaaagatggagtgtgaatcactgtcaataacgacttgacatattgg gcaacatcgtggtgatccatggtaccataaagatcaagaacccgtaacca acgtgctctgccagtgactggctcacgactgagagtactacgaactttct cagacaaggtttggaaagaacaaagtcaatataggagttgaatgcggatc tgtcctcagaagtgtatccatcgtcaacattgtcagaggcaaaagatatg ccacaaattctttccaattggttcgaaaagttgatccattctggtttcca taatgaaaagtcgttgatggaagtcaacatttgttctgaaggaaacgaga ttgagtagttgaacttcaggtgacggctcataacctgttgaagttcagaa gcattcatagtgtcttacgtgtaataattgttaacagtaaaggtagaact tgtaagttgttctagttatcgttattaaaacatttagaaagtctatctaa ctctaaggggataccaccdtatttatgttgttgtdcacactcacatgctc catgtgattcttgttcaatatctcatggatcctattctctgcatcacgtt catctcatagctgtggggttgagaccttctccacatctgttccatatgtc cgtgtggggttctcctatcatctctgtatacctgccattgtgttttctat taccaccatatcctcattatgatatatgattggctctcacaagagttgca gccaaatctattagattatcaatatccggtatctacgatattttctagat catgcatattcatgcattatcaaactttatctaataccggatttcaacag tgcgtgaacaatgactgaacgtcaggcttcatacacttgaggataagctc acggagcttgtggcttaacgcctgctggtccgtaaaggtgatggaaagtt cttctctgaaagataagcagcaatctctgtagccaagacacagctactga acataccagtcatccagtcttccattccagaaagttctcacggcctctga ggagaagagtatcaatgaccatgaggccggaatttaattggctcataacc tgttgaactgtttgcttggaagctcagtagattgaatcggattgttcata atgtaggacagtatattgattaacttatttaagatagataatttccatat agaagaagaaaagttatagaaagttagaaaggagaagggggagtaagacc cccttaaatagatgccaaatacaatcacaggctgacccctcatcgggatg aaatgaaacgacatgaccagaatttcaggttagtcggacataattgattc tcattggtagatgttatcttatcacattactgtgcacaatt CEN7-1.6kb
(SEQ ID NO: 7)
agcagcgaagcatgttcttcgatatctcaagggaaccaggtctcttgggc aacgttactcaaagaccggacaacttgaagtatttgtagacgcagattgg ggatcttcaacagacaataggaaatccatcacgggctatgcagtgaagtt cggaggaggattgattcttggaaatcgaagaagcaagctatagtcgcaac TABLE 2-continued The sequences of the key genetic elements in this work. The 125-bp CEN cores are highlighted.

| Genetic elements | Sequences(5'→3') |
|---|---| ttctaccactgaagccgaatatatcgcactagcagaagccgtgaaagaag
tgcttggttgagaaccctatttggtgaactacagataccactaacattac
ctataggaattcatgaggataatgtatcctgtataaaactaagtgaacat
ccaaccgttcatctgaggactaagcatatcgacataagataccatttcat
ccgtgaaaggataaaagaggagactatcaaattaatacctgtcaaatctg
aattcaatatagctgacatattcacaaaggctctagcaaaaccacaacac
ataaaattaagagcgttagcagggatttcgtgaagagactattagattaa
gggaggctgttgaaatccggtattagataaagtttgataatgcatgaata
tgcatgatctagaaaatatcgtaaataccggatattgataatctaataga
ttggctacaactcttgtgagagcaaatcatatatcataataaggatatgg
tggtaatagaaaacacaatggcaggtatacagagaggataatagaacccc
acacggacatacggaaatagatgtggagaaaggtttcaataccacagcta
tgaaacaaatgtgaaacatgagaacaagaatccatggagcatgtgaatgt
gagacaacaccataaataagggtgatatcctctcagagttagatagactt
tcttaatgttttaataacgataactagaacaacttacaagttctacctttt
actgttaacaattattacacgtaagacactatgaatgcttctgaattaca
acataaaggtgatggaaagttcttttctgaaagataagcagcaatctctg
tagccaagacgcagctactgaacataccagtcatccagtcttccattcca
gaaagttctcacggcctctgagaagaagagtatcaatgaccatgaggccg
gaatttaattggctcataacctgttgaactgtttgctttggaagctcagt
agattgaatcggattattcataatgtaggacagtatattgattaacttat
ttaagatagataatttccatatagaagaagaaaagttatagaaagttaga
aaggagaaggggggagtaagaccccttatatagatgccaaatacaatcac
aggctgacccctcatcaggatgaaatgaaacgacatgaccagaattcagg
ttagtctgacataattgattctcattggtagatgttatcttatcacatta
ctgtgcacaattatttcagaatggctgcaaatcctgcattcataaagttt
acgcattggattaaaaatagaatatagaatatgcttttaggtttgatatc
agcatattcaacaacca CEN8-3kb (SEQ ID NO: 8)
ctcataacctgttgaactgtttgctttggaagctcagtagattgaatcgg
attgttcataatgtaggacagtatattgattaacttatttaagatagata
attccatatagaagaagaaaagttatagaaagttagaaaggagaaggggg
agtaagaccccttatatagatgccaaatacaatcacaggctgacccctc
atcaggatgaaatgaaacgacatgaccagaattcaggttagtaggacata
attgattctcattggtagatgttatcttatcacattactgtgcacaatta
tgtctgaatggctgcaaatcctgcattcataaagtttacgcattggatta
aaaatagaatatagaatatgctttaggttgatatcagcatattcaacact atcaagtttaggtctgctgatgagactatagtccttcaggaagtatgcta
tgttccagaatgcactaaaaatcttatctccgtgcatgctgctgttcgtg
tctctggttcgccccttaccaccaaagtagacggaatctatcatccacgg
attggtagtttggtgtatatagggacgatcttggactttccgtccttgat
atgacacctgtaccaccttagtctccgccttatctgttcttcataaccgt
cttggtcatccgcatcaggctattgaacagcaagttcttcgtgacaatta
ctcgcttgctgatattgagaaaattggtgatgtaacgaagagttgtgcca
gctgtctggaatataagaagacacgtatattgaaatgtgaattgttgata
tgatggactctagtttatgtagacctcttgattgcctatccatgttgtaa
tttgtctgtcttcttctttatcttgatacaactgtttaaacaaggcgcgc
aacttgtctatatggatacagcgtatcctacagttgttcaatatgttatt
ctctacatctctagaataacctccctcaaatgaatcgtaaattgattaat
tataaacgtataaacttttcaagactttgaggatttcagcttctttatac
ctcagagttgcctgcacatcagtgcggcttaatttgcaacctgtgcgttt
ctgaataatgcttctaatctgaaatattattcttgcattcgcagttcttg
cacgctcagttcttgttatataactaaacttcaatctattggattactct
agatttccaatctcaacattcccccataatctaatggttattgaagtttg
catctgatccagctcttagttcaaatcagtagcatctgtttgaaagtatt
tgtgaacttcactctttgcacttcctgatagactggtaataatcttcgtg
atgtatagtcccttatttcagattccatttggagcatcttgatcactagtg
attattcttaaattcctgttaaatttcatccaggagtagtattccatcac
ttacgtgatggtcatattgttgttgggtaggatacccacattgtgttgtg
attatcgagatcaacattatatccgataacgatgttagtatggtataatg
tagatataagaatgaggttattgtgtgtacggcacactgtagacataacc
atatctaacgatgaatcaattcaacattactattagattagatcatttga
tatttccaatgttcaatactcctgctcttaatctaatagtcgttcattttt
actcttacacatttgtaagggcaactgtgtaatcaagtactcttggatta
gaacagcaatctattcacattcccccataatctaaaagtacaacattcgt
aattcacagattgtagttgcacacgcaatgttcactatcatcctcacagt
aaataaaggtagtgatgatagttcagtcagaacatagactcatgtttctt
atcagaaccggtgagtactgcaccgcttgtgcagattttataacagcgca
tactattctatattcgagaataggggttgctatcttagcagatactcctt
gaattggagtagaaagtaattcagatgatacacgtagactgcatgggccc
aacagactgacgtggaatcatatggttaatatggactdcggagcaccata
ttgtaggttaaatggaacgcgacataaggttccaaatagcaccgcaacca
tggaatgactgcgagtgtatcattctaggtaagcgagaacacaatcaggt
tctcgcagaatacagagaatacagtcacagtagactgtagcaattaatcg
taaaagaattaagaatgaccgggtgtcactttaaaatacagaaggaatac TABLE 2-continued The sequences of the key genetic elements in this work. The 125-bp CEN cores are highlighted.

| Genetic elements | Sequences(5'→3') |
| --- | --- | ccaagttgtttgggtaagacgagaggtagtagtaacggactacagtaggga
gccacggcaggctcagcaataaataataggagaacactaggggatctdca
tatcagatgatatagttatagaagactagcatcaataaatagtggcagtc
ttctataactagtcgcaaaggaataatagtaagtagtaataacagaccga
aagcaagtaaccattatgagcttgcagtaaacagatgggaacgaccactg
caaatggtcacatagagctgacaggaagtaattactcgtcacccacagta
aatggtcctacagtactagcagcatagtcacaagtgactaacaatagcaa
ctattcacacaggactaacgagaatcagtcagtggattgtcaaaaactag
ttactcaggaccagaaggaatcagccaagatagtgggcagtaggtagtca
ctagggaccagaaggaagcagcctcggcaggctgttaataagtaagatgt
cgttcgcgacaaatagagatccgccaagagggccgtccataagaagtagt
cgctcgggactagtagagagcagccagagggccgttcagaagtatgatgt
cgctcgggactagtagagatcaggcaagagggccgtcaataagaagtagt
cgt CEN1-2.6kb'

(SEQ ID NO: 31)
cctgatcaagcaccaactacgtctgcttcaactattcctatgggggtgtc
cggtatcctcgcattttaccggttgttcccacgacttcacgaactgaaca
tttgtcgagtgatgaacatgaaaattccttgggtgatcactcacaagaaa
caatcaacagatatgaacagggcaaattctcttgcgacctcttgtctatt
tcggacaatttactaccactaccttcgtcctgatgcgtctcttctctc
ctttgattccactgatactgaatttgcacaaataccatctaatcgactcg
catccgattctacgggggtgaggttctcaccaaacactcattgacaccag
tgataagtcctaaccacaatcagagggctggaaacaagagaaagcaggtg
ccatcaacgaatttgacaaagagagtcctataggaattcatgaggataat
gtatcctgtataaaacttagtaaacattctgttgaaattttataccccaa
taatgcaccttcttcttatatgcagaatggctgcaaaatctaacataatc
tcaagcaacgataaggtatgccctggactctgaggacttcacctctcgga
tatccttgttcttcataatgacctgctgtagccacctgtcccaaacctgt
taatattaattccagtcgcacgaatagcccaacagttataactcctggac
agtcctcatcccgccctgcgtggctcagtgtactacctgtcaaactat
cccgctcttcttcccgcgtctacctcaggggggaagcacctactgcatca
cggcctactccactggtcaatgaaatgtaacttgttcgtacgaacctctt
ggtgagcgagaacaacgcattgttcggaagcgcaaactcacaccagttcc
gtctcgagtccctctgtagtggaatgacataattctttcttaatactta
tgaagctggtatgtgtatcagtgttaagtacttcatatagctatagacaa
ttctctaaacagggaattcttgaagaattgtacagaattcgcagcacgta
gattttttgtgttacgatgaggtcggagaaaactgctaatctctaggccgt tgaccggacattgctgataaaaaacatccagtcttggtcctagtactttaa
cctcaatcatttatcgttccttgagattatgtcagattttgctgctattc
tgtatataagaacatagcgaatcatgttgaataagttttgatgaatattt
gctaatccactacttaaactatacaagtgcaaaattgctgccatttaacg
tgattctgatctacattgagaaaatctcctccattgtgaaggtaaacatt
ctatcttttagctttccctccttgtatctatgcaaaataactacccgtaa
ataagtaactcaatagaataacttaacaataattttaaagaatctgatccg
cttccaaagtaaacagctaaacacatcgttgtagcataaactcgttcaac
aagatttgacacctattcttcaaaatcgctctcggtttaaactctgttga
actgcatttgcaaatgttccagttggcgttcttcacgggagattatcccg
gaattgatcctttcggaaagctcatcttgttattactttgcaactataca
agatattacaatacttcatttcagttccaggagccttcttcctatttgca
aggctgctgaagtctaccccactaggagctcgcctctccatcctccaggt
cctattgtccgtcttcagagaactgatattcctccttctgattccttcga
cctatctgccgactttctaccgctcctggtcctcgtcaggtatcatatcg
tccaacataattcttgtttaaaacacctgtatttgaacatttgcagataa
ggctgcaggtactcatataggatgaatggaagtactacttcaattcatcg
aattacaactattccattagataatcagcactgttggattgcttcaaatt
ttcactacaggataattcagtctcatattgaataaccgaagcttattgtt
ggttattttagatattcaatttcaacaccaaggattcggtatgttaaggt
tccggaacaagattgcaaataggctcttatgcttcaaagtttagaacaat
taatctgcaattgaactcgttctatctactatcaaatgggtgatgactaa
ttttttaacaattccaagagtttctattgatttcaggatattgaatattgc
tctattgtaaaatggcctgtagtggatgggagaaagcactgcgttcctcc
tatacaggcccaactcttcctctactagcatacgcaaaatgcaccaggcc
agtgctaggaatgatgtcatttataatactccatgcttatagaacaatta
tgaattgctttaataaaagttaaaaatgaaatgcatatagcgcttctcat
gtttggaagtctatttggacaatatacatttgaaggtcaaacgttggtat
gctttgaagttcataatggttgagttgagcatacacatagatagacagtc
tgtcaacacccaataaacacaaaca CEN5-3kb'

(SEQ ID NO: 32)
tgactccacaagtgccacgcacctatgaggaagccactaacagtcctcaa
cgagaacgatggattgaagctatgaacaaggaattggtgctcaaatggaa
aactccacgtggactcttgctgagcttcctaagggaaaacgagccctagg
aatgaagtgggtatataccatcaaagatgatggaacttacaaagccagac
tagttgctctaggttttagacaaaaacatggaattgactatgaagaaacc
tttgcgcctgtgatcaggagtgaaagtatcaaacttctactagccatagc
ggctgtacataagatgaagattcatcagatggacgtctcgacggccttcc

TABLE 2-continued

The sequences of the key genetic elements in this work. The 125-bp CEN cores are highlighted.

| Genetic elements | Sequences(5'☐3') |
|---|---| taaatgggaagattgacacagaactctacattaagcagcctaaaggtttc atggatgaacaatatccacatatggtttgtaagttgaacaaatcactcta cggtctaaaacaagctccattgatctggaactcgactattaataaattct tggagaataacggctttattcgatcaaaatccgagttcgggatctacaga agaaataatgtgattcttggccttacgttgatgacctacttattgcgagt cctcgagaaatgaaatctacgaggccaagaaacttctcctgaacaagtt caagatgaaggatcttggattggcacgcaaattcctaggaatcaacatag aacagggccctgaagggatcacagcaaatctttctgactacatcaagaaa acgttggaggaactaaatcttgaagagctcaacagcgtgaaaagtcctat tattcagggacagcatctaaaccagaaatccaaaccctgcgatgcaacaa tttacagaagcatagtaggaaagcttctttatgctagcaataccatacga ggtgatattgcttatattgttggaatgttaagtcggtacttcaacgaacc aacagaggtaactctaactgccgccaaacatgttctccgctatctaaaag gaacacagaaactcggtcagcactacacaaacataaacgatctacaagtg tttgttgactcagactggggaagtgatagcagtgacaggaaatcaatcag tgggtatgccatcaagtatggggggaagcctaatctcttggaaatccaaga aacaaaccaccacagcattgtcaaccactgaagctgagtacatggccctc gcaaccgttataaaagaagttatctggctaataacattcttcagagaact tcgaatcccaatatcactaccaataatgatttgggaagataacacctcgt gtatcaaactcagcgaacatcctgtacaccacgaacgtacgaaacacata gatattcgctatcactttatccgtgacaaaatcatagacaatattgtcaa acttcgccaaatcaaatctgccgacaacgttgcagatatgtttacaaaag gactaactccaggaaccttccaacacttaatccaactatcaggaatgcaa ctaacccaataaaatgaccattggattaagggggatgttgaatatgttg aatatgctgatatcaaacctaaaagcatattctatattctattttaatc caatgcgtaaactttatgaatgcaggatttgcagccattcagacataatt gtgcacagtaatgtgataagataacatctaccaatgagaatcaattatgt ccgactaacctgaaattctggtcatgtcgttcatttcctcctgatgaggg gtcagcctgtgattgtattggcatctatataaggggggtcttactccct tctccttctaacttctataactttcttcttctatatggaaattatctatc ttaaataagttaatcaatatactgtcctacattatgaataatccgattca atctactgagcttccaaagcaaacagttcaacagtgaaagcgtaaacttg taaaggttggagtcaggaagaacagagccaacaagtcctaacacaggatg agagacggcagttggcagaaagttgaaattagatttgctacgagcagcag caacagcaagggaaacgaggttcctggcacatccagggacgtagtagaca tcatgaagttcaacaggagttttaccggcaagaaacttgacagtaccaga accacaaacagggagaggggcgccattagcgccaaaaatagaaccagctt cgacgaaacagtgggcttgaagtcccaaaacaaggtaggatcattacaga tatgatacgaagcaccagaatcaataaggaaatcagtggaggccaataac atagaaggggatacattgagggaatacgcctgggtggatggggtggatgc aaaggcatcaccagcggcagtagaaaaagaatgaacacgaggagacagag aggtacgggacgacaggaaatgtccagtacgaacaggagaaggacagcta gtggccttgtggccattaccaagacaattggtacacttgagaacagggga agtacatgttgaagttcagaagcattcatagtgtcttacgtgtaataatt gttaacagtaaaggtagaacttgtaagttgttctcgttatcgttattaaa acattaagaaagtctatctaactctgagaggataccaccdtatttatgtt gaatatgctgatatcaaacctaaaagcatattctatattctattttaat ccaatgcgtaaactttatgaatgcaggatttgcagccattcagacataat tgtgcacagtaatgtgataagataacatctaccaatgagaatcaattatg tccgactaacctgaaattctggtcatgtcgtttcatttcatcctgatgag gggtcagcctgtgattgtatttggcatctatataaggggggtcttactccc ccttctccttctaacttctataacttttcttcttctatatggaaattatc tatcttaaataagttaatcaatatactgtcctacattatgaacaatccga ttcaatctactgagcttccaaagcaaacagttcaacaggttatgagcca

Example 2: Engineering of *S. stipitis* for High Yield Production of Aromatics Recent advances in metabolic engineering have revolutionized the ability to engineer platform organisms to produce a wide variety of value-added compounds with broad applications as fuel, chemicals, and pharmaceuticals. Among these microbial factories, a number of yeast species, in particular *Saccharomyces cerevisiae*, have been widely successful due to their relatively well-characterized physiology and genetics, fast cell-growth rates, and the availability of tools for genetic manipulation. In terms of industry-scale fermentation, compared to bacterium platforms, yeast-based production brings additional economic advantages, for instance, a greater ease for maintaining phage-free cultivation conditions. In addition, the downstream biomass byproducts (i.e. yeast extract) can often be sold separately as animal feed, therefore further increasing the overall profit. More importantly, yeasts have the unique capabilities of expressing membrane-associated cytochrome P450 enzymes, which enables the synthesis of complex molecules such as plant-derived natural products that often possess important medicinal properties.

Results

Strain Selection and Pathway Design

Figure 9:
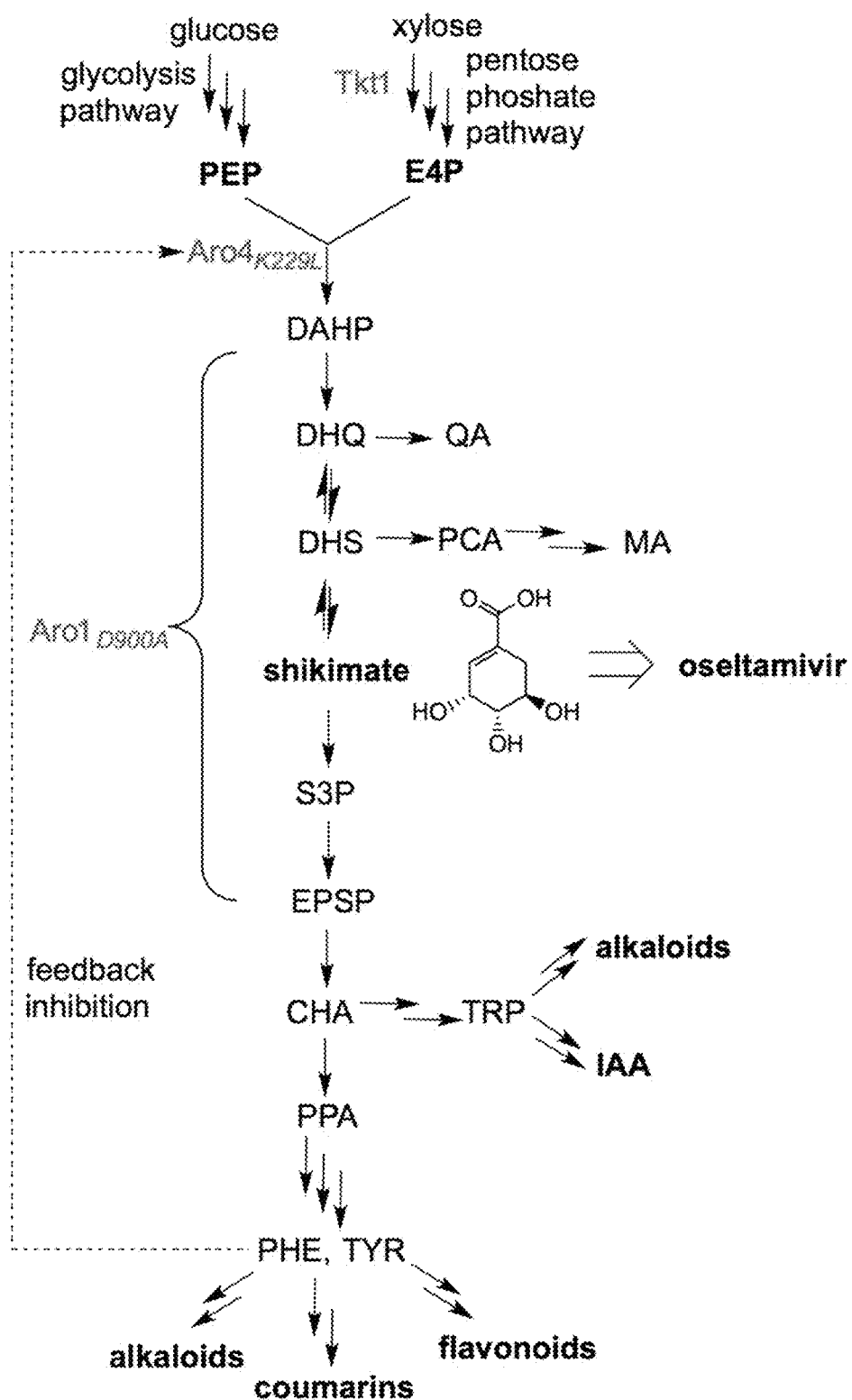
FIG. 9 shows biosynthetic pathways of shikimate and its derivatives. Metabolites: E4P, erythrose-4-phosphate; PEP, phosphoenolpyruvate; DAHP, 3-deoxy-D-arabinoheptulosonate-7-phosphate; DHQ, 3-dehydroquinic acid; DHS, 3-dehydroshikimate; S3P, shikmate-3-phosphate; EPSP, 5-enolpyruvylshikimate-3-phosphate; CHA, chorismate; PPA, prephenic acid; TRP, tryptophan; PHE, phenylalanine; TYR, tyrosine; QA, quinic acid; PCA, protocatechuate; MA, muconic acid; IAA, indole-3-acetic acid. Enzymes: Aro4K229L, DAHP synthase mutant insensitive to feedback inhibition; Aro1D900A, adapted pentafunctional enzyme variant with shikimate kinase domain inactivated; TKL, transketolase. Through ten step chemical conversions, shikimate can be converted to oseltamivir phosphate, more commonly known as Tamiflu® and used for the treatment of seasonal influenza.

Despite the fact that shikimate serves as an important intermediate in the aromatic amino acid biosynthetic pathways of many organisms, its accumulation in yeast species has not been reported to date. Considering that the two precursors of the shikimate pathway, phosphoenolpyruvate (PEP) and erythrose-4-phosphate (E4P), originate from the glycolytic pathway and the pentose phosphate pathway, respectively (FIG. 9), the inventors hypothesized that the highly active xylose-consuming species, S. stipitis, might be a better production host than the regular glucose-utilizing yeasts due to the fact that it has a more active pentose phosphate pathway. In yeasts, the entry into the shikimate pathway via condensation of PEP and E4P is governed by two isozymes of 3-deoxy-D-arabino-heptulosonate-7-phosphate (DAHP) synthase (encoded by aro3 and aro4), which are subject to feedback inhibition by aromatic amino acids. It has previously been shown that overexpressing a tyrosine-insensitive aro4$_{K229L}$ mutant in an aro3/aro4 double knock-out strain successfully alleviated this feedback inhibition in S. cerevisiae. In addition, as evidenced by the production of muconic acid that utilizes 3-dehydro-shikimate (DHS) as its synthetic precursor, overexpression of the transketolase gene (tkt1) in S. cerevisiae contributed an increased flux in the pentose phosphate pathway, consequently improving muconic acid production by increasing the E4P supply (FIG. 9).

To increase the production of shikimate, the flux towards shikimate must be enhanced, but its subsequent conversion to shikimate-3-phosphate (S3P) must be halted. Unlike prokaryotes and higher eukaryotes, in yeasts the single pentafunctional enzyme ARO1 catalyzes the five steps that convert DAHP to 5-enolpyruvylshikimate-3-phosphate (EPSP). Sequence alignment with shikimate kinase genes from prokaryotes and fungi indicates that the aspartate (Asp) at position 900 is the conserved active site in the shikimate kinase subunit of ARO1, corresponding to Asp36 in E. coli AroK. The inventors hypothesized that substitution of Asp900 with alanine would significantly boost shikimate accumulation, without affecting the other catalytic functions of the ARO1 subunits.

Identification of Strong Constitutive Promoters Via Transcriptome Analysis

Although S. stipitis has great potential in the biorenewables field due to its natural capability for xylose fermentation, its broader application as a popular host is limited by a lack of genetic manipulation tools. As a first step to develop a highly productive strain, we sought to identify strong constitutive promoters using RNA-seq. Promoters such as TEF1p, Xyl1p, ADH1p and ADH2p have been used to drive gene expression in S. stipitis in independent studies, but no systematical comparison and characterization have been performed. Previous transcriptomic studies (i.e. DNA microarray) in S. stipitis chose single-sugar (glucose or xylose) conditions and analyzed only one time point during the exponential phase. In the current study, the strong potential of S. stipitis for use as an industrial producer to convert biomass-derived sugars led us to choose mixed-sugar plus industry preferred oxygen-limited condition to culture the strain. The culture was sampled at three defined time points (15, 48, and 72 hr). The absolute counts for 5700 genes were normalized using the upper quartile method, and more than 94% of all reads were uniquely mapped to the reference genome for S. stipitis (v2.0 downloaded from JGI).

Figure 10A:
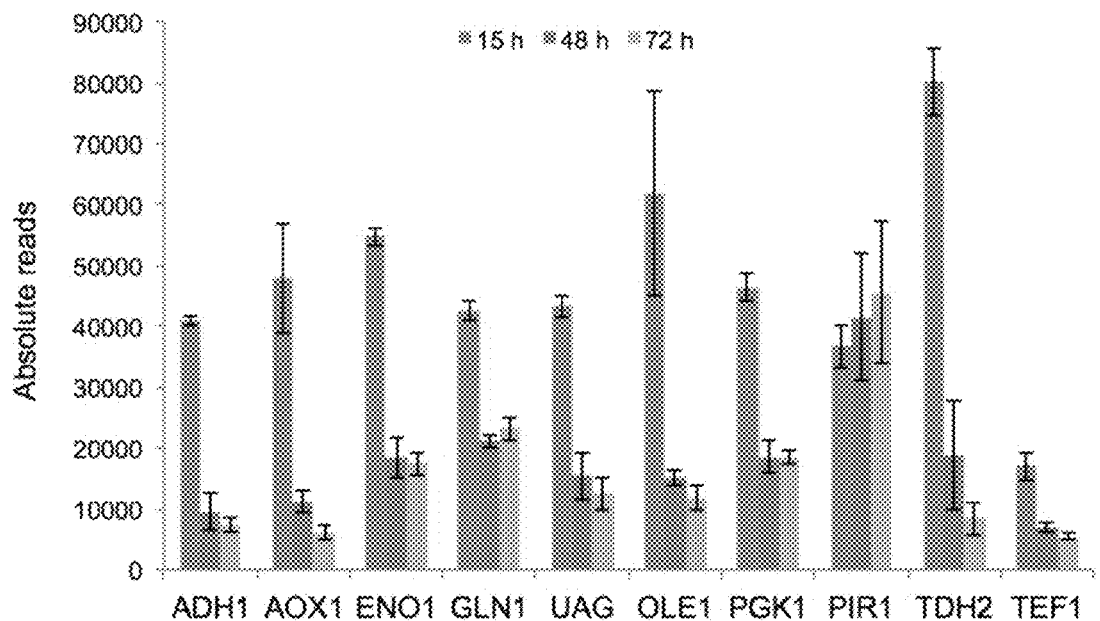
FIG. 10A shows absolute mRNA reads from ten highly expressed genes selected from S. stipitis based on RNA-seq analysis. Error bars represent standard deviations of four biological replicates.

Constitutively and highly expressed genes were selected based on two criteria. First, the transcriptional level of a specific gene should be above the level of tef1 at both sampling time points (48 and 72 hr). This criterion was based on the fact that after 48 hr, glucose was nearly depleted and xylose became the main carbon source. A total of 23 genes were discovered, after which a second threshold was applied to select genes with at least a 2-fold higher expression compared to that of tef1 at 15 hr. Due to carbon catabolite repression (CCR), only glucose was utilized during the first 15 hr. For effective co-sugar conversion, the activities of the desired promoters should not vary significantly with the transition of the sugar option or with sugar concentration. As a result, nine highly expressed genes were identified (FIG. 10a), and their promoters and terminators were isolated for more detailed characterization.

Promoter Characterization and Length Optimization

Figure 10B:
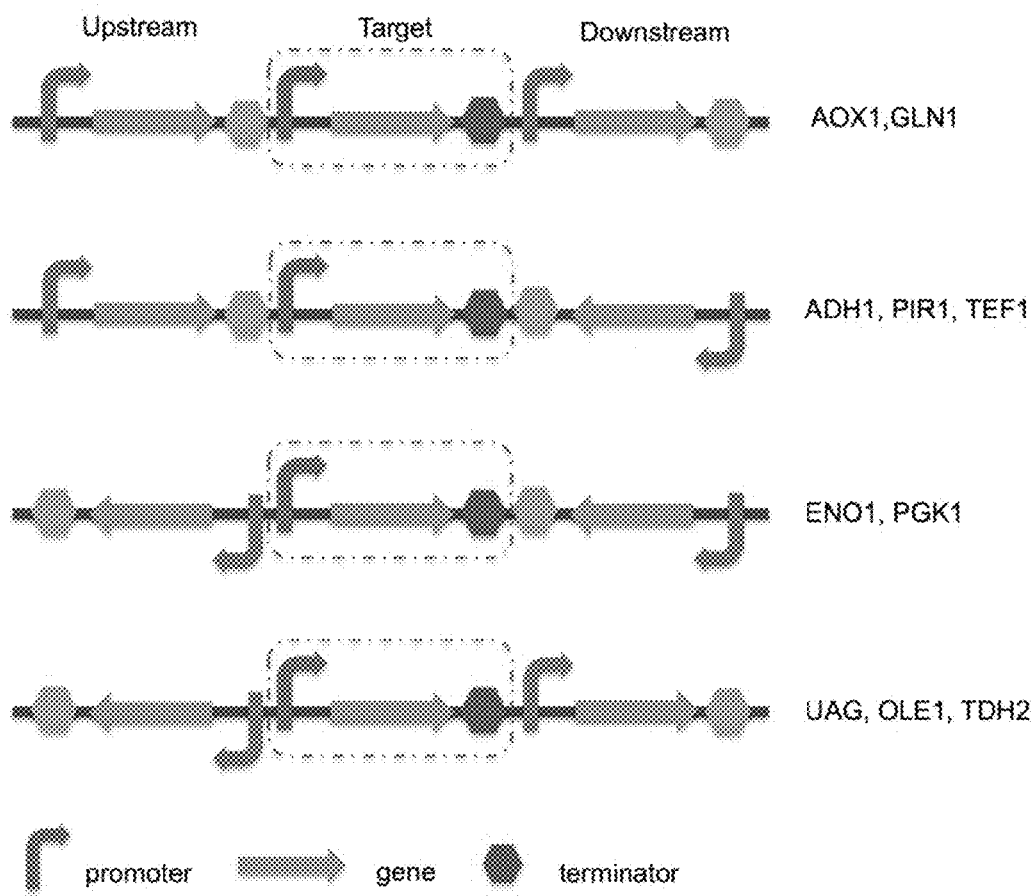
FIG. 10B shows genome context of the selected genes.
Figure 11A:
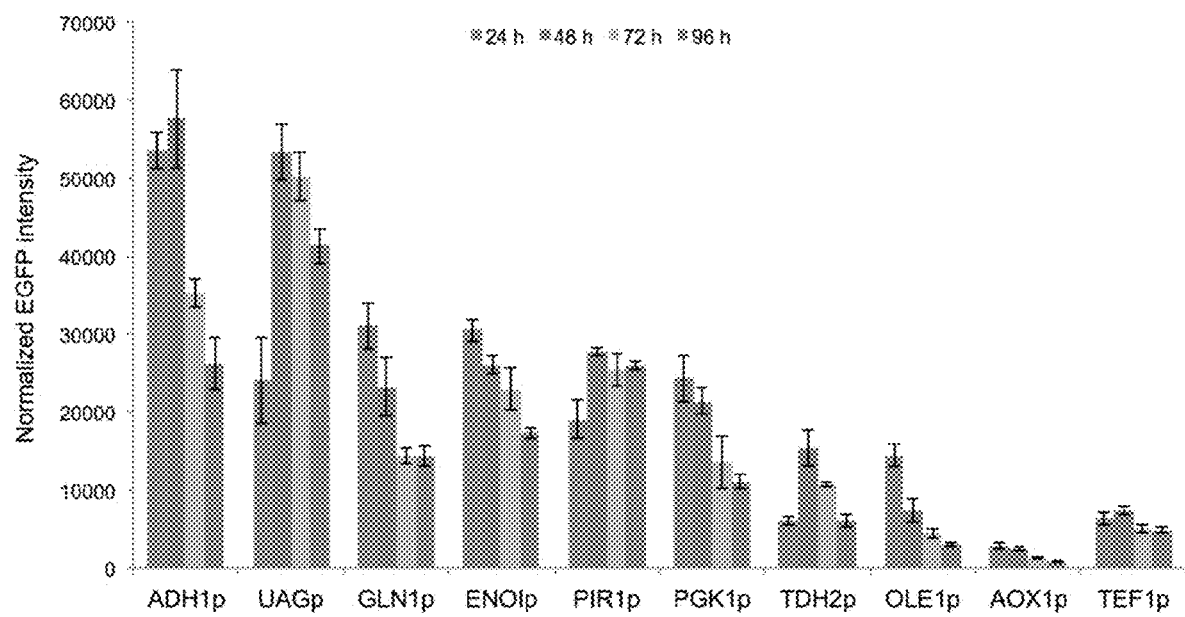
FIGS. 11A-B show EGFP intensity of S. stipitis FPL-UC7 harboring the egfp gene cloned downstream of each of the 10 selected promoters, under mixed-sugar oxygen-limited condition.

The genomic context of the ten selected promoters (including TEF1p) is summarized in FIG. 10b. According to the transcriptional direction of neighboring genes, five of the ten upstream intergenic regions contain the terminators of the upstream genes, while each of the other five regions carries another promoter that runs in the reverse direction. It was challenging to identify the promoter boundaries initially; therefore we began by tagging the entire intergenic region (1.1 to 2.6 kb) with an egfp reporter gene encoding enhanced green fluorescent protein (EGFP) and the same terminator (TEF1t). The EGFP output of the resulting ten strains grown in mixed-sugar oxygen-limited condition was evaluated (FIG. 11a). Largely consistent with RNA-seq results, the majority of these intergenic promoters were much stronger than TEF1p. In particular, ADH1p and UAGp showed the highest activity, more than 7-fold stronger than TEF1p (for individual promoters, the time points giving the highest activities were selected for comparison). Only AOX1p appeared weaker than TEF1p. This could be attributed to the difference in mRNA stability when the native gene and terminator were replaced by egfp and TEF1t.

Figure 11B:
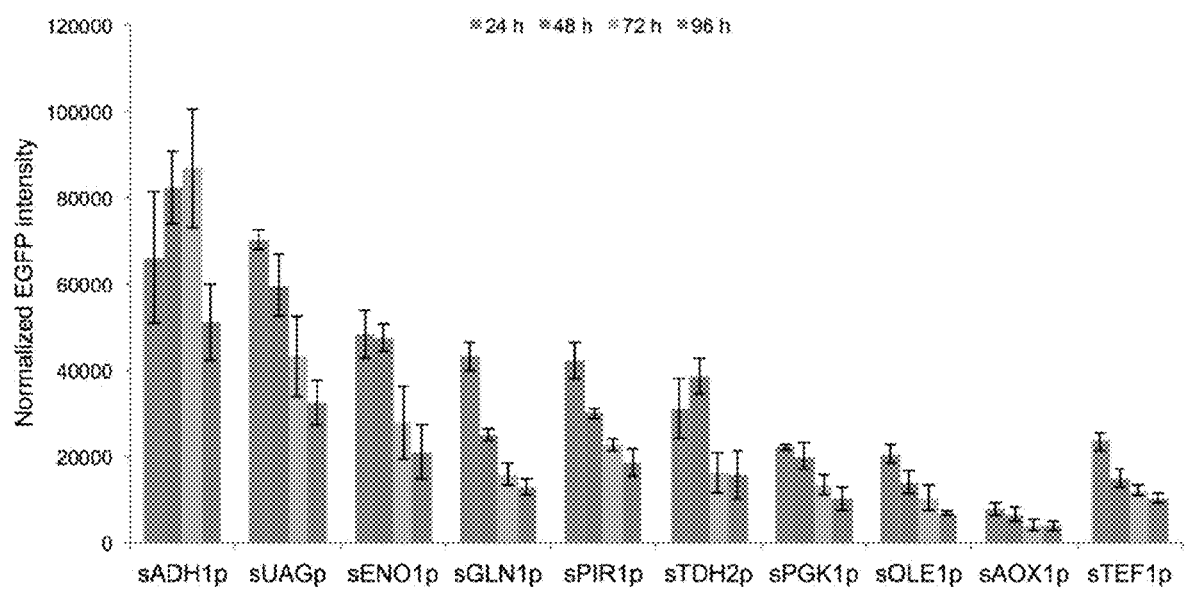

Next, we truncated the 5'-ends of the intergenic promoters so that only 500-800 bp from the 3'-end remained. When these shortened promoters were evaluated under the same mixed-sugar oxygen-limited condition (FIG. 11b), the majority maintained stronger activities than the shortened TEF1p (sTEF1p). When compared with their intergenic counterparts, six of the shortened promoters (sADH1p, sENO1p, sPIR1p, sTDH2p, sAOX1p, and sTEF1p) displayed 1.5- to 3.2-fold higher activities, whereas the other four (sUAG1p, sGLN1p, sOLE1p, and sPGK1p) maintained 0.9-1.4 fold strengths to the full-length promoters. The enhanced strengths seen with the shortened promoters suggest that the deleted regions may have contained repressor-binding sites. We also noticed that although sUAGp produced a strong signal, the EGFP expression peak verified by flow cytometry analysis was abnormally broad (data not shown), indicating potential instability of the plasmid. The full-length intergenic promoter was therefore selected for UAGp. Sequences of the nine shortened promoters and the intergenic UAGp are SEQ ID NO: 9-18. This collection of strong promoters will be useful for building long biosynthetic pathways in S. stipitis.

Terminator Discovery and Characterization

In addition to intensive promoter characterization and engineering, recent attention has been broadened to terminators due to their essential function as transcriptional modulators via the control of mRNA stability and half-life. Therefore, the terminator regions of the ten highly expressed genes previously identified from RNA-seq (FIG. 10a) were selected for detailed characterization at both transcriptional and translational levels. Again, the genomic context revealed that five intergenic terminator regions (ADH1t, PIR1t, TEF1t, ENO1t, and PGK1t) contained another terminator running in the opposite direction (FIG. 10b). For this group, if the length was shorter than 500 bp, the intergenic region was left intact; otherwise, the first 500 bp was selected as the putative terminator. The other five intergenic terminator regions (AOX1t, GLN1t, UAGt, OLE1t, and TDH2t) include the promoters of neighboring genes, which could interfere with the downstream gene transcription if the entire region was selected as the terminator, therefore two sequence lengths of 150 bp and 300 bp were chosen for further verification.

Figure 12A:
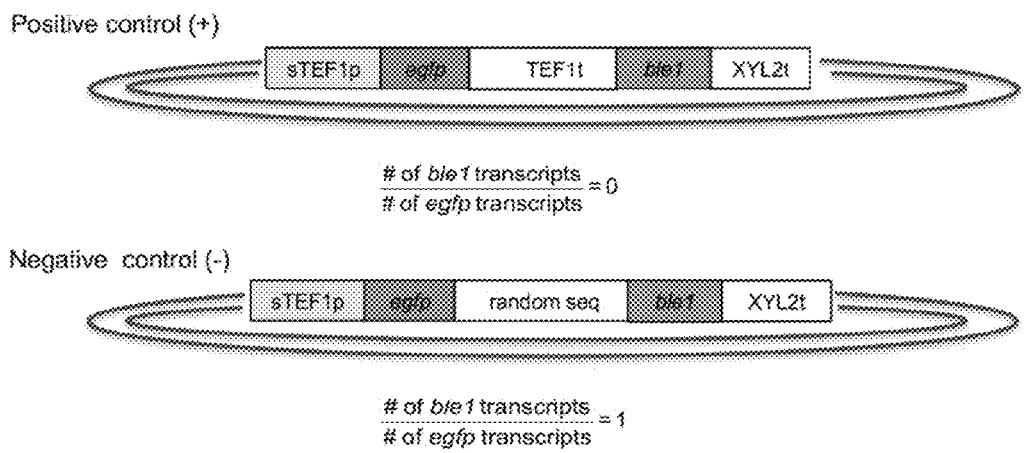
FIG. 12A is a diagram of constructs used to test terminator efficiency. The target terminator is located between two reporter genes, egfp and ble1. If the terminator has high termination efficiency, the transcript ratio of ble1 to egfp should be close to 0. If the target sequence is not functional, the ratio should theoretically be 1.
Figure 12B:
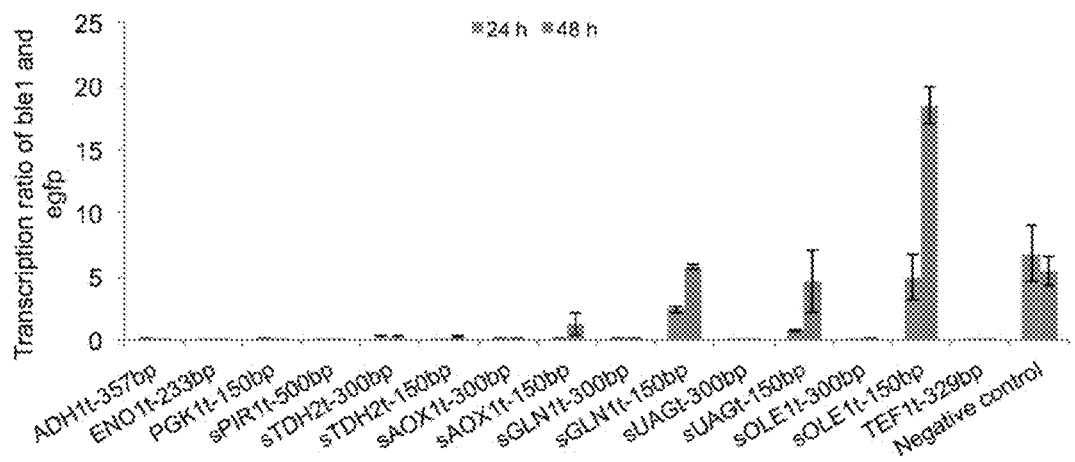
FIG. 12B shows termination efficiency of the selected terminators at the transcriptional level.
Figure 12C:
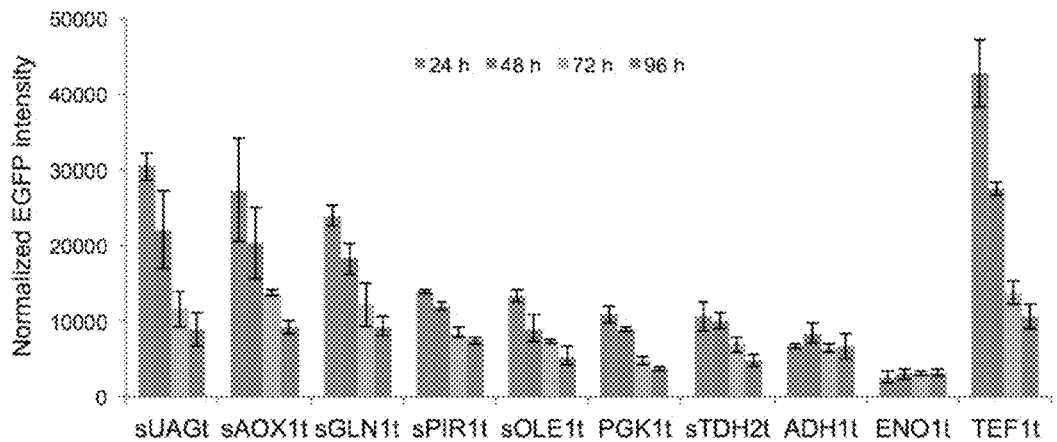
FIG. 12C shows terminator characterization based on EGFP intensity. S. stipitis harboring the egfp gene upstream of each of the 10 select terminators, cultured under mixed-sugar oxygen-limited condition. Error bars represent standard deviations of three biological replicates.

To verify termination efficiency, we devised a method that utilizes two reporter genes, egfp and ble1 (FIG. 12a). The putative terminator was inserted between the two reporter genes, which share a common promoter (sTEF1p) and terminator (XYL2t). In principle, if the inserted sequence is not functional, the two reporter genes will be co-transcribed, and thus the transcription ratio of ble1 to egfp should be close to 1. Conversely, if a strong terminator is inserted, the ratio will be close to 0. Accordingly, the transcription ratio for each construct carrying a putative terminator or a random, non-functional sequence was calculated using real-time PCR (FIG. 12b). A transcription ratio of almost 7 (instead of 1) was observed for the negative control construct (a random sequence inserted between the two reporter genes). This result was not totally unexpected when considering the bias towards the 3' end of mRNA during reverse transcription using oligo(dT)s as a primer. The ratio for the positive control, TEF1t, was very close to zero, indicating that transcription read through was minimal. For AOX1t, GLN1t, UAGt, and OLE1t, the 150 bp versions presented low transcription termination abilities with ratios of at least 1. The 300 bp lengths were therefore selected for these four terminators, named correspondingly as sAOX1t, sGLN1t, sUAGt, and sOLE1t. The transcription ratios of the remaining terminators ranged from 0.003 to 0.21, therefore qualifying them as strong terminators to efficiently block transcription. The strains carrying these tailored terminators were then cultured under the mixed-sugar oxygen-limited condition. According to EGFP intensity, the strengths of the terminators ranged from 0.07- to 0.7-fold with respect to TEF1t, and of these newly discovered terminators, sUAGt was 9.6-fold stronger than the weakest terminator ENO1t (FIG. 12c). These results demonstrate that, as for promoter selection, choosing an appropriate terminator is also important for modulating gene expression to optimize metabolic pathways. The optimized terminator lengths and sequences are SEQ ID NO: 19-28.

Shikimate Production in *S. stipitis*

Figure 13:
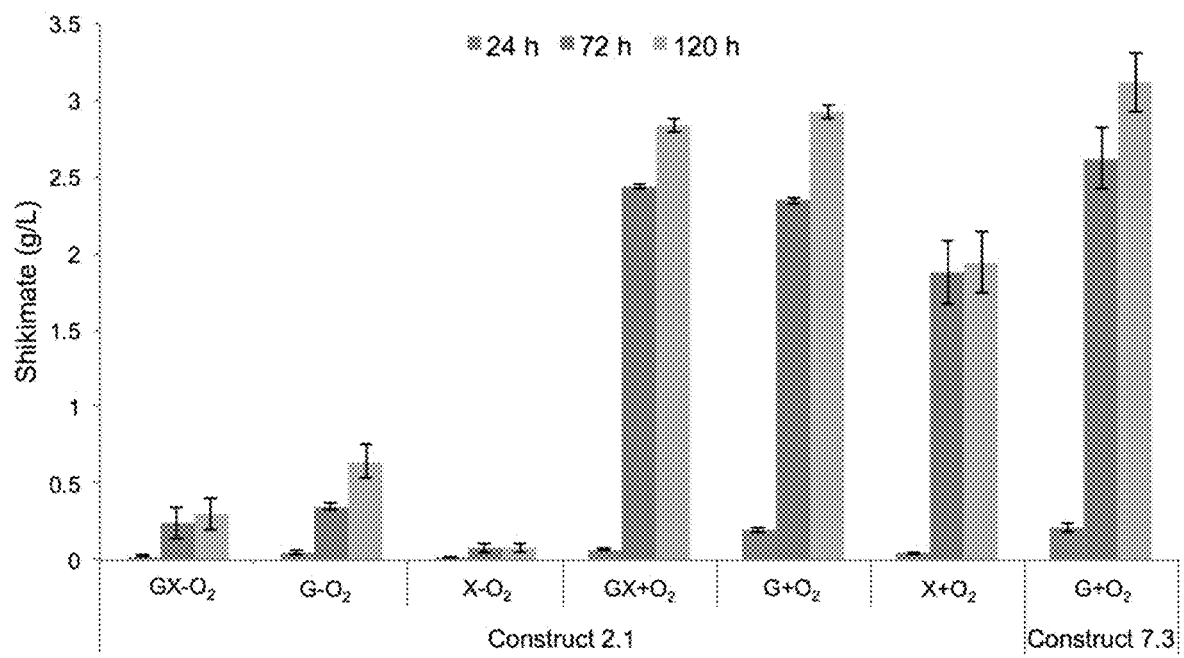
FIG. 13 shows shikimate production under various culture conditions. Construct 2.1: sADH1p-tkt1-sUAGt, sPIR1p-aro4K220L-sAOX1t, and UAGp-aro1D900A-sOLE1t; Construct 7.3: sADH1p-tkt1-PGK1t, sPIR1p-aro4K220L-ADH1t, and UAGp-aro1D900A-sPIR1t. −O2, oxygen limited; +O2, oxygen-rich; G, 4% glucose; GX, 2.8% glucose plus 1.2% xylose; X, 4% xylose. Error bars represent standard deviations of three biological replicates.
Figure 14A:
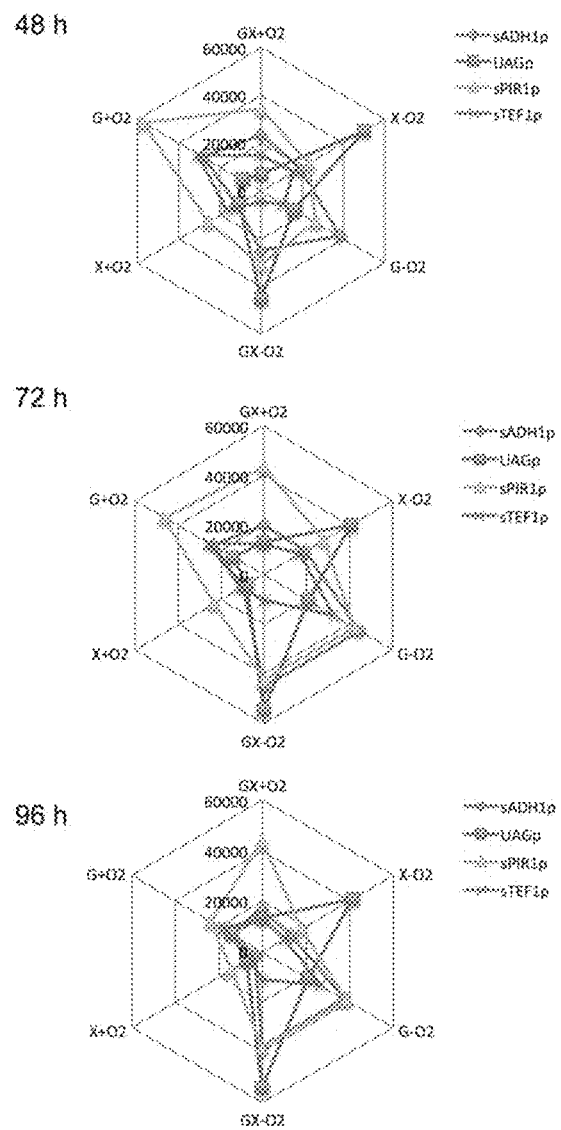
FIG. 14A shows characterization of the selected promoters under six culture conditions.
Figure 14B:
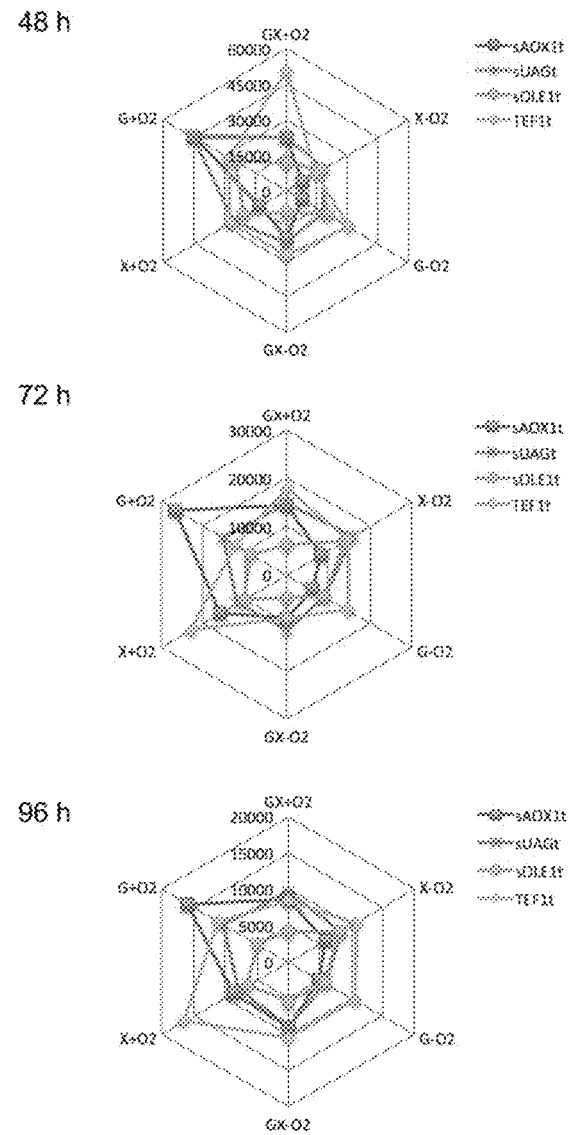
FIG. 14B shows characterization of the selected terminators under six culture conditions. Abbreviations: −O2, oxygen-limited; +O2, oxygen-rich; G, 1.4% glucose; GX, 1.4% glucose plus 0.6% xylose; X, 0.6% xylose.
Figure 15A:
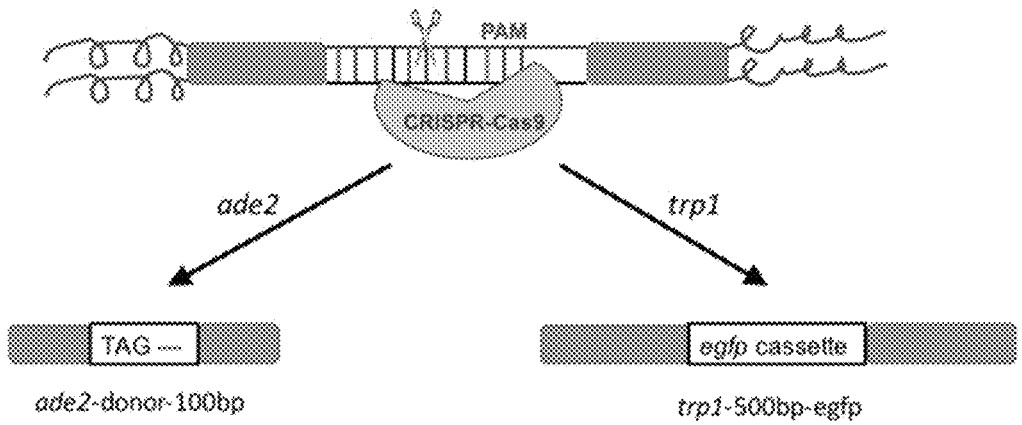
FIGS. 15A-B show HR efficiency in S. stipitis strains.
Figure 15B:
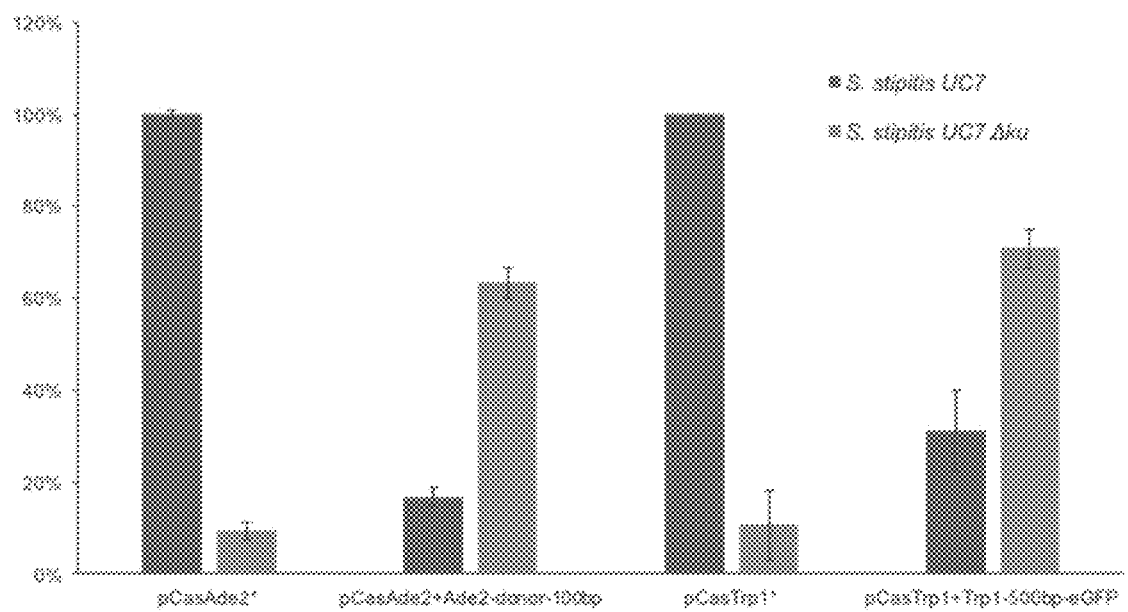

Based on the characterization described above, the strong promoters (sADH1p, UAGp and sPIR1p) and terminators (sAOX1t, sUAGt, and sOLE1t) were subsequently used to reconstitute the shikimate pathway in *S. stipitis*. The recombinant strain carrying aro4$_{K220L}$, aro1$_{D900A}$ and tkt1, each flanked by the selected promoter and terminator, was first cultured under mixed-sugar oxygen-limited condition, leading to shikimate production at a titer of 0.30±0.10 g/L after 120 hr of fermentation (construct 2.1 in FIG. 13). Interestingly, although the strong promoters and terminators were identified using the mixed-sugar oxygen-limited condition, their strengths were maintained under other commonly used laboratory conditions. As shown in FIG. 6a, the selected promoters and terminators, together with sTEF1p and TEF1t, were evaluated in single-sugar (glucose or xylose) or mixed-sugar in combination with oxygen-rich or oxygen-limited conditions. The promoter sPIRp drove a constitutive EGFP expression under all six conditions, roughly independent of oxygen level or sugar option; sADH1p appeared to be oxygen-sensitive, although even in the presence of oxygen the EGFP intensity was still similar to that of sTEF1p; and UAGp demonstrated a preference on xylose-containing media in the oxygen-limited condition. Moreover, except that sAOX1t and TEF1t demonstrated a preference on glucose oxygen-rich condition and xylose oxygen-rich condition, respectively, the variation of the EGFP intensity associated with the four terminators in different culture conditions was minimal (FIG. 14b). However, shikimate production levels varied strongly, with the highest titers of 2.83±0.04 and 2.93±0.04 g/L achieved under the mixed-sugar oxygen-rich condition and the pure glucose oxygen-rich fermentation, respectively (FIG. 13). The implications of shikimate production preference on fermentation conditions are two-fold: (1) regardless of the sugar option, PEP and E4P supplies might be much more abundant in oxygen-rich conditions than in oxygen-limited conditions, resulting in significantly higher production titers when the oxygen supply was sufficient, even though enzyme expression might prefer oxygen-limited conditions; (2) the mixed-sugar (2.8% glucose+1.2% xylose) condition did not produce titers above those seen with 4% glucose conditions, at both oxygen levels, which was mainly due to CCR. At this stage, precursor availability rather than enzyme expression seems to be the rate-limiting parameter for shikimate production: a slightly higher titer (3.11±0.19 g/L, FIG. 13) was observed even after replacing the three strong terminators with three medium level terminators (PGK1t, ADH1t, and sPIRt). Nevertheless, to the best of our knowledge, this platform could potentially permit production of much higher levels of shikimate pathway products compared to those achieved with any other yeast platforms to date.

Stepping into Oseltamivir Phosphate Synthesis

The relatively high titer of shikimate encouraged us to begin to investigate downstream processes including product recovery and further derivatization. Sequentially passing the cell-free medium through activated carbon, an anion-exchange resin, and a cation-exchange resin resulted in a shikimate purity of 81%. The inventors then attempted the first two steps of oseltamivir phosphate synthesis according to the process developed by Roche. The 81% pure shikimate was first esterified to ethyl shikimate in the presence of ethanol and thionyl chloride. Without further purification, the crude ethyl shikimate was treated with 2,2-dimethoxypropane in the presence of catalytic p-toluenesulfonic acid to form ethyl 3, 4-Oisopropylidene shikimate, giving a final yield of 97% (based on 81% purity shikimate) over two steps and a purity of >97% after purification by silica gel chromatography. Being able to synthesize this key intermediate with simple procedures in such a high yield and purity indicates a feasible process of implementing yeast-produced shikimate for Tamiflu production.

Despite a clear discrepancy between the two conditions that produced shikimate at the highest titer and that provided the strongest promoter activities, the data from the current study suggest that future work to improve shikimate production should be focused on improving precursor availability and balancing pathway expression. Although the promoter and terminator pairs were identified from the mixed-sugar oxygen-limited condition, their activities were stronger or at least comparable to those of sTEF1p and TEF1t standards under glucose oxygen-rich conditions. This observation raises an interesting question—whether those very strong promoters and terminators are even needed, especially considering the extra energy burden involved in gene overexpression. An abundance of evidence from previous studies suggests that, in order to achieve balanced pathway expression, it is much easier to mutagenize strong promoters and tailor their strengths than to try to improve the strength of weaker promoters. Exemplary success has been achieved using this method to improve isoprenoid production, and boost xylose and cellobiose utilization efficiency. The combination of promoters and terminators of various strengths, therefore, provides a great opportunity to modulate the expression of individual genes in a pathway. Considering the lack of a comprehensive evaluation of promoters and terminators that are applicable in S. stipitis, we further performed a systematic characterization of all the newly isolated promoters and terminators in the six routinely used culture conditions, which provides a valuable resource for designing biosynthetic pathways and modulating gene expression in S. stipitis.

Many nonconventional microorganisms have highly desirable biosynthetic and metabolic features that are not shared by model hosts. Recent advances in platform technologies, such as CRISPR-Cas9 and next-generation sequencing, have catalyzed a growing interest in exploring nonconventional organisms as microbial factories. In the current study, we demonstrate that S. stipitis would be particularly well suited to produce shikimate derivatives, compared to the relatively low yields achieved in S. cerevisiae. However, even in S. stipitis the main factor that prohibits a high production level is the limited availability of PEP and E4P. Future work will be focused on relieving CCR in order to synchronize glycolysis and pentose phosphate pathway, mainly for the purpose of increasing the E4P level. Replacing the promoters of the genes sensitive to CCR with the constitutive promoters isolated from the mixed-sugar condition might relieve CCR on the transcriptional level. A fully resolved CCR would also involve the incorporation of xylose transporters that are not sensitive to glucose. Furthermore, to increase PEP level, several strategies could be investigated, including (1) replacing the promoter of pyk (pyruvate kinase) with an inducible one or expressing a mutant pyk with reduced activity to retain flux for the reaction catalyzed by Aro4K220L; (2) overexpressing ppck (PEP carboxykinase) and pc (pyruvate carboxylase) to recirculate pyruvate to PEP. Both strategies have been demonstrated with some success in bacteria, and the former will rely on the ongoing development of CRISPR-Cas9 technology to achieve genome-specific modification. This, however, has been challenging for nonconventional organisms with high non-homologous end joining efficiency. Nevertheless, our work represents advances into expanding the current collection of microbial factories and emphasizes the rationale for selecting a host that is best suited to producing a particular group of compounds.

Materials and Methods

S. stipitis Cultivation and RNA Isolation

The S. stipitis was initially grown on YPAD plate for 3-4 days. A single colony was inoculated into a 500 mL baffled flask (VWR, Chicago, Ill.) containing 50 mL YPAD liquid medium and cultured at 30° C. with 250 rpm orbital shaking for 4 days. The resulting culture was transferred to 1 L anaerobic bottles (Chemglass Life Sciences, Vineland, N.J.) containing 600 mL of either YPA plus 3.5% glucose, YPA plus 3.5% glucose and 1.5% xylose, or YPA plus 1.5% xylose with an initial $OD_{600}$~0.2. The ratio of glucose to xylose was selected according to the approximate abundance of the two sugars in commonly studied biomass. Cells were grown at 30° C. with 200 rpm orbital shaking and the anaerobic bottles were covered with double layers of foil to maintain oxygen-limited condition. Cell pellets with a total $OD_{600}$~50 were harvested at three time points (15 hr, 48 hr, and 72 hr) and stored at −80° C. Total RNA was isolated using RNeasy mini kit (Qiagen, Valencia, Calif.) followed by removal of genomic DNA contamination with Turbo DNA-free kit (Life Technologies, Carlsbad, Calif.) according to the manufacturer's instructions.

Plasmid Construction and Transformation

A single colony of S. stipitis was initially grown in 3 mL YPAD liquid media with 250 rpm orbital shaking until $OD_{600}$ reached ~3.0. Genomic DNA was extracted from S. stipitis using a Wizard genomic DNA purification kit (Promega, Madison, Wis.). Promoters of various lengths were amplified from S. stipitis genomic DNA, cotransformed with the amplified egfp and TEF1t fragments, and assembled into the plasmid pMG1 linearized by XhoI and ClaI (Thermo Scientific, Waltham, Mass.). The assembly was performed in S. cerevisiae using the DNA assembler approach previously described, in which 40 bp homologous regions were designed between adjacent fragments. The verified constructs were transformed into S. stipitis. Transformants were selected on SC-Ura plates for 3-5 days until colonies appeared. For terminator characterization, a total of 15 terminators of various lengths were amplified from S. stipitis genomic DNA, and co-transformed with the sTEF1p-egfp and the ble1-XYL2t fragments. The ble1-XYL2t fragment was amplified from the pJML545 backbone and the control random sequence was amplified from a non-functional region on the same plasmid. To construct the shikimate pathway, genes (tkt1, aro4$_{K220L}$ and aro1$_{D900A}$), promoters (sADH1p, sPIR1p, and UAGp), and terminators (sUAGt, sAOX1t, sOLE1t, PGK1t, ADH1t, and sPIR1t) were amplified from S. stipitis genomic DNA. Site-directed mutagenesis was performed by overlap extension PCR (OE-PCR) to introduce the corresponding mutations into aro1 and aro4. Expression cassettes (sADH1p-tkt1-sUAGt, sPIR1p-aro4K220L-sAOX1t, and UAGp-aro1D900A-sOLE1t, or sADH1p-tkt1-PGK1t, sPIR1p-aro4K220L-ADH1t, and UAGp-aro1D900A-sPIR1t) were constructed by OE-PCR and assembled into pMG1 linearized by XhoI and ClaI using the DNA assembler approach.

Terminator Characterization Via qPCR

Sixteen recombinant S. stipitis strains harboring 15 selected terminators and the non-functional control sequence were evaluated using qPCR. Strains were grown on SC-Ura plates for 3 days, and single colonies were inoculated into 15 mL SC-Ura liquid media and grown until $OD_{600}$ reached ~3. The resulting cultures were transferred to 50 mL SC-Ura liquid media with an initial $OD_{600}$~0.2. Cell pellets with a total $OD_{600}$~50 were collected at 24 hr and 48 hr and stored at −80° C. Total RNA extraction and removal of DNA contamination were performed as described above. cDNA libraries were generated by reverse transcription using a RevertAid first strand cDNA synthesis kit (ThermoScientific, Waltham, Mass.). qPCR was performed on a StepOnePlus Real-Time PCR systems (ThermoScientific, Waltham, Mass.). Primers were designed using the free online PrimerQuest tool provided by Integrated DNA Technologies. qPCR reactions were carried out in a volume of 25 µL, containing 12.5 µL 2×SYBR Green Mix, 100 ng cDNA in an appropriate volume, 1.25 µL 20 µM forward primer, and 1.25 µL 20 µM reverse primer. Thermal cycling conditions were as follows: initial denaturation, 1 cycle of 95° C. for 20 s; amplification, 40 cycles of 95° C. for 3 s, and 60° C. for 30 s; and final dissociation, 1 cycle of 95° C. for 15 s, 60° C. for 15 s, and 95° C. for 15 s. Relative quantification of egfp and ble1 transcripts was determined using the corresponding standard curves followed by calculation of the ratio of egfp to ble1 transcripts for each cDNA library. All assays were performed in triplicate.

Promoter and Terminator Characterization Using EGFP Assay

Recombinant S. stipitis strains carrying individual promoter-egfp-terminator cassette were grown on synthetic complete (SC) without uracil (SC-Ura) plates for 3-4 days, and single colonies were inoculated into 250 mL baffled flasks (VWR, Chicago, Ill.) containing 25 mL SC-Ura liquid media and grown until $OD_{600}$ reached ~3. The resulting cultures were transferred to 250 mL baffled flasks containing 50 mL of one of the three specified liquid media (oxygen-rich condition), or to 100 mL serum bottles (VWR, Chicago, Ill.) containing 60 mL of one of the three specified liquid media (oxygen-limited condition) with initial $OD_{600}$~0.2. The specified media were SC-Ura plus 1.4% glucose, SC-Ura plus 1.4% glucose and 0.6% xylose, and SC-Ura plus 0.6% xylose. Note that here sugar concentrations were reduced to 40% of those used in the RNA-seq experiment. This was because SC medium instead of rich media were used to maintain plasmids, and the cells were not able to deplete 35 g/L glucose in the SC media during fermentation. Baffled flasks were used with 250 rpm orbital shaking to maintain oxygen-rich conditions; serum bottles were used with 200 rpm orbital shaking to maintain oxygen-limited conditions. Samples (200 μL) were collected every 24 hr, and total EGFP intensity was measured on a 96-well black polystyrene plate (Fisher Scientific, Pittsburgh, Pa.) using a Synergy HTX multi-mode reader (BioTek, Winooski, Vt.). The excitation and the emission wavelengths were 485 nm and 516 nm, respectively.

Shikimate Production

A single colony of *S. stipitis* harboring the three enzymes involved in the shikimate pathway was inoculated into 3 mL SC-Ura liquid media until $OD_{600}$ reached ~3. Cells were washed three times with water, transferred to 50 mL SC-Ura liquid media with an initial $OD_{600}$~0.2, and cultivated at 30° C. with 250 rpm orbital shaking. Samples were collected every 24 hr. After centrifugation at 12,000-rpm for 10 min, the supernatant was filtered through a 0.2 μm syringe filter (XPERTEK, St. Louis, Mo.) prior to HPLC analysis. Waters HPLC system (Waters, Milford, Mass.) was equipped with a binary HPLC pump, a 717plus auto sampler, a column heater module, and a 2998 photodiode array detector, and an Aminex HPX-87H column (300×7.8 mm) (Bio-Rad, Hercules, Calif.). The HPLC program was as follows: flow rate, 0.3 mL/min; column temperature, 30° C.; sample size, 10 μL; mobile phase, 5 mM sulfuric acid; and running time, 60 min/sample. PDA data extracted at 210 nm were compared to a standard curve made from commercially available shikimate (Sigma-Aldrich, St. Louis, Mo.).

TABLE 3

The sequences of the strong constitutive promoters and terminators.

| Promoter | Sequence (5'-3') |
| --- | --- |
| sADH1p (SEQ ID NO: 9) | cagcatcatcaccatgttgtccaattacagcccgaagcacagtctaatgctgaattttgatagagctcatc gtgaacagccagattcgaagaaaggggggatgagatccgggttcatctgcaagagacacagaaaata aaaaacatacgatccgttcagctacctggcgcttaaccaggaaaatcactgctggagtggccagcatgt cacgaggtggcagaatccgataatgtgtgattgcgtgtagcatcggcgcaagtcgaatttcggtcatatt ccgtgtctggatattattccactattttttaattttttcaggttggatgcgattgttccctttacgtctggacgatg cctgaagcccaggtatatataagggggctcgaaagtcctttgaccagctggttgatttgactttgtttgttcc tttctttctttcatctactcatcactcaattgcattcgcaatttcccattaatacatatttcacttgctccacatatt gcacccaattgcataagtgctgcgatccatccaaattatc |
| sENO1p (SEQ ID NO: 10) | tacatcaccagccaccgtatcactgctccattatcagtgccatctcatgagcattggagctgttgatgcaa gctgtcgctaatatgccgcaacaaattggactcattttagggcaattctatccagtaccaataaagcacg aatcgctttatgaatcatagcctggccgtagcatttcagcaatttcgcaggttatggtttaacagcgacgta caaaacttttcacagtcatatacggtatacccaaacatggattcgtggacttcggctcctccgttgaactca tattcgtaatccccattcagattgccctctcatgatgcccaccagttgcaatctggtgatcgcattatgcaca ctcttcgggtatcgggactgagtggtccagtttcgcacaaaattcgcacacggtgaacaagatggccca cactttttttcactcgacatataaagggaacgagatttcctccttgatttctcctggcattgcgtactgtgtatttt ttgcatctagtcaattatctgatttccagctaattacttgcttctttatcgattcccgcactaaca |
| sPIR1p (SEQ ID NO: 11) | aaggctctttgaatttactttgcctatttatagatatgtaattggatacatgacatttatttggtgcacataatcg actggttttgtaattgtatggccattaacattttagcaccccggcccttgttatgcggagcgcagcaattggt tacgttttatcttaatcgtaccgaagcacaatgatgtcaggcttcctgtagcccattagctttctttattgcggt taattggctctttgagcccctcactctgcaccctccttttgcaccttattggttttgtcagctccgcttgttctt ccggtcatattcctaatggcggagcttgtaggttgttattttgccgcaaaatcatgacctttctggtataaata ttcaacttttttccctgttacagtaattttttgctgttgctggtttaaccaagtagcgaacattttactaagcacttttt tttgcatccgttacatacattcgctatctacaataaacctgattgatttaca |
| sTDH2p (SEQ ID NO: 12) | aatcggaaaatagaatcagccgctgtccccattgtgtcccattaaccaatggtggggggtgtgaaagcgtt agtgtaaaagcgtttcatccagcgaaatgcattctaatcaacagatgccatttatctgtcacctgatacttac caggagactcccacagcatttggagcctgagggatttacatccgagccgttcaatgtctctctagtgtag aaacggggacgaaattttttaaagccttttatgcagaatcatgtatagatactttgcatctcctgatgttgaatta actctaagcttaaccatgggaatggccagatgggggtagggcagtatctaaatcggatgaggtgtattaga agaggagaaggagaggaattatacacacgagacgagagagaaccacgagttgaaaaatttgttgccct gccaattcacatttgaatactataaaagggctatgttgcagccatcttacttttacattttacttagaattttctt ctacagtgtcactattcacataatatagtagtataaataaaaatttcaag |
| sAOX1p (SEQ ID NO: 13) | aaactggagtcatggattagattacgctgtacggccattggtcaaaatggcagacgagccagcgctcaa ctgatgtaaagaggaagaactcggaaacggaatatggcttccatgctctgaatgaaactccgtattccct agctaatacccgcaccccagccgtatggctgtaccagtgactccgagacatctgcttgtagagtaagcg attttcaccaaaaagtcgaattgaaaacgaatccaactatcagtccatatttctctaccggtcttttccatgaag acatctgagttactgttacactcgacaagctacactctactaaatggctgttccaaaaaagcccttcagat ggaagtatggccgcgggaatcaatggtatataaataaatgtaaaattgcgcaaagctaatactcaaattata atattataatattatatctaagtctgcaatgttttttctgttgctcatagactctcgtaattcctataaatataactg attccagtgcaattccatctttatcccttttctcctcttcctcatccagtctagcaattcaattaaattaca |
| sTEF1p (SEQ ID NO: 14) | ttcatgaagtacgataaggttggtaaccgattgactcattggttcgtggcggagaagtacgcagagtaaa accggggccgattcgtggtaaattctggaatgatccagaggcgcgacatttatgcagacaatttgtgtttt |

TABLE 3-continued

The sequences of the strong constitutive promoters and terminators.

|  |  |
|---|---|
|  | gtcgcaaacgatgttatagcgaaattttcactctgtcagataaatggattttgtcaaaagggggaagtaga<br>aggagaatgggcccgagatgttctgccaaattctcagtagcataatgtgaaagaagcccttacattgtcc<br>agcctctggcatcattaaaaaccgtagcggaaaccaattgtctctgttcttccctggcacaccctggtagc<br>cccatccagttgtagtacatctcacacgctggcaacttgggacaatcagcaactttttttttcttttaatttttttca<br>gcgcgacattttgcctcttctgcgagaacagacttttcacctccatctcaccccctttgcacttatataaat<br>tggaccagttcctcccattgtagaaaaaattttgctggaccttttctctttttttttgtcctttagtttcatacaatc<br>taagtctatctaca |
| sGLN1p<br>(SEQ ID NO: 15) | aaaaaaaactgtcggtgtcttcctgaaaacacaggggtgcacctcgctatgtgcacccggacggagtct<br>caattccggagcaggggaggttcctgtcttgtcgggaagttgctttgtgcagcgcacacctgcgataa<br>ccgcagcgacaagctcccattggctgtgataaccgcctcggtcacaaattgcctctgtgcaccctccta<br>cagggaggacgcaggacgcactcccaaaaagaaacccacatagcggctgaagctaccgatccag<br>tttgcgaccatctggatgcaatatatatatgaagcgaatcctctcggaatttcgaaatcagttgctttctc<br>tcccattcttattgtttacgtctaaacaacaaacaaccaaaccctagacttactattgtctgtctgacctt<br>gcttcgcttcccgccttgctacccaatcttagcttcaacttttgtctgttgagccatctcgcaacctgcatttt<br>ctaactattagaatcacatacaatttccatc |
| sOLE1p<br>(SEQ ID NO: 16) | tcttttctgacattggtgcgtatgctaatagttccaccaccacattacatacagacacaaaaccgttttcgatt<br>gtaggccgtagtcgtcagcttccgttcttaaggcgaaacttctctaaaatcgaataagcgtccgcttcact<br>ggtcccaccttggtcttctcttcaaactcgtcgtctctctggcctccagcgcctggctctctggtgtccccat<br>attcgttcggaaacattagcagattcccaacggttgctcccttcggcttacatgcacgccgctccggcac<br>acacctccgtctttggcgtagaaaatttgttgggatttcttttgtcgactaaattgtgttatctctgggtgcgaa<br>acatgcgttacccggccatgggccatagtttttttaattgccatatgcatctgcctacatgcataccatac<br>tgggaaaatttttgacaaactatataatggcaccaggatcgaggattgcaaactaccgggagacttttgUtt<br>gcttgtttgtttgttgtttgtagcttcaacttctgattctatttcgatttcagt |
| sPGK1p<br>(SEQ ID NO: 17) | agcgtgttcaattgcaaaatgtgttccacggtctgctctcatcagcttgtgtgtctcgctgggaattcccca<br>ctaattctcaccaaatctcggtagccatctgtgaagtgttcagtaatgctcgccattttcttcactaacaatc<br>tctaaggaaagatcggtgtatttcaaagagtccggctaatagccagaattctacgtaaccactatatacac<br>agaagcattctacgataaccactatatatcgagtgtcttgcacgctctcagtacactttctctgccattacgt<br>ggtgcactaatttcagtcaaatctggtgagccgggctccacgacttttacccaattgcacctgggcctgaa<br>aatatatgggatgaaaaatatataagtgcaccgatttctacacaaccagattcgctacaagtttcgctttcttt<br>cttcttttctctagtctgtacaacgtttgtgcgtagtttgtttcttcatcgatctcaagcttatcctcattcacatc<br>gctatctctacata |
| UAGp<br>(SEQ ID NO: 18) | ttcaaatcaggaagtaagctattttcatcgagagagggaaagtcaacagaccccctcttttcggcctcccg<br>agaatgaagtcgacgaagacgtcgacgcgtggcacatgagcacccctgcgcccttgtaaatttagat<br>gtacgtcctcgtataccttcgctaatatattggcgcattcaaccatacgatcatgagtcggaaaaactcgc<br>gttcggacacacgagcccagccttcatgtatgacggaaaaaccactccagtcatgaatcacgctacttg<br>atcacactgttgcgcagtatcatcacgaaacctgcatataacaacatgtgtctcgataagagtatagagct<br>ggagtagtggttccacccgataacagagaagcctgtttaaacctgcttgactcacaaatgaatcagacg<br>gccagtttcgggtttagatggaaatgtgccactaggagttgacgttctcttgactcatatacgcctacgag<br>ctggggggcgattagccgaatgccttcatttcttctgcggagcggagacgctagcagcacaaattaccgt<br>ggtgggatgacattcacaatcctggctaatttggtgatgtcattagaggggagagaaatctcattctgacac<br>acacttctggtgtctagcatctagtattgtcctctctcgtacaatatcacactctcatggtagaactcaatccg<br>cttttctcttgtagcccgctcatacagtgccctagtagcccgctctcaatacccgagtagcctcaacttgcgt<br>tccaccacattgtcgagacctggactcacaccttgggatatccccattggctgggattactgtggggtgg<br>cagatctccgcttgcgcgacttttggtgggtgaaattggccactgtcatttcttttttgcaattcgaggggttccc<br>ttctaggcgatggtagtggattgacaaacctgctggtggtgggattggggtgctctggagcccgtgccgc<br>agtactgatggcaggagaaatagtagtcgcactaccagccggaacttctccgatgtggagtgacttgttt<br>ggcttattttctgctgctcttgtgcgacatttcccaagtggagtattttcctgtgggctacttcctgtattctcc<br>ttaagtgcatcgcatcacgataccaatgaggagactttttctggggccatgtcatgttccctattgtttacga<br>cggcaattcacgaatagggacgaataatatagaacgatgaaattcttgggcgtagccagaatgtgtcg<br>gttccttttacctgctacggatttgagggatttagcctgggttggctggttttctgtggttgcatcattctgatg<br>cggcgcagatatatagttgcaaattaactatgcgccccagcaatataaatagtctagttttcccactggtgt<br>gtaactactttcacttttctttcttcactactgatcaacaccaagatctaaccaaacaactctcatatatatata<br>cgtctcctgctgtatatatattttacaaaggcaccctgtcgctgttacacaactacaactacttcatataacc<br>ctaatcgacc |
| Terminator | Sequence (5'-3') |
| ADH1t<br>(SEQ ID NO: 19) | acaagccgtgctagatagtgctttgttctattccacctcgtgtttttatttaccattaactagtgctaatttacga<br>ataatgtacgttagaaaaattgacctgttttatatatgggtgcaaaaaagttgcgtcctgtccaaaggttgcat<br>ttccctcaagcaaccaaaaggagttaggatctgggaactatttaacgccgctggggcaacaattgaga<br>tgtcgtagacgccatgccccacctaaccaatgcactctaatactgtagttatatccttaagattagttctcac<br>cgtgaagtaaagatggtgaacgttttctaagaaattttctaggaaaaagcaaactttaagaggcta |
| sAOX1t<br>(SEQ ID NO: 20) | gaattgctcaggtttcccgatttctttctacatcattttttgtatcgttgttcatagttaggttttttacgaagaatga<br>agtcatgattagcacgaagttgattgcaccgtagtagccgctggaaacagctgcagtttaatcgagagta<br>gctgcaagtcagacctgtatggaatcaaaatcggagttgcagcaatatcaaatcccgcgcaagttgaga<br>gacatctcttagcaatatcgagaccaatacgatgaagttaggaattggccgataagagaacggagaaat<br>attatacaaagcaga |
| ENO1t<br>(SEQ ID NO: 21) | tcatgtcaatgacattttactattcaaaaaagctttaatacgttcacgagtcttacatagatatttgagatattt<br>attatgaacaaattgcactgtagaattaatatctcaaactgtgaagtcgtgtgatactttgtatacgactactt<br>ttataccaatgatatttctaacttttctagatgttcatggttctatcatagattttgacgttctatacactttaaaatt<br>ctat |

TABLE 3-continued

The sequences of the strong constitutive promoters and terminators.

| | |
|---|---|
| sGLN1t (SEQ ID NO: 22) | atgtctggctggtttccttctgctgtactttacccttttacatagtcctttagttcgtgcttccttttttttcttaatctg tttttcatgcttatcgttaatgccaactacaaaactgctgcttagcaacaacttctcttcatctacaaacttcat aaaagttaagtttattcattgtatagtaatgctataatttgctactactgttcactttcgattttttgctgtagaaag tagtaaaatgattcaatatcaatattgctcaatctgcatttttggtggtactaatgttcattattcgtta |
| sUAGt (SEQ ID NO: 23) | ttttattttctcctttccttaaatctccgatgaagtgactagacttcattagatttatttctacttgtttgtcttttacga atgataattacgaaatttacgtttacgccgctcatgtttatatgttattatgagatatacgtcattgtatataatt gaattgtagcagtttgtaggtattcgtagataccagttggtataatttgctgatttattccaaagtccggttag ggggttgtacgatttgtctggacatgtgacccttccaaaaatggagcaatcggaatctacccaagattg |
| sOLE1t (SEQ ID NO: 24) | actatactagccaagatagcacattagagaatagagaaagatttcaggtatggttggttatatttaagaatt atggagtatgtcattgaagagtttattgtttgcgagtttggtcctttttgtttatattcctatccatagcttcgtttta tattaccttgtatttttcattatcaaatctacaaacagctcaatattatgacaacaaaaaatattcggaaattatt cagtgtagaaagagagatagcaaaaggagcccggatcaattttcggttttttaatttgttcatcgtatgcga aa |
| PGK1t (SEQ ID NO: 25) | ttgatgtaagactttaattataagaatacaattgtgataaagacaatgtagaagtactgtagaagtcatgga atagctgatcaactgtactgttatacaaaggtactattaacaaaatagacatatagtttctataacatatataa acat |
| sPIR1t (SEQ ID NO: 26) | tggtctcttggcttaatttcactcctcattgacttcttttgattacgttgcccccatatttgttttcggtatccttac ttaattttcttaataataattcttgcacccaagtttgaaaagtctgctctgatgttttttttcatgtaccacagaga tcaattcttgcatccacatagtttaactaattggcaataaacatgatttcgcttacctaacagctatagaac acgtgtagtaattaaaatcttcaggtcttccaaattgttggggtatataattcctttattttcacaatagatatac tgtaaatctcagtttggttaacttctcatacaattaattcaccctgatcattcttttcacagtaccttattaatag aattaactattgaatgttccctttgaaaattatttcctaagcgacttcttgtattttaccaataactaagtaaatc ttcaaaaaatagaattaaactttgcatccagcaaataaaat |
| sTDH2t (SEQ ID NO: 27) | ttgtagtatttgttatttcatatatatgtctctcattatgaacttctttattgaatacgatgttaatgacattagtttt ttaggcggtgaaaaatatctacctaattccaacgtacgaatgagtcagaaacgaactcaataatagaagt |
| TEF1t (SEQ ID NO: 28) | gctgattaatttacgtatattcagtttaatatcaatacgttagctacatttccaatgaacgatactagatattgtt taggattattgaactggtatagataattttagtgtatattcatgtacttgataaatgtaataatatgtgaaaatgt agttgtacattaactgatagacaacatgctggagtatatggcattaaggttgctacaaagtagaagcaacc tagacacacctcagaagatagattgggcgagtgatcgtattatatgagaacttctatgtgatacacttccaa gtatgattagtgtctacaataaccttatattatc |

Example 3: CRISPR-Mediated Genome Editing and Gene Repression in S. stipitis

Results

In the previous design, the pre-optimized small nucleolar RNA 52 (SNR52) promoter has a length of 1000 bp, which is not an ideal length for convenient cloning. Ideally, the 122 bp coding region for single guide RNA (SgRNA) can be purchased from gene synthesis companies and directly ligated with the backbone containing the SNR52 promoter. However, we suspected that introducing an extra restriction enzyme site between SNR52 promoter and SgRNA would leave a few bp scar at 5' end of SgRNA and potentially interfere subsequent Cas9 binding. Presumably if the SNR52 promoter can be shortened to a few hundred bp, then it could be synthesized together with the SgRNA coding sequence as a single piece with a low cost. It was reported that the functional SNR52 promoter in S. cerevisiae is only 269 bp (DiCarlo et al. 2013). The inventors hence selected two lengths (378 bp and 298 bp) and tested their function on editing ade2. The result showed that the two shortened promoters functioned equally well to introduce indel mutations to ade2 locus with an efficiency of 74% (Table 1), similar to that achieved via using the 1000 bp-SNR52 promoter. Another technical hurdle to developing S. stipitis as a chassis is the low transformation efficiency. Transforming 1 μg of 10 kb-plasmid DNA (ARS/CEN5-500 bp-eGFP) only led to 40 colonies when using the standard 1.5 kv electroporation voltage (750 v/mm). The efficiency was even lower when transforming CRISRP-Cas9 plasmid due to the chromosomal double strand break (DSB) induced by Cas9. In the previous ade2 and trp1 knockout efforts, only 10~20 and 2~5 colonies were obtained, respectively (Cao et al., 2017). Here we applied higher voltages, 2 kv and 2.5 kv, and found that 2.5 kv could dramatically increase the transformation efficiency of S. stipitis by almost 25-fold ($1.0 \times 10^3$ cfu/μg for a 10 kb-plasmid).

With this optimized CRISPR-Cas9 system, we proceeded to create individual ura3 and leu2 auxotrophic strains by single round knockout. The N20 target sequences and knockout efficiencies were summarized in Table 4. In addition, we investigated the possibility of double-gene knockout by connecting two SgRNA expression cassettes corresponding to ade2 and trp1 into one vector backbone through Golden Gate Assembly (Engler et al. 2009). The resulting number of transformants dropped to only 5 for this purpose, among which 2 (40%) were phenotypically screened and sequencing-confirmed as the desired double indel mutants, while the other 3 colonies contained single gene disruption of either ade2 or trp1.

In S. stipitis, non-homologous end joining (NHEJ) is the dominant mechanism for repairing DSB, which led to indel mutations even if a donor DNA is provided. Strictly speaking, modification by indel mutations is not real editing because it just messes up the site where DSB occurs. Besides, random genome integration is inevitably associated with expression inconsistency across individual clones and the integration site is hard to be traced. In this regard, site-specific integration is important but cannot be easily achieved until homologous recombination (HR) plays the leading role. Ku is a dimeric protein complex composed of Ku70 and Ku80 that bind to DSB ends to facilitate NHEJ-mediated genome repair (Di Primio et al. 2005). It was reported that deletion of ku genes could impair NHEJ and consequently reinforce HR (Gao et al. 2016; Maassen et al. 2008). The inventors performed two rounds of transformation to step-wisely knock out ku70 and ku80. In the first round, ku70 and ku80 were targeted in parallel and the corresponding DSB was repaired by NHEJ-mediated indel mutation with high efficiency (100% and 83% Table 4). In the second round, donor DNA fragments, ku70-100 bp or ku80-1 kb, were transformed along with the CRISPR-Cas9 plasmid to the Δku80 strain and Δku70 strain, respectively, and high efficiencies were achieved again (80% and 100%, Table 4). The ade2 and trp1loci were subsequently chosen for further evaluation of HR frequency in the Δku strain. As shown in FIG. 1, the indel mutation efficiencies in the Δku strain were decreased to 10% of those achieved in NHEJ-dominant strain. The remaining function of NHEJ might be granted by other NHEJ-relevant proteins. The HR efficiencies were improved by 3.8-fold and 2.3-fold in the Δku mutants, with co-transforming CRISPR-Cas9 plasmid and the donor DNA fragments ade2-donor-100 bp and trp1-500 bp-eGFP, respectively.

The CRISPR-Cas9 system has been recognized as an efficient genome-editing tool for mutation and insertion. However, in many cases, repression or knockdown, rather than actual gene deletion, is more desirable for synthetic biology and metabolic engineering applications. For example, elimination of certain genes or pathways is not always feasible, because they could be essential for metabolism and the deletion would be lethal to the cells (Wang et al. 2016). To address this issue, CRISPR-dCas9 was developed as an efficient, tunable and reversible tool for executing gene transcription repression. We introduced D10A and H840A mutations to the active sites of Cas9 (Dominguez et al. 2016) and developed the CRISPR-dCas9 version specific for S. stipitis.

Figure 16A:
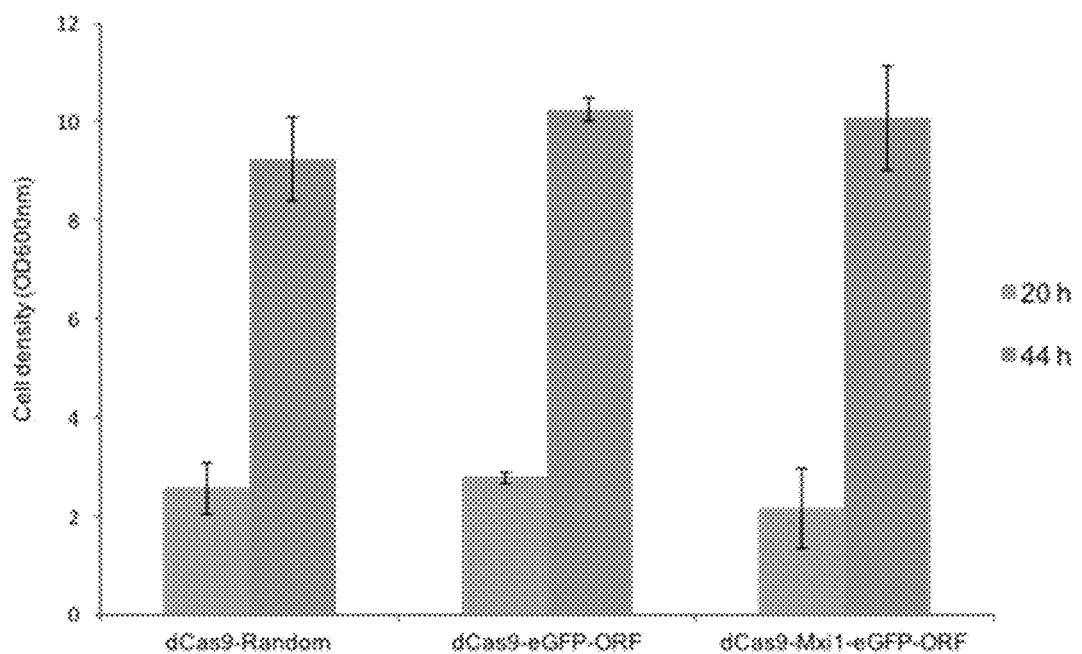
FIGS. 16A-B show gene transcription repression by dCas9 in S. stipitis ΔKuΔtrp1::egfp strain.
Figure 16B:
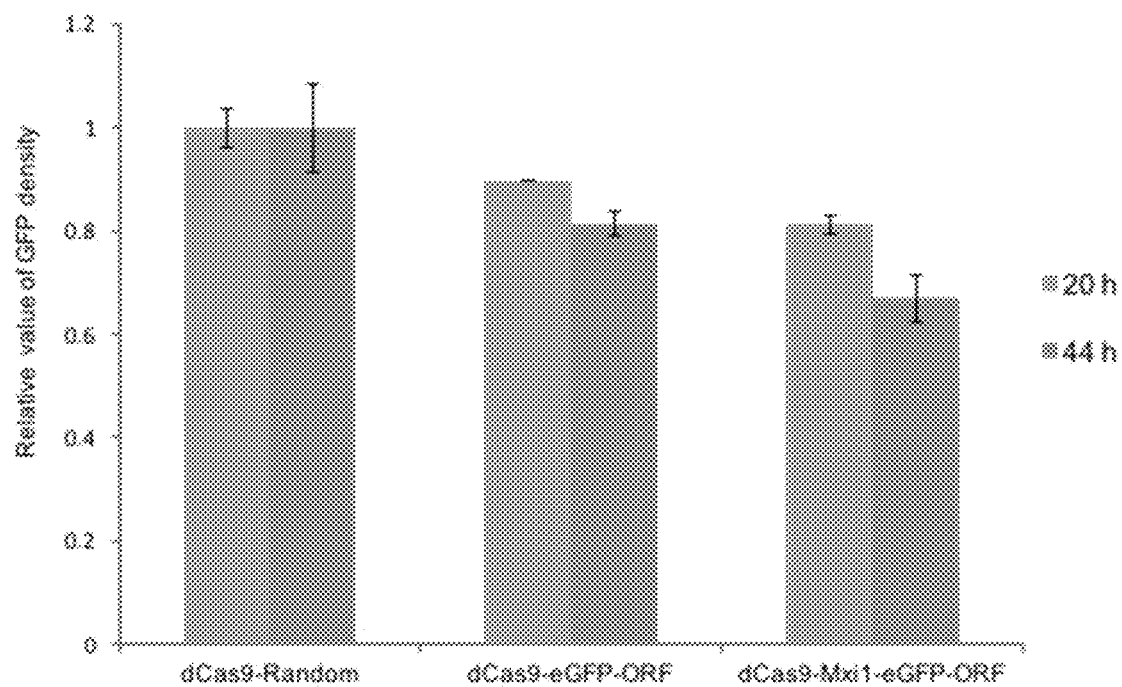
Figure 17A:
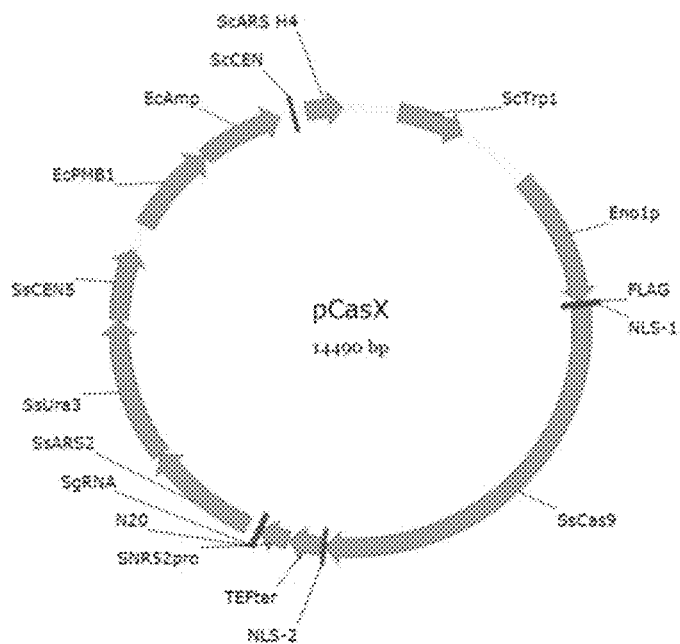
FIGS. 17A-D show plasmid maps of the main Cas9 and dCas9 constructs.
Figure 17B:
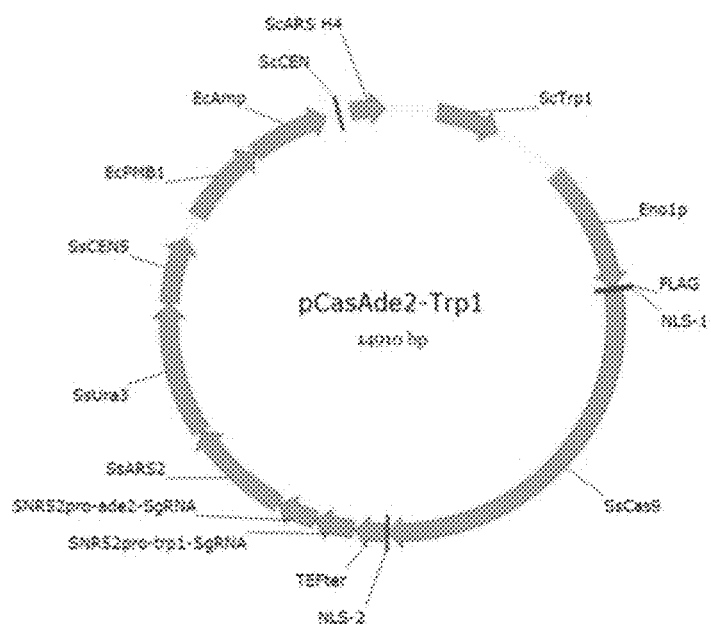
Figure 17C:
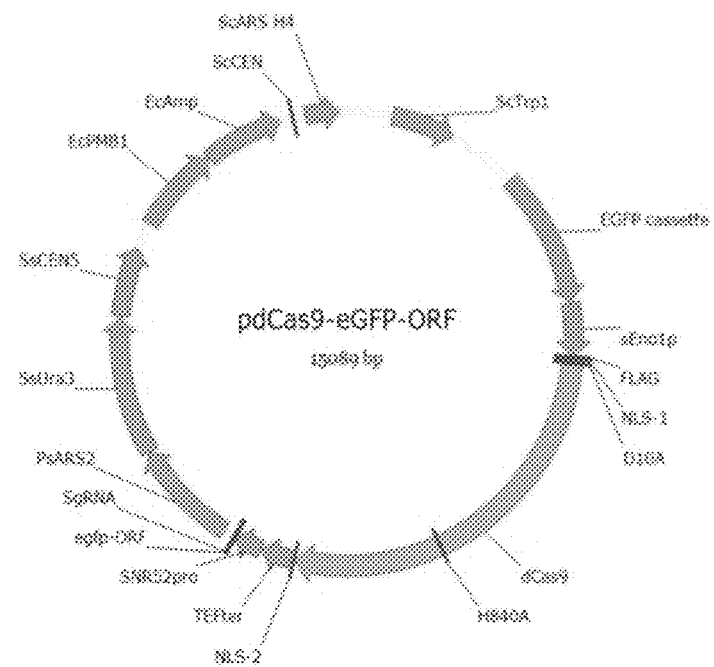
Figure 17D:
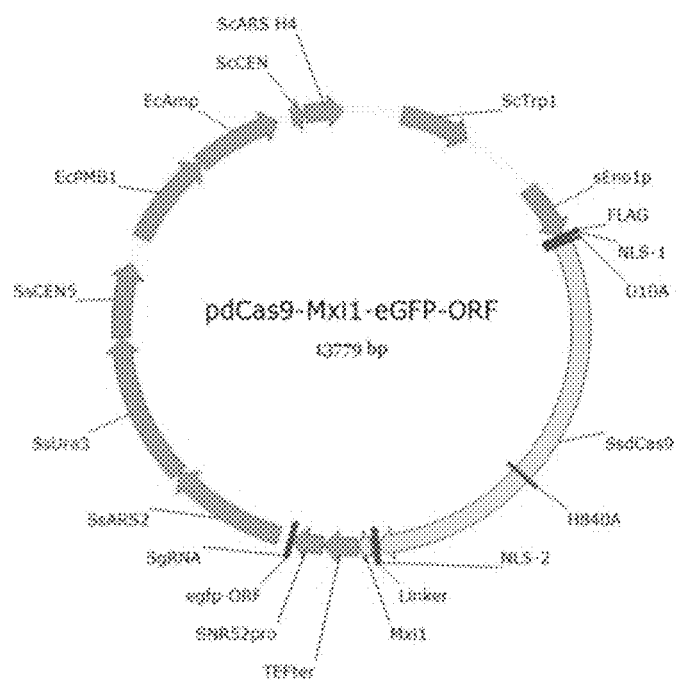

A Tef1p-eGFP-Pgkt expression cassette was then integrated to genome (Δtrp1::egfp) as a reporter for monitoring the repression role of dCas9. An N20 was designed to target at the open reading frame (ORF) region, 4-23 bp downstream of the start codon (dCas9-eGFP-ORF, Table 4). It was noticed that N20 sequences with stronger repression impacts were mostly located at the promoter region (Cress et al. 2016; Deaner and Alper 2017; Smith et al. 2016). However, we did not take that design because while targeting the Tef1 promoter that drives eGFP expression, repression would also occur at the native tef1 gene, encoding for the essential translation elongation factor. A control (dCas9-Random) was designed with one random 8 bp sequence (tcaggtac) replacing N20. Furthermore, to enhance dCas9 repression activity, we fused a well-characterized transcription repressor, Mxi1, to the C-terminal of dCas9 (dCas9-Mxi1-eGFP-ORF) via a 11 aa GSS linker. As shown in FIG. 16, the cells densities (OD600 nm) were almost identical among three strains harboring plasmids dCas9-Random, dCas9-eGFP-ORF and dCas9-Mxi1-eGFP-ORF, which indicated that expression of dCas9 or dCas9-Mxi1 along with SgRNA did not affect much on cell growth. In contrast, dCas9-eGFP-ORF repressed eGFP expression by 11% and 19% at 20 h and 40 h, respectively, whereas dCas9-Mxi1-eGFP-ORF repressed eGFP expression by 19% and 33% when compared to the control strain transformed with dCas9-Random plasmid, indicating Mxi1 could promote dCas9 repression by 1.7-fold. Since dCas9 target sites affect repression efficiency, greater repression could be achieved via thoroughly screening the binding sites throughout promoter and ORF loci (Bikard et al. 2013; Deaner and Alper 2017).

In conclusion, the inventors successfully tailored the CRISPR-Cas9 system for ready implementation in S. stipitis. This system enabled efficient single-gene and double-gene editing through either NHEJ or HR. The Ku mutant strain exhibited deficient DNA repair function via NHEJ, and enhanced HR efficiency by at least 2~4-fold. The derived CRISPR-dCas9 system was established for executing transcription repression in S. stipitis, which is particularly valuable for modulating essential gene expression and brings various applications in metabolic engineering, synthetic biology and functional genomic studies of S. stipitis. This readily applicable CRISPR-Cas9/dCas9 systems encourages further exploration of a broad collection of nonconventional yeasts that are naturally associated with various desired traits.

Materials and Methods

Strains, Media and Chemicals

E. coli BW25141 transformants were growing in LB medium supplemented with 100 μg/mL ampicillin. The S. cerevisiae YSG50, S. stipitis UC7 and its mutants were propagated at 30° C. in YPAD media (1% yeast extract, 2% peptone, 0.01% adenine hemisulphate, and 2% dextrose). Yeast transformants were cultured or selected in Synthetic complete dropout media lacking uracil, adenine, tryptophan, or leucine (SC-URA, SC-ADE, SC-TRP, or SC-LEU). DNA polymerase and restriction enzymes were purchased from Thermo Scientific (Waltham, Mass.), DNA extraction/purification kits were purchased from Zymo Research (Irvine, Calif.), and all the other chemicals were provided by Fisher Scientific (Pittsburgh, Pa.).

Plasmid Construction

All plasmids constructed in this study were derived from the previously developed pCasAde2 vector (Cao et al., 2017). To assemble the genetic cassettes, the DNA Assembler technique (Shao and Zhao 2013) was implemented. Briefly, the gene fragments with overlapping ends were co-transformed with a digested plasmid backbone into S. cerevisiae for plasmid assembly via electroporation method. The isolated yeast plasmids were then transformed into E. coli for enrichment, and their identities were verified by restriction digestion or sequencing. The correctly assembled plasmids were subsequently transformed into S. stipitis for target gene expression. For single-gene editing plasmid construction, the gBlock (IDT, Coralville, Iowa) synthesized fragment of SNR52 promoter-SgRNA was assembled with pCas9 backbone, which was obtained from NcoI-PstI digested pCasAde2, While, for double-genes editing, the combined SNR52 promoter-SgRNA for ade2 and trp1 was preassembled by Golden Gate Assembly Kit (NEB, Beverly, Mass.), and then assembled to pCas9 backbone. Codon-optimized genes, and plasmid maps are summarized in Table 5 and FIG. 17.

Yeast Transformation and Mutant Screening

Different electroporation voltages, 1.5 kv, 2 kv and 2.5 kv, were utilized to evaluate the transformation efficiency of S. stipitis. 1 μg plasmid was electroporated via 2 mm cuvette to S. stipitis, the transformants were first selected on SC-URA solid medium, and then re-streaked on SC-URA (Δura3), SC-ADE (Δade2), SC-TRP (Δtrp1), or SC-LEU (Δleu2). The indel mutations were confirmed by colony-PCR and sequencing the target loci. For eGFP integration mutants, the colonies were pre-screened by a DR46B Transilluminator (Clare Chemical Research, Dolores, Colo.), and confirmed by flow cytometry and DNA sequencing. For sequential knockout of ku, the first-round CRISPR plasmid was cured by culturing the cells in rich YPAD medium and screened on SC+FOA (1 g/L, 5-Fluoroorotic Acid); then the second-target CRISPR plasmid was electroporated with 300~500 ng donor-DNA to the ku70 or ku80 mutant strain.

CRISPR-dCas9-Based Gene Repression

Followed by CRISPR-Cas9 design (Cao et al., 2017), dCas9 was expressed under Eno1 promoter and Tef1 terminator. The two mutations D10A and H840A were introduced into Cas9 via PCR primers D10A-F/D10A-R and H840A-F/H840A-R. The amplified fragments, together with SgRNAs of 8 bp random sequence or eGFP-ORF were assembled to ApaI-NcoI digested pCasAde2 backbone, and the resultant vectors were named as pdCas9-Random and pdCas9-eGFP-ORF. In addition, the codon-optimized Mxi1 sequence (Life Technologies, Carlsbad, Calif.) was also fused to dCas9 by 11 aa-linker (GSSKLGGSGGS: SEQ ID NO: 45) to form pdCas9Mxi1-eGFP-ORF. The plasmids were electroporated to *S. stipitis* ΔkuΔtrp1::egfp strain to track the eGFP expression repression by fluorescence plate reader (BioTek, Winooski, Vt.) and flow cytometry. The flow cytometry was performed at 488 nm on a FACSCanto flow cytometer (BD Biosciences, San Jose, Calif.), and the fluorescence-intensity distribution was calculated by BD FACSCanto Clinical Software.

TABLE 4

Gene knockout efficiency by CRISPR-Cas9 in *S. stipitis*

| Gene name | N20 + PAM (NGG) sequence | Knockout Efficiency | References |
|---|---|---|---|
| Δade2-SNR52pro-1000 bp | actgcgttgatctgtttcgcAGG (SEQ ID NO: 33) | 83.3% | Cao et al., 2017 |
| Δtrp 1 | acgtactattcaagaaccagTGG (SEQ ID NO: 34) | 100% | Cao et al., 2017 |
| Δade2-SNRpro-378 bp | actgcgttgatctgtttcgcAGG (SEQ ID NO: 33) | 74% | This study |
| Δade2-SNRpro-298 bp | actgcgttgatctgtttcgcAGG (SEQ ID NO: 33) | 74% | This study |
| Δleu2 | agcagttggtggtcccaagtGGG (SEQ ID NO: 35) | 33% | This study |
| Δura3 | aactaacttgtgtgcttcagTGG (SEQ ID NO: 36) | 29% | This study |
| ΔKu70 | actcgaccaaagagaacttgTGG (SEQ ID NO: 37) | 100% | This study |
| ΔKu80 | atttgtaggcatagacttccTGG (SEQ ID NO: 38) | 83% | This study |
| ΔKu70-ΔKu80-1 kb | atttgtaggcatagacttccTGG (SEQ ID NO: 38) | 80% | This study |
| ΔKu80-ΔKu70-100 bp | actcgaccaaagagaacttgTGG (SEQ ID NO: 37) | 100% | This study |
| Δade2Δtrp1 | actgcgttgatctgtttcgcAGG(ade2) (SEQ ID NO: 33) acgtactattcaagaaccagTGG(trp1) (SEQ ID NO: 34) | 40% | This study |
| egfp-ORF | aaaggtgaagaattattcacTGG (SEQ ID NO: 39) | 33%* | This study |

*represents the egn, repression efficiency, not gene knckoutout efficiency.

TABLE 5

The sequences of the key genetic elements in this work.

| Genetic elements | Sequences (5'→3') |
|---|---|
| SNR52-pro-378 bp (SEQ ID NO: 40) | aacctcttttttttacgaaatggcatgtattatgatctgctacagagtatataaatcttcctctaatccataccgaaa ggtggagggaatcctaggataaaaacctccgaatgacattacctaaaaaaacacataagtgatatctttggaa agcaacagaagttacaactattttatttttacacgtgactgaccgcgtgattaggcacgtgactaatcacgt gctgtataatgacaattggagtgaatgtgtaattttgtgcgatattttgctggatggcgcattcgctggaccggc gagtttggagttcccgtcagctgacggtgcctttgaacgagtcgcaggttcgtttccaacaagatacatttattt c |
| SNR52-pro-298 bp (SEQ ID NO: 41) | tggagggaatcctaggataaaaacctccgaatgacattacctaaaaaaacacataagtgatatctttggaaag caacagaagttacaactattttatttttacacgtgactgaccgcgtgattaggcacgtgactaatcacgtgc tgtataatgacaattggagtgaatgtgtaattttgtgcgatattttgctggatggcgcattcgctggaccggcga gtttggagttcccgtcagctgacggtgcctttgaacgagtcgcaggttcgtttccaacaagatacatttattc |
| dCas9-linker-Mxi1 (codon-optimized) (SEQ ID NO: 42) | atg<u>gactacaaggatgacgatgacaag</u>cctccaaagaaaaagagaaaggttgacaagaagtactctatc ggtttggctatcggcactaactctgttggttgggctgttatcactgacgagtacaaggtcccatccaagaagtt caaggtatgggtaacaccgacagacactccatcaagaagaacttgatcggcgccttgttgttcgactctggt gaaactgctgaagccaccagattgaagagaaccgccagaagaagatacaccagaagaaagaacagaatc tgctacttgcaagagatcttctcaacgaaatggccaaggtcgacgactcgttcttccacagattggaagaat ccttcttggtcgaagaggacaagaagcacgaaagacaccaatcttcggtaacatcgttgacgaagtcgcct accacgaaaagtacccaaccatctaccacttgagaaagaagttggtcgactctaccgacaaggccgacttg agattgatctacttggctttggcccacatgatcaagttcagaggtcacttcttgatcgagggcgacttgaaccc agataactctgacgttgacaagttgttcatccagttggtccagacctacaaccagttgttcgaagaaacccaa tcaacgcttctggtgtcgacgctaaggctatcttgtctgccagattgtccaagtccagaagattggaaaacttg atcgcccagttgccaggcgaaaagaagaacggtttgttcggcaacttgatcgctttgtccttgggcttgaccc caacttcaagtctaacttcgacttggctgaggacgccaagttgcagttgtctaaggatacttacgacgacga cttggacaacttgttggctcaaatcggtgaccagtacgctgacttgttcttggctgctaagaacttgtctgacgc catcttgttgtccgacatcttgagagtcaacaccgaaatcaccaaggccccattgtctgcctctatgatcaaga gatacgacgaacaccaccaggacttgaccttgttgaaggctttggttagacagcagttgcccgagaagtaca aagaaatcttcttcgaccagtccaagaacggttacgctggttacatcgatggtggtgcctcccaagaagagtt ctacaagttcatcaagcccatcttggaaaagatggacggcaccgaagagttgttggtcaagttgaacagaga ggacttgttgagaaagcagagaaccttcgacaacggttctatcccacatcagatccacttgggtgaattgcac gccatcttgagaagacaagaggacttctacccattcttgaaggacaacagagaaaagatcgagaagatcttg accttcagaatcccctactacgtcggtccattggccagaggtaattctagattcgcctggatgaccagaaagt ccgaagaaactatcaccccctggaacttcgaagaagttgttgataagggcgcctccgcccagtctttcatcga aagaatgaccaacttcgacaagaacttgcccaacgagaaggtcttgccaaagcactccttgttgtacgagta cttcaccgtctacaacgagttgaccaaggtcaagtacgtcaccgaaggtatgagaaagccagccttcttgtct ggtgaacaagaagaagctatcgtcgacttgttgttcaagaccaacagaaaggtcaccgtcaagcagttgaa agaggactacttcaagaaaatcgagtgcttcgactccgcgaaatctctggtgtcgaagatagattcaacgcc tccttgggtacttaccacgacttgttgaagatcatcaaggacaaggattttcttggacaacgaagagaacgagg acatcttggaggacatcgtcttgactttgaccttgttcgaggacagagagatgatcgaagagattgaaaac ctacgcccacttgttcgacgacaaggtcatgaagcagttgaagagaagaagatataccggctggggcagat tgtccagaaagttgatcaacggtatcagagacaagcagtccgacgaagactatcttggacttcttgaagtctga cggcttcgccaacagaaacttcatgcagttgatccacgacgattccttgaccttcaaagaggacatccagaa ggctcaagtttctggtcaaggtgactccttgcacgaacatatcgctaacttggctggttctccagccatcaaga agggtatcttgcagactgttaaggtcgtcgacgaattggtgaaggtcatgggtagacacaagccagagaac atcgtcatcgaaatggctagagaaaaccagaccacccagaagggtcagaagaactccagagaaagaatg aagagaatcgaagagggcatcaaagagttgggctcccagatcttgaaagaacacccagtcgaaaacaccc agttgcagaacgagaagttgtacttgtactacttgcagaacggcagagacatgtacgtcgaccaagagttgg acatcaacagattgtctgactacgacgttgacgctatcgtcccccaatcttcttgaagtgaagatgactccatcgac aacaaggtcttgaccagatccgacaagaacagaggtaagtctgacaacgttccatccgaagaggtcgtcaa gaagatgaagaactattggagacagttgttgaacgccaagttgatcacccagagaaagttcgacaacttgac taaggccgaaagaggtggtttgtctgaattggacaaggccggcttcatcaagagacagttggtcgaaactag acagatcaccaagcacgtcgctcagatcttggactccagaatgaacaccaagtacgacgagaacgacaag ttgattagagaggtcaaggtcatcaccttgaagtccaagttggtgtccgacttcagaaaggacttccagttcta caaggtcagagagatcaacaactaccaccacgctcatgacgcttacttgaacgctgttgtcggtactgccttg atcaagaagtacccaaagttggaatccgagttcgtctacggtgactacaaggtctacgacgtcagaaagatg atcgccaagtccgaacaagaaatcggtaaggctaccgccaagtacttcttctactccaacatcatgaatttctt caagaccgagatcaccttggccaacggcgagatcagaaaaagaccattgatcgaaactaacggcgaaacc ggtgaaatcgtttgggataagggtagagacttcgccaccgtcagaaaggttttgtctatgccccaggtcaaca tcgtcaagaaaactgaagtccagaccggcggatctcaaagaatctatcttgccaaagagaaactcggaca agttgatcgccagaaagaaggactgggaccccaaagaaatacggtggtttcgactctccaaccgtcgcttact ctgtttggttgtcgctaaggtcgagaagggcaagtctaagaagttgaagtccgtcaaagagttgttgggcat caccatcatggaaagatcctcgagaagaaacccaatcgacttcttggaagccaagggctacaaagagg tgaagaaggacttgatcatcaagttgcccaagtactcgttgttcgagttggagaacggtagaaagagaatgtt ggcttccgctggtgaattgcagaagggtaacgaattggcttgccctccaagtacgtcaacttcttgtacttgg cctcccactacgaaaagttgaagggttcccctgaagataacgagcgaagcagttgttcgtcgagcagcata agcactacttggacgaaatcatcgagcagatctccgagttctctaagagagtcatcttggctgacgccaactt ggacaaggtcttgtctgcttacaacaagcacagagacaagccaatcagagagcaggccgaaaacatcatc cacttgttcactttgaccaacttgggtgctccagctgcttcaagtacttcgacactaccatcgacagaaagag atacacctccaccaaagaagtcttggacgctaccttgatccaccagtctatcactggcttgtacgaaaccaga TABLE 5-continued The sequences of the key genetic elements in this work.

| Genetic elements | Sequences (5'→3') |
|---|---|
| | atcgacttgtctcaattgggtggtgac*gatcctaagaagaaaagaaaagtt*ggtagttccaagcttggcg ggcagcggcggcagcatggaaagagtcaagatgatcaacgtccagagattgcttgaagccgccgaattctt ggagagaagagaaagagaatgcgaacacggctacgcctcttcattcccatctatgccatctccaagaggct ga<br>FLAG: DYKDDDDK (underlined sequence; SEQ ID NO: 43); NLS: P/DPKKKRKV (italic sequence; SEQ ID NO: 44); Linker: GSSKLGGSGGS (bold sequence; SEQ ID NO: 45) |
| ade2-donor-100 bp (SEQ ID NO: 46) | ttaacattaacacagttatcttggatgcccccaactctt<u>agc</u>gaaacagatcaacgcagtgagtgaccatgttg atggctctttcacacactatgagtct<br>The mutations in donor DNA: CCTG to TA-G (stop codon, and missing 1 bp, underlined sequence) |
| trp1-500-egfp (SEQ ID NO: 47) | *aactacagctcactctagatgatggtaccttgacaaaccaaaaccagttactatctaatttagaagacga agaagagtcgggatcggttagtatttctcaggtcagcacacctaccccagactttaagtcaccaaaattg cttcctacgaaaatcaacaactttgagaaaaatctccgagaatttgctatcactggagaaagccatgtca ataagttaaacgagaacttcaagaactttggtaagttcttcagaaaggataacgactagcatagatagttt tatatagctttggttatatatggttgtatatgcagtattccatcaaaatcattagtcataagatttagagggtta tacaaatttaatagctttacttctatcttcaaaagtcattggatatgcccaaaattgtaaagatatgtggaac cagaacagttgaagctgctgctaaagctatagagtcaggaacggatttactcggggtaattcttgtaccc* attcatgaagtacgataaggttggtaaccgattgactcattggttcgtggcggagaagtacgcagagtaaaac cggggccgattcgtggtaaattctggaatgatccagaggcgcgacatttatgcagacaatttgtgttttgtcgc aaacgatgttatagcgaaattttttcactctgtcagataaattggattttgtcaaaaggggggaagtagaaggagaa tgggcccgagatgttctgccaaattctcagtagcataatgtgaaagaagcccttacattgtccagcctctggca tcattaaaaaccgtagcggaaaccaattgtctctgttcttccctggcacaccctggtagcccatccagttgta gtacatcttcacacgctggcaacttgggacaatcagcaactttttttctcttttaatttttttcagcgcgacattttgcct cttctgcgagaacagacttttttcacctccatctcaccccccttttgcacttatataaattggaccagttcctcccatt gtagaaaaaatttgctggaccttttttctctttttttttgtccttttagtttcatacaatctaagtctatctacaatgtc taaaggtgaagaattattcactggtgttgtcccaatttttggttgaattagatggtgatgttaatggtcacaaatttc tgtctccggtgaaggtgaaggtgatgctacttacggtaaattgacctttaaaattttatttgtactactggtaaattgcc agttccatggccaaccttagtcactacttcgcttatggtgttcaatgtttgctagataccagatcatatgaaaca acatgacttttttcaagtctgccatgccagaaggttatgttcaagaaagaactatttttttcaaagatgacggtaac tacaagaccagagctgaagtcaagttgaaggtgataccttagttaatagaatcgaattaaaaggtattgatttt aaagaagatggtaacattttaggtcacaaattggaatacaactataactctcacaatgtttacatcatggctgac aaacaaaagaatggtatcaaagttaacttcaaaattagacacaacattgaagatggttctgttcaattagctgac cattatcaacaaaatactccaattggtgatggtccagtccttgttaccagcaaccattacttatccactcaatctg cctatccaaagatccaaacgaaaagagagaccacatggtcttgttagaatttgttactgctgctggtattaccc atggtatggatgaattgtacaaataattgatgtaagactttaattataagaatacaattgtgataaagacaatgta gaagtactgtagaagtcatggaatagctgatcaactgtactgttatacaaaggtactattaacaaaatagacat atagttttctataacatatataaacat*cttattaggattcgatgtcagcggaggtgtagaggatctgaatggag *ataaggatttgcaaaaagttgaggatttcattaagattggaaagactttatagatgtaaatagtgttaatga tatatgattattagcatgatttttgcgtagagtgtgttcaagcgttaggtgggatattttgatacggttaacattt tactacgacgtactttctactatactttattccttttgctttaatattttttattactaaaatgcacttattgcggtat ctgaatttaatcatcttgatcccagttaccaggtctaggctgctttggcatctgagggcctccagctctcttggc catgatgattgatctatagacaatatggtgttggtggcatctacagccaagttaatggcagacttcttactg gagtacaagtcgtagataccagcttgggtgacatcaagtaaatcgtcattgtcgatgtcgataccgaggtt gatgttgtc*<br>500 bp up/down stream sequence of trp1 gene (italic sequence); egfp cassette of tef1 promoter-egfp-pgk terminator (underlined sequence) |
| ku70-donor-100 bp (SEQ ID NO: 48) | aagtgctttggtttactacaaacgacaagccatacaccaagaactcgacc<u>taatag</u>gcgtattatcaacgatta ctataactatggctactttattcgtc<br>The mutations in donor DNA: AAAGAGAACTTGTG (SEQ ID NO: 49) to TAATAG-------- (two stop codons, and missing 8 bp, underlined sequence) |
| ku80-donor-1 kb (SEQ ID NO: 50) | *cacaagattccaaacgatatagagccgaatgggaaaaaagattccaattataagcctaacacagagat gacaaaaacagcaagcttgctctcctacgtttcttcaagtcttgacataagggtattctttagtattgcagtg cgcattacttctataaactttgttttttatgatcacgtgaatatgtacagagatttatgcacttcaggcacgtctg gttcttgattgtaattcaaacgtcttctgtagcctattataacaattttaaaaccaattgactccccaaccatgct gtccaaagagatgacgttcttcgtcattgataccacactggagatggtcaataggtcaaatcccgtttcaa aaagatcaagcccttgagagaggattaggctactttcatgatcatactgcgactctattgcttaagaacagg aagattgaccgcgtaggcataatttgtgcctcagatgctggtaaccatgtctacagtgctgatgaggc*catt cgagcgatatttccaagacattgatcgatgcccttgatgtgaaatatcttgagaaggacgagaagaaacaca agcgtcgtaagtacgaaggaactgcattcgaacgattcttccgtaatgaaggcgactctgcgaactccgatat gaaggctgactttgatgaattttttcgacgttaaagacttattgggtggtagtatagatagtaaataaaggtca atattggtactcaatacctgaaagctgttagttctatgtacatgattccttactaatatttaaacaaacgatttttc aaatgtattccctatccttttgctgttctccttcctatgttttgatcttttgatcgaaccgtcttcccccaaactattac aattttttcggataccttcatggttgtaaccccgttccctttcgttcttgaagatctgtttgaggtcgtttccattgat gtccaagatggcttgcaagtcaaagacagccttatatttctggga<br>500 bp upstream sequence of ku80 gene (italic sequence); 500 bp upstream sequence of ku80 gene (underlined sequence) |

Example 4: Engineering *S. cerevisiae* for High Production of Polymer and Drug Precursors Introduction Engineering microbial factories for the production of valuable chemicals often requires the optimization of long metabolic pathways. Splitting the pathways into modules can allow for faster optimization, leading to higher overall yields and titers. Grouping genetic elements permits a more precise analysis of bottlenecks, rate-limiting steps, and metabolic imbalances (Biggs et al., 2014). Moreover, studying metabolic pathways as independent modules facilitates the analysis of transcriptional regulators that may act on the genes within distinct modules, hence enabling a multilevel approach encompassing engineering at both transcriptional and metabolic levels.

Modular approaches for engineering microbes have been implemented in a variety of cases. In *Escherichia coli*, for example, implementing a modular design strategy led to significant increases in the production of total fatty acids (Xu et al., 2013). In *Saccharomyces cerevisiae*, the most recent example was observed for the de novo production of benzylisoquinoline alkaloids (BIAs), which required the coordinated overexpression of more than 20 endogenous and heterologous genes (Galanie et al., 2015). Partitioning the pathway into several modules allowed efficient optimization of precursor and cofactor availability, and reduction of pathway bottlenecks. In fact, the aromatic amino acid pathway from which BIAs are originated is a source of a great variety of chemicals that range from polymer precursors to nutraceuticals and pain-relief drugs (Suástegui and Shao, 2016). Previous metabolic engineering efforts in *S. cerevisiae* have enabled the production of chemicals derived from this pathway including, but not limited to, shikimic acid (SA) (Suástegui et al., 2016a), muconic acid (MA) (Curran et al., 2012; Suástegui et al., 2016b), vanillin (Brochado et al., 2010), L-tyrosine (L-tyr) (Gold et al., 2015), coumaric acid (Rodriguez et al., 2015), and secondary metabolites from the flavonoid and stilbenoid families, as well as BIAs (Galanie et al., 2015; Jiang et al., 2005; Koopman et al., 2012; Li et al., 2015; Trantas et al., 2009; Yan et al., 2005).

Figure 18:
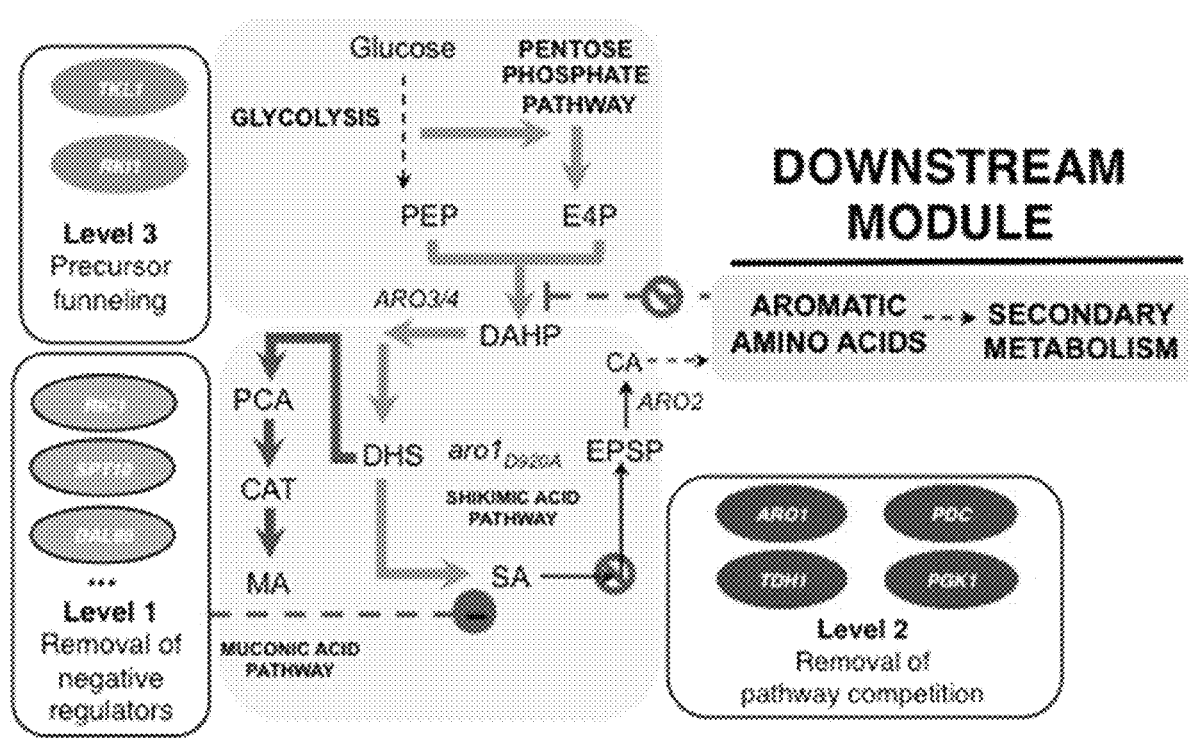
FIG. 18 is a schematic representation of the metabolic engineering rationale for enhancing the carbon flux into the aromatic amino acid biosynthetic pathway. To establish the boundaries, the pathway was visualized in two main modules, namely the precursor module, and the downstream module. The multilevel engineering strategy consisted of removing pathway repressors (level 1), removing pathway competition (level 2), and increasing precursor funneling (level 3). Color codes: green, gene overexpression; red, gene knockout. Metabolite abbreviations: PEP, phosphoenolpyruvate; E4P, erythrose-4-phosphate; DAHP, 3-deoxy-D-arabino-heptulosonate-7-phosphate; DHS, 3-dehydroshikimic acid; SA, shikimic acid; EPSP, 5-enolpyruvyl-3-shikimate phosphate; CA, chorismic acid. Gene abbreviations: TKL1, transketolase; RKI1, ribose-5-phosphate ketol-isomerase; ZWF1, glucose-6-phosphate dehydrogenase; PFK1, phosphofructokinase; ARO1, pentafunctional aromatic enzyme; aro1D920A, mutant version of ARO1 with disrupted shikimate kinase activity; ARO2, chorismate synthase, PDC, pyruvate decarboxylase; PGK1, 3-phophoglycerate kinase; TDH1, glyceraldehyde-3-phosphate dehydrogenase.

One major metabolic engineering strategy employed to unlock the production of derivatives spun off the aromatic amino acid biosynthetic pathway is the overexpression of the feedback insensitive enzymes 3-deoxy-D-arabino-heptulosonate-7-phosphate (DAHP) synthase, Aro3/4, and chorismate mutase, Aro7, catalyzing the first committed step in the pathway, and the branching point towards the production of L-tyr and phenylalanine (L-phe), respectively (Brown and Dawes, 1990; Luttik et al., 2008). As shown in FIG. 18, other strategies include rewiring the pentose phosphate pathway (PPP) for increasing the pool of erythrose-4-phosphate (E4P), and the overexpression of mutant versions of the pentafunctional protein Aro1 to halt the activity at specific subunits for accumulating the desired intermediates (Suástegui and Shao, 2016). Despite the implementation of these strategies, the yields of the compounds based on carbon sources in *S. cerevisiae* still remain low, suggesting that higher carbon fluxes into the pathway are constrained by other unknown factors. Therefore, a more comprehensive investigation needs to be prosecuted to determine novel transcriptional and metabolic targets, which will benefit the design of microbial cell factories for producing many high-value compounds from such a resourceful pathway.

Herein, we have focused the attention on engineering the precursor module of the aromatic amino acid pathway using SA as a reporter product. The target metabolic module is composed of the genes in the glycolytic pathway (up to the production of phosphoenolpyruvate, PEP), the PPP (leading to the production of erythrose-4-phosphate, E4P), and the genes in the SA pathway including ARO2, ARO3, ARO4, and the pentafunctional ARO1 (FIG. 18). Besides implementing a comprehensive engineering strategy at the metabolic level (i.e. deletion or overexpression of structural genes), we identified that the protein Ric1, involved in regulating the efficient localization of trans-Golgi network proteins (Bensen et al., 2001), can act as a transcriptional repressor of multiple genes in the aromatic amino acid pathway. Furthermore, the incorporation of in silico modeling and pathway analysis led to the discovery of a novel genetic target. Overexpression of ribose-5-phosphate ketolisomerase, RKI1, in addition to other tested interventions, facilitated PPP flux redirection into the aromatic amino acid pathway through E4P. The combination of these novel, multilevel interventions led to the high production of SA, MA, and its intermediate. Such a multilevel intervention strategy thoroughly removes the constraints in the upstream precursor module of the aromatic amino acid pathway, maximize the carbon flux flowing to the downstream, and therefore pave the way for synthesizing high-value molecules from the downstream branches.

Results

Identification of a Novel Transcriptional Regulator

Figure 19A:
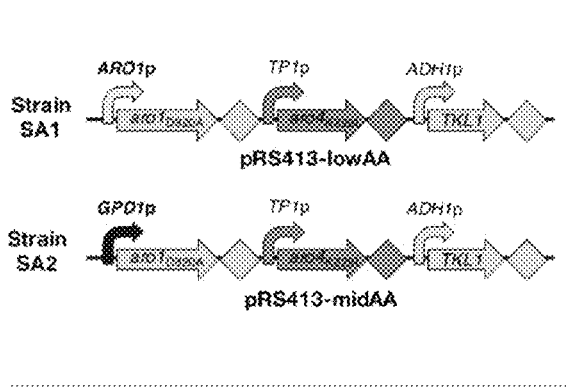
FIGS. 19A-C show engineering the production of SA at the transcriptional level.
Figure 19B:
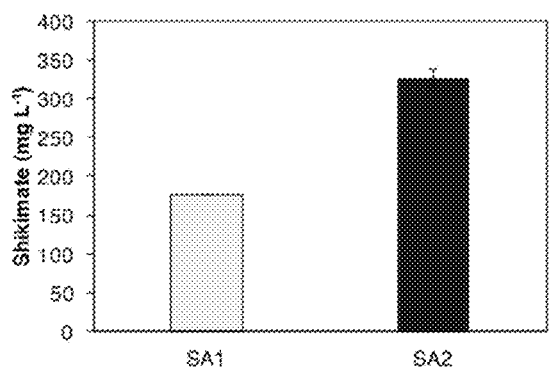

SA was selected as the reporter molecule to track the entrance of carbon into the precursor module. Initially, to study the transcriptional regulation upon this module, we focused the attention to the ARO1 promoter as it controls the expression of the pentafunctional gene ARO1, the main core of the module. Table 6 shows the plasmid design based on the previously reported platform in *S. cerevisiae* for production of SA (Suástegui et al., 2016a). The promoter controlling the expression of the mutant gene aro1$_{D920A}$ was switched from the strong constitutive GPD1 promoter (GPD1 encodes glycerol-3-phosphate dehydrogenase, strain SA2) to the native ARO1 promoter, yielding plasmid pRS413-lowAA (strain SA1, Table 7 and FIG. 19a). The titer after 3 days of fermentation with strain SA1 reached 176.27±0.50 mg L-1 of SA (FIG. 19b), a reduction of almost 46% compared to strain SA2. This indicated that, indeed, the two promoters had different strengths, presumably due to distinct responses to transcriptional regulatory elements. Hence we proceeded to investigate which specific transcription factors (TFs) could be involved in the regulation of the upstream precursor module of the aromatic amino acid biosynthesis, including ARO1, ARO2, ARO3, and ARO4 (FIG. 18), as a direct approach to discerning the cause of the repressive regulation of carbon flux into the pathway.

A list of TFs with reported evidence of acting as repressors was retrieved from the Yeast Search for Transcriptional Regulators and Consensus Tracking (YEASTRACT) website (Teixeira et al., 2014). YEASTRACT is a repository of over 200,000 regulatory associations between transcription factors and target genes in *S. cerevisiae*, developed based on more than 1300 references. The list contained 66 unique TFs from which 21 were selected for further analysis according to the criteria described in the Materials and Methods Section.

Figure 19C:
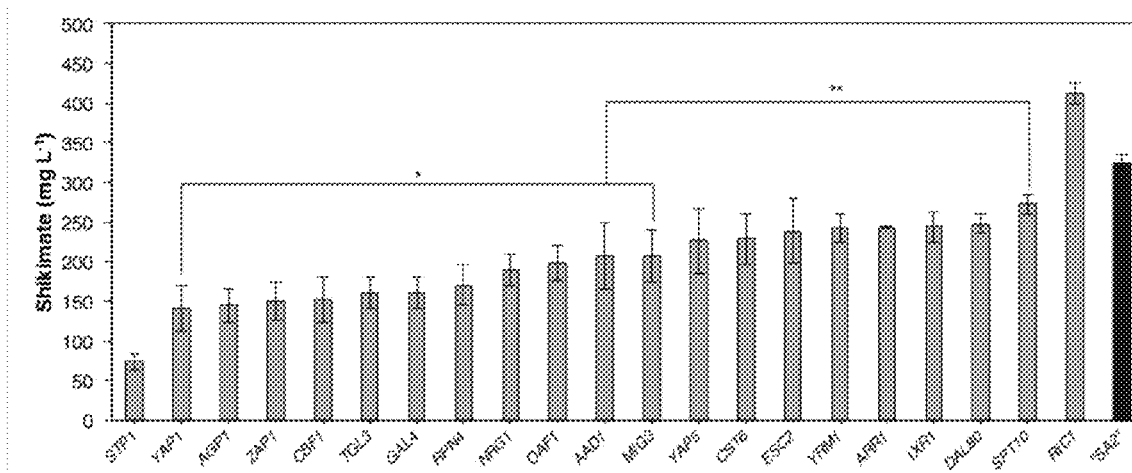
Figure 20A:
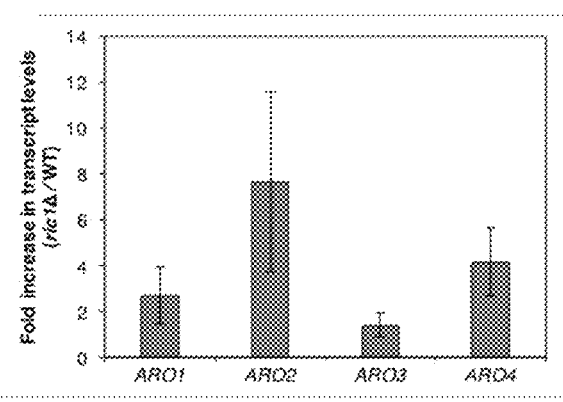
FIG. 20A shows the effect of RIC1 deletion on the transcript levels of the ARO genes. The strain BY4741 ric1Δ and BY4741 wildtype were cultured (as indicated in the Materials and Methods section) and samples for RNA extraction were taken after 24 h. The transcript levels of the ARO genes were measured with RT-qPCR using the housekeeping gene ALG9 as the reference. An increase in the transcript levels of all four ARO genes was observed in the BY4741 ric1Δ strain.
Figure 20B:
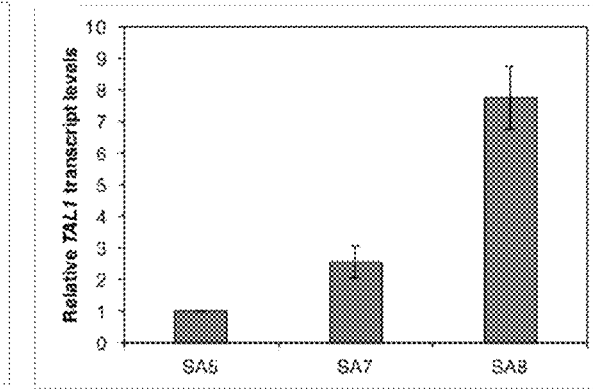
FIG. 20B shows transcript levels of TAL1. The strain SA7 (pho13Δ) showed a 2.56-fold increase in TAL1 transcript levels compared to strain SA5, which lacked the deletion. The strain SA8 showed a 7.72-fold increase due to overexpressing TAL1 under the control of the constitutive promoter PGK1p. The increases in TAL1 transcript levels in strains SA7 and SA8 correlate with the decreases in SA titers (FIG. 22). The variation is represented by the standard deviation from three biological replicates

The plasmid pRS413-midAA (FIG. 19) was transformed into the selected TF single knockout strains, which were independently assayed for SA accumulation (FIG. 19c). In general, the majority of the knockout strains resulted in reduced SA titers, ranging from −77% to −16% when compared to strain SA2. The drops could be related to the decrease in nutrient uptake (de Boer et al., 2000), as well as reduced competitive fitness in minimal media (Qian et al., 2012).

A positive outcome was observed in strain BY4741 ric1Δ (strain SA3), which was able to accumulate 413.2±13.4 mg L-1 SA, representing a 27% increase compared to strain SA2 (FIG. 19c). Ric1 is a protein involved in the activation of the Ras-like GTP binding protein Ypt6, and its deletion has shown to cause a reduction in heat tolerance (Bensen et al., 2001). Further analysis with the "Rank Genes by TF" tool in YEASTRACT revealed that Ric1 was ranked as the second top TF, only after the global regulator Gcn4p that stimulates many genes involved in amino acid biosynthesis (Hinnebusch and Natarajan, 2002). This enrichment-based ranking takes into consideration the effect and interaction of each TF with other regulons, and prioritizes those with fewer and less complex regulations while covering as many of the genes in query as possible (Teixeira et al., 2014). Indeed, Ric1 was the only shared transcriptional repressor obtained from our analysis by multiple promoters of the genes in the aromatic amino acid precursor pathway (ARO2, ARO3, and ARO4) and with the lowest impact on other regulatory networks.

TABLE 6

List of plasmids used in this study.

| Production plasmids | Genetic elements | Reference |
| --- | --- | --- |
| pRS413 | | |
| pRS413-lowAA | pRS413-ARO1p-aro1$_{D920A}$/ TP1p-aro4$_{K229L}$/ADH1p-TKL1 | This study |
| pRS413-midAA | pRS413-GPD1p-aro1$_{D920A}$/ TP1p-aro4$_{K229L}$/ADH1p-TKL1 | (Suástegui et al., 2016a) |
| pRS413-highAA | pRS413-GPD1p-aro1$_{D920A}$/ TP1p-aro4$_{K229L}$/ADH1p-TKL1/PGK1p-RKI1 | This study |
| pRS413-midAA_1 | pRS413-GPD1p-aro1$_{D1409A, D920A}$/ TP1p-aro4$_{K229L}$/ ADH1p-TKL1 | This study |
| pRS413-highAA_1 | pRS413-GPD1p-aro1$_{D1409A, D920A}$/ TP1p-aro4$_{K229L}$/ADH1p-TKL1/PGK1p-RKI1 | This study |
| pRS425-MA | pRS425-PYK1p-AROZ/GPD1p-HQD2/TEF1p-AROY | (Suástegui et al., 2016b) |
| CRISPR plasmids | | |
| pCRCT | | (Bao et al., 2014) |
| pCRCT_aro1 | | This study |
| pCRCT_pho13 | | This study |
| pCRCT_zwf1 | | This study |

TABLE 7

Strains constructed in this work.

| Strain | Description | Genotype | Source |
| --- | --- | --- | --- |
| AA_001 | BY4741 BY4741 ric1Δ | ric1Δ:: KanMX | GE Dharmacon |
| AA_002 | BY4741 aro1Δ | aro1Δ::KanMX | GE Dharmacon |
| AA_003 | BY4741 ric1Δ aro1Δ | ric1Δ:: KanMX, aro1Δ | This study |
| AA_004 | BY4741 zwf1Δ | zwf1Δ::KanMX | GE Dharmacon |
| AA_005 | BY4741 pho13Δ aro1Δ ric1Δ | ric1Δ::KanMX, aro1Δ, pho13Δ | This study |
| AA_006 | BY4741 zwf1Δ aro1Δ ric1Δ | ric1Δ::KanMX, aro1Δ, zwf1Δ | This study |

Shikimic acid producing strains

| Strain | Genotype | Plasmid | Parent |
| --- | --- | --- | --- |
| SA1 | BY4741 | pRS413-ARO1p-aro1$_{D920A}$, TP1p-aro4$_{K229L}$, ADH1p-TKL | BY4741 |
| SA2 | BY4741 | pRS413-GPD1p-aro1$_{D920A}$, TP1p-aro4$_{K229L}$, ADH1p-TKL | BY4741 |
| SA3 | ric1Δ:: KanMX | pRS413-GPD1p-aro1$_{D920A}$, TP1p-aro4$_{K229L}$, ADH1p-TKL | AA_001 |
| SA4 | aro1Δ::KanMX | pRS413-GRD1p-aro1$_{D920A}$, TP1p-aro4$_{K229L}$, ADH1p-TKL | AA_002 |
| SA5 | ric1Δ::KanMX, aro1Δ | pRS413-GRD1p-aro1$_{D920A}$, TP1p-aro4$_{K229L}$, ADH1p-TKL | AA_003 |
| SA6 | zwf1Δ::KanMX | pRS413-GRD1p-aro1$_{D920A}$, TP1p-aro4$_{K229L}$, ADH1p-TKL | AA_004 |
| SA7 | ric1Δ::KanMX. aro1Δ, pho13Δ | pRS413-GRD1p-aro1$_{D920A}$, TP1p-aro4$_{K229L}$, ADH1p-TKL | AA_005 |
| SA8 | ric1Δ::KanMX, aro1Δ | pRS413-GRD1p-aro1$_{D920A}$, TP1p-aro4$_{K229L}$, ADH1p-TKL PGK1p-TAL | AA_003 |
| SA9 | ric1Δ::KanMX, aro1Δ | pRS413-GPD1p-aro1$_{D920A}$, TP1p-aro4$_{K229L}$, ADH1p-TKL PGK1p-RKI1 | AA_003 |
| SA10 | ric1Δ::KanMX, aro1Δ, pho13Δ | pRS413-GPD1p-aro1$_{D920A}$, TP1p-aro4$_{K229L}$, ADH1p-TKL PGK1p-RKI1 | AA_005 |

Muconic acid producing strains

| Strain | Genotype | Plasmid | Parent |
| --- | --- | --- | --- |
| MA1 | BY4741 | pRS413-GPD1p-aro1$_{D1409A, D920A}$, TP1p-aro4$_{K229L}$, ADH1p-TKL pRS425-PYK1p-AROZ, GPD1p-HQD2, TEF1p-AROY pRS413-GPD1p-aro1$_{D1409A, D920A}$, TP1p-aro4$_{K229L}$, ADH2p | BY4741 |

TABLE 7-continued

| MA2 | BY4741 | -TKL, PGK1p-RKI1<br>pRS425-PYK1p-AROZ, GPD1p-HQD2, TEF1p-AROY | BY4741 |
|---|---|---|---|
| MA3 | BY4741 aro1Δ | pRS413-GPD1p-aro1$_{D1409A,\ D920A}$, TP1p-aro4$_{K229L}$, ADH1p-TKL, PGK1p-RKI1<br>pRS425-PYK1p-AROZ, GPD1p-HQD2, TEF1p-AROY | AA_002 |
| MA4 | BY4741 aro1Δ<br>ric1 A | pRS413-GPD1p-aro1$_{D1409A,\ D920A}$, TP1p-aro4$_{K229L}$,<br>ADH1p-TKL, PGK1p-RKI1<br>pRS425-PYK1p-AROZ, GPD1p-HQD2, TEF1p-AROY | AA_003 |
| MA5 | BY4741 aro1Δ<br>ric1Δ zwf1Δ | pRS413-GPD1p-aro1$_{D1409A,\ D920A}$, TP1p -aro4$_{K229L}$, ADH1p-TKL, PGK1p-RKI1<br>pRS425-PYK1p-AROZ, GPD1p-HQD2, TEF1p-AROY | AA_006 |

To further support the evidence observed from deleting RIC1, we quantified the transcript levels of the ARO genes (ARO1-4) in the BY4741 ric1Δ strain and compared them to the wildtype strain, both transformed with an empty pRS413 shuttle vector to maintain the consistency with our SA-producing strains. As observed in FIG. 3a, the transcript levels of all four genes were increased. This strongly suggests that the major contributions of ric1Δ to the enhancement of SA and MA titers came from the increase in the transcription levels of ARO4 (4.16-fold), ARO1 (2.68-fold), and ARO3 (1.4-fold), whereas the highest change corresponded to the gene ARO2 (catalyzing a conversion downstream of SA) with a 7.65-fold increase in strain BY4741 ric1Δ. This represents the first evidence reported in literature that directly links the deletion of RIC1 with an increase in ARO transcript levels, leading to enhanced titers from molecules in the shikimic acid pathway.

Removal of Competing Pathways

Figure 21A:
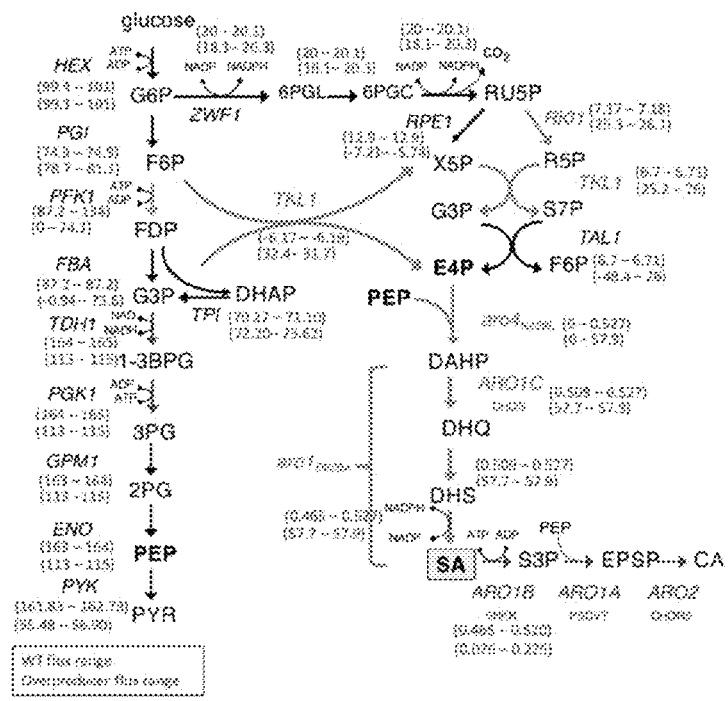
FIGS. 21A-C show metabolic interventions identified with OptForce for production of SA.
Figure 21B:
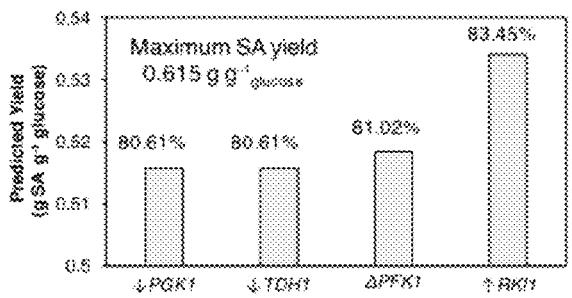
Figure 21C:
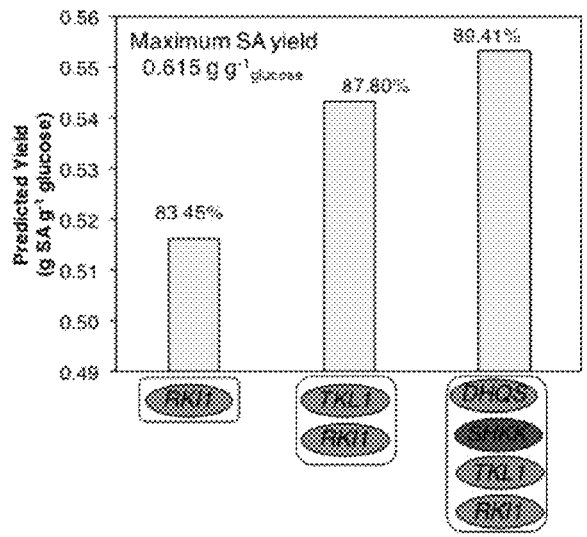
Figure 22:
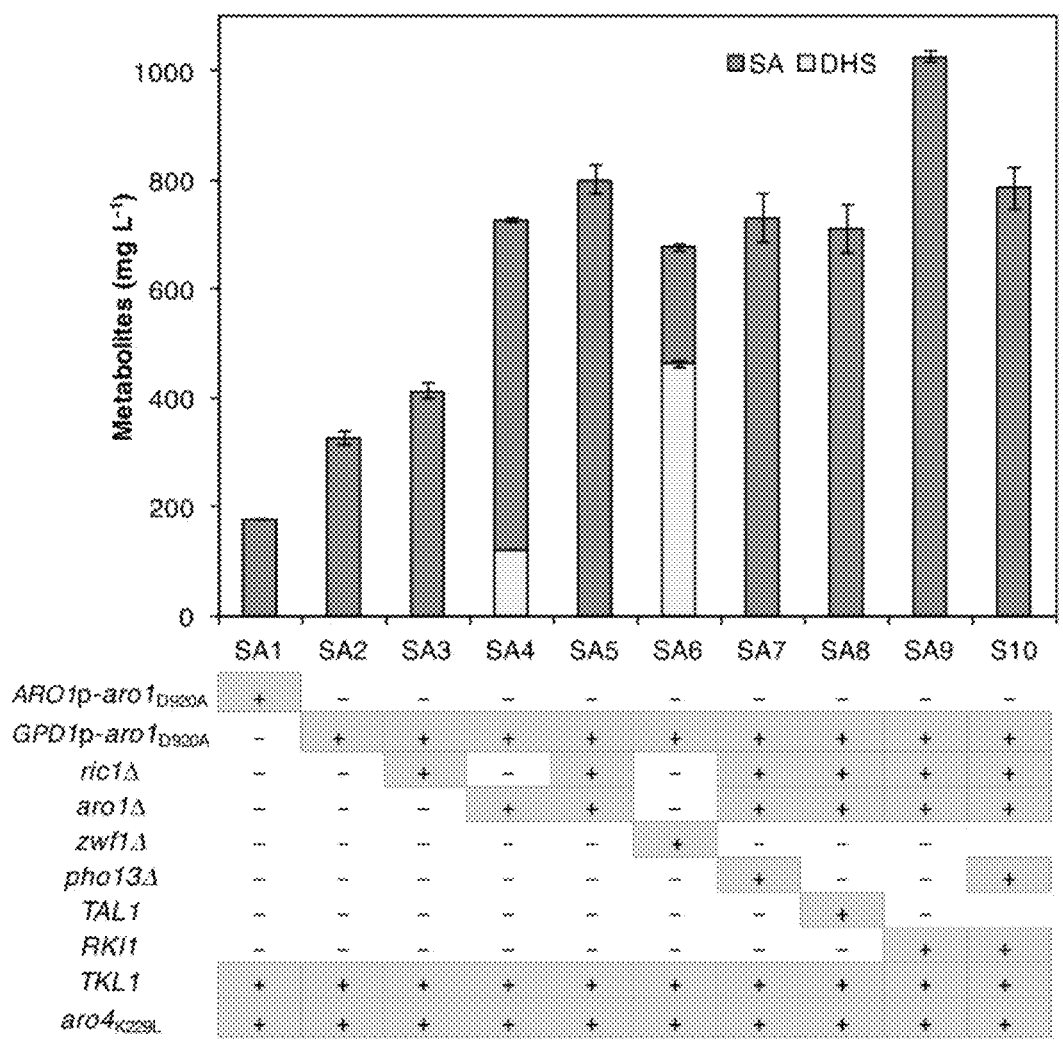
FIG. 22 shows fermentation results from *S. cerevisiae* B47471 strains engineered to produce SA. The strains were grown in 3 mL minimal media (lacking histidine and supplemented with uracil) in a shaker incubator at 250 RPM and 30° C. The three aromatic amino acids (L-phe, L-tyr, and L-trp) were added to the media (50 mg L-1 each) to grow only the strains carrying the ARO1 deletion (SA4, SA5, and SA7 to SA10). Samples were collected at 72 h and stored at −20° C. until analyzed with HPLC. The accumulation of DHS was only included for strain SA4 and SA6 as main comparison to illustrate the effect of the deletion of ZWF1. The variation is represented by the standard deviation from three biological replicates.
Figure 23:
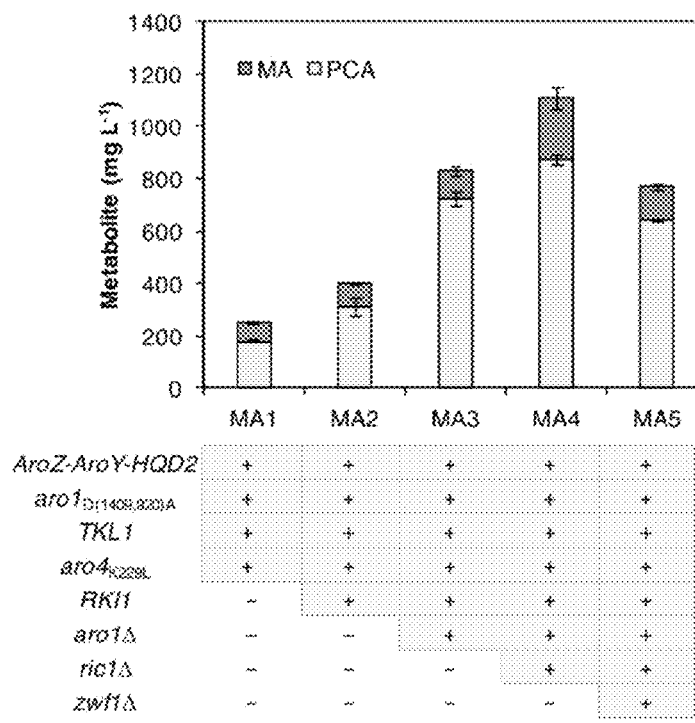
FIG. 23 shows fermentation results from *S. cerevisiae* BY4741 strains engineered to produce MA. The strains were grown in 3 mL minimal media (lacking histidine and leucine and supplemented with uracil), in a shaker incubator 250 RPM and at 30° C. The three aromatic amino acids (L-phe, L-tyr, and L-trp) were added to the media (50 mg L-1 each) to grow only the strains carrying the ARO1 deletion (MA3, MA4, and MA5). Samples were collected at 72 h and stored at −20 □C until analyzed with UPLC. The variation is represented by the standard deviation from three biological replicates.

The precursor module in the aromatic amino acid pathway can be exploited for the production of molecules such as drug precursors (e.g. SA), polymer precursors (e.g. MA), and flavoring agents (e.g. vanillin). It is evident that to divert more flux towards the target molecules, deletion of the competing pathways (i.e. the biosynthesis of L-tyr, L-trp, and L-phe) is required. To validate this assumption, the inventors employed the OptForce procedure, which is a computationally tractable and deterministic algorithm that can identify knockout, overexpression or down-regulation strategies. The procedure incorporates experimental flux measurement in its prediction to better characterize the reference strain and has been successfully applied in several case studies (Ranganathan et al., 2012; Xu et al., 2011). In fact, OptForce also suggested the down-regulation of shikimate kinase (SHKK) or 3-phosphoshikimate 1-carboxyvinyltransferase (PSCVT) to restrict flux drainage towards biomass precursors and competitive products during SA overproduction (FIG. 21). This intervention can be achieved by knocking out the gene ARO1, which catalyzes the five intermediate steps in the SA pathway, in combination with overexpression of ARO1 variant (aro1$_{D920A}$) that maintains the catalytic functions of the first three conversions from DAHP to SA (Suástegui et al., 2016a). The strain BY4741 aro1Δ overexpressing aro1$_{D920A}$, TKL1, and aro4$_{K229L}$ (Strain SA4), reached a titer of 606.0±4.8 mg L-1 SA (FIG. 22). Note this required the addition of the three aromatic amino acids, each at a level of 50 mg L-1, even when the cells were grown in synthetic complete media. By supplementing the extra aromatic amino acids, we were able to restore the growth level of the aro1Δ strain to that of the wildtype strain. Finally, combining the deletions of RIC1 and ARO1 (Strain SA5) elevated the titer to 800.3±26.8 mg L-1 SA, which represented a 4.5-fold increase compared to the initial strain SA1 (FIG. 22).

Clarification of the Role of the Oxidative PPP

The next level of engineering was directed towards enabling higher availability of the precursor E4P. Previously, we have identified that between the two precursors PEP and E4P, the latter is the rate limiting one constraining the entrance flux into aromatic amino acid biosynthesis pathway in S. cerevisiae (Suástegui et al., 2016a). The inventors began with the deletion of the gene ZWF1 encoding glucose-6-phosphate dehydrogenase (G6PDH2), a strategy that has been previously implemented to increase the availability of E4P (Curran et al., 2012; Gold et al., 2015). Deletion of ZWF1 (strain SA6) caused a reduction in SA titer to 213.8±6.75 mg L-1, but the total titer of 3-dehydroshikimic acid (DHS) and SA (676.81 mg L-1) increased ~2.1-fold when compared to strain SA2 (FIG. 5). The reaction catalyzed by G6PDH2 is the main source for generating reducing power in the form of NADPH (Zhang et al., 2015), which in turn serves as the cofactor for the SA dehydrogenase subunit of Aro1 protein. A reduction in the NADPH pool directly translated into significantly reduced cell growth and a lower catalytic conversion of the SA dehydrogenase, resulting in a higher accumulation of DHS. Very interestingly, this result was consistent with our computational study. In contrary to the prediction of Genetic Design by Local Search (GDLS) (Gold et al., 2015), OptForce did not suggest the knockout of ZWF1 because SA production requires the cofactor NADPH. Knocking out ZWF1 in silico reduced the theoretical maximum yield of SA by 4.8% (from 64.0 mmol g DW-1 h-1 to 60.9 mmol g DW-1 h-1) because metabolic flux has to be drained towards competitive metabolic pathways such acetaldehyde dehydrogenase to supply the required NADPH.

Clarification of the Role of Transaldolase

Previous studies have shown that deletion of the haloacid dehalogenase encoded by PHO13 can increase the transcription rates of the genes in the PPP (Kim et al., 2015). The inventors hypothesized that such manipulation could increase the push of carbon into the aromatic amino acid biosynthesis pathway. Accordingly, deletion of PHO13 as a new alternative to rewiring the PPP to enhance the production of pathway precursor. However, the strain SA7 (pho13Δ) accumulated 731≠444 mg L-1 of SA, which represented an 11% reduction compared to strain SA5 (ric1Δaro1Δ) (FIG. 5).

Re-inspecting the mechanism of gene up-regulation in a pho13Δ strain (Kim et al., 2015) led to the hypothesis that the decrease in SA titer could be due to channeling of the carbon flux into glycolysis rather than into the aromatic amino acid pathway. In fact, in a pho13Δ background, the transcript levels of transaldolase (TAL1) were increased (Kim et al., 2015), which has also been correlated with increased growth and ethanol titers in yeast engineered to efficiently use pentose sugars as carbon source (Vilela Lde et al., 2015). This could be an indication that the transaldolase is pivotal in connecting the flux from PPP to glycolysis. To prove this, we overexpressed TAL1 in strain SA5 (resulting in strain SA8), leading to a SA titer of 709.4±45 mg L-1 (FIG. 5); no statistical difference was observed when compared to strain SA7 (Student's t-test, p>0.05). To further support this correlation between TAL1 and pho13Δ, we tested the TAL1 transcript levels in strain SA7 (pho13Δ) and in strain SA8. We observed an increase of TAL1 expression in strain SA7 (2.56-fold) consistent to what has been reported previously (Kim et al., 2015), and an even higher increase in the strain carrying the overexpression (7.72-fold) (FIG. 3b). This confirms that the reduction in SA titer was likely related to the increase in TAL1 overexpression.

Discovery of Novel Metabolic Interventions by OptForce

The OptForce algorithm intends to scope out non-intuitive interventions generally overlooked in manual investigation. For SA hyper-accumulation, OptForce first suggested two interventions consistent with what has been successfully implemented for producing aromatic amino acid pathway derivatives in the previous studies. These include, up-regulation of transketolase (TKL1) and 3-dehydroquinate synthase (DHQS, by replacing native ARO1 with $aro1_{D920A}$). In addition, down-regulation of pyruvate kinase (PYK) by 2.9-fold was identified as one of the single interventions that could improve SA titer. Down-regulation of PYK allows for the accumulation of precursor PEP. Note that while this intervention appeared to be detrimental towards up-regulating the aromatic amino acid pathway as observed previously (Gold et al., 2015), we believe that it was because this intervention was combined with the deletion of ZWF1, causing an NADPH deficiency in the organism as explained supra.

In this work, the primary focus was on identifying interventions that, have not been previously linked to the production of aromatic amino acid pathway derivatives. In this regard, manipulations of four individual metabolic targets in the central carbon metabolism were identified, including: downregulation of the reactions 3-phophoglycerate kinase (PGK1) and glyceraldehyde-3-phosphate dehydrogenase (TDH1), knockout of phosphofructokinase 1 (PFK1), and overexpression of ribose-5-phosphate ketol-isomerase (RKI1) (FIGS. 21a and 21b).

Overall, the intention of all these interventions was to divert carbon flux from glycolysis towards the biosynthesis of the precursor E4P. Although all four interventions individually demonstrated an increase in the titer of SA compared to the wild-type scenario based on in silico analysis, overexpression of RKI1 seemed to be most feasible. Considering the type of fermentation regime studied here (aerobic and glucose-rich), deletion or knockdown of the genes PGK1, TDH1, and PFK1, could drastically reduce cell growth given their key roles in glycolysis. Hence, only the overexpression of RKI1 was selected as the new intervention to be tested.

RKI1 catalyzes the interconversion of ribose-5-phosphate and ribulose-5-phosphate in the PPP (FIG. 4a). According to OptForce, overexpressing RKI1 could help direct carbon flux towards the formation of E4P and preventing it from recirculating back into glycolysis. The in silico overexpression of RKI1 resulted in the highest increase in SA compared to the other individual manipulations, achieving 83.45% of the theoretical yield. Furthermore, its combination with TKL1 overexpression, DHQS upregulation (enabled by $aro1_{D920A}$ overexpression), and SHKK knockout (enabled by aro1 deletion) increased the yield to 0.55 g SA g-1glucose, representing 89.41% of the maximum theoretical yield based on in silico prediction (FIG. 21c).

Experimentally indicated by RT-qPCR analysis, the overexpression of RKI1 in strain SA5 (yielding strain SA9) increased the transcript levels 6.95-fold leading to a SA titer of 1,026.6±51 mg L-1 (FIG. 22). This strain constituted the highest-producing strain in this work with a yield of 51 mg g-1glucose, an increase of 4.82-fold compared to the initial strain. In a final attempt to increase the flux into the SA titers, we deleted PHO13 in strain SA9 (yielding strain SA10). Although this strain improved the SA titer by 11% compared to strain SA8, there was a decrease of about 23% compared to strain SA9 (FIG. 22). This indicates that overexpression of RKI1 resulted in a consistent, beneficial manipulation for improving the flux in the aromatic amino acid pathway, but the higher transcription rate of TAL1 resulting from PHO13 deletion channeled the flux back into glycolysis, leading to a lower titer. Finally, the initial carbon concentration was increased in fermentations with the best producer (SA9) and the titers reached 2.0 g L-1 (4% glucose) and 2.4 g L-1 (4% sucrose). These SA titers represent the highest level reported in *S. cerevisiae* by batch fermentation (Table 10).

Case Study: Muconic Acid

To show the applicability of the manipulations that yielded the SA producing platform strain, we introduced the genetic elements to switch the production towards MA (Table 9). It is important to mention that unlike SA, MA is not an endogenous product in *S. cerevisiae*, hence the introduction of three heterologous genes from diverse microorganisms was required. According to previous studies, and also observed in this work, the gene aroY from the bacterium *Klebsiella pneumoniae* is the rate-limiting step in the pathway (Curran et al., 2012; Suástegui et al., 2016b). This gene encodes for protocatechuic acid (PCA) decarboxylase, and due to its oxygen sensitivity, it prevents an efficient conversion of PCA into catechol. Therefore, to fully capture the effects of the metabolic manipulations, the comparison of titers will include the sum of PCA and MA from here on.

Figure 6:
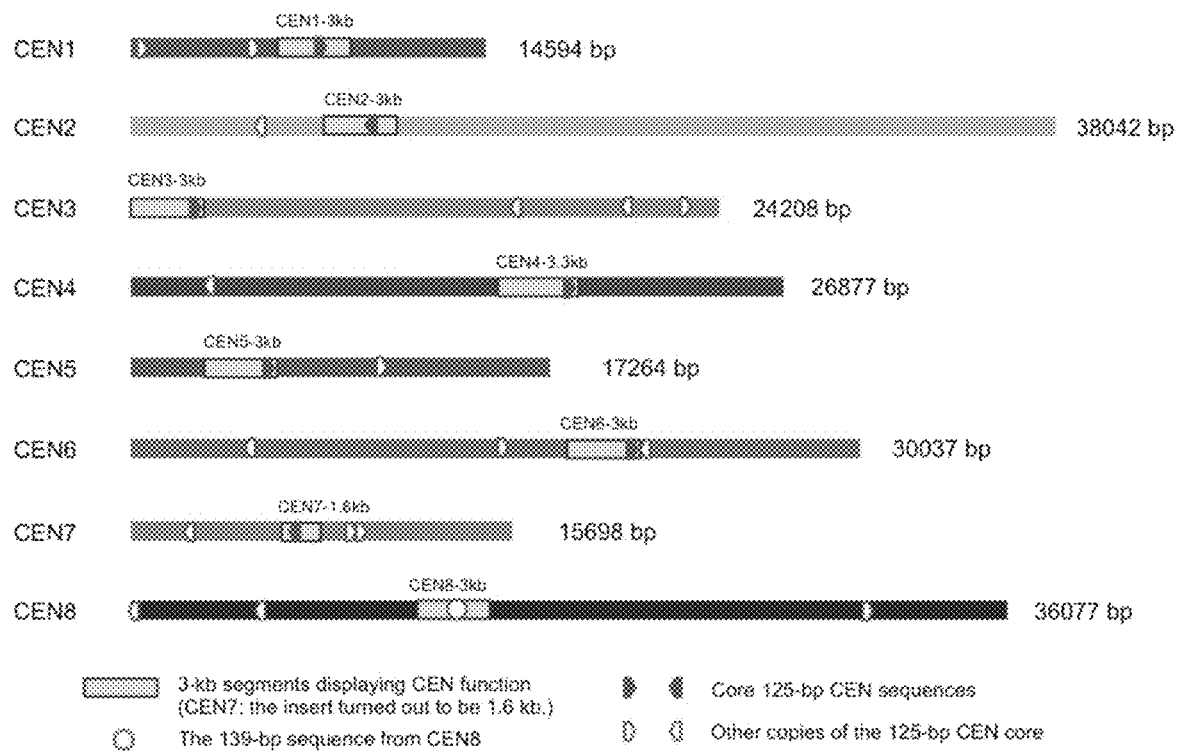
FIG. 6 shows the locations and the repeats of the 125-bp core CEN in the corresponding predicted $GC_3$ valleys. The point angel of a pentagon marks that the 125-bp core CEN was found from the sense strand or the antisense strand.

Initially, the single-copy plasmid for DHS accumulation (pRS413-midAA 1) was co-transformed with the multiple-copy plasmid pRS425-MA to channel DHS into the production of MA. Compared to the platform strains for the production of SA, the MA strains harbored the mutant $aro1_{D1409A-D920A}$ to ensure complete blockage of the SA dehydrogenase subunit for accumulating DHS for MA synthesis (Suástegui et al., 2016b). This yielded the reference strain MA1, capable of accumulating 247.24 mg L-1 of MA and PCA. Overexpression of RKI1, yielding strain MA2, increased the titer by 47%, achieving 363.97 mg L-1 (FIG. 6). Further deletion of ARO1 increased the composite titer to 826 mg L-1 (Strain MA3). Finally, deletion of RIC1 and ARO1 (strain MA4) increased the titer reaching 1,105 mg L-1 (873 mg L-1 PCA plus 232 mg L-1 MA), a similar titer observed from strain SA9, indicating that the set of metabolic engineering strategies for the SA platform are translatable to other products from the same module. The strategies implemented here were consistent with OptForce predictions, wherein different combinations of interventions involving transketolase (TKL1/TKL2), ribose-5-phosphate isomerase (RKI1), and 3-dehydroquinate synthase (ARO1 mutant) led to the highest yield of MA.

In strain SA6 (FIG. 22), DHS was accumulated due to an imbalance in reducing power caused by ZWF1 deletion. Here for MA production, this manipulation was presumed to be beneficial since DHS is the precursor of MA pathway (also suggested by the OptForce analysis. Surprisingly, deletion of ZWF1 (strain MA5) did not increase the titers of PCA and MA in experiment; rather, it decreased the overall titer by 31%. This could be a result of removing the primary source of NADPH, in combination with a higher metabolic burden imposed on the MA producing strain, which carries the three-gene heterologous pathway in a multiple-copy plasmid along with multiple gene deletions. In fact, there was a significant reduction in growth rate caused by deleting the gene ZWF1 accompanied with a longer lag phase when compared to the wildtype strain.

Figure 24:
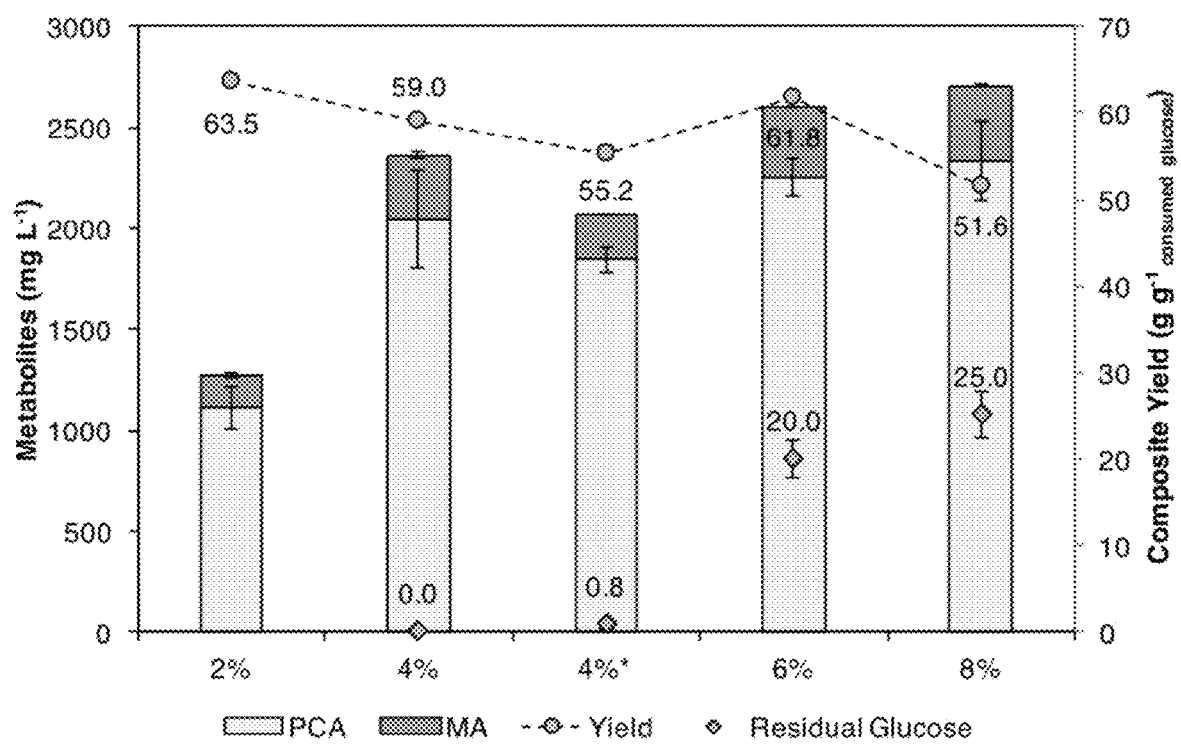
FIG. 24 shows production of MA and the intermediate PCA by strain MA4 with glucose concentration increasing. The strain MA4 was grown for 72 h in 250 mL flasks containing 25 mL of minimal media supplemented with uracil, the three aromatic amino acids, and an increasing concentration of glucose from 20 g L-1 to 80 g L-1. The composite yield (PCA+MA) was calculated based on consumed glucose. 20 g/L and 25 g/L were left when 60 g/L and 80 g/L of glucose were used, respectively. The variation is represented by the standard deviation of three biological replicates. The asterisk (*) represents an experiments in which the pH in the media was controlled at ~5.0 using the citric acid-sodium citrate buffer. Otherwise, the pH in the media was not controlled, reaching values ~2.5 during the first 24 hours of growth. The low pH did not affect cell growth.

We subjected our highest MA producing strain, MA4, to fermentations in a larger scale (25 mL in 250 mL shake flasks) to better gauge the production limit by controlling the pH of the media, and by increasing the initial glucose concentration. Compared to the small fermentation experiments in 3 mL tubes, the composite titers obtained in flasks were very similar, with a slight increase from 1,105 g L-1 to 1,269.3 mg L-1 (FIG. 24). By increasing the glucose concentration to 4%, we achieved a titer of 2361.87 mg L-1, which dropped to 2,068 mg L-1 when we controlled the pH of the media at a level of 5 using the citric acid-citrate buffer. This indicates that the production of the acids PCA and MA, which may cause a drop in pH does not affect cell growth. Finally, increasing the glucose concentrations to 6% and 8% slightly increased the titers to 2,596.1 mg L-1 and 2,705 mg L-1, respectively. However, we observed that the efficiency of carbon utilization was reduced, as residual glucose was observed in the media after 72 h fermentations (FIG. 24). Overall, the yields based on consumed glucose were maintained from 63.5 mg g-1glucose to 51.6 mg g-1glucose, which in parallel with the SA yields, represents the highest level reported in literature in batch fermentation (Table 10).

PHO13, and ZWF1 was performed using the plasmid pCRCT containing the CRISPR/Cas9 system (Bao et al., 2014). The CRISPR RNA (crRNA) cassettes for gene deletion were composed of 100 bp of the donor fragment lacking 8-bp to induce a frame shift and a 20-bp guide sequence. The guide sequences were designed based on the CHOPCHOP web tool (Montague et al., 2014). After plasmid transformation (1 µg), the yeast cells were grown for two days in liquid SC-Uracil medium. After this period, 200 µL of culture was transferred to fresh liquid medium and incubated for two more days. Finally, 100 µL of 104-fold diluted cells were plated on selective medium. Individual colonies were picked and inoculated in YPD plus 5-fluoroorotic acid and grown for 2 days to ensure plasmid loss. Genomic DNA was extracted by two cycles of freeze/boil and the supernatant was used as a template for diagnostic PCR. The PCR product was recovered from agarose gel and sent for Sanger sequencing at the DNA facility at Iowa State University.

Analysis of Transcriptional Repressors

The genes ARO1, ARO2, ARO3, and ARO4 were chosen for analysis of TFs using the YEASTRACT website (Teixeira et al., 2014). The search for TFs by target gene was performed in the Regulatory Associations tool by filtering the regulation type to only those acting as repressors (referred as 'inhibitors' on the website) with 'evidence of DNA binding plus expression'. This resulted in a list of 66 TFs, from which only 21 were selected for further analysis based on evidence of knockout viability and availability in the MATa yeast library.

TABLE 10

Comparison of highest SA and MA *S cerevisiae* producing strains reported in literature in batch fermentations.

| Compound | Strain | Titer MG L$^{-1}$ | Yield Mg g$^{-1}$ | Reference |
|---|---|---|---|---|
| Shilimi c acid | INVSCL-SA3 | 380 | 19 | (Suástegui et al., 2016a) |
|  | SA9[&] | 1,979 | 54.4 | This work |
|  | INVSC1-MA4 | 559-5 (759-5 | 14 18.9 | (Suástegui er al., 2016b) |
| Muconic acid | MuA- 5.01.1.02 + ARO1t + ScPAD1[#] | 557 (~1,200) | 13.9 (~30) | Leavitt et al., 2017 |
|  | BY47471-MA4* | 320.0 (2,362) | 8.0 (59) | This work |

[&]This strain can accumulate 2.5 g L$^{-1}$ in 4% sucrose.
[#]This strain could produce 2.1 g L$^{-1}$ of MA in fed-batch fermentation.
*This strain could produce 2.7 g L$^{-1}$ of MA and PCA in 8% glucose (FIG. 7). The numbers in the parenthesis represent the total pathway composite titers and yields.

Material and Methods

Plasmid Construction

The plasmids constructed in this work were assembled via DNA assembler (>4 fragments) (Shao et al., 2012; Shao and Zhao, 2013; Shao and Zhao, 2014) or Gibson assembly (2-3 fragments) (Gibson et al., 2009). The pCRCT plasmids containing the CRISPR/Cas9 system for gene editing were constructed via Golden Gate assembly (Engler et al., 2009; Engler et al., 2008) following the previously reported design (Bao et al., 2014). A list of the plasmids used in this work is displayed in Table 8. Transformation of plasmids into yeast was performed following the "quick and dirty" protocol (Amberg et al., 2006). All yeast genetic fragments (promoters, genes, and terminators) were amplified by PCR using the genomic DNA of strain BY4741. For gene knockouts using plasmid pCRCT, gBlocks® containing the donor DNA and the guide RNA were synthesized by IDT DNA (Coralville, Iowa).

Gene Deletion Using CRISPR/Cas9

The engineered strains with single or multiple gene deletions are listed in Table 9. Deletion of the genes ARO1, RT-qPCR Analysis The mRNA quantification of the endogenous genes studied in this work was performed using RT-qPCR. The strains were cultured in selective media and samples equivalent to an OD600~0.5 were harvested during late exponential phase (~24 h) for immediate extraction of total RNA using the RNeasy mini kit (Qiagen, Valencia, Calif.). Removal of residual genomic DNA was performed with Turbo DNA-free kit (Life Technologies, Carlsbad, Calif.), followed by cDNA generation by reverse transcription using a RevertAid first strand cDNA synthesis kit (ThermoScientific, Waltham, Mass.). The qPCR reactions (20 µL final volume) were setup according to the specifications of the Maxima SYBR Green/ROX qPCR master mix and processed on a StepOnePlus Real-Time PCR system (ThermoScientific, Waltham, Mass.). The primers used for qPCR were designed using the IDT PrimerQuest online tool (http://www.idtdna.com/PrimerQuest/Home/Index).

Computational Modeling

The optimization-based OptForce algorithm (Ranganathan et al., 2010) was implemented to identify target reaction-level interventions leading to the overproduction of SA and MA individually. In particular, the objective of the computational study was to identify key motifs in the intervention strategies that were conserved, and those that differed due to cofactor or energy equivalent requirements, when attempting to overproduce two metabolites in the same branch of metabolism (i.e. aromatic amino acid pathway). The genome-scale metabolic model iAZ900 (Zomorrodi and Maranas, 2010) was used to simulate the metabolic flux profiles in *S. cerevisiae* for both target molecules. For the case of SA production, the base model was modified by adding the SA exchange and transport reactions. Likewise, for simulation of MA production, the MA production pathway was included in the model by adding DHS dehydratase (SKHL), PCA decarboxylase (PCC) and catechol 1,2-dioxygenase (CATO) reactions, along with the corresponding exchange and transport reactions. All simulations were performed in the aerobic minimal media with glucose as the sole carbon substrate mimicking the experimental fermentation conditions. The CPLEX optimization software was used to solve the mixed integer optimization programming problems to optimality, and was accessed through the General Algebraic Modeling System optimization package. Note that the reaction-level intervention strategy suggested by OptForce was converted to gene-level suggestion using the gene-protein-reaction relationship information mined from iAZ900 model, as well as from the most recent curation of *S. cerevisiae* metabolism reported in literature (Chowdhury et al., 2015).

Fermentation and Strain Characterization

Single colonies were picked from transformation plates and inoculated into 3 mL of SC-Histidine or SC-Histidine-Leucine for seed culturing of the SA and MA production strains, respectively. After overnight growth, 30 µL of the saturated cultured was transferred into 3 mL of minimal medium lacking the corresponding amino acids grown in an incubator at 30° C. and a shaking speed of 250 RPM. 1 mL of samples were collected after 72 h and centrifuged at 5,000 rpm for 5 min; the supernatant was stored at −20° C. for chromatographic analysis.

SA and DHS were analyzed by High Performance Liquid Chromatography (HPLC) (Waters, Milford, Mass.) with an Aminex HPX-87H column (300×7.8 mm) (Bio-Rad, Hercules, Calif.) as previously reported (Gao et al., 2016). An ACQUITY Ultra Performance Liquid Chromatography (UPLC) with a BEH-C18 column (Waters) as the stationary phase was used to analyze MA and PCA. The mobile phase program was implemented as described previously (Suástegui et al., 2016b). Standard curves of PCA (MP Biomedicals, Santa Clara, Calif.), SA, DHS, and MA (Sigma-Aldrich, St. Louis) with authentic compounds were generated for metabolite quantification.

Example 5

*Scheffersomyces stipitis* is recognized as an important yeast species in the field of biorenewables due to its desired capacity for utilizing xylose [1], the second most abundant sugar in lignocellulosic biomass. While its previous applications were mainly demonstrated as a repository for isolating genes involved in xylose assimilation and transport, its potential as a better-suited microbial host than *Saccharomyces cerevisiae* for producing compounds derived from the shikimate pathway was recently proposed [2]. The much more active pentose phosphate pathway associated with the native xylose assimilating ability in *S. stipitis* renders a higher availability of the precursor erythrose 4-phosphate (E4P), which was identified as the rate-limiting precursor of the shikimate pathway in *S. cerevisiae* [3]. Considering that in plants the downstream products of the shikimate pathway include many kinds of flavonoids and alkaloids with important pharmaceutical and nutraceutical properties [4-6], finding a well-suited microbial chassis that can potentially synthesize these high-value natural products at sufficient titers is very important. For engineering nonconventional microbial species, the challenges ahead mainly include low transformation efficiency and the lack of genetic manipulation tools. Recently, we developed a CRISPR-based gene knockout system in *S. stipitis* and improved the gene knockout efficiency from <1% to more than 80% based on indel mutations [7].

However, strictly speaking, genome modification by an indel mutation based on the NHEJ mechanism should not be regarded as accurate genome editing because an indel mutation simply disrupts the target locus where DNA DSB occurs, resulting in random insertions and/or deletions. Until an HR-mediated genome modification method is established, many genome-engineering purposes, such as targeted integration, site-specific mutation, and functional replacement, cannot be achieved. Considering the growing interest in expanding the current collection of microbial cell factories, we implement *S. stipitis* here as an example and provide a step-wise procedure to overcome the major technical hurdles often encountered in the exploration of a novel microbial chassis.

Results

Improving transformation efficiency for *S. stipitis* by adjusting electroporation voltage Like many nonconventional microbial species, *S. stipitis* has a very low transformation efficiency. Transforming 1 µg of 10 kb plasmid DNA only led to approximately 40 colonies when using the standard electroporation voltage (750 v/mm, 1.5 kv for 2 mm cuvettes) for yeast transformation. The efficiency was even lower when transforming a CRISPR-Cas9 plasmid due to the DSB induced by Cas9. In the previous NHEJ-mediated knockout endeavors, very few colonies were obtained when 1 µg of plasmid DNA was transformed[7]. Such a low efficiency prohibits the development of the multi-locus gene disruption protocol, which is often desired in the complete toolbox. We tested higher voltages, 2 kv and 2.5 kv, and found that 2.5 kv could dramatically increase the transformation efficiency of *S. stipitis* by 25-fold (1.0×10³ cfu/µg for a 10 kb plasmid, Figure S2A). This improvement not only enabled simultaneous double-gene knockout (trp1/ade2) at an efficiency of 40% (Figure S3), and later appeared as a critical improvement for performing the HR-mediated gene disruption because the elimination of the NHEJ mechanism in *S. stipitis* dramatically reduced the number of transformants. At a later stage of our endeavors, the transformation efficiency was improved by 191-fold using 1.38 kv and 1 mm cuvettes.

Knocking Out Ku70/Ku80 Genes to Improve Homologous Recombination

*S. stipitis* is one of the microbial species that rely on NHEJ as the dominant mechanism to repair DSB[8]. Unlike *S. cerevisiae*, in which multi-locus specific genome integration can be achieved via HR-mediated CRISPR editing [9], when a target gene carrying a selection marker is transformed to *S. stipitis*, the selection marker will randomly insert into the genome, sometimes without carrying the target gene along. Even if the target gene is successfully integrated, random genome integration is inevitably associated with expression inconsistency across individual clones due to the genomic context dependency [10]. The location where integration occurs is hard to be traced and varies from one transformation to another. In this regard, site-specific integration is important but cannot be easily accomplished in NHEJ-dominant hosts until HR plays the leading role.

Ku is a dimeric protein complex composed of Ku70 and Ku80 subunits that bind to DSB ends to facilitate NHEJ-mediated genome repair [11]. Deletion of ku genes to impair NHEJ and consequently reinforce HR nowadays becomes a practical solution [8, 12]. We performed two rounds of transformation and sequentially knocked out ku70 and ku80. In the first round, ku70 (N20: actcgaccaaagagaacttg; SEQ ID NO: 51) and ku80 (N20: atttgtaggcatagacttcc; SEQ ID NO: 52) were targeted in two parallel transformations and the DSBs were repaired by NHEJ-mediated indel mutations with high efficiencies (100% and 83%, respectively, Table 1). In the second round, donor DNA fragments had to be provided because the NHEJ mechanism would be impaired post ku70Δku80Δ double knockout. Two donor DNA fragments (namely donor-ku70-50 bp and donor-ku80-500 bp, Table 51) that carried the homologous arms (HAs) of 50 bp and 500 bp flanking the cleavage sites, were transformed to the ku80Δ strain and the ku70Δ strain, respectively, along with the CRISPR-Cas9 plasmid designed to express an appropriate SgRNA. High efficiencies were achieved again (100% and 78%, Table 1), but this time through HR.

Figure 25A:
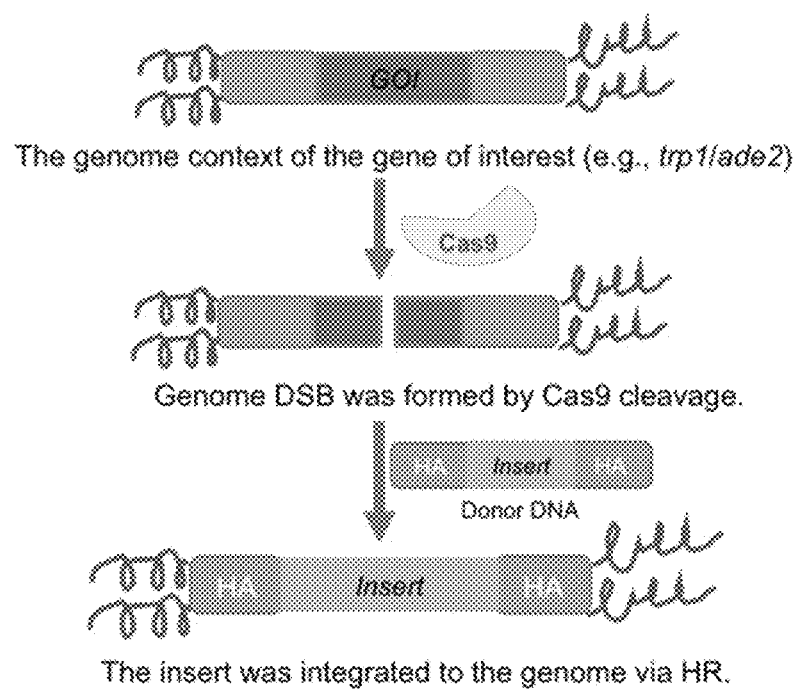
FIGS. 25A-D show establishing the HR-mediated gene knockout tool and the dCas9-mediated gene knockdown tool in *S. stipitis*.

This ku70Δku80Δ strain was subsequently used as a platform to assess the enhancement of the HR-mediated genome editing. We first chose trp1 as the evaluation target, whose disruption will lead to tryptophan auxotrophy. The donor DNA was designed to carry an enhanced green fluorescence protein (eGFP) expression cassette (i.e., Tef1p-eGFP-Pgkt), flanked by HAs (FIG. 25A). We first choose HAs of 50 bp, 100 bp, 500 bp, and 1 kb and transformed each of the integration fragments along with the CRISPR-Cas9 plasmid carrying the SgRNA designed to target trp1 into the ku70Δku80Δ strain. The positives clones were confirmed by colony PCR followed by sequencing. The result showed that very similar HR efficiencies (73%-83%) were obtained among the different HA lengths, and HA-500 bp and HA-1 kb exhibited higher transformation efficiencies (Figure S5). Therefore we chose 500 bp as the desired length and compared to the result obtained with the parental strain without ku gene deletions. It was found that the number of transformants for the ku70Δku80Δ strain was only 6.0% of that obtained from transforming the parental strain without ku gene deletions (FIG. 1B), indicating that the indel mutation efficiency and NHEJ in the ku70Δku80Δ strain were minimized. When the donor DNA was co-transformed with the CRISPR-Cas9 plasmid, the HR-mediated gene knockout efficiency reached 71% in the ku70Δku80Δ mutant strain, representing an improvement of 4.5-fold, compared to the efficiency achieved in the parental strain without ku gene deletion (Table 1 and FIG. 25C).

Figure 25B:
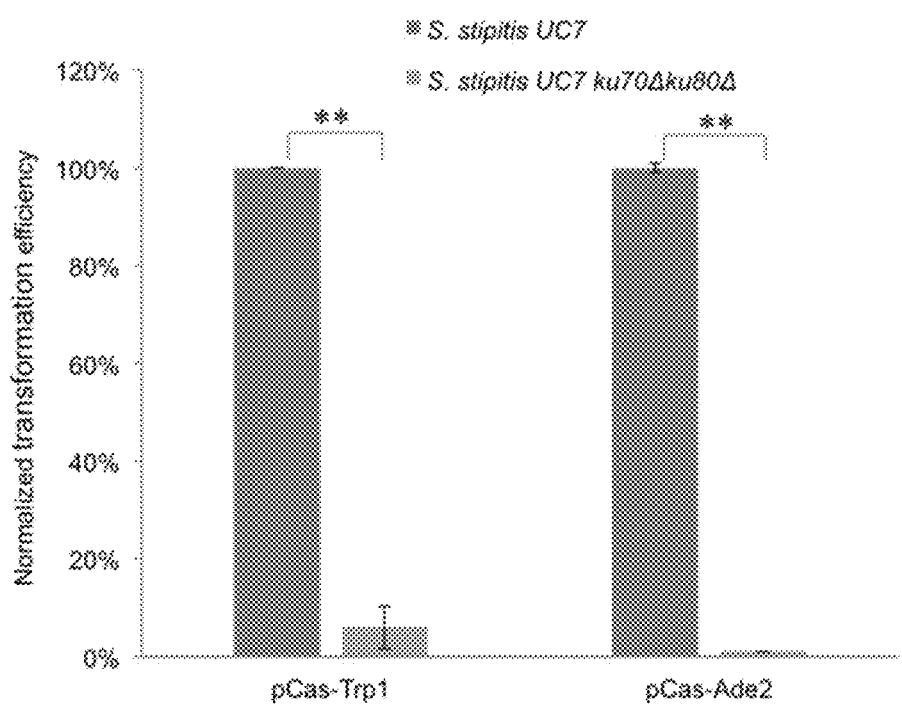
Figure 25C:
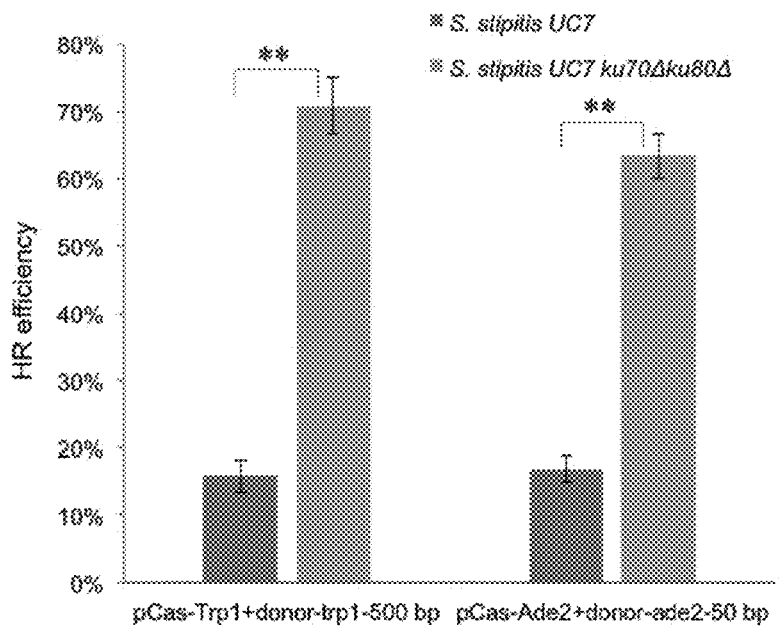
Figure 25D:
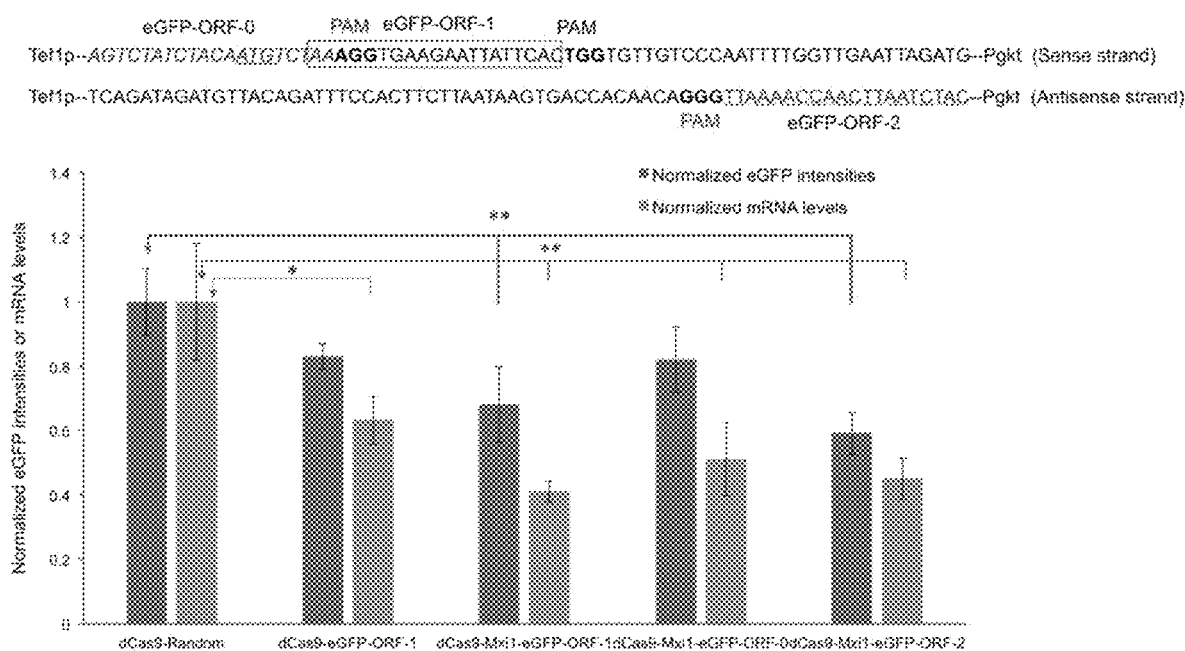
Figure 26A:
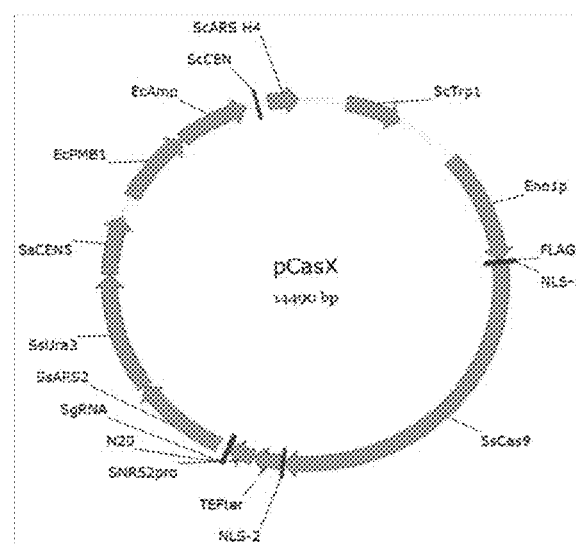
FIGS. 26A-D show plasmid maps of the main Cas9 and dCas9 constructs.
Figure 26B:
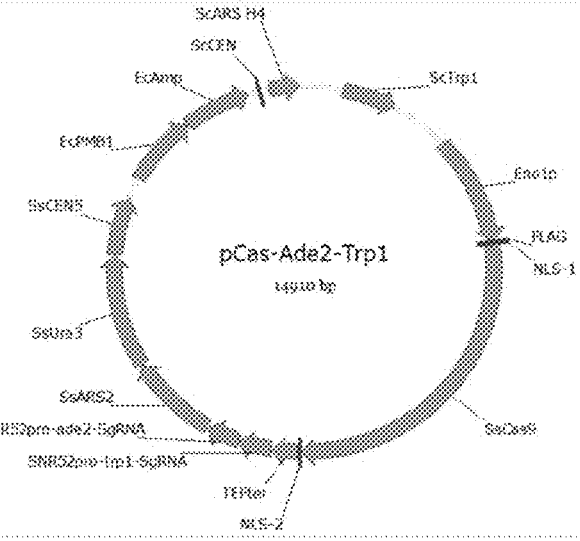
Figure 26C:
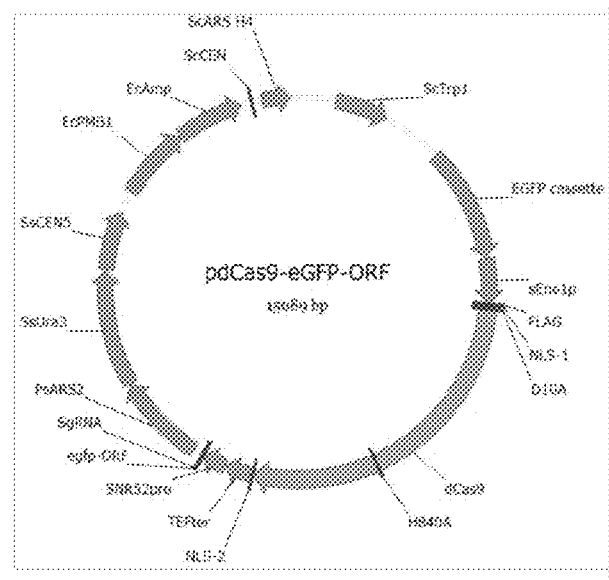
Figure 26D:
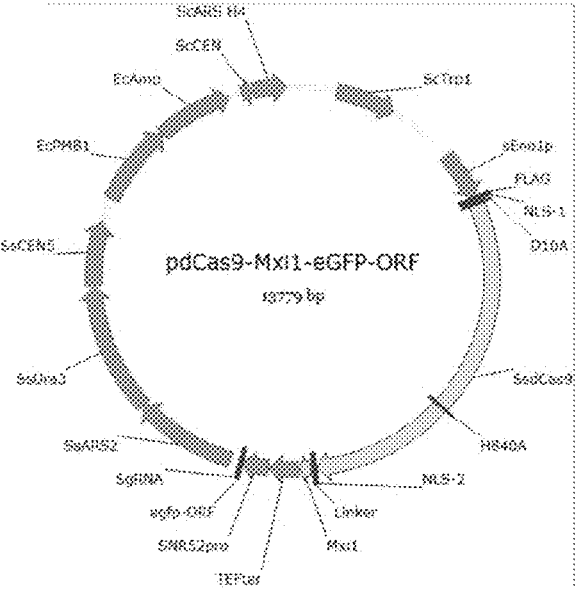
Figure 27A:
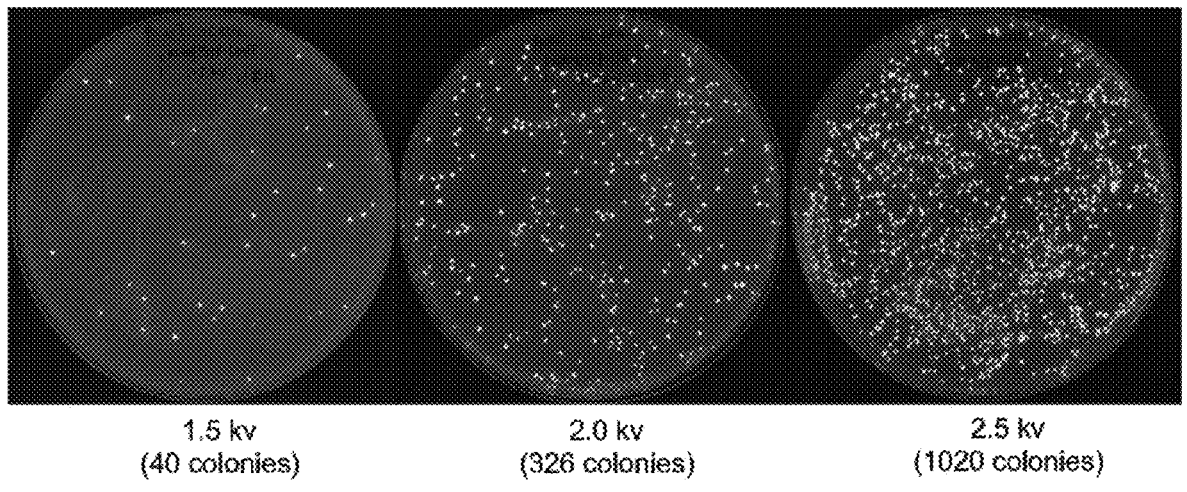
FIG. 27A shows the efficiency of transforming 1 μg of pARS/CEN5-500 bp-eGFP (10 kb) to *S. stipitis* UC7. Three voltages, including 1.5 kv, 2.0 kv, and 2.5 kv, were chosen to test the electroporation efficiency using 2 mm cuvettes.
Figure 27B:
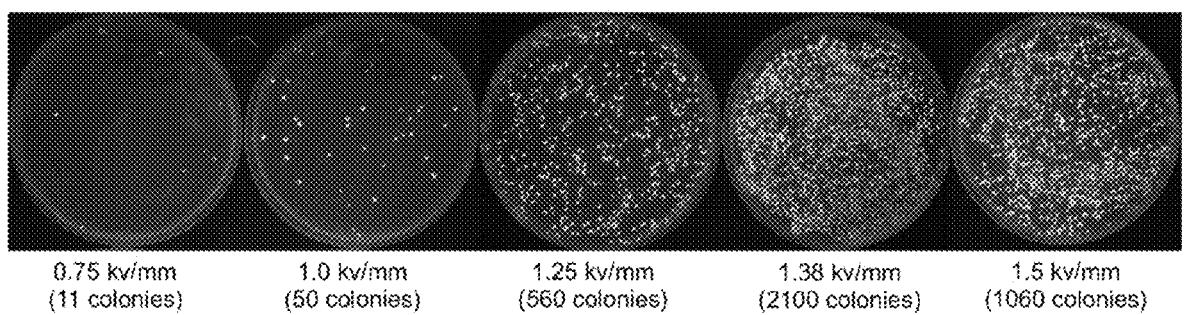
FIG. 27B shows the efficiency of transforming 600 ng of pARS/CEN5-500 bp-eGFP (10 kb) to *S. stipitis* UC7 (data from a later test). Five voltages, including 0.75 kv, 1.0 kv, 1.25, 1.38 kv, and 1.5 kv, were chosen to test the electroporation efficiency using 1 mm cuvettes.
Figure 30A:
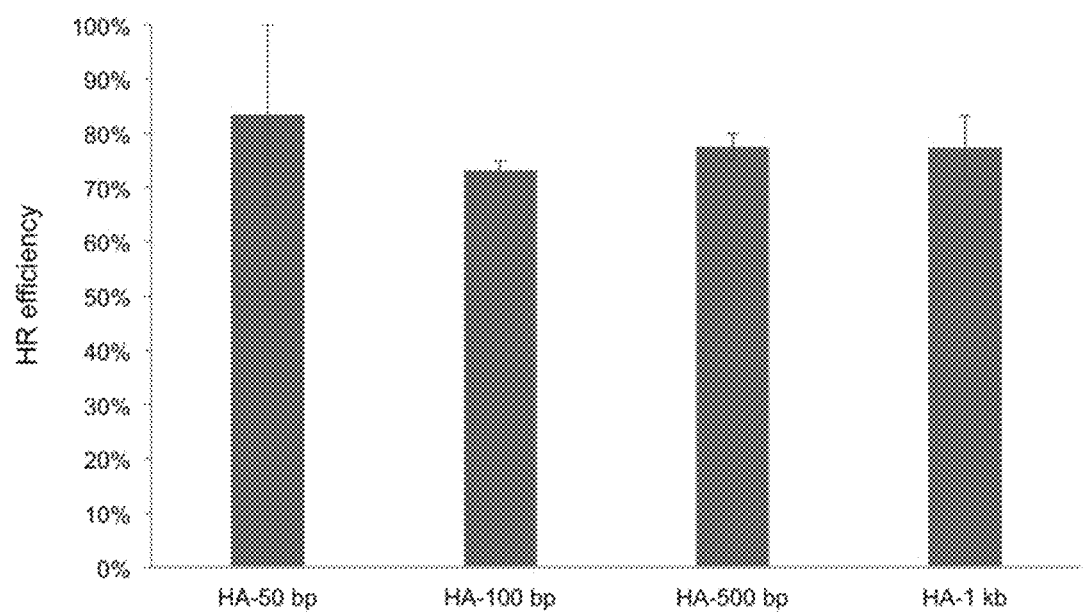
FIGS. 30A-B shows effects of the lengths of the HAs on transformation and HR efficiency. The egfp cassette was integrated to the genome of the ku70Δku80Δ strain, replacing the trp1 gene through the HR mechanism. The positive colonies with eGFP integration were confirmed by colony-PCR (Figure S4B).
Figure 30B:
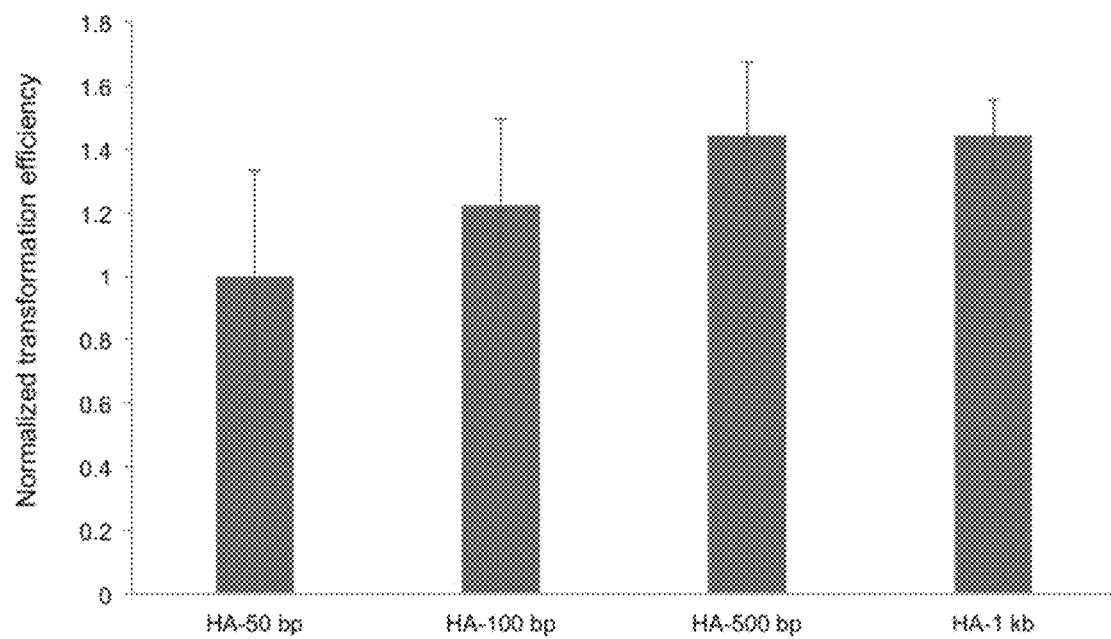

Another locus ade2 was selected to assess the HR-mediated genome editing. Disruption of ade2 grants cells a pink color due to the accumulation of the intermediate phosphoribosylaminoimidazole. Observing the high efficiency obtained with the 50 bp HAs in the trp1 deletion experiment, donor DNA was designed to embed a stop codon between two 50 bp HAs flanking the Cas9 cleavage site and also omitted a single base to generate a frame shift in the open reading frame (ORF) of ade2. Consistent with trp1 deletion, a high HR efficiency of 64% was obtained with the ku70Δku80Δ mutant, representing a 3.8-fold enhancement despite the transformation efficiency dropped to 1% compared to the transformation efficiency achieved in the parental strain without ku gene deletion (FIGS. 25B and 25C). Consistent with the result in the last step of creating the ku70Δku80Δ strain (Table 1), 50 bp HAs were sufficient for HR-mediated DSB repair in S. stipitis.

In eukaryotes, Rad51/Rad52 complex plays an important role in HR-mediated DNA repair. However, literature did not provide consistent answers regarding the benefit of overexpressing Rad51 and/or Rad52 to promote HR [11, 13, 14]. We also attempted the overexpression of Rad proteins in the ku70Δku80Δ strain. Since the proposed homologs from S. stipitis share merely 27% and 32% similarity with Rad51 and Rad52 from S. cerevisiae in which HR is the dominant mechanism for DSB repair, the codon-optimized rad51 and rad52 genes from S. cerevisiae were overexpressed separately and in combination in the ku70Δku80Δ strain. However, no obvious improvement in HR efficiency was observed. DSB repair in eukaryotes is tightly regulated by Ku, Rad, and other recombinases and binding proteins. Therefore, either low-level expression of the Rad proteins in S. stipitis is not the limiting factor or S. stipitis uses a completely different mechanism to conduct HR. Another possibility is that overexpression of Rad proteins may interfere the normal chromosomal recombination [11, 13, 14]. In this scenario, promoters of different strengths might be helpful to fine-tune Rad expression to stimulate HR at an appropriate level.

Enabling Gene Repression by CRISPR-dCas9

In many synthetic biology and metabolic engineering applications, gene repression or knockdown, rather than knockout, is needed. Elimination of genes essential for metabolism is not always feasible, because such deletion would be lethal to the cells [15, 16]. To address this issue, CRISPR interference (CRISPRi) has been developed as an efficient, tunable, and reversible tool for executing transcription repression [17] and regulating metabolic networks [15, 18-20]. In CRISPRi, the mutant dCas9 lacking the endonuclease activity but still retaining the DNA binding capability replaces Cas9 as the key functional unit.

We introduced D10A and H840A mutations to the active sites of Cas9[16] and developed the CRISPR-dCas9 version specific for S. stipitis. The Tef1p-eGFP-Pgkt expression cassette that was integrated to the genome (trp1Δ::egfp) was used as a reporter to monitor the repression efficiency of dCas9. An N20 sequence (aaaggtgaagaattattcac; SEQ ID NO: 53, FIG. 1D, and Table S1) targeting the ORF 4-23 bp downstream of the eGFP start codon was used to create the plasmid, pdCas9-eGFP-ORF-1 (FIG. 51). A control plasmid, pdCas9-Random, was designed with one random 8 bp sequence (tcaggtac) replacing the N20 in the plasmid pdCas9-eGFP-ORF-1. Furthermore, to enhance dCas9 repression activity, we fused a well-characterized transcription repressor, Mxi1 [21], to the C-terminal of dCas9 via a GSS linker composed of 11 amino acids (GSSKLGGSGGS; SEQ ID NO: 45) with the resulting plasmid named pdCas9-Mxi1-eGFP-ORF-1. As a result, pdCas9-eGFP-ORF-1 repressed eGFP expression by 17%, whereas pdCas9-Mxi1-eGFP-ORF-1 repressed eGFP expression by 32% when compared to the control strain transformed with the pdCas9-Random plasmid, indicating Mxi1 could enhance dCas9 repression by 1.9-fold (FIG. 1D and Table S3).

It has been previously noted that an N20 sequence targeting the promoter region could be associated with stronger repression [18, 22, 23]. However, we did not target the Tef1 promoter that drove eGFP expression here, because repression could also occur at the native tef1 gene (encoding the essential translation elongation factor), which presumably would cause the deficient cell growth. Moreover, considering that the binding of dCas9 to the N20 sequence and the target locus is the most important parameter that affects repression efficiency [18, 24], we choose two more loci, one covering the start codon of egfp (eGFP-ORF-0, N20: agtctatctacaatgtctaa; SEQ ID NO: 54), the other sitting 36-55 bp downstream of ATG (eGFP-ORF-2, N20: catctaattcaaccaaaatt; SEQ ID NO: 55, Table 1 and Table S1). Compared to the eGFP-ORF-1 region, targeting the eGFP-ORF-2 region from the antisense strand granted the greatest repression on eGFP fluorescence (FIG. 1D and Table S3). Lastly, to prove that the repression was indeed mediated at the transcriptional level by dCas9-Mxi1, real-time PCR was performed with the results largely consistent with the eGFP expression evaluated by flow cytometry analysis (FIG. 1D and Table S3).

TABLE 11

Gene knockout efficiency by CRISPR-Cas9 in *S. stipitis*.

| Target gene | Host strains | Donor DNA (DSB repair mechanism) | Knockout efficiency (the number of the positive clones/total colony number) |
|---|---|---|---|
| ku70Δ | *S. stipitis* UC7 | No (NHEJ) | 100% (4/4) |
| ku80Δ | *S. stipitis* UC7 | No (NHEJ) | 83% (5/6) |
| ku80Δ | *S. stipitis* UC7 ku70Δ | donor-ku80-500 bp (HR) | 78% (7/9) |
| ku70Δ | *S. stipitis* UC7 ku80Δ | donor-ku70-50 bp (HR) | 100% (3/3) |
| trp1Δ | *S. stipitis* UC7 ku70Δ ku80Δ | donor-trp1-500 bp-egfp (HR) | 71% (5/7) |
| ade2Δ | *S. stipitis* UC7 ku70Δ ku80Δ | donor-ade2-50 bp (HR) | 64% (14/22) |

TABLE 12

Strains and plasmids used in this study.

| Strains/plasmids | Features | Sources |
|---|---|---|
| Strains | 1 | 1 |
| *S. stipitis* UC7 | ura3-3, NRRL Y-21448, host for most plasmids in this study | [25] |
| *S. stipitis* UC7 ku70Δ | Derived from *S. stipitis* UC7, with ku70 knocked out | This study |
| *S. stipitis* UC7 ku80Δ | Derived from *S. stipitis* UC7, with ku80 knocked out | This study |
| *S. stipitis* UC7 ku70Δ ku80Δ | Derived from *S. stipitis* UC7, with ku70 and ku80 knocked out | This study |
| *S. stipitis* UC7 kuΔ trp1Δ::egfp | Derived from *S. stipitis* UC7 ku70Δ ku80Δ, with egfp integrated to the trp1 locus | This study |
| Plasmids | | |
| pARS/CEN5-500bp-eGFP | eGFP expression plasmid, used for electroporation efficiency testing | [7] |
| pCas-Ku70 | CRISPR plasmid containing SNR52 promoter upstream of the SgRNA designed to target ku70, used for ku70-deficient strain construction | This study |
| pCas-Ku80 | CRISPR plasmid targeting ku80, used for ku80-deficient strain construction | This study |
| pCas-Ade2 | CRISPR plasmid targeting ade2, used for ade2 gene editing | [7] |
| pCas-Trp1 | CRISPR plasmid targeting trp1, used for trp1 gene editing | [7] |
| pCas-Ade2-Trp1 | CRISPR plasmid targeting ade2 and trp1, used for double-gene knockout | This study |
| pdCas9-Random | CRISPR-dCas9 plasmid, with a random 8 bp sequence (tcaggtac) replacing the N20 sequence as a control plasmid | This study |
| pdCas9-eGFP-ORF-1 | CRISPR-dCas9 plasmid (Cas9 mutated at D10A/H840A) targeting the egfp-ORF-1 locus | This study |
| pdCas9-Mxi1-eGFP-ORF-0, 1, or 2 | dCas9 fused with the transcription repressor Mxi1, targeting the locus egfp-ORF-0, 1, or 2 | This study |

Supporting Information

TABLE S1

The sequences of the key genetic elements in this work.

| Genetic elements | Sequences (5'→3') |
|---|---|
| SNR52-pro (SEQ ID NO: 41) | tggagggaatcctaggataaaaacctccgaatgacattacctaaaaaaacacataagtgatat ctttggaaagcaacagaagttacaactattttattttattttacacgtgactgaccgcgtgattaggcacgtg actaatcacgtgctgtataatgacaattggagtgaatgtgtaattttgtgcgatattttgctggatggcgcat tcgctggaccggcggcgagtttggagttcccgtcagctgacggtgcctttgaacgagtcgcaggttcgtttccaa caagatacatttatttc |
| dCas9-linker-Mxi1 (codon-optimized) (SEQ ID NO: 42) | atggactacaaggatgacgatgacaagcctccaaagaaaaagagaaaggttgacaagaa gtactctatcggttttggctatcggcactaactctgttggttgggctgttatcactgacgagtacaaggtccca tccaagaagttcaaggtcttgggtaacaccgacagacactccatcaagaagaacttgatcggcgccttgtt gttcgactctggtgaaactgctgaagccaccagattgaagagaaccgccagaagaagatacaccagaag aaagaacagaatctgctacttgcaagagatcttctccaacgaaatggccaaggtcgacgactcgttcttcc acagattggaagaatccttcttggtcgaagaggacaagaagcacgaaagacacccaatctcggtaaca tcgttgacgaagtcgcctaccacgaaaagtacccaaccatctaccacttgagaaagaagtggtcgactct |

TABLE S1-continued

The sequences of the key genetic elements in this work.

| Genetic elements | Sequences (5'→3') |
|---|---|
| | accgacaaggccgacttgagattgatctacttggctttggcccacatgatcaagttcagaggtcacttcttg<br>atcgagggcgacttgaacccagataactctgacgttgacaagttgttcatccagttggtccagacctacaa<br>ccagttgttcgaagaaaacccaatcaacgcttctggtgtcgacgctaaggctatcttgtctgccagattgtc<br>caagtccagaagattggaaaacttgatcgcccagttgccaggcgaaaagaagaacggtttgttcggcaac<br>ttgatcgctttgtccttgggcttgaccccccaacttcaagtctaacttcgacttggctgaggacgccaagttgc<br>agttgtctaaggatacttacgacgacgacttggacaacttgttggctcaaatcggtgaccagtacgctgac<br>ttgttcttggctgctaagaacttgtctgacgccatcttgttgtccgacatcttgagagtcaacaccgaaatca<br>ccaaggccccattgtctgcctctatgatcaagagatacgacgaacaccaccaggacttgaccttgttgaag<br>gctttggttagacagcagttgcccgagaagtacaaagaaatcttcttcgaccagtccaagaacggttacgc<br>tggttacatcgatggtggtgcctcccaagaagagttctacaagttcatcaagcccatcttggaaaagatgg<br>acggcaccgaagagttgttggtcaagttgaacagagaggacttgttgagaaagcagagaaccttcgaca<br>acggttctatcccacatcagatccacttgggtgaattgcacgccatcttgagaagacaagaggacttctac<br>ccattcttgaaggacaacagagaaaagatcgagaagatcttgaccttcagaatcccctactacgtcggtcc<br>attggccagaggtaattctagattcgcctggatgaccagaaagtccgaagaaactatcacccctggaac<br>ttcgaagaagttgttgataagggcgcctccgcccagtctttcatcgaaagaatgaccaacttcgacaagaa<br>cttgcccaacgagaaggtcttgccaaagcactccttgttgtacgagtacttcaccgtctacaacgagttgac<br>caaggtcaagtacgtcaccgaaggtatgagaaagccagccttcttgtctggtgaacagaagaaggctatc<br>gtcgacttgttgttcaagaccaacagaaaggtcaccgtcaagcagttgaaagaggactacttcaagaaaa<br>tcgagtgcttcgactccgtcgaaatctctggtgtcgaagatagattcaacgcctccttgggtacttaccacg<br>acttgttgaagatcatcaaggacaaggattcttggacaacgaagagaacgaggacatcttggaggacat<br>cgtcttgacttttgaccttgttcgaggacagagagatgatcgaagagagattgaaaacctacgcccacttgt<br>tcgacgacaaggtcatgaagcagttgaagagaagaagatatccggctggggcagattgtccagaaagt<br>tgatcaacggtatcagagacaagcagtccggcaagactatcttggacttcttgaagtctgacggcttcgcc<br>aacagaaacttcatgcagttgatccacgacgaattccttgaccttcaaagaggacatccagaaggctcaag<br>tttctggtcaaggtgactccttgcacgaacatatcgctaacttggctggttctccagccatcaagaagggta<br>tcttgcagactgttaaggtcgtcgacgaattggtgaaggtcatgggtagacacaagccagagaacatcgt<br>catcgaaatggctagagaaaaccagaccaccccagaagggtcagaagaactccagagaaagaatgaag<br>agaatcgaagagggcatcaaagagttgggctcccagatcttgaaagaacacccagtcgaaaacacccag<br>ttgcagaacgagaagttgtacttgtactacttgcagaacggcagagacatgtacgtcgaccaagagttgg<br>acatcaacagattgtctgactacgacgttgacgctatcgtcccccaatctttcttgaaggatgactccatcg<br>acaacaaggtcttgaccagatccgacaagaacagaggtaagtctgacaacgttccatccgaagaggtcg<br>tcaagaagatgaagaactattggagacagttgttgaacgccaagttgatcacccagagaaagttcgaca<br>acttgactaaggccgaaagaggtggtttgtctgaattggacaagagccggcttcatcaagagacagttggtc<br>gaaactagacagatcaccaagcacgtcgctcagatcttggactccagaatgaacaccaagtacgacgag<br>aacgacaagttgattagagaggtcaaggtcatcaccttgaagtccaagttggtgtccgacttcagaaagg<br>acttccagttctacaaggtcagagagatcaacaactaccaccacgctcatgacgcttacttgaacgctgtt<br>gtcggtactgccttgatcaagaagtacccaaagttggaatccagatcgtctacggtgactacaaggtcta<br>cgacgtcagaaagatgatcgccaagtccgaacaagaaatcggtaaggctaccgccaagtacttcttctac<br>tccaacatcatgaatttcttcaagaccgagatcaccttggccaacggcgagatcagaaaaagaccattga<br>tcgaaactaacggcgaaaccggtgaaatcgtttgggataagggtagagacttcgccaccgtcagaaagg<br>ttttgtctatgccccaggtcaacatcgtcaagaaaactgaagtccagaccggcggcttctccaaagaatct<br>atcttgccaaagagaaactcggacaagttgatcgccagaaagaaggactgggacccaaagaaatacgg<br>tggttcgactctccaaccgtcgcttactctgttttggttgtcgctaaggtcgagaagggcaagtctaagaa<br>gttgaagtccgtcaaagagttgttgggcatcaccatcatggaaagatcgtccttcgagaagaacccaatcg<br>acttcttggaagccaagggctacaaagaggtgaagaaggacttgatcatcaagttgcccaagtactcgtt<br>gttcgagttggagaacggtagaaagagaatgttggcttccgctggtgaattgcagaagggtaacgaattg<br>gccttgccctccaagtacgtcaacttcttgtacttggcctcccactacgaaaagttgaagggttcccctgaa<br>gataacgagcagaagcagttgttcgtcgagcagcataagcactacttggacgaaatcatcgagcagatct<br>ccgagttctctaagagagtcatcttggctgacgccaacttggacaaggtcttgtctgcttacaacaagcac<br>agagacaagccaatcagagagcaggccgaaaacatcatccacttgttcactttgaccaacttgggtgctc<br>agctgcttttcaagtacttcgacactaccatcgacagaaagagatacacctccaccaaagaagtcttgga<br>cgctaccttgatccaccagtctatcactggcttgtacgaaaccagaatcgacttgtctcaattgggtggtga<br>*cgatcctaagaagaaaagaaaagtt*ggtagttccaagcttggcggcagcggcggcagcatggaaaga<br>gtcaagatgatcaacgtccagagattgcttgaagccgccgaattcttggagagaagagaaagagaatgc<br>gaacacggctacgcctcttcattcccatctatgccatctccaagaggctga<br>FLAG: DYKDDDDK (underlined sequence; SEQ ID NO: 43); NLS:<br>P/DPKKKRKV (italic sequence; SEQ ID NO: 44); Linker: GSSKLGGSGGS (bold<br>sequence; SEQ ID NO: 45) |
| donor-<br>trp1-500 bp-egfp<br>(SEQ ID NO: 47) | *aactacagctcactctagatgatggtaccttgacaaaccaaaaccagttactatctaattta<br>gaagacgaagaagagtcgggatcggttagtatttctcaggtcagcacacctacccccagactttaagt<br>caccaaaattgcttcctacgaaaatcaacaactttgagaaaaatctccgagaatttgctctatcactgga<br>gaaagccatgtcaataagttaaacgagaacttcaagaactttggtaagttcttcagaaaggataacg<br>actagcatagatagtttatatagctttggttatatatggttgtatatgcagtattccatcaaaatcatta<br>gtcataagatttagagggttatacaaaatttaatagctttacttctatcttcaaaagtcattggatatgcc<br>caaaattgtaaagatatgtggaaccagaacagttgaagctgctgctaaagctatagagtcaggaac<br>ggatttactcggggtaattcttgtaccc*attcatgaagtacgataaggttggtaaccgattgactcattgg<br>ttcgtggcggagaagtacgcagagtaaaaccggggccgattcgtggtaaattctggaatgatccagaggc<br>gcgacatttatgcagacaatttgtgttttgtcgcaaacgatgttatagcgaaatttttcactctgtcagataa<br>atggattttgtcaaaaggggaagtagaaggagaatctccgagatgttctgccaaattctcagtagca<br>taatgtgaaagaagcccttcacttgtccagcctctggcatcattaaaaaccgtagcggaaaccaattgtct<br>ctgttcttccctggcacaccctggtagcccatccagttgtagtacatctcacacgctggcaacttgggaca<br>atcagcaactttttttttctttttaattttttcagcgcgacattttgcctcttctgcgagaacagacttttcacctc<br>catctcaccccctttgcacttatataaattggaccagttcctcccattgtagaaaaattttgctggacctttt<br>ttctcttttttttgtccttagtttcatacaatcta*agtctatcacaatgtctaaaggtgaagaattattca |

TABLE S1-continued

The sequences of the key genetic elements in this work.

| Genetic elements | Sequences (5'→3') |
|---|---|
| | *ctgg*tgttgt*cccaattttggttgaattagatg*gtgatgttaatggtcacaaattttctgtctccggtgaag<br>gtgaaggtgatgctacttacggtaaattgacctttaaaatttatttgtactactggtaaattgccagttccatg<br>gccaaccttagtcactactttcggttatggtgttcaatgttttgctagataccagatcatatgaaacaacat<br>gactttttcaagtctgccatgccagaaggttatgttcaagaaagaactatttttttcaaagatgacggtaac<br>tacaagaccagagctgaagtcaagtttgaaggtgataccttagttaatagaatcgaattaaaaggtattg<br>attttaaagaagatggtaacattttaggtcacaaattggaatacaactataactctcacaatgtttacatca<br>tggctgacaaacaaaagaatggtatcaaagttaacttcaaaattagacacaacattgaagatggttctgtt<br>caattagctgaccattatcaacaaaatactccaattggtgatggtccagtcttgttaccagacaaccattac<br>ttatccactcaatctgccttatccaaagatccaaacgaaaagagagaccacatggtcttgttagaatttgtt<br>actgctgctggtattacccatggtatggatgaattgtacaaataattgatgtaagactttaattataagaat<br>acaattgtgataaagacaatgtagaagtactgtagaagtcatggaatagctgatcaactgtactgttatac<br>aaaggtactattaacaaaatagacatatagtttctataacatatataaacatcttattaggattcgatgtc<br>*agcggaggtgtagaggatctgaatggagataaggatttgcaaaaagttgaggatttcattaagatt<br>ggaaagactttatagatgtaaatagtgttaatgatatatgattattagcatgattttgcgtagagtgtg<br>ttcaagcgttaggtgggatattttgatacggttaacattttctactacgacgtactttctactatactttatt<br>cctttgctttaatattttttattactaaaatgcacttattgcggtatctgaatttaatcatcttgatcccagtt<br>accaggtctaggctgcttttggcatctgagggcctccagctctcttggccatgatgatttgatctatagac<br>aatatggtgttggtggcatctcacagccaagttaatggcagacttcttactggagtacaagtcgtagat<br>accagcttgggtgacatcaagtaaatcgtcattgtcgatgtcgataccgaggttgatgttgtc*<br>500 bp upstream and downstream sequences of trp1 gene (italic sequences); egfp expression cassette: Tef1p-egfp-Pgkt (underlined sequence)<br>N20 + PAM of pdCas9-Mxi1-eGFP-ORF-1 (green, italic and bold sequence): aaggtgaagaattattcactgg; SEQ ID NO: 56; N20 + PAM of pdCas9-Mxi1-eGFP-ORF-0 (purple, italic and bold sequence): agtctatctacaatgtctaaaagg; SEQ ID NO: 57; N20 + PAM of pdCas9-Mxi1-eGFP-ORF-2 (red, italic and bold sequence): 5'-catctaattcaaccaaaattggg (SEQ ID NO: 58; based on the antisense strand) |
| donor-ade2-50 bp (SEQ ID NO: 46) | ttaacattaacacagttatcttggatgccccaactctt<u>tag</u>cgaaacagatcaacgcagtgagt<br>gaccatgttgatggctctttcacacactatgagtct<br>The original CCTG was mutated to TAG- (stop codon, and omitting 1 bp, underlined sequence) |
| donor-ku70-50 bp (SEQ ID NO: 48) | aagtgctttggtttactacaaacgacaagccatacaccaagaactcgacc<u>taatag</u>gcgtatta<br>tcaacgattactataactatggctactttattcgtc<br>The mutations in the donor DNA: AAAGAGAACTTGTG (SEQ ID NO: 49) to TAATAG-------- (two stop codons, and omitting 8 bp, underlined sequence) |
| donor-ku80-500 bp (SEQ ID NO: 50) | *cacaagattccaaacgatatagagccgaatgggaaaaaagattccaattataagcctaa<br>cacagagatgacaaaaacagcaagcttgctctcctacgtttcttcaagtcttgacataagggtattcttt<br>agtattgcagtgcgcattacttctataaactttgtttttatgatcacgtgaatatgtacagagatttatgc<br>acttcaggcacgtctggttcttgattgtaattcaaacgtcttctgtagcctattatacaatttaaaaccaa<br>ttgactccccaaccatgctgtccaaagagatgacgttcttcgtcattgataccacactggagatggtca<br>ataggtcaaatcccgtttcaaaaagatcaagccttgagagaggattaggctactttcatgatcatact<br>gcgactctattgcttaagaacaggaagattgaccgcgtaggcataatttgtgcctcagatgctggtaa<br>ccatgtctacagtgctgatgaggc*<u>cattcgagcgatatttccaagacattgatcgatgccttgatgtgaa<br>atatcttgagaaggacgagaagaaacacaagcgtcgtaagtacgaaggaactgcattcgaacgattcttc<br>cgtaatgaaggcgactctgcgaactccgatatgaaggctgactttgatgaattttttcgacgttaaagactta<br>ttgggtgggtagtatagatagtaaataaagggtcaatattggtactcaatacctgaaagctgttagttctat<br>gtacatgattcttactaatatttaaacaaacgattttcaaatcgtattccctatcctttgctgttctccttct<br>atgttttgatctagcggtaccgtcttcccccaaactatttacaatttttcggataccttcatggttgtaaccc<br>gttcccttttcgttcttgaagatctgtttgaggtcgtttccattgatgtccaagatggcttgcaagtcaaagac<br>agccttatatttctggga</u><br>500 bp upstream sequence of ku80 gene (italic sequence); 500 bp downstream sequence of ku80 gene (underlined sequence) |

TABLE S2

List of the main primers used for confirming genome editing and creating the dCas9 mutant. The bold and underlined letters mark the mutations in Cas9.

| Name | Sequence (5'→3') |
|---|---|
| trp1-PCR-F/HR-P1-F | Gatatgtggaaccagaacag (SEQ ID NO: 59) |
| trp1-PCR-R/HR-P1-R | ccaatcttaatgaaatcctc (SEQ ID NO: 60) |
| ade2-PCR-F | Cctcttctagaacacgttcttagtc (SEQ ID NO: 61) |

TABLE S2-continued

List of the main primers used for confirming genome editing and creating the dCas9 mutant. The bold and underlined letters mark the mutations in Cas9.

| Name | Sequence (5'→3') |
|---|---|
| ade2-PCR-R | ccaaggatctgacaaccatcac (SEQ ID NO: 62) |
| HR-P2-F | Cttgttgaaggtcttgatgg (SEQ ID NO: 63) |
| HR-P2-R | tgacctaaaatgttaccatc (SEQ ID NO: 64) |
| ku70-PCR-F | Gtttgaaatcctcagctcca (SEQ ID NO: 65) |
| ku70-PCR-R | cctctggtgtataacatgag (SEQ ID NO: 66) |
| ku80-PCR-F | Aggattaggctactttcatg (SEQ ID NO: 67) |
| ku80-PCR-R | tcctgttctccagccatttc (SEQ ID NO: 68) |
| qPCR-alg9-F | Taggcttgacatttggactctac (SEQ ID NO: 69) |
| qPCR-alg9-R | tattggctgttgtaggtgtagtc (SEQ ID NO: 70) |
| qPCR-egfp-F | ctttcggttatggtgttcaatgt (SEQ ID NO: 71) |
| qPCR-egfp-R | aactacaagaccagagctgaag (SEQ ID NO: 72) |
| dCas9-D10A-F | ggttgacaagaagtactctatcggtttggctatcggcactaactctgttggttgggctgt; (SEQ ID NO: 73) |
| dCas9-D10A-R | acagcccaaccaacagagttagtgccgatagccaaaccgatagagtacttcttgtcaacc (SEQ ID NO: 74) |
| dCas9-H840A-F | caacagattgtctgactacgacgttgacgctatcgtcccccaatctttcttgaaggatga; (SEQ ID NO: 75) |
| dCas9-H840A-R | tcatccttcaagaaagattgggggacgatagcgtcaacgtcgtagtcagacaatctgttg (SEQ ID NO: 76) |

TABLE S3

Gene repression by dCas9 and dCas9-Mxi1 in *S. stipitis* UC7 kuδtrp1δ::epfp strain.

| The transformed plasmids | Cell density (OD$_{600\ nm}$) | Normalized eGFP expression | Normalized mRNA level |
|---|---|---|---|
| dCas9-Random | 6.50 ± 0.82 | 1.00 ± 0.10 | 1.00 ± 0.18 |
| dCas9-eGFP-ORF-1 | 6.50 ± 0.63 | 0.83 ± 0.04 | 0.63 ± 0.07 |
| dCas9-Mxi1-eGFP-ORF-1 | 6.18 ± 0.72 | 0.68 ± 0.12 | 0.41 ± 0.03 |
| dCas9-Mxi1-eGFP-ORF-0 | 7.66 ± 0.42 | 0.83 ± 0.10 | 0.51 ± 0.11 |
| dCas9-Mxi1-eGFP-ORF-2 | 5.69 ± 0.19 | 0.59 ± 0.06 | 0.45 ± 0.06 |

Materials and Methods (1) Strains, Media, and Chemicals

The strains used in this study are listed in Table 2. *E. coli* transformants were grown in LB media supplemented with 100 μg/mL ampicillin. *S. cerevisiae* YSG50, *S. stipitis* UC7, and its mutants were propagated at 30° C. in YPAD media (1% yeast extract, 2% peptone, 0.01% adenine hemisulphate, and 2% dextrose). Yeast transformants were cultured or selected in the Synthetic Complete dropout media lacking uracil, tryptophan, leucine or with a low concentration of adenine (~10 mg/L) (corresponding to SC-URA, SC-TRP, SC-LEU, or SC-ADE). DNA polymerase and restriction enzymes were purchased from Thermo Scientific (Waltham, Mass.). DNA extraction and purification kits were purchased from Zymo Research (Irvine, Calif.). All the other chemicals were purchased from Fisher Scientific (Pittsburgh, Pa.). Oligonucleotides including gBlocks and primers were all synthesized by Integrated DNA Technologies (IDT, Coralville, Iowa). Mxi1 was codon-optimized and synthesized by Life Technologies (Carlsbad, Calif.).

(2) Plasmid Construction

All the plasmids constructed in this study (Table 2) were derived from the previously developed pCas-Ade2 vector[1]. The DNA assembler technique[2-4] was implemented to assemble various constructs. Briefly, the gene fragments with overlapping ends were co-transformed with a digested plasmid backbone into *S. cerevisiae* via electroporation method. The isolated yeast plasmids were then transformed into *E. coli* for enrichment, and their sequences were verified by restriction digestion or sequencing. The correctly assembled plasmids were subsequently transformed into *S. stipitis* for expression. For the construction of a gene knockout plasmid, a gBlock composed of the SNR52 promoter and SgRNA was assembled into the pCas9 backbone, which was obtained from pCas-Ade2 digested by NcoI and PstI. Key primer sequences, codon-optimized genes, and plasmid maps are summarized in Supporting Information Table S1, Table S2, and FIG. 26.

(3) Yeast Transformation and Mutant Screening

Different electroporation voltages (1.5 kv, 2.0 kv, and 2.5 kv), were utilized to evaluate the transformation efficiency of S. stipitis. One microgram of plasmid pARS/CEN5-500 bp-eGFP (Table 2) was electroporated using 2 mm cuvette and the transformants were spread on SC-URA solid media. The transformation efficiency was later further improved by using 2.75 kv and 1 mm cuvette. For gene knockout studies, the transformants were first spread on SC-URA solid media to select transformants carrying the CRISPR plasmid, and then re-streaked on SC-ADE (for ade2Δ screening) and SC-TRP (for trp1Δ screening). The indel mutations were confirmed by colony PCR and sequencing of the target loci (See primer sequences in Table S2). For eGFP integration mutants, the colonies were pre-screened using a DR46B Transilluminator (Clare Chemical Research, Dolores, Colo.), and confirmed by flow cytometry and DNA sequencing. For sequential knockout of ku70 and ku80 genes, the first-round CRISPR plasmids were cured by culturing in YPAD media and screened on SC solid media supplemented with 5-fluoroorotic acid (FOA) at 1 g/L. The second-round CRISPR plasmids were electroporated together with 300-500 ng of donor DNA fragments to the ku70 and ku80 mutant strains in parallel. For the transformation efficiency, gene knockout efficiency and homologous recombination (HR) efficiency experiments, three independent biological replicates were run. Student's t-test was employed to analyze the significant difference between S. stipitis UC7 and S. stipitis UC7 ku70Δku80Δ.

(4) CRISPR-dCas9-Mediated Gene Repression

Following CRISPR-Cas9 design[1], pdCas9 was expressed under the Eno1 promoter and Tef1 terminator. The two mutations, D10A and H840A, were introduced into Cas9 via PCR primers D10A-F/D10A-R and H840A-F/H840A-R (Table S2). The amplified fragments, together with the SgRNA carrying the negative control 8 bp random sequence or the N20 sequence targeting at egfp-ORF were assembled to the pCas-Ade2 backbone digested by ApaI and NcoI, and the resultant vectors were named as pdCas9-Random and pdCas9-eGFP-ORF. In addition, the codon-optimized Mxi1 sequence was fused to dCas9 at the C-terminal through a linker of 11 amino acids (GSSKLGGSGGS; SEQ ID NO: 45), resulting in pdCas9-Mxi1-eGFP-ORF (FIG. 26). The plasmids were electroporated to S. stipitis UC7 kuΔtrp1Δ::egfp strain, and the repression of eGFP expression was monitored by a fluorescence plate reader (BioTek, Winooski, Vt.) and a flow cytometer. The flow cytometry analysis was performed at 488 nm on a FACSCanto flow cytometer (BD Biosciences, San Jose, Calif.), and the fluorescence intensity distribution was calculated by the software BD FACSCanto Clinical. qPCR was performed on a StepOnePlus System (Life Technologies, Carlsbad, Calif.) following the previously reported protocol [1]. Briefly, $2\times10^7$ yeast cells were harvested and digested by Zymolyase, and followed by RNA extraction using QIAGEN RNeasy Mini Kit (Hilden, Germany). The RNA was first treated by DNase I (TURBO DNA-Free™ Kit) to remove genomic DNA, and then reversely transcribed to cDNA using Thermo Scientific RevertAid First Strand cDNA Synthesis Kit. qPCR was performed using SYBR green detector and the primers for alg9 as the internal control and egfp as the target, with the following condition: 50° C. for 2 min, 95° C. for 10 min, 40 cycles of 95° C. for 15 sec and 60° C. for 1 min, and a final dissociation stage at 95° C. for 15 sec, 60° C. for 15 sec and 95° C. for 15 sec. Data were analyzed using the ΔΔCT method. The significant difference was measured through the Student's t-test between the random sequence and the individual locus of egfp-ORF targeted by dCas9 or dCas9-Mxi1. For the transcriptional repression, 3 independent biological replicates were used.

REFERENCE

[1] Cao, M., Gao, M., Lopez-Garcia, C. L., Wu, Y., et al., Centromeric DNA facilitates nonconventional yeast genetic engineering. *ACS Synth Biol* 2017, 6, 1545-1553.

[2] Shao, Z., Zhao, H., Construction and engineering of large biochemical pathways via DNA assembler. *Methods Mol. Biol.* 2013, 1073, 85-106.

[3] Shao, Z., Zhao, H., DNA assembler: a synthetic biology tool for characterizing and engineering natural product gene clusters. *Methods Enzymol.* 2012, 517, 203-224.

[4] Shao, Z., Zhao, H., Manipulating natural product biosynthetic pathways via DNA assembler. *Current Protocols in Chemical Biology* 2014, 6, 65-100.

The inventions being thus described, it will be obvious that the same may be varied in many ways. Such variations are not to be regarded as a departure from the spirit and scope of the inventions and all such modifications are intended to be included within the scope of the following claims.

The above specification provides a description of the manufacture and use of the disclosed compositions and methods. Since many embodiments can be made without departing from the spirit and scope of the invention, the invention resides in the claims.

What is claimed is:

1. A modified recombinant yeast cell for producing an aromatic compound, comprising
   a) an expression system that comprises at least one nucleotide sequence that encodes a transketolase, TKL1, capable of being expressed;
   b) an expression system that comprises at least one nucleotide sequence that encodes a pentafunctional protein for aromatic amino acid biosynthesis (ARO1), wherein the nucleotide sequence has the mutation $aro1_{D920A}$, capable of being expressed; wherein the expression of a protein involved in regulating the efficient localization of Golgi network proteins (RIC1), a pentafunctional protein for aromatic amino acid biosynthesis (ARO1) and a 3-deoxy-D-arabino-heptulosonate-7-phosphate (DAHP) synthase (ARO4) are downregulated or absent, and wherein said modified yeast cell produces higher titers of aromatic compounds compared to wild-type yeast cell of the same strain.

2. The modified yeast cell of claim 1, wherein said cell further comprises a third expression system that comprises at least one nucleotide sequence that encodes ribose-5-phosphate ketol-isomerase (RKI1).

3. The modified yeast cell of claim 1, wherein said cell is of Saccharomyces spp.

4. The modified yeast cell of claim 1, wherein said mutant pentafunctional protein for aromatic amino acid biosynthesis (ARO1) is $aro1_{D1409A-D920A}$.

5. The modified yeast cell of claim 3, wherein said cell is Saccharomyces cerevisiae.

6. The modified yeast cell of claim 1, wherein said cell is of Scheffersomyces spp.

7. The modified yeast cell of claim 6, wherein said cell is Scheffersomyces stipitis.

8. The modified yeast cell of claim 1, wherein said cell is Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida sp., Candida utilis, Candida cacaoi, Geotrichum sp., and/or Geotrichum fermentans.

9. The modified yeast cell of claim 1, wherein said modified yeast cell produces higher titers of shikimic acid compared to wild-type yeast cell of the same strain.

10. The modified yeast cell of claim 1, wherein said modified yeast cell produces higher titers of muconic acid compared to wild-type yeast cell of the same strain.

11. The modified yeast cell of claim 1, wherein said cell further comprises a third expression system that comprises at least one nucleotide sequence that encodes $aro4_{K220L}$.

12. A cell, tissue, or organ comprising the modified yeast cell of claim 1.

* * * * *

SEQUENCE LISTING

<160> NUMBER OF SEQ ID NOS: 77

<210> SEQ ID NO 1
<211> LENGTH: 3000
<212> TYPE: DNA
<213> ORGANISM: Scheffersomyces stipitis

<400> SEQUENCE: 1
aaacttgtta tctctcatga tgacattgtt caccctaagt atggccaact tgctaccaga    60
gacctgagaa atctttactt gctgtgtctc gaaattgtcc gcccctcgac tgtctcgcgg   120
gctaaccact ctgcctactc ggcccccgct cctgttacgg tcgctgctcc tgctgcggac   180

```
cctggtgtgg cacctatttc tgcctctgct cttgtccatg ctcgccttgg ccacccttct    240
ccgactgtcg ttcgtctggc cttgaaatat ccgaacatgc ctcgcacggc tgttcacgac    300
tcgatttcat gtgaagcatg tcttagctcc aagaacactc gggttattcc caaaacgacc    360
accggtccag tcacatctgc tcccttgcaa cttcttcact gtgatttgtc cggtcctcat    420
gccggtggtc cctcctcgtt gttttatttt tgtattcttc ttgacgactt tactcgcttc    480
aaggctgttg gccctattct caagaaatcg gatgctgcgg acttcattat caaagttatt    540
aaggcatgga caaaccactt ctccagtcgt ggtggctacc gtgtctgtaa ctttcgttct    600
gacaatggag gtgagtttgt caatctgacg cttacttctt tctttgcggc agaagggatc    660
cagacccagc tcactgtgcc tggtaactca caccaaaatg gacgtgctga agagcgatt     720 cgctccgttc ttgacaaaac gcgtaccatg atcactgcgt gttctcttcc ttcaccgctc    780
ttcccgcatg cactccaaca tgctgcattt ctcctaaacc ggctaccaac acctgttctc    840
caaaatcgct cgccatttga actctggcat ggcgcgaggc ctatcttatc tcaacttaaa    900
gtgtttgggt gtgctgcctt tgtgaatgtt ccacccaatc accgtcaact gaagttggtc    960
gctcgtgcaa tcaagggtgt ttatcttgga tctgatccgt ttcggaaggc tcatcttgtt   1020
tatgatctcg ctaccagaca agtgattacc tcttctcatg ttcggttcca ggaaaatgtc   1080
tttccttttg taagacctct gacgtcaact gtcgtgtcgg ctacctccat ggtggtgga    1140 ggtagtggtg gtggaagttt tccttctatt ctggcacctg ctccattttg aagttcagaa   1200
gcattcatag tgtcttacgt gtaataattg ttaacagtaa aagtagaact tgtaagttgt   1260
tctagttatc gttattaaaa cattttgaaa gtctatctaa ctctaagggg ataccaccat   1320
tatttatgtt gttgtctcac actcacatgc tccatgtgat tcttgttcaa tatctcatgg   1380
atcctattct ctgcatcacg ttcatctcat agctgtgggg ttgagacctt tctccacatc   1440
tgtttccata tgtccgtgtg gggttctcct atcatctctg tatacctgcc attgtgtttt   1500
ctattaccac catatcctta ttatgatatt tgattggctc tcacaagaat tgcagccaaa   1560
tctattagat tatcaatatc cggtatctac gatattttcc gaatcatgca tatactcatg   1620
cattatcaaa cttatctaa taccggattt cgacaaactt ctcctcacag atgtggggtt    1680
tgacctttct ccacatctat ttccatatat atatttatat atccgtgtgg gattctcctc   1740
tcatctctgt ataccagcct ttatgttttc tgttactacc atattcttat catgatcatt   1800
tgattggctc tcacaagaat tgcaaccaaa tctattagat tatcaatatc cggtatatac   1860
tgtatttatc atgcatattc atgcatacca actttatctc ataccggatt tcaacagttt   1920
cataggttat gttgttcaat agtgtttctg aattcagaca tattttggag catccagatt   1980
catacagaac tcgatttcag tgcttcgtta cctaggtaga aaatttgacg aattgggtga   2040
ccaccaaacc tttagttttt attttatgtg gatttgtgaa attcagcatt tgtttcttc   2100 ttgaaacggt gttgattatt cttccttgtt gtgttgtcga tgttgtgttt ggatggttct   2160
atgaacgctg aatcaccgtg aattttcatg gaagtttgac ttatgtcgac cgcacctttg   2220
tttggaaagg ggcttttttat acttgaaact gttcattcta ttgtcgaccc aagacttta   2280 tattgttagc ttcaccgctg tttccgacaa agatacagta ttcaatagag taatgagggt   2340
ctattgtctt gaagaacagt tttggtgtat catcgtgatt tgatgtcaac tgttcaggat   2400 tatttttcacg ttcggttgtt ttgagagact tacttttttt cataaatcct ttgatgtaat   2460
taatgatttc ttctgaagca tcttttttctt cattattttc aatgtacggt ttatttcatt   2520
caaaataggt tcttaagatt ccttattgat agcctcttct gtttttgtca tcaatatgca   2580
```

```
tttgactgaa tcggccaaat atttgtaata taatgcttta gtaatcgcat tgtgacttct    2640
ttgattgaat ttaatgttga agtcattcag aataaccttt ttaaatgttg taaatgcttc    2700
caatattcca tccaatttat actttttgttt tcgaactatc caaatttggc aaattctcaa    2760
gtttctcgtt atgcacaatc attacagcgc ttaccgcttt ttgaatttct ttcttactac    2820
gtttcttgat tcctttgaat tcattgggcg taagagtgtc aacaccatcc agcagatctt    2880
cttcttcagg ctccagcgat gactccgaat tcagcgtag acctgatccg ttccagcgtt    2940
tgtaccgtca acctttccta tctcgttaaa caactcccga attgtcttta ggatgtcatc    3000

<210> SEQ ID NO 2
<211> LENGTH: 3000
<212> TYPE: DNA
<213> ORGANISM: Scheffersomyces stipitis

<400> SEQUENCE: 2
gaagatgaca agaaagtga gatatgaata cattgaagat gacaatgagt tttggaacga      60
gactttagaa tcgaatagcg atgatccgaa tgatgataca tatgatgaag ctaatatttg     120
catccaaggt catgcttatc aaatgtcggt tgaatctaca gagagcaaga agtaccaaa     180 cacatacgaa gaagccatta attcttcaga ttctgagaaa tggattgaag ccatgaatac     240
cgaaatggct gctcattctg aaaatgacac atggacatta gtggatctcc cggaaaagaa     300
aacgaaagtc cttggagtaa gatgggtgta caccatcaag gatggaggaa aatacaaagc     360
taggcttgtg gtacgaggat ttcaacaaag atatggagtt gattacaaag agacgtttgc     420
tccagtaatt aggagtgaga gtgtcaagtt gttacttgca cttgcggcca tgtatggaaa     480
gaaggtacac cagatggatg tgtcaactgc attcttgaat ggtaagattg atcttaagat     540
ctacatgaag caaccatctg ggtaccagga ttgtagtgcc tttgagaagg tgtgtcagct     600
taataagtcc ttgtacggat tgaaacaggc tccattgata tggaatgaaa caatgaatag     660
tttccttgag aagatcggtt ttaaaaggtc tttgtcagag tatggactat acacgagaag     720
aagtgtgatc attggacttt atgtcgatga tttattgatt gctggagaca atcagaatga     780
gataaaagaa atcaagggac agttgagtgc ccagttcaag atgaaagatc ttggaatagc     840
taggaagttc ctaggcatta atatcactca agggagtgat ggaataaaag cagacttagg     900
ggattatatt gataagatcc tagaagagtt cggaatggag aactgtaacc cagtatcaac     960
accaggtttg cctggattga aacttgaaaa taacgagact gcgttattgg agaatcctac    1020
cttataccga tcaatagttg gaagttgct atatgctagc aacacggtaa gaggagacat    1080
aagttttatt acaggagttc tcagtagata cttaaagag ccaagagagg cacatcttac    1140
agcagcgaag catgttcttc gatatctcaa gggaaccagg tctcttgggc aacgttactc    1200
aaagactgga caacttgaag tatttgtaga cgcagattgg ggatcttcaa cagacaatag    1260
gaaatccatc acgggctatg cagtgaagtt cggaggagga ttgatttctt ggaaatcgaa    1320
gaagcaagct atagtcgcaa cttctaccac tgaagccgaa tatatcgcac tagcagaagc    1380
cgtgaaagaa gtgctttggt taagaaccct atttggtgaa ctacagatac cactaacatt    1440
acctatagga attcatgagg ataatgtatc ctgtataaaa ctaagtgaac atccaaccgt    1500
tcatctgagg actaagcata tcgacataag ataccatttc atccgtgaaa ggataaaaga    1560
ggagaccata aaattaatac ctgtcaaatc tgaattcaat atagccgaca tattcacaaa    1620
ggcgctagca aaaccacaac acataaaatt aagagcgtta gcagggattt cgtgaagaga    1680
```

```
ctattagatt aagggaggct gttgaaatcc ggtattagat aaagtttgat aatgcatgaa    1740
tatgcatgat ctagaaaata tcgtagatac cggatattga taatctaata gatttggctg    1800
caactcttgt gagagcaaat catatatcat aataaggata tggtggtaat agaaaacaca    1860
atggcaggta tacagagagg ataatagaac cccacacgga catatggaaa cagatgtgga    1920
gaaaggtctc aaccccacag ctatgagatg aacgtgatgt tgaaattcag agaattgaaa    1980
ctataattgt aatctaacaa tcagataact atgtgcagta ctggctgcaa atttacaaat    2040
aaggaagttc cactggtcct atctctgaga ataggagtaa ccccttatca gacccgcctc    2100
aacggaatag aacttatccg taatgaaatt ggaggcgggc tagagataag aataggggga    2160
gataagaata tgaataaggg ggaagataag gggttctgaa caatataaat atggtaggat    2220
attctccaat atcagaagaa taatcagaac ttgaaattga acttcattat caagagttaa    2280
ctatatcttt attaatatac aatgtctaat tttcaacagg ttatgagcca atccgtctca    2340
aacatcaagt tgatgactc ccagaaacta gtttcgcgtt tcaactatcg tgaatggcgt    2400
acgcgtatgg aggtcactat tgggactctt ggtatggagt tccggggttt cattgaaaaa    2460
tctgaaccac ctaccgaggc ttcgttgttt attcttttta acctgacgct tcagctgctt    2520
attgacaaga cggtgtctaa agagattgtt gattctcttc ttgccgagaa tctttctggt    2580
caggctcttt gggaggctat ccacgtcaat tattcggtta tgacgtactc tgagaaggtc    2640
gagtacgtta ctggtttggt cgctaagatt agtgacacgt cggtcagtac tactgttcag    2700
ttatcggctg ccaagctgct ttctacctac tttgctgagc agcctcctac tgacattcct    2760
ggtctcctct atcttacaca ctgtaagctg gaccatattt tgtctaagtt caaggaactt    2820
ggtgctacct tggatctcac tgacctcaaa tcgttcctaa aacggatcga tgcctcactg    2880
tcttccacgc ctgggtctgt gttcacggtg actactctct cctctgctgg actgaagtct    2940
caccagaaag ctcctgccac ctctcctatc tggaataccc gttgctatac gtgctctggt    3000
```

<210> SEQ ID NO 3
<211> LENGTH: 3000
<212> TYPE: DNA
<213> ORGANISM: Scheffersomyces stipitis

<400> SEQUENCE: 3

```
atacataagt gactacgaag gagattctcc tgagtctttg aatgatgatc caaatgatga      60
agattaccaa atgtcagaag caaatgtggt aattcgagga catgcgttca cggctacaac     120
aagtgtttta ggtagcccca agattcccag aagctatagc gaagctgtcg gaagccaaga     180
cgctgggaaa tggatagaag caatgaacga tgaaatgtct gcacatgaaa tgaaccagac     240
gtgggttctt gcagacaagc caaatgataa aacaaaagtg ttaggtgtga gatgggtgta     300
taccatcaag gatgatggtc gatacaaagc aagattagtc gcaagaggtt ttcaacagag     360
atatggtgtt gattacgaag aaacctttgc tccagtaatc agaagtgaga gtgtaaaggt     420
gctactctcc gtatctgctg tgtatgggat gaaagttcat cagatggatg taacgacagc     480
attcctaaat ggaaaaatcg atttaccaat attcatgaat caaccagatg gattcaagca     540
tacaaatgaa cttgggaaag tatgcaaact caacaagtca ctctatggtc taaagcaagc     600
tccgttgata tggaacaaga caataaatgc gtttctcgag aaggtggggt tgttaggtc      660 acaagctgaa ttcggattat acaaaagaaa gaacactatt gtcggtttat atgtggatga     720
cctattgata gcaagcagta atgaaaatga gatcaaggc atcaaagaat tgttgaagaa     780
ggaattcaaa atgaaagacc tcggcattgc acagaaattc cttggaataa acatacagca     840
```

```
atcagaaaaa ggtattagag cccatttggg agactacatt gacaaaatct tggaggaatt      900
ctcaatgcaa gattgcaacc cagttggaac tgcagcaatt ccaaatgctc agttagataa      960
agatgaaacc aagattcttg ccaatcctac aatttacaga tccattgttg caagttatt     1020 atatgctagt aacaccattc ggggagatat tagcttcatt actggcatgc tcagccggta     1080
ctttcagaat cctagagagg gacatctagt agcagctaag catgtacttc ggtacctaaa     1140
aggaacaaag actgtgggcc aggtatatgg aaaactggat aaattcgagg tgtacgttga     1200
tgcagattgg ggttcttcgc tgtcagatag aaaatcaata acaggatatg caattaagtt     1260
cggaggaagt ctaatctcgt ggaaatcaaa gaaacaacca acagttgcac tatctacaac     1320
agaagccgag tatatggcac ttgctgaagc agttaaggag gtcctctggt tggtgactct     1380
atttaaagaa ttggaaatcc ctgtaaccct tccaattata gtacatgaag ataatacgtc     1440
atgtattaac ttaacgaatc atccaacaac tcatcaacgt acaaaacaca ttgatatcag     1500
atatcacttt ataagagagc aggtacagaa agaattgatc aaggttgtcc aagttcagtc     1560
aacaaataat atcgcggaca tctttacgaa ggcagttccc aagccattac tccagcaact     1620
acgaaactca gcaggaatga tggatattga ataatccgat tattagatta tgggggatg     1680 ttgaaattca gagaattgaa actataattg taatctaaca atcagataac tatgtgcagt     1740
actggctgca aatttacaaa taaggaagtt ccactggtcc tatctctgag aataggagta     1800 acccccttatc agacccgcct caacggaata gaacttatcc gtaatgaaat tggaggcggg     1860
ctagagataa gaataggggg agataagaat atgaataagg gggaagataa ggggatctga     1920
acaatataaa tatggtagga tattctccaa tatcagaaga ataatcagaa cttgaaattg     1980
aacttcatta tcaagagtta actatatctt tattaatata caatgtctaa ttttcaacag     2040
aacttgtaag ttgttctcgt tatcgttatt aaaacattaa gaaagtctat ctaactctga     2100
gaggatacca cccttattta tggtgttgtc tcacattcac atgctccacg gattcttgtt     2160
ctcatgtttc acatttgttt catagctgtg gtattgaaac ctttctccac atctatttcc     2220
gtatgtccgt gtggggttct attatcctct ctgtatacct gccattgtgt tttctattac     2280
caccatatcc ttattatgat atatgaatgg ctctcacaag agttgcagcc aaatctatta     2340
gataatcaat atccggtatc tacgatattt tctagatcat gcatattcat gcattatcaa     2400
actttatcta ataccggatt tcaacaacag agaggtacgg gacgcacagga aatgtccagt     2460 acgaacagga gaaggacagc tagtggcctt gtggccatta ccaagacaat tggtacactt     2520
gagaacaggg gaagtacaaa cattcgaacg gtggccctta ccagagcacg tatagcaacg     2580
ggtattccag ataggagagg tggcaggagc tttctggtga gacttcagtc cagcagagga     2640
gagagtagtc accgtgaaca cagacccagg cgtggaagac agtgaggcat cgatccgttt     2700
taggaacgat ttgaggtcag tgagatccaa ggtagcacca agttccttga acttagacaa     2760
aatatggtcc agcttacagt gtgtaagata gaggagacca ggaatgtcag taggaggctg     2820
ctcagcaaag taggtagaaa gcagcttggc agccgataac tgaacagtag tactgaccga     2880
cgtgtcacta atcttagcga ccaaaccagt aacgtactcg accttctcag agtacgtcat     2940
aacccaataa ttgacgtgga tagcctccca aagagcctga ccagaaagat tctcggcaag     3000
```

<210> SEQ ID NO 4
<211> LENGTH: 3300
<212> TYPE: DNA
<213> ORGANISM: Scheffersomyces stipitis

```
<400> SEQUENCE: 4
ctagtttttg acaatccact gactgattct cgttagtcct gtgtgaatag ttgctattgt      60
tagtcacttg tgactatgct gctagtactg taggaccatt tactgtgggt gacgagtaat     120
tacttcctgt cagctctatg tgaccatttg cagtggtcgt tcccatctgt ttactgcaag     180
ctcataatgg ttacttgctt tcggtctgtt attactactt actattattc ctttgcgact     240
agttatagaa gactgccact atttattgat gctagtcttc tataactata tcatctgata     300
tgagagatcc ccgagtgttc tcctattatt tattgctgag cctgccgtgg ctccctactg     360
tagtccgtta cgactacctc tcgtcttacc aacaaacttg ggtattcct tctgtatttt      420 aaagtgacac ccggtcattc ttaattcttt tacgattaat tgctacagtc tactgtgact     480
gtattctctg tattctgcga gaaacctgat tgtgttctcg cttacctaga atgatacact     540
cgcagtcatt ccatggttgc ggtggtattt ggaaccttat gtcgcgttcc atttaaccta     600
caatatggtg ctccgagagt ccatattaac catatgattc cacgtcagtc tgttgggccc     660
atgcagtcta cgtgtatcat ctgaattact ttctactcca aattcaagga gtatctgcta     720
aagatagcaa ccctattctc gaatatagaa tagtatgcgc tgttataaaa tctgcacaag     780
cggtgcagta ctcaccggtt ctgataagaa acatgagtct atgttctgac tgaaactatc     840
atcactacct ttatttactg tgaggatgat agtgaacatt gcgtgtgcaa actacaaatc     900
tgtgaattac gaatgttgta cttttagatt atggggaat gtgaatagat tgctgttcta      960
atccaagagt acttgattac acagttgccc ttacaaaatg tgtaagagta aaatgaacga    1020
ctattagatt aagagcagga gtattgaaca ttggaaatat caaatgatct aatctaatag    1080
taatgttgaa ttgattcatc gttagatatg gttatgtcta cagtgtgccg tacacacaaa    1140
taacctcatt cttatatcta cattatacca tactaacatc gttatcggat ataatgttga    1200
tctcgataat cacaacacaa tgtgggtatc ctacccaaca acaatatgac catcacgtaa    1260
gtgatggaat actactcctg gatgaaattt aacaggaaat ttaagaaata atcactagtg    1320
atcaagatgc tccaaatgga atctgaaaat aaggactata catcacgaag attattacca    1380
gtctatcagg aagtgcaaag agtgaaagtt cacaaatact ttcaaaacag atgctactga    1440
tttgaactaa gagctggatc agatgcaaac ttcaataacc attagattat gggggaatgt    1500
tgagattgga atctagagt aatccaatag attgaagttt agttatataa caagaaactg     1560
agcgtgcaag aaactgcgaa tgcaagaaat aatatttcag attagaagca ttattcagaa    1620
acgcacaggt tgcaaattaa gccgcactga tgtgcaggca actctgaggt ataaaagaaa    1680
gctgaaatcc tcaaagtctt gaaaaagttt atacgtttat aatgaatcaa tttacgattc    1740
atttgaggga ggttattcta gagatgtaga gaataacata ttgaacaact gtaggatacg    1800
ctgtatccat atagacaagt tgcgcgcctt gtttaaacag ttgtatcaag ataaagaaga    1860
agacagacaa attacaacat ggataggcaa tcaagaggtc tacataaact agagtccatc    1920
atatcaacaa ttcacatttc aatatgaaac cccggaactc cataccaaga gtcccaatag    1980
tgacctccat acgcgtacgc cattcacgat agttgaaacg cgaaactagt ttctgggagt    2040
catcaaactt gatgtttgag acggattggc tcataacctg ttgaaaatta gacattgtat    2100
attaataaag atatagttaa ctcttgataa tgaagttcaa tttcaagttc tgattattct    2160
tctgatattg gagaatatcc taccatattt atattgttca gatcccctta tcttcccct     2220 tattcatatt cttatctccc cctattctta tctctagccc gcctccaatt tcattacgga    2280
taagttctat tccgttgagg cgggtctgat aagggggttac tcctattctc agagatagga    2340
```

| | |
|---|---|
| ccagtggaac ttccttattt gtaaatttgc agccagtact gcacatagtt atctgattgt | 2400 |
| tagattacaa ttatagtttc aattctctga atttcaacaa gtcggacata attgattctc | 2460 |
| attggtagat gttatcttat cacattactg tgcacaatta tgtctgaatg gctgcaaatc | 2520 |
| ctgcattcat aaagtttacg cattggatta aaaatagaat atagaatatg cttttaggtt | 2580 |
| tgatatcagc atattcaaca gaatatgcat gatctagaaa atatcataga taccggatat | 2640 |
| tgataatcta atagatttgg ctgcaactct tgtgagagca aatcatatat cataataagg | 2700 |
| atatggtggt aatagaaaac acaatggcag gtatacagag atgataggag aaccccacac | 2760 |
| ggacatatgg aaacagatgt ggagaaaggt ctcaaccccca cagctatgag atgaacgtga | 2820 |
| tgcagagaat aggatccatg agatattgaa caagaatcac atggagcatg tgagtgtgag | 2880 |
| acaacaacat aaataagggt ggtatcccct tagagttaga tagactttct aaatgtttaa | 2940 |
| taacgataac tagaacaact tacaagttct acctttactg ttaacaatta ttacacgtaa | 3000 |
| gacactatga atgcttctga acttcaacat ctattaccat catatcctta atatgatatg | 3060 |
| tgattggcta tcacaagagt tgcagccaaa tctattagat tatcaatatc cggtatctac | 3120 |
| gatattttct agatcatgca tattcatgca ttatcaaact ttatctatta ccggatttca | 3180 |
| acagcctccc ttaatctaat agtctcttca cgaaatccct gctaacgctc ttaattttat | 3240 |
| gtgttgtggt tttgctagcg cctttgtgaa tatgtcggct atattgaatt cagatttgac | 3300 |

<210> SEQ ID NO 5
<211> LENGTH: 3000
<212> TYPE: DNA
<213> ORGANISM: Scheffersomyces stipitis

<400> SEQUENCE: 5

| | |
|---|---|
| aacagttcaa caggttatga gccaattaaa ttccggcctc atggtcattg atactcttct | 60 |
| tctcagaggc cgtgagaact ttctggaatg gaaagactgg atgactggta tgttcagtag | 120 |
| ctgtgtcttg gctacagaga ttgctgctta tctttcagag aaagaacttt ccatcacctt | 180 |
| tacggaccag caggcgttga gccacaagct ccgtgagctt attctcaagt gtatgaagcc | 240 |
| tgacgttcag tcattgttca cgcactactc tctgggtgtc gaaacttgga aagctgtcga | 300 |
| aactgttgaa attcagagaa ttgaaactat aattgtaatc taacaatcag ataactatgt | 360 |
| gcagtactgg ctgcaaatttt acaaataagg aaattccact ggtcctatct ctgagaatag | 420 |
| gagtaacccc ttatcagacc cgcctcaacg gaatagaact tatccgtaat gaaattggag | 480 |
| gcgggctaga gattgttgat tctcttcttg ccgagaatct ttctggtcag gctcataac | 540 |
| ctgttgaaaa ttagacattg tatattaata agatatagt taactcttga taatgaagtt | 600 |
| caatttcaag ttctgattat tcttctgata ttggagaata tcctaccata tttatattgt | 660 |
| tcagaacccc ttatcttccc ccttattcat attcttatct ccccctatcg gagcttgctt | 720 |
| tagaccatag agtgacttgt tgagtttgca tactttccca agttcatttg tatgcttgaa | 780 |
| tccatctggt tgattcatga atattggtaa atcgattttt ccatttagga atgctgtcgt | 840 |
| tacatccatc tgatgaactt tcatcccata cacagcagat acggagagta gcaccttac | 900 |
| actctcactt ctgattactg gagcaaaggt ttctccgtaa tcaacaccat atctctgttg | 960 |
| aaaacctctt gcgactaatc ttgctttgta tcgaccatca tccttgatgg tatacaccca | 1020 |
| tctcacacct aacactttgt tttattattt ggcttgtctg caagaaccca cgtctggttc | 1080 |
| atttcatgtg cagacatttc atcatccgcc tcaggagaaa tatccgagtc ataagaatag | 1140 |

| | |
|---|---|
| cacagacgac agcatacggc aagaacacag caggcaccga accatgagtc agaagagttc | 1200 |
| gggctttatc aagaatggta cgaatactac cgacacggta tccaccacga gtggagaaga | 1260 |
| aagaatgaaa gagctcggca ttgcacagaa attccttgga ataaacatac agcaatcaga | 1320 |
| aaaaggtatt agagcccatt tgggagacta cattgacaaa atcttggagg aattctcaat | 1380 |
| gcaagattgc aacccagttg gaactgcagc aattccaaat gctcagttag ataaagatga | 1440 |
| aaccaagatt cttgccaatc ctacaattta cagatccatt gttggcaagt tatgttgaga | 1500 |
| ttggaaatct agagtaatcc aatagattga agtttagtta tataacaaga aactgagcgt | 1560 |
| gcaagaaact acgaatgcaa gaaataatat ttcagattag aagcattatt cagaaacgca | 1620 |
| caggttgcaa attaagccgc actgatgtgc aggcaactct gaggtataaa agaaagctga | 1680 |
| aatcctcaaa gtcttgaaaa agtttatacg tttataatta atcaatttac gattcatttg | 1740 |
| atggaggtta ttctagagat gcagagaata acatattgaa cgactgtagg atacgctgta | 1800 |
| tccatataga caagttgcgc gccttgttta acagttgta tcaagataaa gaagaagaca | 1860 |
| gacaaattac aacatggata ggcaatcaag aggtctacat aaactagagt ccatcatatc | 1920 |
| aacaattcac atttcaaaat gctcagcaaa gtaggtagaa agcagcttgg cagccgataa | 1980 |
| ctgaacagta gtactgaccg acgtgtcact aatcttagcg accaaaccag taacgtactc | 2040 |
| gaccttctca gagtacgtca taaccgaata attgacgtgg atagcctccc aaagagcctg | 2100 |
| accagaaaga ttctcggcaa gaagagaatc aacaatctct ttagacaccg tcttgtcaat | 2160 |
| aagctgttga agttcagaag cattcatagt gtcttacgtg taataattgt taacagtaaa | 2220 |
| ggtagaactt gtaagttgtt ctcgttatcg ttattaaaac atttagaaag tctatctaac | 2280 |
| tctaagggga taccacccctt atttatgttg ttgtctcaca ctcacatgct ccatgtgatt | 2340 |
| cttgttcaat atctcatgga tcctattctc tgcatcacgt tcatctcata gctgtggggt | 2400 |
| tgagaccttt ctccacatct gtttccatat gtccgtgtgg ggttctccta tcatctctgt | 2460 |
| atacctgcca ttgtgttttc tattaccacc atatcctcat tatgatatat gattggctct | 2520 |
| cacaagagtt gcagccaaat ctattagatt atcaatatcc ggtatctacg atattttcta | 2580 |
| gatcatgcat attcatgcat tatcaaactt tatctaatac cggatttcaa cagcctccct | 2640 |
| taatctaata gtctcttcac gaaatccctg ctaacgctct taattttatg tgttgcggtt | 2700 |
| ttgctagcgc ctttgtgaat atgtcggcta tattgaattc agatttgaca ggtattaatt | 2760 |
| ttatggtctc ctctttatc cttttcacgga tgaaatggta tcttatgtcg atatgcttag | 2820 |
| tcctcagatg aacggttgga tgttcactta gttttataca ggatacatta tcctcatgaa | 2880 |
| ttcctatagg taatgttagt ggtatctgta gttcaccaaa tagggttctc aaccaaagca | 2940 |
| cttctttcac ggcttctgct agtgcgatat attcggcttc agtggtagaa gttgcgacta | 3000 |

<210> SEQ ID NO 6
<211> LENGTH: 2962
<212> TYPE: DNA
<213> ORGANISM: Scheffersomyces stipitis

<400> SEQUENCE: 6

| | |
|---|---|
| cgaggtgcaa tagttcgaac agcgtcttgt cagcaatagt cctggaggga agcctattca | 60 |
| ataaatatgc ggcacattta acagcgtagg gccagaatgc ttgaggaaca gaagcatgtc | 120 |
| caagtagcgt cctggcctta tcgattaccg agcggatcga acgctctgcg gttccattct | 180 |
| gataagaatt gtgagcaacc gtacgctgat gtgctatacc ttcctgttca aggaagctcc | 240 |
| tgagactatg gttgacaaat tcaccccat tatctgtacg aagagcacca acacgatatc | 300 |

```
caccacgagt agagaaaaat gagtgtaata gccgaatatg gataataatc tggtgggcca    360
catccgactt cctaacgatt gggaacaccc acttaaactt gctataatca tccacaagca    420
cacagaaata actttcagaa gagattcctg gcgtattatg agggccggag acatccgagt    480
gaagaatttg taaaggagtt gttgtatccg atttatggga aaccttcggg atactacgtg    540
tcttcttata ttccagacag ctggcacaac tcttcgttac atcaccaatt ttctcaatat    600
cagcaagcga gtaattgtca cgaagaactt gctgttcaat agcctgatgc ggatgaccaa    660
gacggttatg aagaacagat aaggcggaga ctaaaggtgg tacaggtgtc atatcaagga    720
cggaaagtcc aagatcgtcc ctatagacac caaaacgacc aatccgtgga tgatagattc    780
cgtctacttt ggtggtaagg ggcgaaccag agacacgaac agcagcatgc acggagataa    840 gattttagt gcattctgga acatagcata cttcctgaag gactatagtc tcatcagcag    900
acctaaactt gatagaccct ctacctaaga caggaagacg aactccgcca gcacaagaaa    960
caaaactacc ggactccggt ttaaaagtcc aaaacaagga ccgatcatga caaatgtgaa   1020
tcgaagcacc agagtcaaag atgaactccg gtgaatgaga tgtcgtggag ccggtggttg   1080
tagtgagcac gaaggcactt tcgttaacag caacatttgc agtagcacct gacttgtatt   1140
gcttcttgcg ctcattgtca ctaaaggagc gcttcttgga cgtattggtc agccatccag   1200
tatacttacc aacacgaata ggcgagcaac acacatcacg tctgtgacca cgaccaccac   1260
agttgtaaca cttagtgttc caaagcggat cattggcatc aacagaagga cgtctggtgt   1320
cagtggaaaa ggtagcagca agaactgatg gagcagtagg agtttcggta gaattctctg   1380
cttttgctag aaatttgaaa acatcatcat acttcaacga ttcgttgccc aggtggaagt   1440
aattttgcat gagattaggg gaacttcgag taactagaag gtgaagaccc ttaatttcat   1500
caaaggtata ggattcgttc aaggaataaa gagagtcaaa aaccggctta acaacgtcag   1560
ttgtcaaaga tggagtgtga atcactgtca ataacgactt gacatattgg gcaacatcgt   1620
ggtgatccat ggtaccataa agatcaagaa cccgtaacca acgtgctctg ccagtgactg   1680
gctcacgact gagagtacta cgaactttct cagacaaggt tttggaaaga acaaagtcaa   1740
tataggagtt gaatgcggat ctgtcctcag aagtgtatcc atcgtcaaca tttgtcagag   1800
gcaaaagata tgccacaaat tcttttccaa ttggttcgaa aagttgatcc attctggttt   1860
tccataatga aaagtcgttg atggaagtca acatttgttc tgaaggaaac gagattgagt   1920
agttgaactt caggtgacgg ctcataacct gttgaagttc agaagcattc atagtgtctt   1980
acgtgtaata attgttaaca gtaaaggtag aacttgtaag ttgttctagt tatcgttatt   2040
aaaacattta gaaagtctat ctaactctaa ggggatacca cccttattta tgttgttgtc   2100
tcacactcac atgctccatg tgattcttgt tcaatatctc atggatccta ttctctgcat   2160
cacgttcatc tcatagctgt ggggttgaga cctttctcca catctgtttc catatgtccg   2220 tgtgggttc tcctatcatc tctgtatacc tgccattgtg ttttctatta ccaccatatc   2280
ctcattatga tatgattg gctctcacaa gagttgcagc caaatctatt agattatcaa    2340
tatccggtat ctacgatatt ttctagatca tgcatattca tgcattatca aactttatct   2400
aataccggat ttcaacagtg cgtgaacaat gactgaacgt caggcttcat acacttgagg   2460
ataagctcac ggagcttgtg gcttaacgcc tgctggtccg taaaggtgat ggaaagttct   2520
ttctctgaaa gataagcagc aatctctgta gccaagacac agctactgaa cataccagtc   2580
atccagtctt tccattccag aaagttctca cggcctctga ggagaagagt atcaatgacc   2640
```

| | |
|---|---|
| atgaggccgg aatttaattg gctcataacc tgttgaactg tttgctttgg aagctcagta | 2700 |
| gattgaatcg gattgttcat aatgtaggac agtatattga ttaacttatt taagatagat | 2760 |
| aatttccata tagaagaaga aaagttatag aaagttagaa aggagaaggg ggagtaagac | 2820 |
| ccccttaaat agatgccaaa tacaatcaca ggctgacccc tcatcgggat gaaatgaaac | 2880 |
| gacatgacca gaatttcagg ttagtcggac ataattgatt ctcattggta gatgttatct | 2940 |
| tatcacatta ctgtgcacaa tt | 2962 |

<210> SEQ ID NO 7
<211> LENGTH: 1573
<212> TYPE: DNA
<213> ORGANISM: Scheffersomyces stipitis

<400> SEQUENCE: 7

| | |
|---|---|
| agcagcgaag catgttcttc gatatctcaa gggaaccagg tctcttgggc aacgttactc | 60 |
| aaagaccgga caacttgaag tatttgtaga cgcagattgg ggatcttcaa cagacaatag | 120 |
| gaaatccatc acgggctatg cagtgaagtt cggaggagga ttgatttctt ggaaatcgaa | 180 |
| gaagcaagct atagtcgcaa cttctaccac tgaagccgaa tatatcgcac tagcagaagc | 240 |
| cgtgaaagaa gtgctttggt tgagaaccct atttggtgaa ctacagatac cactaacatt | 300 |
| acctatagga attcatgagg ataatgtatc ctgtataaaa ctaagtgaac atccaaccgt | 360 |
| tcatctgagg actaagcata tcgacataag ataccatttc atccgtgaaa ggataaaaga | 420 |
| ggagactatc aaattaatac ctgtcaaatc tgaattcaat atagctgaca tattcacaaa | 480 |
| ggctctagca aaaccacaac acataaaatt aagagcgtta gcagggattt cgtgaagaga | 540 |
| ctattagatt aagggaggct gttgaaatcc ggtattagat aaagtttgat aatgcatgaa | 600 |
| tatgcatgat ctagaaaata tcgtaaatac cggatattga taatctaata gatttggcta | 660 |
| caactcttgt gagagcaaat catatatcat aataaggata tggtggtaat agaaaacaca | 720 |
| atggcaggta tacagagagg ataatagaac cccacacgga catacggaaa tagatgtgga | 780 |
| gaaaggtttc aataccacag ctatgaaaca aatgtgaaac atgagaacaa gaatccatgg | 840 |
| agcatgtgaa tgtgagacaa caccataaat aagggtgata tcctctcaga gttagataga | 900 |
| cttttcttaat gttttaataa cgataactag aacaacttac aagttctacc tttactgtta | 960 |
| acaattatta cacgtaagac actatgaatg cttctgaatt acaacataaa ggtgatggaa | 1020 |
| agttctttt ctgaaagata agcagcaatc tctgtagcca agacgcagct actgaacata | 1080 |
| ccagtcatcc agtcttttcca ttccagaaag ttctcacggc ctctgagaag aagagtatca | 1140 |
| atgaccatga ggccggaatt taattggctc ataacctgtt gaactgtttg ctttggaagc | 1200 |
| tcagtagatt gaatcggatt attcataatg taggacagta tattgattaa cttatttaag | 1260 |
| atagataatt tccatataga agaagaaag ttatagaaag ttagaaagga aaggggggag | 1320 |
| taagaccccc ttatatagat gccaaataca atcacaggct gacccctcat caggatgaaa | 1380 |
| tgaaacgaca tgaccagaat ttcaggttag tctgacataa ttgattctca ttggtagatg | 1440 |
| ttatcttatc acattactgt gcacaattat ttcagaatgg ctgcaaatcc tgcattcata | 1500 |
| aagtttacgc attggattaa aaatagaata tagaatatgc ttttaggttt gatatcagca | 1560 |
| tattcaacaa cca | 1573 |

<210> SEQ ID NO 8
<211> LENGTH: 2980
<212> TYPE: DNA
<213> ORGANISM: Scheffersomyces stipitis

<400> SEQUENCE: 8

```
ctcataacct gttgaactgt ttgctttgga agctcagtag attgaatcgg attgttcata    60
atgtaggaca gtatattgat taacttattt aagatagata atttccatat agaagaagaa   120
aagttataga aagttagaaa ggagaagggg gagtaagacc cccttatata gatgccaaat   180
acaatcacag gctgacccct catcaggatg aaatgaaacg acatgaccag aatttcaggt   240
tagtcggaca taattgattc tcattggtag atgttatctt atcacattac tgtgcacaat   300
tatgtctgaa tggctgcaaa tcctgcattc ataaagttta cgcattggat taaaaataga   360
atatagaata tgcttttagg tttgatatca gcatattcaa cactatcaag tttaggtctg   420
ctgatgagac tatagtcctt caggaagtat gctatgttcc agaatgcact aaaaatctta   480
tctccgtgca tgctgctgtt cgtgtctctg gttcgcccct taccaccaaa gtagacggaa   540
tctatcatcc acggattggt cgttttggtg tatatagggca cgatcttgga ctttccgtcc   600
ttgatatgac acctgtacca cctttagtct ccgccttatc tgttcttcat aaccgtcttg   660
gtcatccgca tcaggctatt gaacagcaag ttcttcgtga caattactcg cttgctgata   720
ttgagaaaat tggtgatgta acgaagagtt gtgccagctg tctggaatat aagaagacac   780
gtatattgaa atgtgaattg ttgatatgat ggactctagt ttatgtagac ctcttgattg   840
cctatccatg ttgtaatttg tctgtcttct tctttatctt gatacaactg tttaaacaag   900
gcgcgcaact tgtctatatg gatacagcgt atcctacagt tgttcaatat gttattctct   960
acatctctag aataacctcc ctcaaatgaa tcgtaaattg attaattata aacgtataaa  1020
cttttttcaag actttgagga tttcagcttt cttttatacc tcagagttgc ctgcacatca  1080
gtgcggctta atttgcaacc tgtgcgtttc tgaataatgc ttctaatctg aaatattatt  1140
tcttgcattc gcagtttctt gcacgctcag tttcttgtta tataactaaa cttcaatcta  1200
ttggattact ctagatttcc aatctcaaca ttcccccata atctaatggt tattgaagtt  1260
tgcatctgat ccagctctta gttcaaatca gtagcatctg ttttgaaagt atttgtgaac  1320
tttcactctt tgcacttcct gatagactgg taataatctt cgtgatgtat agtccttatt  1380
ttcagattcc atttggagca tcttgatcac tagtgattat ttcttaaatt tcctgttaaa  1440
tttcatccag gagtagtatt ccatcactta cgtgatggtc atattgttgt tgggtaggat  1500
acccacattg tgttgtgatt atcgagatca acattatatc cgataacgat gttagtatgg  1560
tataatgtag atataagaat gaggttattt gtgtgtacgg cacactgtag acataaccat  1620
atctaacgat gaatcaattc aacattacta ttagattaga tcatttgata tttccaatgt  1680
tcaatactcc tgctcttaat ctaatagtcg ttcattttac tcttacacat tttgtaaggg  1740
caactgtgta atcaagtact cttggattag aacagcaatc tattcacatt cccccataat  1800
ctaaaagtac aacattcgta attcacagat ttgtagtttg cacacgcaat gttcactatc  1860
atcctcacag taaataaagg tagtgatgat agtttcagtc agaacataga ctcatgtttc  1920
ttatcagaac cggtgagtac tgcaccgctt gtgcagattt tataacagcg catactattc  1980
tatattcgag aataggggttg ctatctttag cagatactcc ttgaatttgg agtagaaagt  2040
aattcagatg atacacgtag actgcatggg cccaacagac tgacgtggaa tcatatggtt  2100
aatatggact ctcggagcac catattgtag gttaaatgga acgcgacata aggttccaaa  2160
tagcaccgca accatggaat gactgcgagt gtatcattct aggtaagcga aacacaatc   2220
aggtttctcg cagaatacag agaatacagt cacagtagac tgtagcaatt aatcgtaaaa  2280
```

-continued

| | |
|---|---|
| gaattaagaa tgaccgggtg tcactttaaa atacagaagg aatacccaag tttgttgggt | 2340 |
| aagacgagag gtagtcgtaa cggactacag tagggagcca cggcaggctc agcaataaat | 2400 |
| aataggagaa cactcgggga tctctcatat cagatgatat agttatagaa gactagcatc | 2460 |
| aataaatagt ggcagtcttc tataactagt cgcaaaggaa taatagtaag tagtaataac | 2520 |
| agaccgaaag caagtaacca ttatgagctt gcagtaaaca gatgggaacg accactgcaa | 2580 |
| atggtcacat agagctgaca ggaagtaatt actcgtcacc cacagtaaat ggtcctacag | 2640 |
| tactagcagc atagtcacaa gtgactaaca atagcaacta ttcacacagg actaacgaga | 2700 |
| atcagtcagt ggattgtcaa aaactagtta ctcaggacca gaaggaatca gccaagatag | 2760 |
| tgggcagtag gtagtcactc gggaccagaa ggaagcagcc tcggcaggct gttaataagt | 2820 |
| aagatgtcgt tcgcgacaaa tagagatccg ccaagagggc cgtccataag aagtagtcgc | 2880 |
| tcgggactag tagagagcag ccagagggcc gttcagaagt atgatgtcgc tcgggactag | 2940 |
| tagagatcag gcaagagggc cgtcaataag aagtagtcgt | 2980 |

<210> SEQ ID NO 9
<211> LENGTH: 544
<212> TYPE: DNA
<213> ORGANISM: Scheffersomyces stipitis

<400> SEQUENCE: 9

| | |
|---|---|
| cagcatcatc accatgttgt ccaattacag cccgaagcac agtctaatgc tgaattttga | 60 |
| tagagctcat cgtgaacagc cagattcgaa gaaaggggg atgagatccg ggttcatctg | 120 |
| caagagacac agaaaataaa aaacatacga tccgttcagc tacctggcgc ttaaccagga | 180 |
| aaatcactgc tggagtggcc agcatgtcac gaggtggcag aatccgataa tgtgtgattg | 240 |
| cgtgtagcat cggcgcaagt cgaatttcgg tcatattccg tgtctggata ttattccact | 300 |
| atttttaat ttttcaggtt ggatgcgatt gttccctta cgtctggacg atgcctgaag | 360 |
| ccccaggtat atataagggg ctcgaaagtc ctttgaccag ctggttgatt tgactttgtt | 420 |
| tgttcctttc tttctttcat ctactcatca ctcaattgca ttcgcaattt cccattaata | 480 |
| catatttcac ttgctccaca tattgcaccc aattgcataa gtgctgcgat ccatccaaat | 540 |
| tatc | 544 |

<210> SEQ ID NO 10
<211> LENGTH: 570
<212> TYPE: DNA
<213> ORGANISM: Scheffersomyces stipitis

<400> SEQUENCE: 10

| | |
|---|---|
| tacatcacca gccaccgtat cactgctcca ttatcagtgc catctcatga gcattggagc | 60 |
| tgttgatgca agctgtcgct aatatgccgc aacaaattgg actcattttt agggcaattc | 120 |
| tatccagtac caataaagca cgaatcgctt tatgaatcat agcctggccg tagcatttca | 180 |
| gcaatttcgc aggttatggt ttaacagcga cgtacaaaac ttttcacagt catatacggt | 240 |
| atacccaaac atggattcgt ggacttcggc tcctccgttg aactcatatt cgtaatcccc | 300 |
| attcagattg ccctctcatg atgcccacca gttgcaatct ggtgatcgca ttatgcacac | 360 |
| tcttcgggta tcgggactga gtggtccagt ttcgcacaaa attcgcacac ggtgaacaag | 420 |
| atggcccaca cttttttcac tcgacatata aagggaacga gatttcctcc ttgatttctc | 480 |
| ctggcattgc gtactgtgta ttttttgcat ctagtcaatt atctgatttc cagctaatta | 540 |
| cttgcttctt tatcgattcc cgcactaaca | 570 |

<210> SEQ ID NO 11
<211> LENGTH: 503
<212> TYPE: DNA
<213> ORGANISM: Scheffersomyces stipitis

<400> SEQUENCE: 11

```
aaggctcttt gaatttactt tgcctattta tagatatgta attggataca tgacatttat      60
ttggtgcaca taatcgactg gttttgtaat tgtatggcca ttaaccttt tagcacccgg      120
cccttgttat gcggagcgca gcaattggtt acgttttatc ttaatcgtac cgaagcacaa     180
tgatgtcagg cttcctgtag cccattagct ttctttattg cggttaattg gctctttgag    240
cccctcact ctgcaccctc cttttgcac cttattggtt tgtcagctcc gcttgttctt      300
ccggtcatat tcctaatggc ggagcttgta ggttgttatt ttgccgcaaa atcatgacct   360
ttctggtata aatattcaac ttttttcctg ttacagtaat ttttgctgtt gctggtttaa  420
ccaagtagcg aacattttac taagcacttt ttttgcatcc gttacataca ttcgctatct  480
acaataaacc tgattgattt aca                                            503
```

<210> SEQ ID NO 12
<211> LENGTH: 552
<212> TYPE: DNA
<213> ORGANISM: Scheffersomyces stipitis

<400> SEQUENCE: 12

```
aatcggaaaa tagaatcagc cgctgtcccc attgtgtccc attaaccaat ggtgggggtg    60
tgaaagcgtt agtgtaaaag cgtttcatcc agcgaaatgc attctaatca acagatgcca   120
tttatctgtc acctgatact taccaggaga ctcccacagc atttggagcc tgagggattt   180
acatccgagc cgttcaatgt ctctctagtg tagaaacggg gacgaaattt ttaaagcctt   240
tatgcagaat catgtataga tactttgcat ctcctgatgt tgaattaact ctaagcttaa   300
ccatgggaat ggccagatgg ggtagggcag tatctaaatc ggatgaggtg tattagaaga   360
ggagaaggag aggaattata cacacgagac gagagagaac cacgagttga aaaatttgtt   420
gccctgccaa ttcacctttt gaatactata aaagggctat gttgcagcca tcttactttt   480
acattttact tagaattttc ttctacagtg tcactattca cataatatag tagtataaat   540
aaaaatttca ag                                                        552
```

<210> SEQ ID NO 13
<211> LENGTH: 573
<212> TYPE: DNA
<213> ORGANISM: Scheffersomyces stipitis

<400> SEQUENCE: 13

```
aactggagtc atggattaga ttacgctgta cggccattgg tcaaaatggc agacgagcca    60
gcgctcaact gatgtaaaga ggaagaactc ggaaacggaa tatggcttcc atgctctgaa   120
tgaaactccg tattccctag ctaatacccg caccccagcc gtatggctgt accagtgact   180
ccgagacatc tgcttgtaga gtaagcgatt tcaccaaaaa gtcgaattga aaacgaatcc   240
aactatcagt ccatatttct ctaccggtct ttccatgaag acatctgagt tactgttaca   300
ctcgacaagc tacactctac taaatggctg ttccaaaaaa gccccttcag atggaagtat   360
ggccgcggaa tcaatggtat ataaataaat gtaaaattgc gcaaagctaa tactcaaatt   420
ataatattat aatattatat ctaagtctgc aatgtttttt ctgttgctca tagactctcg   480
```

```
taattcctat aaatataact gattccagtg caattccatc tttatccctt ttctcctctt    540
cctcatccag tctagcaatt caattaaatt aca                                 573

<210> SEQ ID NO 14
<211> LENGTH: 596
<212> TYPE: DNA
<213> ORGANISM: Scheffersomyces stipitis

<400> SEQUENCE: 14
ttcatgaagt acgataaggt tggtaaccga ttgactcatt ggttcgtggc ggagaagtac     60
gcagagtaaa accggggccg attcgtggta aattctggaa tgatccagag gcgcgacatt   120
tatgcagaca atttgtgttt tgtcgcaaac gatgttatag cgaaattttt cactctgtca   180
gataaatgga ttttgtcaaa aggggaagt agaaggagaa tgggcccgag atgttctgcc   240
aaattctcag tagcataatg tgaaagaagc ccttacattg tccagcctct ggcatcatta   300
aaaaccgtag cggaaaccaa ttgtctctgt tcttccctgg cacaccctgg tagccccatc   360
cagttgtagt acatctcaca cgctggcaac ttgggacaat cagcaacttt ttttttcttt    420
aattttttca gcgcgacatt ttgcctcttc tgcgagaaca gacttttca cctccatctc    480 accccctt gcacttatat aaattggacc agttcctccc attgtagaaa aaattttgct    540
ggaccttttt ctctttttt tgtcctttag tttcatacaa tctaagtcta tctaca         596

<210> SEQ ID NO 15
<211> LENGTH: 530
<212> TYPE: DNA
<213> ORGANISM: Scheffersomyces stipitis

<400> SEQUENCE: 15
aaaaaaaact gtcggtgtct tcctgaaaac acaggggtgc acctcgctat gtgcacccgg     60
acggagtctc aattccggag cagggggagg ttcctgtctt gtcgggaagt tgctttgtgc   120
agcgcacacc tgcgataacc gcagcgacaa gctcccattg gctgtgataa ccgcctcggt   180
cacaaattgc ctctgtgcac ccctcctaca gggaggacgc aggacgcact ccccaaaaaa   240
gaaacccaca tagcggctga agctaccgat ccagtttgcg accatctgga tgcaatatat   300
atatatggaa gcgaatcctc tcggaatttc gaaatcagtt gctttctctc cttttctttt   360
attgttttac gtctaaacaa caaacaacca aacccctaga cttactttt gtctgtctga    420 ccttgcttcg cttcccgcct tgctacccaa tcttagcttt caacttttgt ctgttgagcc   480
atctcgcaac ctgcatttc taactattag aatcacatac aatttccatc                530

<210> SEQ ID NO 16
<211> LENGTH: 561
<212> TYPE: DNA
<213> ORGANISM: Scheffersomyces stipitis

<400> SEQUENCE: 16
tctttctgac attggtgcgt atgctaatag ttccaccacc acattacata cagacacaaa     60
accgttttcg attgtaggcc gtagtcgtca gcttccgttc ttaaggcgaa acttctctaa   120
aatcgaataa gcgtccgctt cactggtccc accttggtct tctcttcaaa ctcgtcgtct   180
ctctggcctc cagcgcctgg ctctctggtg tccccatatt cgttcggaaa cattagcaga   240
ttcccaacgg ttgctccctt cggcttacat gcacgccgct ccggcacaca cctccgtctt   300
tggcgtagaa aatttgttgg gatttctttt gtcgactaaa ttgtgttatc tctgggtgcg   360
aaacatgcgt taccggcca tggggcccat agttttttta attgccatat gcatctgcct   420
```

```
acatgcatac catactggga aaattttgac aaactatata atggcaccag gatcgaggat    480
tgcaaactac cgggagactt ttgttttgct tgtttgtttg ttgtttgtag cttcaacttc    540
tgattctatt tcgatttcag t                                              561
```

<210> SEQ ID NO 17
<211> LENGTH: 526
<212> TYPE: DNA
<213> ORGANISM: Scheffersomyces stipitis

<400> SEQUENCE: 17

```
agcgtgttca attgcaaaat gtgttccacg gtctgctctc atcagcttgt gtgtctcgct     60
gggaattccc cactaattct caccaaatct cggtagccat ctgtggaagt gttcagtaat    120
gctcgccatt tcttcacta acaatctcta aggaaagatc ggtgtatttc aaagagtccg    180
gctaatagcc agaattctac gtaaccacta tatacacaga agcattctac gataaccact    240
atatatcgag tgtcttgcac gctctcagta cactttctct gccattacgt ggtgcactaa    300
tttcagtcaa atctggtgag ccgggctcca cgacttttac ccaattgcac ctgggcctga    360
aaatatatgg gatgaaaaat atataagtgc accgatttct acacaaccag attcgctaca    420
agtttcgctt tctttcttct tttctctagt ctgtacaacg tttgtgcgta gtttgtttct    480
tcatcgatct caagcttatc ctcattcaca tcgctatctc tacata                  526
```

<210> SEQ ID NO 18
<211> LENGTH: 1582
<212> TYPE: DNA
<213> ORGANISM: Scheffersomyces stipitis

<400> SEQUENCE: 18

```
ttcaaatcag gaagtaagct attttcatcg agagagggaa agtcaacaga cccctctttt     60
cggcctcccg agaatgaagt cgacgaagac gtcgacgcgt ggcacatgag cacccccctgc   120 gcccttgtaa atttagatgt acgtcctcgt ataccttcg ctaatatatt ggcgcattca    180
accatacgat catgagtcgg aaaaactcgc gttcggacac acgagcccag ccttcatgta    240
tgacggaaaa accactccag tcatgaatca cgctacttga tcacactgtt gcgcagtatc    300
atcacgaaac ctgcatataa caacatgtgt ctcgataaga gtatagagct ggagtagtgg    360
ttccacccga taacagagaa gcctgtttaa acctgcttga ctcacaaatg aatcagacgg    420
ccagtttcgg gtttagatgg aaatgtgcca ctaggagttg acgttctctt gactcatata    480
cgcctacgag ctgggggcga ttagccgaat gccttcattt tcttctgcgg agcggagacg    540
ctagcagcac aaattaccgt ggtgggagac attcacaatc ctggctaatt tggtgatgtc    600
attagagggg agagaaatct cattctgaca cacacttctg gtgtctagca tctagtattg    660
tcctctctcg tacaatatca cactctcatg gtagaactca atccgctttc tcttgtagcc    720
cgctcataca gtggccctag tagcccgctc tcaataccga gtagcctcaa cttgcgttcc    780
accacattgt cgagacctgg actcacacct tgggatatcc ccattggctg ggattactgt    840
ggggtggcag atctccgctt gcggcagttt ggtgggtgaa atggccactg tcattctctt     900
tgcaattcga gggttccct tctaggcgat ggtagtggat tgacaaacct gctggtggtg    960
ggattgggtg ctctggagcc cgtgccgcag tactgatggc aggagaaata gtagtcgcac   1020
taccagccgg aacttctccg atgtggagtg acttgtttgg cttatttct gctgctcttg   1080 tgcgacattt cccaagtgga gtattttcc tgtgggctac ttcctgtatt ctccttaagt   1140
```

```
gcatcgcatc acgataccaa tgaggagact ttttctgggg ccatgtcatg ttccctattg    1200
tttacgacgg caattcacga ataggggacg aataatatag aacgatgaaa ttcttgggcg    1260
tagccagaat gtgtcggttc ctttacctgc tacggatttg agggatttag cctgggttgg    1320
ctggttttct gtggttgcat cattctgatg cggcgcagat atatagttgc aaattaacta    1380
tgcgccccag caatataaat agtctagttt tcccactggt gtgtaactac tttcactttt    1440
cttttcttca ctactgatca acaccaagat ctaaccaaac aactctcata tatatatacg    1500
tctcctgctg tatatatata tttacaaagg caccctgtcg ctgttacaca actacaacta    1560
cttcatataa ccctaatcga cc                                            1582

<210> SEQ ID NO 19
<211> LENGTH: 357
<212> TYPE: DNA
<213> ORGANISM: Scheffersomyces stipitis

<400> SEQUENCE: 19
acaagccgtg ctagatagtg ctttgttcta ttccacctcg tgttttattt acctttaac     60 tagtgctaat ttacgaataa tgtacgttag aaaaattgac ctgtttatat atgggtgcaa   120
aaaagttgcg tcctgtccaa aggttgcatt tcccctcaag caaccaaaag gagttaggat   180
ctgggaacta tttaacgccg ctggggcaac aattgagatg tcgtagacgc catgccccac   240
ctaaccaatg cactctaata ctgtagttat atccttaaga ttagttctca ccgtgaagta   300
aagatggtga acgttttcta agaaattttc taggaaaaag caaactttaa gaggcta      357

<210> SEQ ID NO 20
<211> LENGTH: 300
<212> TYPE: DNA
<213> ORGANISM: Scheffersomyces stipitis

<400> SEQUENCE: 20
gaattgctca ggtttcccga tttcttccta catcattttt gtatcgttgt tcatagttag    60 gttttttacga agaatgaagt catgattagc acgaagttga ttgcaccgta gtagccgctg   120
gaaacagcta cagtttaatc gagagtagct gcaagtcaga cctgtatgga atcaaaatcg   180
gagttgcagc aatatcaaat cccgcgcaag ttgagagaca tctcttagca atatcgagac   240
caatacgatg aagttaggaa ttggccgata agagaacgga gaaatattat acaaagcaga   300

<210> SEQ ID NO 21
<211> LENGTH: 233
<212> TYPE: DNA
<213> ORGANISM: Scheffersomyces stipitis

<400> SEQUENCE: 21
tcatgtcaat gacatttta ctattcaaaa aagctttaat acgttcacga gtcttacata     60
gatatttgag atatttatta tgaacaaatt gcactgtaga attaatatct aaacttgtag   120
aagtcgtgtg atactttgta tacgactact tttataccaa tgatatttct aactttctag   180
atgttcatgg ttctatcata gattttgacg ttctatacac tttaaaattc tat           233

<210> SEQ ID NO 22
<211> LENGTH: 300
<212> TYPE: DNA
<213> ORGANISM: Scheffersomyces stipitis

<400> SEQUENCE: 22
atgtctggct ggtttccttc tgctgtactt taccctttac atagtccttt agttcgtgct     60
```

```
tcctttttttt cttaatctgt ttttcatgct tatcgttaat gccaactaca aaactgctgc      120
ttagcaacaa cttctcttca tctacaaact tcataaaagt taagtttatt cattgtatag      180
taatgctata atttgctact actgttcact ttcgattttt gctgtagaaa gtagtaaaat      240
gattcaatat caatattgct caatctgcat tttggtggta ctaatgttca ttattcgtta      300

<210> SEQ ID NO 23
<211> LENGTH: 300
<212> TYPE: DNA
<213> ORGANISM: Scheffersomyces stipitis

<400> SEQUENCE: 23
ttttattttt cctttcctta aatctccgat gaagtgacta gacttcatta gatttatttc       60
tacttgtttg tcttttacga atgataatta cgaaatttac gtttacgccg ctcatgttta      120
tatgttatta tgagatatac gtcattgtat ataattgaat tgtagcagtt tgtaggtatt      180
cgtagatacc agttggtata atttgctgat ttattccaaa gtccggttag ggggttgtac      240
gatttgtctg gacatgtgac ccttccaaaa atggagcaat cggaatctac cccaagattg      300

<210> SEQ ID NO 24
<211> LENGTH: 300
<212> TYPE: DNA
<213> ORGANISM: Scheffersomyces stipitis

<400> SEQUENCE: 24
actatactag ccaagatagc acattagaga atagagaaag atttcaggta tggttggtta       60
tatttaagaa ttatggagta tgtcattgaa gagtttattg tttgcgagtt tggtcctttt      120
gtttatattc ctatccatag cttcgtttta tattaccttg tattttccat tatcaaatct      180
acaaacagct caatattatg acaacaaaaa atattcggaa attattcagt gtagaaagag      240
agatagcaaa aggagcccgg atcaattttt cggtttttaa tttgttcatc gtatgcgaaa      300

<210> SEQ ID NO 25
<211> LENGTH: 150
<212> TYPE: DNA
<213> ORGANISM: Pichia stipitis

<400> SEQUENCE: 25
ttgatgtaag actttaatta taagaataca attgtgataa agacaatgta gaagtactgt       60
agaagtcatg gaatagctga tcaactgtac tgttatacaa aggtactatt aacaaaatag      120
acatatagtt tctataacat atataaacat                                       150

<210> SEQ ID NO 26
<211> LENGTH: 500
<212> TYPE: DNA
<213> ORGANISM: Scheffersomyces stipitis

<400> SEQUENCE: 26
tggtctcttg gcttaatttc actcctcatt gacttctttt gattacgttg cccccatatt       60
tgttttcggt atccttactt aattttctta ataataattc ttgcacccaa gtttgaaaag      120
tctgctctga tgttttttt catgtaccac agagatcaat tcttgcatcc acatagttta      180
actaattggc aataaacatg atgtttcgct tacctaacag ctatagaaca cgtgtagtaa      240
ttaaaatctt caggtcttcc aaattgttgg ggtatataat tcctttatt tcacaataga      300 tatactgtaa atctcagttt ggttaacttt catacaatta attcacccct gatcattctt      360
```

```
tttcacagta ccttattaat agaattaact attgaatgtt cccttttgaa aattatttcc      420
taagcgactt cttgtatttt accaataact aagtaaatct tcaaaaaata gaattaaact      480
ttgcatccag caaataaaat                                                   500

<210> SEQ ID NO 27
<211> LENGTH: 150
<212> TYPE: DNA
<213> ORGANISM: Scheffersomyces stipitis

<400> SEQUENCE: 27
ttgtagtatt tgttatttca tatatatgtc tctcattatg aacttctttt attgaatacg       60
atgttaatga cattagtttt ttaggcggtg aaaaatatct acctaattcc aacgtacgaa      120
tgagtcagaa acgaactcaa taatagaagt                                       150

<210> SEQ ID NO 28
<211> LENGTH: 329
<212> TYPE: DNA
<213> ORGANISM: Scheffersomyces stipitis

<400> SEQUENCE: 28
gctgattaat ttacgtatat tcagtttaat atcaatacgt tagctacatt tccaatgaac       60
gatactagat attgtttagg attattgaac tggtatagat aattttagtg tatattcatg      120
tacttgataa atgtaataat atgtgaaaat gtagttgtac attaactgat agacaacatg      180
ctggagtata tggcattaag gttgctacaa agtagaagca acctagacac acctcagaag      240
atagattggg cgagtgatcg tattatatga gaacttctat gtgatacact tccaagtatg      300
attagtgtct acaataacct tatattatc                                        329

<210> SEQ ID NO 29
<211> LENGTH: 717
<212> TYPE: DNA
<213> ORGANISM: Artificial Sequence
<220> FEATURE:
<223> OTHER INFORMATION: Synthetic Construct

<400> SEQUENCE: 29
atgtctaaag gtgaagaatt attcactggt gttgtcccaa ttttggttga attagatggt       60
gatgttaatg gtcacaaatt ttctgtctcc ggtgaaggtg aaggtgatgc tacttacggt      120
aaattgacct taaaatttat ttgtactact ggtaaattgc cagttccatg gccaacctta      180
gtcactactt tcggttatgg tgttcaatgt tttgctagat acccagatca tatgaaacaa      240
catgactttt tcaagtctgc catgccagaa ggttatgttc aagaaagaac tatttttttc      300
aaagatgacg gtaactacaa gaccagagct gaagtcaagt ttgaaggtga taccttagtt      360
aatagaatcg aattaaaagg tattgatttt aagaagatg gtaacatttt aggtcacaaa      420
ttggaataca actataactc tcacaatgtt tacatcatgg ctgacaaaca aaagaatggt      480
atcaaagtta acttcaaaat tagacacaac attgaagatg gttctgttca attagctgac      540
cattatcaac aaaatactcc aattggtgat ggtccagtct tgttaccaga caaccattac      600
ttatccactc aatctgcctt atccaaagat ccaaacgaaa agagagacca catggtcttg      660
ttagaatttg ttactgctgc tggtattacc catggtatgg atgaattgta caaataa         717

<210> SEQ ID NO 30
<211> LENGTH: 972
<212> TYPE: DNA
<213> ORGANISM: Artificial Sequence
```

<220> FEATURE:
<223> OTHER INFORMATION: Synthetic Construct

<400> SEQUENCE: 30

| | | |
|---|---|---|
| atggccagag aagaaaagcc aagaaaggtc atcttggtcg gtgatggtgc tgtcggttct | 60 |
| actttcgctt tctctatggt tcagcagggt atcgccgaag aattgggtat catcgatatc | 120 |
| gccaaagaac acgtcgaagg tgacgctatc gatttggctg atgctactcc atggacctcc | 180 |
| ccaaagaata tctacgctgc tgattaccca gactgtaagg acgctgactt ggttgttatc | 240 |
| actgctggtg ctccacaaaa gccaggtgaa actagattgg acttggtcaa caagaacttg | 300 |
| aagatcttgt cctccatcgt cgaaccagtc gtcgaatctg gtttcgaagg tatcttcttg | 360 |
| gtcgtcgcta acccagtcga catcttgact catgctactt ggagaatgtc cggtttccca | 420 |
| aaggacagag ttatcggttc tggtacttct ttggacaccg gtagattgca aaaggtcatc | 480 |
| ggtaagatgg aaaacgtcga cccatcttct gtcaacgcct acatgttggg tgaacacggt | 540 |
| gatactgaat cccagcctg tcttacaac aacgttgctg tgttaaggt tgccgactgg | 600 |
| gttaaggctc ataacatgcc agaatccaag ttggaagata ccaccaaga ggtcaaggac | 660 |
| atggcctacg acatcatcaa caagaagggg gctaccttct acggtatcgg tactgcttct | 720 |
| gctatgatcg ctaaggccat cttgaacgac gaacacagag tcttgccatt gtctgttcca | 780 |
| atggacggtg aatacggatt gcacgacttg catatcggta ctccagctgt tgttggtaga | 840 |
| aagggtttgg aacaggtcat cgaaatgcca ttgtccgaca agaacaaga attgatgacc | 900 |
| gcttctgccg accagttgaa gaaagttatg gacaaggcct tcaaagaaac cggtgtcaag | 960 |
| gttagacagt aa | 972 |

<210> SEQ ID NO 31
<211> LENGTH: 2594
<212> TYPE: DNA
<213> ORGANISM: Scheffersomyces stipitis

<400> SEQUENCE: 31

| | | |
|---|---|---|
| cctgatcaag caccaactac gtctgcttca actattccta tgggggtgtc cggtatcctc | 60 |
| gcattttacc ggttgttccc acgacttcac gaactgaaca tttgtcgagt gatgaacatg | 120 |
| aaaattcctt gggtgatcac tcacaagaaa caatcaacag atatgaacag gcaaattct | 180 |
| cttgcgacct ctttgtctat ttcggacaat ttactaccac taccttcgtc tcctgatgcg | 240 |
| tctcttctct ccttttgattc cactgatact gaatttgcac aaataccatc taatcgactc | 300 |
| gcatccgatt ctacggggt gaggttctca ccaaacactc attgacacca gtgataagtc | 360 |
| ctaaccacaa tcagagggct ggaaacaaga gaaagcaggt gccatcaacg aatttgacaa | 420 |
| agagagtcct ataggaattc atgaggataa tgtatcctgt ataaaactta gtaaacattc | 480 |
| tgttgaaatt ttataccca ataatgcacc ttcttcttat atgcagaatg gctgcaaaat | 540 |
| ctaacataat ctcaagcaac gataaggtat gccctggact ctgaggactt tcacctctcg | 600 |
| gatatccttg tttcttcata tgacctgct gtagccacct gtcccaaacc tgttaatatt | 660 |
| aattccagtc gcacgaatag cccaacagtt ataactcctg acagtcctc atccccggcc | 720 |
| ctgcgtggct cagtgtacta cctgtcaaac tatcccgctc ttcttcccgc gtctacctca | 780 |
| ggggggaagc acctactgca tcacggccta ctccactggt caatgaaatg taacttgttc | 840 |
| gtacgaacct ctttggtgcg cgagaacaac gcattgttcg gaagcgcaaa ctcacaccag | 900 |
| ttccgtctcg agtccctctg tagtggaatg acataattct tttcttaata ctttatgaag | 960 |

-continued

| | |
|---|---|
| ctggtatgtg tatcagtgtt aagtacttca tatagctata gacaatttct ctaaacaggg | 1020 |
| aatttcttga agaatttgta cagaattcgc agcacgtaga ttttttgtgt tacgatgagg | 1080 |
| tcggagaaaa ctgctaatct ctaggccgtt gaccggacat tgctgataaa aacatccagt | 1140 |
| cttggtccta gtactttaac ctcaatcatt tatcgttcct tgagattatg tcagattttg | 1200 |
| ctgctattct gtatataaga acatagcgaa tcatgttgaa taagttttga tgaatatttg | 1260 |
| ctaatccact acttaaacta tacaagtgca aaattgctgc catttaacgt gattctgatc | 1320 |
| tacattgaga aaatctcctc cattgtgaag gtaaacattc tatctttta gcttttccct | 1380 |
| ccttgtatct atgcaaaata actacccgta aataagtaac tcaatagaat aacttaacaa | 1440 |
| taatttaaa gaatctgatc cgcttccaaa gtaaacagct aaacacatcg ttgtagcata | 1500 |
| aactcgttca acaagatttg acacctattc ttcaaaatcg ctctcggttt aaactctgtt | 1560 |
| gaactgcatt tgcaaatgtt ccagttggcg ttcttcacgg gagattatcc cggaattgat | 1620 |
| ccttttcgga aagctcatct tgtttattac tttgcaacta tacaagatat tacaatactt | 1680 |
| catttcagtt ccaggagcct tcttcctatt tgcaaggctg ctgaagtcta ccccactagg | 1740 |
| agctcgcctc tccatcctcc aggtcctatt gtccgtcttc agagaactga tattcctcct | 1800 |
| tctgattcct tcgacctatc tgccgacttt tctaccgctc ctggtcctcg tcaggtatca | 1860 |
| tatcgtccaa cataattctt gttttaaaac acctgtattt gaacatttgc agataaggct | 1920 |
| gcaggtactc atataggatg aatggaagta ctacttcaat tcatcgaatt acaactattt | 1980 |
| ccattagata tcagcactg ttggattgct tcaaattttc actacaggat aattcagtct | 2040 |
| catattgaat aaccgaagct tattgttggt tattttagat attcaatttc aacaccaagg | 2100 |
| attcggtatg ttaaggttcc ggaacaagat tgcaatagg ctctttatgc ttcaaagttt | 2160 |
| agaacaatta atctgcaatt gaactcgttc tatctactat caaatgggtg atgactaatt | 2220 |
| tttaacaatt ccaagagttt ctattgattt caggatattg aatattgctc tattgtaaaa | 2280 |
| tggcctgtag tggatgggag aaagcactgc gtttcctcct atacaggccc aactcttcct | 2340 |
| ctactagcat acgcaaaatg caccaggcca gtgctaggaa tgatgtcatt tataatactc | 2400 |
| catgcttata gaacaattat gaattgcttt aataaaagtt aaaaatgaaa tgcatatagc | 2460 |
| gcttctcatg tttggaagtc tatttggaca atatacattt gaaggtcaaa cgttggtatg | 2520 |
| ctttgaagtt cataatggtt gagttgagca tacacataga tagacagtct gtcaacaccc | 2580 |
| aataaacaca aaca | 2594 |

<210> SEQ ID NO 32
<211> LENGTH: 3060
<212> TYPE: DNA
<213> ORGANISM: Scheffersomyces stipitis

<400> SEQUENCE: 32

| | |
|---|---|
| tgactccaca agtgccacgc acctatgagg aagccactaa cagtcctcaa cgagaacgat | 60 |
| ggattgaagc tatgaacaag gaatttggtg ctcaaatgga aaactccacg tggactcttg | 120 |
| ctgagcttcc taagggaaaa cgagccctag gaatgaagtg ggtatatacc atcaaagatg | 180 |
| atggaactta caaagccaga ctagttgctc taggttttag acaaaaacat ggaattgact | 240 |
| atgaagaaac ctttgcgcct gtgatcagga gtgaaagtat caaacttcta ctagccatag | 300 |
| cggctgtaca taagatgaag attcatcaga tggacgtctc gacggccttc ctaaatggga | 360 |
| agattgacac agaactctac attaagcagc ctaaggttt catggatgaa caatatccac | 420 |
| atatggtttg taagttgaac aaatcactct acggtctaaa acaagctcca ttgatctgga | 480 |

```
actcgactat taataaattc ttggagaata acggctttat tcgatcaaaa tccgagttcg    540
ggatctacag aagaaataat gtgattcttg gcctttacgt tgatgaccta cttattgcga    600
gtcctcgaga aaatgaaatc tacgaggcca agaaacttct cctgaacaag ttcaagatga    660
aggatcttgg attggcacgc aaattcctag gaatcaacat agaacagggc cctgaaggga    720
tcacagcaaa tctttctgac tacatcaaga aaacgttgga ggaactaaat cttgaagagc    780
tcaacagcgt gaaaagtcct attattcagg acagcatct  aaaccagaaa tccaaaccct    840
gcgatgcaac aatttacaga agcatagtag gaaagcttct ttatgctagc aataccatac    900
gaggtgatat tgcttatatt gttggaatgt taagtcggta cttcaacgaa ccaacagagg    960
taactctaac tgccgccaaa catgttctcc gctatctaaa aggaacacag aaactcggtc   1020
agcactacac aaacataaac gatctacaag tgtttgttga ctcagactgg ggaagtgata   1080
gcagtgacag gaaatcaatc agtgggtatg ccatcaagta tgggggaagc ctaatctctt   1140
ggaaatccaa gaaacaaacc accacagcat tgtcaaccac tgaagctgag tacatggccc   1200
tcgcaaccgt tataaagaa  gttatctggc taataacatt cttcagagaa cttcgaatcc   1260
caatatcact accaataatg atttgggaag ataacacctc gtgtatcaaa ctcagcgaac   1320
atcctgtaca ccacgaacgt acgaaacaca tagatattcg ctatcacttt atccgtgaca   1380
aaatcataga caatattgtc aaacttcgcc aaatcaaatc tgccgacaac gttgcagata   1440
tgtttacaaa aggactaact ccaggaacct tccaacactt aatccaacta tcaggaatgc   1500
aactaaccca ataaaatgac cattggatta agggggatg  ttgaatatgt tgaatatgct   1560
gatatcaaac ctaaaagcat attctatatt ctattttta  tccaatgcgt aaactttatg   1620
aatgcaggat ttgcagccat tcagacataa ttgtgcacag taatgtgata agataacatc   1680
taccaatgag aatcaattat gtccgactaa cctgaaattc tggtcatgtc gtttcatttc   1740
ctcctgatga ggggtcagcc tgtgattgta tttggcatct atataagggg gtcttactcc   1800
cccttctcct ttctaacttt ctataacttt tcttcttcta tatggaaatt atctatctta   1860
aataagttaa tcaatatact gtcctacatt atgaataatc cgattcaatc tactgagctt   1920
ccaaagcaaa cagttcaaca gtgaaagcgt aaacttgtaa aggttggagt caggaagaac   1980
agagccaaca agtcctaaca caggatgaga gacggcagtt ggcagaaagt tgaaattaga   2040
tttgctacga gcagcagcaa cagcaaggga acgaggttc  ctggcacatc cagggacgta   2100
gtagacatca tgaagttcaa caggagtttt accggcaaga aacttgacag taccagaacc   2160
acaaacaggg agagggcgc  cattagcgcc aaaaatagaa ccagctttcg acgaaacagt   2220
gggcttgaag tcccaaaaca aggtaggatc attacagata tgatacgaag caccagaatc   2280
aataaggaaa tcagtggagg ccaataacat agaaggggat acattgaggg aatacgcctg   2340
ggtggatggg gtggatgcaa aggcatcacc agcggcagta gaaaaagaat gaacacgagg   2400
agacagagag gtacgggacg acaggaaatg tccagtacga acaggagaag gacagctagt   2460
ggccttgtgg ccattaccaa gacaattggt acacttgaga acagggggaag tacatgttga   2520 agttcagaag cattcatagt gtcttacgtg taataattgt taacagtaaa ggtagaactt   2580
gtaagttgtt ctcgttatcg ttattaaaac attaagaaag tctatctaac tctgagagga   2640
taccaccctt atttatgttg aatatgctga tatcaaacct aaaagcatat tctatattct   2700
atttttaatc caatgcgtaa actttatgaa tgcaggattt gcagccattc agacataatt   2760
gtgcacagta atgtgataag ataacatcta ccaatgagaa tcaattatgt ccgactaacc   2820
```

```
tgaaattctg gtcatgtcgt ttcatttcat cctgatgagg ggtcagcctg tgattgtatt    2880
tggcatctat ataagggggt cttactcccc cttctccttt ctaactttct ataacttttc    2940
ttcttctata tggaaattat ctatcttaaa taagttaatc aatatactgt cctacattat    3000
gaacaatccg attcaatcta ctgagcttcc aaagcaaaca gttcaacagg ttatgagcca    3060
```

<210> SEQ ID NO 33
<211> LENGTH: 23
<212> TYPE: DNA
<213> ORGANISM: Scheffersomyces stipitis

<400> SEQUENCE: 33

```
actgcgttga tctgtttcgc agg                                              23
```

<210> SEQ ID NO 34
<211> LENGTH: 23
<212> TYPE: DNA
<213> ORGANISM: Scheffersomyces stipitis

<400> SEQUENCE: 34

```
acgtactatt caagaaccag tgg                                              23
```

<210> SEQ ID NO 35
<211> LENGTH: 23
<212> TYPE: DNA
<213> ORGANISM: Scheffersomyces stipitis

<400> SEQUENCE: 35

```
agcagttggt ggtcccaagt ggg                                              23
```

<210> SEQ ID NO 36
<211> LENGTH: 23
<212> TYPE: DNA
<213> ORGANISM: Scheffersomyces stipitis

<400> SEQUENCE: 36

```
aactaacttg tgtgcttcag tgg                                              23
```

<210> SEQ ID NO 37
<211> LENGTH: 23
<212> TYPE: DNA
<213> ORGANISM: Scheffersomyces stipitis

<400> SEQUENCE: 37

```
actcgaccaa agagaacttg tgg                                              23
```

<210> SEQ ID NO 38
<211> LENGTH: 23
<212> TYPE: DNA
<213> ORGANISM: Scheffersomyces stipitis

<400> SEQUENCE: 38

```
atttgtaggc atagacttcc tgg                                              23
```

<210> SEQ ID NO 39
<211> LENGTH: 23
<212> TYPE: DNA
<213> ORGANISM: Artificial Sequence
<220> FEATURE:
<223> OTHER INFORMATION: Synthetic Construct

<400> SEQUENCE: 39

```
aaaggtgaag aattattcac tgg                                              23
```

<210> SEQ ID NO 40
<211> LENGTH: 378
<212> TYPE: DNA
<213> ORGANISM: Scheffersomyces stipitis

<400> SEQUENCE: 40

```
aacctctttt ttttacgaaa tggcatgtat tatgatctgc tacagagtat ataaatcttc      60
ctctaatcca taccgaaagg tggagggaat cctaggataa aaacctccga atgacattac     120
ctaaaaaaac acataagtga tatctttgga aagcaacaga agttacaact attttatttt     180
attttacacg tgactgaccg cgtgattagg cacgtgacta atcacgtgct gtataatgac     240
aattggagtg aatgtgtaat tttgtgcgat attttgctgg atggcgcatt cgctggaccg     300
gcgagtttgg agttcccgtc agctgacggt gcctttgaac gagtcgcagg ttcgtttcca     360
acaagataca tttatttc                                                   378
```

<210> SEQ ID NO 41
<211> LENGTH: 298
<212> TYPE: DNA
<213> ORGANISM: Scheffersomyces stipitis

<400> SEQUENCE: 41

```
tggagggaat cctaggataa aaacctccga atgacattac ctaaaaaaac acataagtga      60
tatctttgga aagcaacaga agttacaact attttatttt attttacacg tgactgaccg     120
cgtgattagg cacgtgacta atcacgtgct gtataatgac aattggagtg aatgtgtaat     180
tttgtgcgat attttgctgg atggcgcatt cgctggaccg gcgagtttgg agttcccgtc     240
agctgacggt gcctttgaac gagtcgcagg ttcgtttcca acaagataca tttatttc      298
```

<210> SEQ ID NO 42
<211> LENGTH: 4338
<212> TYPE: DNA
<213> ORGANISM: Artificial Sequence
<220> FEATURE:
<223> OTHER INFORMATION: Synthetic Construct

<400> SEQUENCE: 42

```
atggactaca aggatgacga tgacaagcct ccaaagaaaa agagaaaggt tgacaagaag      60
tactctatcg gtttggctat cggcactaac tctgttggtt gggctgttat cactgacgag     120
tacaaggtcc catccaagaa gttcaaggtc ttgggtaaca ccgacagaca ctccatcaag     180
aagaacttga tcggcgcctt gttgttcgac tctggtgaaa ctgctgaagc caccagattg     240
aagagaaccg ccagaagaag atacaccaga agaagaaca gaatctgcta cttgcaagag     300
atcttctcca acgaaatggc caaggtcgac gactcgttct ccacagatt ggaagaatcc     360
ttcttggtcg aagaggacaa gaagcacgaa agacacccaa tcttcggtaa catcgttgac     420
gaagtcgcct accacgaaaa gtacccaacc atctaccact tgagaaagaa gttggtcgac     480
tctaccgaca aggccgactt gagattgatc tacttggctt ggcccacat gatcaagttc     540
agaggtcact tcttgatcga gggcgacttg aacccagata actctgacgt tgacaagttg     600
ttcatccagt tggtccagac ctacaaccag ttgttcgaag aaaacccaat caacgcttct     660
ggtgtcgacg ctaaggctat cttgtctgcc agattgtcca gtccagaag attggaaaac     720
ttgatcgccc agttgccagg cgaaaagaag aacggtttgt tcggcaactt gatcgctttg     780
tccttgggct tgacccccaa cttcaagtct aacttcgact tggctgagga cgccaagttg     840
```

```
cagttgtcta aggatactta cgacgacgac ttggacaact tgttggctca aatcggtgac    900
cagtacgctg acttgttctt ggctgctaag aacttgtctg acgccatctt gttgtccgac    960
atcttgagag tcaacaccga aatcaccaag gccccattgt ctgcctctat gatcaagaga   1020
tacgacgaac accaccagga cttgaccttg ttgaaggctt tggttagaca gcagttgccc   1080
gagaagtaca agaaatcttc ttcgaccag tccaagaacg gttacgctgg ttacatcgat   1140
ggtggtgcct cccaagaaga gttctacaag ttcatcaagc ccatcttgga aaagatggac   1200
ggcaccgaag agttgttggt caagttgaac agagaggact gttgagaaa gcagagaacc   1260
ttcgacaacg gttctatccc acatcagatc cacttgggtg aattgcacgc catcttgaga   1320
agacaagagg acttctaccc attcttgaag gacaacagag aaaagatcga agatcttg   1380
accttcagaa tcccctacta cgtcggtcca ttggccagag gtaattctag attcgcctgg   1440
atgaccagaa agtccgaaga aactatcacc ccctggaact tcgaagaagt tgttgataag   1500
ggcgcctccg cccagtcttt catcgaagaa atgaccaact tcgacaagaa cttgcccaac   1560
gagaaggtct tgccaaagca ctccttgttg tacgagtact tcaccgtcta caacgagttg   1620
accaaggtca agtacgtcac cgaaggtatg agaaagccag ccttcttgtc tggtgaacag   1680
aagaaggcta tcgtcgactt gttgttcaag accaacagaa aggtcaccgt caagcagttg   1740
aaagaggact acttcaagaa aatcgagtgc ttcgactccg tcgaaatctc tggtgtcgaa   1800
gatagattca acgcctcctt gggtacttac cacgacttgt tgaagatcat caaggacaag   1860
gatttcttgg acaacgaaga gaacgaggac atcttggagg acatcgtctt gactttgacc   1920
ttgttcgagg acagagagat gatcgaagag agattgaaaa cctacgccca cttgttcgac   1980
gacaaggtca tgaagcagtt gaagagaaga agatataccg gctggggcag attgtccaga   2040
aagttgatca acggtatcag agacaagcag tccggcaaga ctatcttgga cttcttgaag   2100
tctgacggct tcgccaacag aaacttcatg cagttgatcc acgacgattc cttgaccttc   2160
aaagaggaca tccagaaggc tcaagttttct ggtcaaggtg actccttgca cgaacatatc   2220
gctaacttgg ctggttctcc agccatcaag aagggtatct tgcagactgt taaggtcgtc   2280
gacgaattgg tgaaggtcat gggtagacac aagccagaga catcgtcat cgaaatggct   2340
agagaaaacc agaccacca aagggtcag aagaactcca gagaaagaat gaagagaatc   2400
gaagagggca tcaaagagtt gggctcccag atcttgaaag aacacccagt cgaaaacacc   2460
cagttgcaga acgagaagtt gtacttgtac tacttgcaga acggcagaga catgtacgtc   2520
gaccaagagt tggacatcaa cagattgtct gactacgacg ttgacgctat cgtcccccaa   2580
tctttcttga aggatgactc catcgacaac aaggtcttga ccagatccga caagaacaga   2640
ggtaagtctg acaacgttcc atccgaagag gtcgtcaaga agatgaagaa ctattggaga   2700
cagttgttga acgccaagtt gatcacccag agaaagttcg acaacttgac taaggccgaa   2760
agaggtggtt tgtctgaatt ggacaaggcc ggcttcatca agacagttg gtcgaaact   2820
agacagatca ccaagcacgt cgctcagatc ttggactcca gaatgaacac caagtacgac   2880
gagaacgaca agttgattag agaggtcaag gtcatcacct gaagtccaa gttggtgtcc   2940
gacttcagaa aggacttcca gttctacaag gtcagagaga tcaacaacta ccaccacgct   3000
catgacgctt acttgaacgc tgttgtcggt actgccttga tcaagaagta cccaaagttg   3060
gaatccgagt tcgtctacgg tgactacaag gtctacgacg tcagaaagat gatcgccaag   3120
tccgaacaag aaatcggtaa ggctaccgcc aagtacttct tctactccaa catcatgaat   3180
ttcttcaaga ccgagatcac cttggccaac ggcgagatca gaaaaagacc attgatcgaa   3240
```

```
actaacggcg aaaccggtga aatcgtttgg gataagggta gagacttcgc caccgtcaga   3300
aaggttttgt ctatgcccca ggtcaacatc gtcaagaaaa ctgaagtcca gaccggcggc   3360
ttctccaaag aatctatctt gccaaagaga aactcggaca agttgatcgc cagaaagaag   3420
gactgggacc caaagaaata cggtggtttc gactctccaa ccgtcgctta ctctgttttg   3480
gttgtcgcta aggtcgagaa gggcaagtct aagaagttga agtccgtcaa agagttgttg   3540
ggcatcacca tcatggaaag atcgtccttc gagaagaacc caatcgactt cttggaagcc   3600
aagggctaca agaggtgaa gaaggacttg atcatcaagt tgcccaagta ctcgttgttc   3660
gagttggaga acgtagaaa gagaatgttg gcttccgctg gtgaattgca aagggtaac    3720 gaattggcct tgccctccaa gtacgtcaac ttcttgtact tggcctccca ctacgaaaag   3780
ttgaagggtt cccctgaaga taacgagcag aagcagttgt tcgtcgagca gcataagcac   3840
tacttggacg aaatcatcga gcagatctcc gagttctcta agagagtcat cttggctgac   3900
gccaacttgg acaaggtctt gtctgcttac aacaagcaca gagacaagcc aatcagagag   3960
caggccgaaa acatcatcca cttgttcact ttgaccaact tgggtgctcc agctgctttc   4020
aagtacttcg acactaccat cgacagaaag agatacacct ccaccaaaga agtcttggac   4080
gctaccttga tccaccagtc tatcactggc ttgtacgaaa ccagaatcga cttgtctcaa   4140
ttgggtggtg acgatcctaa gaagaaaaga aagttggta gttccaagct tggcggcagc    4200
ggcggcagca tggaaagagt caagatgatc aacgtccaga gattgcttga agccgccgaa   4260
ttcttggaga aagagaaag agaatgcgaa cacggctacg cctcttcatt cccatctatg    4320
ccatctccaa gaggctga                                                 4338
```

<210> SEQ ID NO 43
<211> LENGTH: 8
<212> TYPE: PRT
<213> ORGANISM: Artificial Sequence
<220> FEATURE:
<223> OTHER INFORMATION: Synthetic Construct

<400> SEQUENCE: 43

Asp Tyr Lys Asp Asp Asp Asp Lys
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

Asp Pro Lys Lys Lys Arg Lys Val
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic Construct

<400> SEQUENCE: 45

Gly Ser Ser Lys Leu Gly Gly Ser Gly Gly Ser
1               5                   10

```
<210> SEQ ID NO 46
<211> LENGTH: 100
<212> TYPE: DNA
<213> ORGANISM: Scheffersomyces stipitis

<400> SEQUENCE: 46
ttaacattaa cacagttatc ttggatgccc ccaactctta gcgaaacaga tcaacgcagt      60
gagtgaccat gttgatggct ctttcacaca ctatgagtct                          100

<210> SEQ ID NO 47
<211> LENGTH: 2463
<212> TYPE: DNA
<213> ORGANISM: Artificial Sequence
<220> FEATURE:
<223> OTHER INFORMATION: Synthetic Construct

<400> SEQUENCE: 47
aactacagct cactctagat gatggtacct tgacaaacca aaaccagtta ctatctaatt      60
tagaagacga agaagagtcg ggatcggtta gtatttctca ggtcagcaca cctaccccag     120
actttaagtc accaaaattg cttcctacga aaatcaacaa ctttgagaaa aatctccgag     180
aatttgctat cactggagaa agccatgtca ataagttaaa cgagaacttc aagaactttg     240
gtaagttctt cagaaaggat aacgactagc atagatagtt ttatatagct ttggttatat     300
atggttgtat atgcagtatt ccatcaaaat cattagtcat aagatttaga gggttataca     360
aatttaatag ctttacttct atcttcaaaa gtcattggat atgcccaaaa ttgtaaagat     420
atgtggaacc agaacagttg aagctgctgc taaagctata gagtcaggaa cggatttact     480
cggggtaatt cttgtaccca ttcatgaagt acgataaggt tggtaaccga ttgactcatt     540
ggttcgtggc ggagaagtac gcagagtaaa accggggccg attcgtggta aattctggaa     600
tgatccagag gcgcgacatt tatgcagaca atttgtgttt tgtcgcaaac gatgttatag     660
cgaaattttt cactctgtca gataaatgga ttttgtcaaa agggggaagt agaaggagaa     720
tgggcccgag atgttctgcc aaattctcag tagcataatg tgaaagaagc ccttacattg     780
tccagcctct ggcatcatta aaaaccgtag cggaaaccaa ttgtctctgt tcttccctgg     840
cacaccctgg tagccccatc cagttgtagt acatctcaca cgctggcaac ttgggacaat     900
cagcaacttt tttttctttt aatttttttca gcgcgacatt tgcctcttc tgcgagaaca     960 gacttttcca cctccatctc acccccttt gcacttatat aaattggacc agttcctccc    1020
attgtagaaa aaattttgct ggaccttttt ctcttttttt tgtcctttag tttcatacaa    1080
tctaagtcta tctacaatgt ctaaaggtga agaattattc actggtgttg tcccaatttt    1140
ggttgaatta gatggtgatg ttaatggtca aatttttct gtctccggtg aaggtgaagg    1200
tgatgctact tacggtaaat tgaccttaaa atttatttgt actactggta aattgccagt    1260
tccatggcca accttagtca ctactttcgg ttatggtgtt caatgttttg ctagataccc    1320
agatcatatg aaacaacatg acttttttcaa gtctgccatg ccagaaggtt atgttcaaga    1380 agaactatt tttttcaaag atgacggtaa ctacaagacc agagctgaag tcaagtttga    1440
aggtgatacc ttagttaata gaatcgaatt aaaaggtatt gattttaaag aagatggtaa    1500
cattttaggt cacaaattgg aatacaacta taactctcac aatgtttaca tcatggctga    1560
caaacaaaag aatggtatca agttaacttt caaaattaga cacaacattg aagatggttc    1620
tgttcaatta gctgaccatt atcaacaaaa tactccaatt ggtgatggtc cagtcttgtt    1680
accagacaac cattacttat ccactcaatc tgccttatcc aaagatccaa acgaaaagag    1740
```

```
agaccacatg gtcttgttag aatttgttac tgctgctggt attacccatg gtatggatga    1800
attgtacaaa taattgatgt aagactttaa ttataagaat acaattgtga taaagacaat    1860
gtagaagtac tgtagaagtc atggaatagc tgatcaactg tactgttata caaaggtact    1920
attaacaaaa tagacatata gtttctataa catatataaa catcttatta ggattcgatg    1980
tcagcggagg tgtagaggat ctgaatggag ataaggattt gcaaaaagtt gaggatttca    2040
ttaagattgg aaagacttta tagatgtaaa tagtgttaat gatatatgat tattagcatg    2100
attttgcgta gagtgtgttc aagcgttagg tgggatattt tgatacggtt aacatttta    2160 ctacgacgta ctttctacta tactttattc ctttgcttta atattttat tactaaaatg     2220 cacttattgc ggtatctgaa tttaatcatc ttgatcccag ttaccaggtc taggctgctt    2280
tggcatctga gggcctccag ctctcttggc catgatgatt tgatctatag acaatatggt    2340
gttggtggca tctacagcca agttaatggc agacttctta ctggagtaca agtcgtagat    2400
accagcttgg gtgacatcaa gtaaatcgtc attgtcgatg tcgataccga ggttgatgtt    2460
gtc                                                                  2463

<210> SEQ ID NO 48
<211> LENGTH: 100
<212> TYPE: DNA
<213> ORGANISM: Scheffersomyces stipitis

<400> SEQUENCE: 48
aagtgctttg gtttactaca aacgacaagc catacaccaa gaactcgacc taataggcgt      60
attatcaacg attactataa ctatggctac tttattcgtc                           100

<210> SEQ ID NO 49
<211> LENGTH: 14
<212> TYPE: DNA
<213> ORGANISM: Scheffersomyces stipitis

<400> SEQUENCE: 49
aaagagaact tgtg                                                        14

<210> SEQ ID NO 50
<211> LENGTH: 1001
<212> TYPE: DNA
<213> ORGANISM: Scheffersomyces stipitis

<400> SEQUENCE: 50
cacaagattc caaacgatat agagccgaat gggaaaaaag attccaatta taagcctaac      60
acagagatga caaaaacagc aagcttgctc tcctacgttt cttcaagtct tgacataagg     120
gtattcttta gtattgcagt gcgcattact tctataaact ttgtttttat gatcacgtga     180
atatgtacag agatttatgc acttcaggca cgtctggttc ttgattgtaa ttcaaacgtc     240
ttctgtagcc tattatacaa tttaaaacca attgactccc caaccatgct gtccaaagag     300
atgacgttct tcgtcattga taccacactg gagatggtca ataggtcaaa tcccgtttca     360
aaaagatcaa gccttgagag aggattaggc tactttcatg atcatactgc gactctattg     420
cttaagaaca ggaagattga ccgcgtaggc ataatttgtg cctcagatgc tggtaaccat     480
gtctacagtg ctgatgaggc cattcgagcg atatttccaa gacattgatc gatgcccttg     540
atgtgaaata tcttgagaag gacgagaaga aacacaagcg tcgtaagtac gaaggaactg     600
cattcgaacg attcttccgt aatgaaggcg actctgcgaa ctccgatatg aaggctgact     660
ttgatgaatt tttcgacgtt aaagacttat tgggtgggta gtatagatag taaataaagg     720
```

```
gtcaatattg gtactcaata cctgaaagct gttagttcta tgtacatgat tccttactaa    780
tatttaaaca aacgattttt caaatcgtat tccctatcct ttgctgttct ccttctatgt    840
tttgatctag cggtaccgtc ttcccccaaa ctatttacaa ttttttcgga taccttcatg    900
gttgtaaccc gttcccttc gttcttgaag atctgtttga ggtcgtttcc attgatgtcc    960
aagatggctt gcaagtcaaa gacagcctta tatttctggg a    1001
```

<210> SEQ ID NO 51
<211> LENGTH: 20
<212> TYPE: DNA
<213> ORGANISM: Scheffersomyces stipitis

<400> SEQUENCE: 51
actcgaccaa agagaacttg    20

<210> SEQ ID NO 52
<211> LENGTH: 20
<212> TYPE: DNA
<213> ORGANISM: Scheffersomyces stipitis

<400> SEQUENCE: 52
atttgtaggc atagacttcc    20

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
aaaggtgaag aattattcac    20

<210> SEQ ID NO 54
<211> LENGTH: 20
<212> TYPE: DNA
<213> ORGANISM: Artificial Sequence
<220> FEATURE:
<223> OTHER INFORMATION: Synthetic Construct

<400> SEQUENCE: 54
agtctatcta caatgtctaa    20

<210> SEQ ID NO 55
<211> LENGTH: 20
<212> TYPE: DNA
<213> ORGANISM: Artificial Sequence
<220> FEATURE:
<223> OTHER INFORMATION: Synthetic Construct

<400> SEQUENCE: 55
catctaattc aaccaaaatt    20

<210> SEQ ID NO 56
<211> LENGTH: 22
<212> TYPE: DNA
<213> ORGANISM: Artificial Sequence
<220> FEATURE:
<223> OTHER INFORMATION: Synthetic Construct

<400> SEQUENCE: 56
aaggtgaaga attattcact gg    22

<210> SEQ ID NO 57
<211> LENGTH: 23
<212> TYPE: DNA
<213> ORGANISM: Artificial Sequence
<220> FEATURE:
<223> OTHER INFORMATION: Synthetic Construct

<400> SEQUENCE: 57
agtctatcta caatgtctaa agg                                           23

<210> SEQ ID NO 58
<211> LENGTH: 23
<212> TYPE: DNA
<213> ORGANISM: Artificial Sequence
<220> FEATURE:
<223> OTHER INFORMATION: Synthetic Construct

<400> SEQUENCE: 58
catctaattc aaccaaaatt ggg                                           23

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gatatgtgga accagaacag                                               20

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
ccaatcttaa tgaaatcctc                                               20

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
cctcttctag aacacgttct tagtc                                         25

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
ccaaggatct gacaaccatc ac                                            22

<210> SEQ ID NO 63
<211> LENGTH: 20
<212> TYPE: DNA
<213> ORGANISM: Artificial Sequence
<220> FEATURE:
<223> OTHER INFORMATION: Primer

```
<400> SEQUENCE: 63
cttgttgaag gtcttgatgg                                               20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
tgacctaaaa tgttaccatc                                               20

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
gtttgaaatc ctcagctcca                                               20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
cctctggtgt ataacatgag                                               20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
aggattaggc tactttcatg                                               20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tcctgttctc cagccatttc                                               20

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
taggcttgac atttggactc tac                                           23

<210> SEQ ID NO 70
```

```
<211> LENGTH: 23
<212> TYPE: DNA
<213> ORGANISM: Artificial Sequence
<220> FEATURE:
<223> OTHER INFORMATION: Primer

<400> SEQUENCE: 70
tattggctgt tgtaggtgta gtc                                            23

<210> SEQ ID NO 71
<211> LENGTH: 23
<212> TYPE: DNA
<213> ORGANISM: Artificial Sequence
<220> FEATURE:
<223> OTHER INFORMATION: Primer

<400> SEQUENCE: 71
ctttcggtta tggtgttcaa tgt                                            23

<210> SEQ ID NO 72
<211> LENGTH: 22
<212> TYPE: DNA
<213> ORGANISM: Artificial Sequence
<220> FEATURE:
<223> OTHER INFORMATION: Primer

<400> SEQUENCE: 72
aactacaaga ccagagctga ag                                             22

<210> SEQ ID NO 73
<211> LENGTH: 60
<212> TYPE: DNA
<213> ORGANISM: Artificial Sequence
<220> FEATURE:
<223> OTHER INFORMATION: Primer

<400> SEQUENCE: 73
ggttgacaag aagtactcta tcggtttggc tatcggcact aactctgttg gttgggctgt    60

<210> SEQ ID NO 74
<211> LENGTH: 60
<212> TYPE: DNA
<213> ORGANISM: Artificial Sequence
<220> FEATURE:
<223> OTHER INFORMATION: Primer

<400> SEQUENCE: 74
acagcccaac caacagagtt agtgccgata gccaaaccga tagagtactt cttgtcaacc    60

<210> SEQ ID NO 75
<211> LENGTH: 60
<212> TYPE: DNA
<213> ORGANISM: Artificial Sequence
<220> FEATURE:
<223> OTHER INFORMATION: Primer

<400> SEQUENCE: 75
caacagattg tctgactacg acgttgacgc tatcgtcccc caatctttct tgaaggatga    60

<210> SEQ ID NO 76
<211> LENGTH: 60
<212> TYPE: DNA
<213> ORGANISM: Artificial Sequence
<220> FEATURE:
<223> OTHER INFORMATION: Primer

<400> SEQUENCE: 76
```

```
tcatccttca agaaagattg ggggacgata gcgtcaacgt cgtagtcaga caatctgttg    60

<210> SEQ ID NO 77
<211> LENGTH: 70
<212> TYPE: DNA
<213> ORGANISM: Artificial Sequence
<220> FEATURE:
<223> OTHER INFORMATION: Synthetic Construct

<400> SEQUENCE: 77
agtctatcta caatgtctaa aggtgaagaa ttattcactg gtgttgtccc aattttggtt    60
gaattagatg                                                          70
```